United States Patent
Kruse et al.

(10) Patent No.: US 10,174,082 B2
(45) Date of Patent: *Jan. 8, 2019

(54) AMYLIN AND CALCITONIN RECEPTOR AGONIST

(71) Applicant: Novo Nordisk A/S, Bagsvaerd (DK)

(72) Inventors: Thomas Kruse, Herlev (DK); Lauge Schaeffer, Lyngby (DK); Kirsten Dahl, Smoerum (DK); Christian Poulsen, Copenhagen K (DK); Kirsten Raun, Lyngby (DK)

(73) Assignee: Novo Nordisk A/S, Bagsvaerd (DK)

( * ) Notice: Subject to any disclaimer, the term of this patent is extended or adjusted under 35 U.S.C. 154(b) by 0 days.

This patent is subject to a terminal disclaimer.

(21) Appl. No.: 15/417,671

(22) Filed: Jan. 27, 2017

(65) Prior Publication Data

US 2017/0145059 A1    May 25, 2017

Related U.S. Application Data

(63) Continuation of application No. 15/151,093, filed on May 10, 2016, now Pat. No. 9,593,149, which is a continuation of application No. PCT/EP2015/069996, filed on Sep. 2, 2015.

(30) Foreign Application Priority Data

Sep. 4, 2014 (EP) .................................... 14183551

(51) Int. Cl.
*A61K 38/00* (2006.01)
*A61K 38/16* (2006.01)
*C07K 14/00* (2006.01)
*C07K 14/575* (2006.01)

(52) U.S. Cl.
CPC .......... *C07K 14/001* (2013.01); *C07K 14/575* (2013.01); *A61K 38/00* (2013.01)

(58) Field of Classification Search
CPC ...... A61K 38/00; A61K 38/16; C07K 14/001; C07K 14/575; C07K 14/00

USPC ................ 514/1.1, 21.3; 530/300, 307, 324
See application file for complete search history.

(56) References Cited

U.S. PATENT DOCUMENTS

| 4,414,149 A | 11/1983 | Orlowski et al. |
| 4,495,097 A | 1/1985 | Orlowski et al. |
| 4,622,386 A | 11/1986 | Orlowski et al. |
| 4,659,804 A | 4/1987 | Orlowski et al. |
| 8,076,288 B2 | 12/2011 | Levy et al. |
| 2010/0311650 A1 | 12/2010 | Mehta et al. |

FOREIGN PATENT DOCUMENTS

| CN | 1167114 A | 12/1997 |
| DE | 68913080 T2 | 9/1994 |
| EP | 0297159 A1 | 1/1989 |
| EP | 0347105 A2 | 12/1989 |
| WO | 2007014051 A2 | 2/2007 |
| WO | 2009/156473 A1 | 12/2009 |
| WO | 2010/103045 A1 | 9/2010 |
| WO | 2012050925 A2 | 4/2012 |

OTHER PUBLICATIONS

Gingell J. J. et al., Activity of Pramlintide, Rat and Human Amylin but not A[beta]1-42 at Human Amylin Receptors, Endocrinology, 2014, vol. 155 No. 1, 21-26.

Roberts et al "Molecular and Functional Characterization of Amylin, a peptide associated with type 2 diabetes mellitus" Proc. Natl. Acad. Sci USA. 1989 vol. 86 pp. 9662-9666.

*Primary Examiner* — Julie Ha
(74) *Attorney, Agent, or Firm* — Jiangjie Hu

(57) ABSTRACT

The present invention relates to peptides comprising an amino acid sequence SEQ ID NO: 1 (EASELSTAALGRL-SAELHELATLPRTETGPESP), analogs and derivatives thereof and pharmaceutical compositions comprising such peptides and derivatives. This invention further regards the use of these peptides according to SEQ ID NO: 1, analogs and derivatives thereof as medicaments.

40 Claims, 1 Drawing Sheet
Specification includes a Sequence Listing.

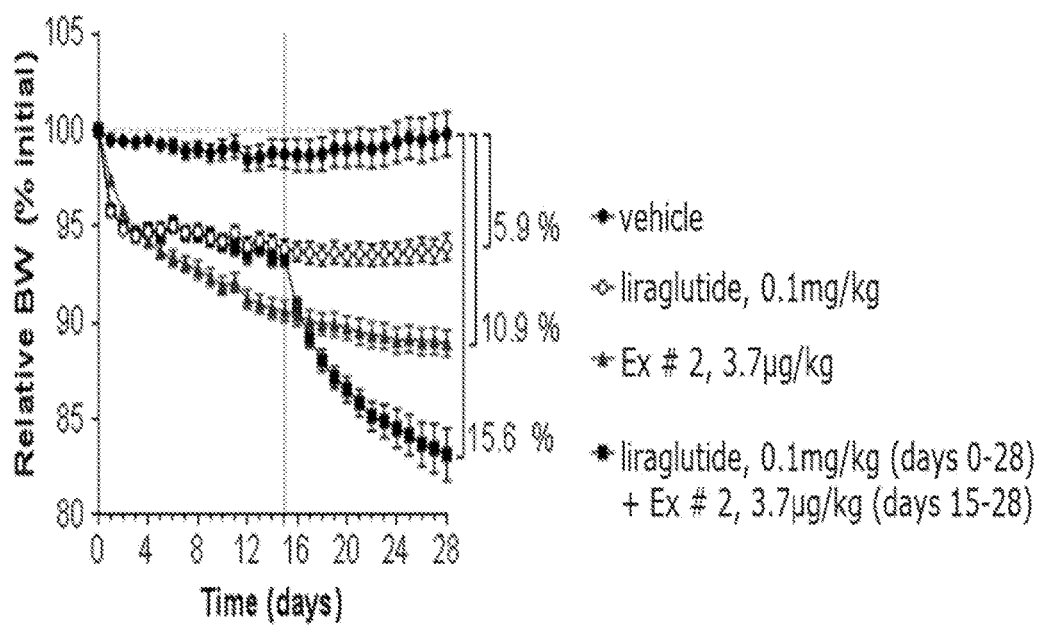

SEQUENCE LISTING

```
<160> NUMBER OF SEQ ID NOS: 119

<210> SEQ ID NO 1
<211> LENGTH: 33
<212> TYPE: PRT
<213> ORGANISM: Artificial Sequence
<220> FEATURE:
<223> OTHER INFORMATION: synthetic

<400> SEQUENCE: 1

Glu Ala Ser Glu Leu Ser Thr Ala Ala Leu Gly Arg Leu Ser Ala Glu
1               5                   10                  15

Leu His Glu Leu Ala Thr Leu Pro Arg Thr Glu Thr Gly Pro Glu Ser
            20                  25                  30

Pro

<210> SEQ ID NO 2
<211> LENGTH: 35
<212> TYPE: PRT
<213> ORGANISM: Artificial Sequence
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: X=E or may be absent
```

-continued

```
<220> FEATURE:
<221> NAME/KEY: MISC_FEATURE
<222> LOCATION: (2)..(2)
<223> OTHER INFORMATION: X=E or A or may be absent
<220> FEATURE:
<221> NAME/KEY: MISC_FEATURE
<222> LOCATION: (3)..(3)
<223> OTHER INFORMATION: X=L, A or P
<220> FEATURE:
<221> NAME/KEY: MISC_FEATURE
<222> LOCATION: (4)..(4)
<223> OTHER INFORMATION: X=S or P
<220> FEATURE:
<221> NAME/KEY: MISC_FEATURE
<222> LOCATION: (5)..(5)
<223> OTHER INFORMATION: X=E, P, K, Q or G
<220> FEATURE:
<221> NAME/KEY: MISC_FEATURE
<222> LOCATION: (6)..(6)
<223> OTHER INFORMATION: X=L, I or V
<220> FEATURE:
<221> NAME/KEY: MISC_FEATURE
<222> LOCATION: (7)..(7)
<223> OTHER INFORMATION: X=S, T or H
<220> FEATURE:
<221> NAME/KEY: MISC_FEATURE
<222> LOCATION: (9)..(9)
<223> OTHER INFORMATION: X=L or A
<220> FEATURE:
<221> NAME/KEY: MISC_FEATURE
<222> LOCATION: (10)..(10)
<223> OTHER INFORMATION: X=A, V, I, S or T
<220> FEATURE:
<221> NAME/KEY: MISC_FEATURE
<222> LOCATION: (11)..(11)
<223> OTHER INFORMATION: X=L, A, I, H or V
<220> FEATURE:
<221> NAME/KEY: MISC_FEATURE
<222> LOCATION: (13)..(13)
<223> OTHER INFORMATION: X=R, H or K
<220> FEATURE:
<221> NAME/KEY: MISC_FEATURE
<222> LOCATION: (15)..(15)
<223> OTHER INFORMATION: X=S, T or E
<220> FEATURE:
<221> NAME/KEY: MISC_FEATURE
<222> LOCATION: (16)..(16)
<223> OTHER INFORMATION: X=A, Q, E, e (d-isoform of E) or T
<220> FEATURE:
<221> NAME/KEY: MISC_FEATURE
<222> LOCATION: (17)..(17)
<223> OTHER INFORMATION: X=E, R, K or Q
<220> FEATURE:
<221> NAME/KEY: MISC_FEATURE
<222> LOCATION: (18)..(18)
<223> OTHER INFORMATION: X=L or I
<220> FEATURE:
<221> NAME/KEY: MISC_FEATURE
<222> LOCATION: (19)..(19)
<223> OTHER INFORMATION: X=H or A
<220> FEATURE:
<221> NAME/KEY: MISC_FEATURE
<222> LOCATION: (20)..(20)
<223> OTHER INFORMATION: X=E, R or K
<220> FEATURE:
<221> NAME/KEY: MISC_FEATURE
<222> LOCATION: (21)..(21)
<223> OTHER INFORMATION: X=L, I or V
<220> FEATURE:
<221> NAME/KEY: MISC_FEATURE
<222> LOCATION: (22)..(22)
<223> OTHER INFORMATION: X=A, Q, S, E or T
<220> FEATURE:
<221> NAME/KEY: MISC_FEATURE
<222> LOCATION: (24)..(24)
<223> OTHER INFORMATION: X=L, Y or T
```

```
<220> FEATURE:
<221> NAME/KEY: MISC_FEATURE
<222> LOCATION: (26)..(26)
<223> OTHER INFORMATION: X=R, P, H or K
<220> FEATURE:
<221> NAME/KEY: MISC_FEATURE
<222> LOCATION: (28)..(28)
<223> OTHER INFORMATION: X=E, Q, G or K
<220> FEATURE:
<221> NAME/KEY: MISC_FEATURE
<222> LOCATION: (29)..(29)
<223> OTHER INFORMATION: X=T or P
<220> FEATURE:
<221> NAME/KEY: MISC_FEATURE
<222> LOCATION: (31)..(31)
<223> OTHER INFORMATION: X=P, S or T
<220> FEATURE:
<221> NAME/KEY: MISC_FEATURE
<222> LOCATION: (32)..(32)
<223> OTHER INFORMATION: X=E, Q, G, A, P or K
<220> FEATURE:
<221> NAME/KEY: MISC_FEATURE
<222> LOCATION: (33)..(33)
<223> OTHER INFORMATION: X=S, T, H, P or A
<220> FEATURE:
<221> NAME/KEY: MISC_FEATURE
<222> LOCATION: (34)..(34)
<223> OTHER INFORMATION: X=P, Y, H, F, L, S, G or A
<220> FEATURE:
<221> NAME/KEY: MISC_FEATURE
<222> LOCATION: (35)..(35)
<223> OTHER INFORMATION: X=G or may be absent

<400> SEQUENCE: 2

Xaa Xaa Xaa Xaa Xaa Xaa Xaa Thr Xaa Xaa Xaa Gly Xaa Leu Xaa Xaa
1               5                   10                  15

Xaa Xaa Xaa Xaa Xaa Xaa Thr Xaa Pro Xaa Thr Xaa Xaa Gly Xaa Xaa
            20                  25                  30

Xaa Xaa Xaa
        35

<210> SEQ ID NO 3
<211> LENGTH: 36
<212> TYPE: PRT
<213> ORGANISM: Artificial Sequence
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: X=E or A or may be absent
<220> FEATURE:
<221> NAME/KEY: MISC_FEATURE
<222> LOCATION: (2)..(2)
<223> OTHER INFORMATION: X=L, A or P
<220> FEATURE:
<221> NAME/KEY: MISC_FEATURE
<222> LOCATION: (3)..(3)
<223> OTHER INFORMATION: X=S or P
<220> FEATURE:
<221> NAME/KEY: MISC_FEATURE
<222> LOCATION: (4)..(4)
<223> OTHER INFORMATION: X=E, P, K, Q or G
<220> FEATURE:
<221> NAME/KEY: MISC_FEATURE
<222> LOCATION: (5)..(5)
<223> OTHER INFORMATION: X=L, I or V
<220> FEATURE:
<221> NAME/KEY: MISC_FEATURE
<222> LOCATION: (6)..(6)
<223> OTHER INFORMATION: X=S, T or H
<220> FEATURE:
<221> NAME/KEY: MISC_FEATURE
<222> LOCATION: (8)..(8)
<223> OTHER INFORMATION: X=A or L
```

-continued

```
<220> FEATURE:
<221> NAME/KEY: MISC_FEATURE
<222> LOCATION: (9)..(9)
<223> OTHER INFORMATION: X=A, V, I, S or T
<220> FEATURE:
<221> NAME/KEY: MISC_FEATURE
<222> LOCATION: (10)..(10)
<223> OTHER INFORMATION: X=L, A, I, H or V
<220> FEATURE:
<221> NAME/KEY: MISC_FEATURE
<222> LOCATION: (12)..(12)
<223> OTHER INFORMATION: X=R, H or K
<220> FEATURE:
<221> NAME/KEY: MISC_FEATURE
<222> LOCATION: (14)..(14)
<223> OTHER INFORMATION: X=S, T or E
<220> FEATURE:
<221> NAME/KEY: MISC_FEATURE
<222> LOCATION: (15)..(15)
<223> OTHER INFORMATION: X=A, Q, E, e (d-isoform of E) or T
<220> FEATURE:
<221> NAME/KEY: MISC_FEATURE
<222> LOCATION: (16)..(16)
<223> OTHER INFORMATION: X=E, R, K or Q
<220> FEATURE:
<221> NAME/KEY: MISC_FEATURE
<222> LOCATION: (17)..(17)
<223> OTHER INFORMATION: X=L or I
<220> FEATURE:
<221> NAME/KEY: MISC_FEATURE
<222> LOCATION: (18)..(18)
<223> OTHER INFORMATION: X=H or A
<220> FEATURE:
<221> NAME/KEY: MISC_FEATURE
<222> LOCATION: (19)..(19)
<223> OTHER INFORMATION: X=E, R or K
<220> FEATURE:
<221> NAME/KEY: MISC_FEATURE
<222> LOCATION: (20)..(20)
<223> OTHER INFORMATION: X=L, I or V
<220> FEATURE:
<221> NAME/KEY: MISC_FEATURE
<222> LOCATION: (21)..(21)
<223> OTHER INFORMATION: X=A, Q, S, E or T
<220> FEATURE:
<221> NAME/KEY: MISC_FEATURE
<222> LOCATION: (23)..(23)
<223> OTHER INFORMATION: X=L, Y or T
<220> FEATURE:
<221> NAME/KEY: MISC_FEATURE
<222> LOCATION: (25)..(25)
<223> OTHER INFORMATION: X=R, P, H or K
<220> FEATURE:
<221> NAME/KEY: MISC_FEATURE
<222> LOCATION: (27)..(27)
<223> OTHER INFORMATION: X=E, Q, G or K
<220> FEATURE:
<221> NAME/KEY: MISC_FEATURE
<222> LOCATION: (28)..(28)
<223> OTHER INFORMATION: X=T or P
<220> FEATURE:
<221> NAME/KEY: MISC_FEATURE
<222> LOCATION: (30)..(30)
<223> OTHER INFORMATION: X=P, S or T
<220> FEATURE:
<221> NAME/KEY: MISC_FEATURE
<222> LOCATION: (31)..(31)
<223> OTHER INFORMATION: X=E, Q, G, A, P or K
<220> FEATURE:
<221> NAME/KEY: MISC_FEATURE
<222> LOCATION: (32)..(32)
<223> OTHER INFORMATION: X=S, T, H, P or A
<220> FEATURE:
<221> NAME/KEY: MISC_FEATURE
<222> LOCATION: (33)..(33)
<223> OTHER INFORMATION: X=P, Y, H, F, L, S, G or A
```

```
<220> FEATURE:
<221> NAME/KEY: MISC_FEATURE
<222> LOCATION: (34)..(34)
<223> OTHER INFORMATION: X=G or may be absent
<220> FEATURE:
<221> NAME/KEY: MISC_FEATURE
<222> LOCATION: (35)..(35)
<223> OTHER INFORMATION: X=T or may be absent
<220> FEATURE:
<221> NAME/KEY: MISC_FEATURE
<222> LOCATION: (36)..(36)
<223> OTHER INFORMATION: X=Y or may be absent

<400> SEQUENCE: 3

Xaa Xaa Xaa Xaa Xaa Xaa Thr Xaa Xaa Xaa Gly Xaa Leu Xaa Xaa Xaa
1               5                   10                  15

Xaa Xaa Xaa Xaa Xaa Thr Xaa Pro Xaa Thr Xaa Xaa Gly Xaa Xaa Xaa
            20                  25                  30

Xaa Xaa Xaa Xaa
        35

<210> SEQ ID NO 4
<211> LENGTH: 33
<212> TYPE: PRT
<213> ORGANISM: Artificial Sequence
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: X=E or A or may be absent
<220> FEATURE:
<221> NAME/KEY: MISC_FEATURE
<222> LOCATION: (2)..(2)
<223> OTHER INFORMATION: X=L, A or P
<220> FEATURE:
<221> NAME/KEY: MISC_FEATURE
<222> LOCATION: (3)..(3)
<223> OTHER INFORMATION: X=S or P
<220> FEATURE:
<221> NAME/KEY: MISC_FEATURE
<222> LOCATION: (4)..(4)
<223> OTHER INFORMATION: X=E, P, K, Q, or G
<220> FEATURE:
<221> NAME/KEY: MISC_FEATURE
<222> LOCATION: (5)..(5)
<223> OTHER INFORMATION: X=L, I or V
<220> FEATURE:
<221> NAME/KEY: MISC_FEATURE
<222> LOCATION: (6)..(6)
<223> OTHER INFORMATION: X=S, T or H
<220> FEATURE:
<221> NAME/KEY: MISC_FEATURE
<222> LOCATION: (8)..(8)
<223> OTHER INFORMATION: X=A or L
<220> FEATURE:
<221> NAME/KEY: MISC_FEATURE
<222> LOCATION: (9)..(9)
<223> OTHER INFORMATION: X=A, V, I, S or T
<220> FEATURE:
<221> NAME/KEY: MISC_FEATURE
<222> LOCATION: (10)..(10)
<223> OTHER INFORMATION: X=L, A, I, H or V
<220> FEATURE:
<221> NAME/KEY: MISC_FEATURE
<222> LOCATION: (12)..(12)
<223> OTHER INFORMATION: X=R, H or K
<220> FEATURE:
<221> NAME/KEY: MISC_FEATURE
<222> LOCATION: (14)..(14)
<223> OTHER INFORMATION: X=S, T or E
```

```
<220> FEATURE:
<221> NAME/KEY: MISC_FEATURE
<222> LOCATION: (15)..(15)
<223> OTHER INFORMATION: X=A, Q, E, e (d-isoform of E) or T
<220> FEATURE:
<221> NAME/KEY: MISC_FEATURE
<222> LOCATION: (16)..(16)
<223> OTHER INFORMATION: X=E, R, K or Q
<220> FEATURE:
<221> NAME/KEY: MISC_FEATURE
<222> LOCATION: (17)..(17)
<223> OTHER INFORMATION: X=L or I
<220> FEATURE:
<221> NAME/KEY: MISC_FEATURE
<222> LOCATION: (18)..(18)
<223> OTHER INFORMATION: X=H or A
<220> FEATURE:
<221> NAME/KEY: MISC_FEATURE
<222> LOCATION: (19)..(19)
<223> OTHER INFORMATION: X=E, R or K
<220> FEATURE:
<221> NAME/KEY: MISC_FEATURE
<222> LOCATION: (20)..(20)
<223> OTHER INFORMATION: X=L, I or V
<220> FEATURE:
<221> NAME/KEY: MISC_FEATURE
<222> LOCATION: (21)..(21)
<223> OTHER INFORMATION: X=A, Q, S, E or T
<220> FEATURE:
<221> NAME/KEY: MISC_FEATURE
<222> LOCATION: (23)..(23)
<223> OTHER INFORMATION: X=L, Y or T
<220> FEATURE:
<221> NAME/KEY: MISC_FEATURE
<222> LOCATION: (25)..(25)
<223> OTHER INFORMATION: X=R, P, H or K
<220> FEATURE:
<221> NAME/KEY: MISC_FEATURE
<222> LOCATION: (27)..(27)
<223> OTHER INFORMATION: X=E, Q, G, or K
<220> FEATURE:
<221> NAME/KEY: MISC_FEATURE
<222> LOCATION: (28)..(28)
<223> OTHER INFORMATION: X=T or P
<220> FEATURE:
<221> NAME/KEY: MISC_FEATURE
<222> LOCATION: (30)..(30)
<223> OTHER INFORMATION: X=P, S or T
<220> FEATURE:
<221> NAME/KEY: MISC_FEATURE
<222> LOCATION: (31)..(31)
<223> OTHER INFORMATION: X=E, Q, G, A, P or K
<220> FEATURE:
<221> NAME/KEY: MISC_FEATURE
<222> LOCATION: (32)..(32)
<223> OTHER INFORMATION: X=S, T, H, P or A
<220> FEATURE:
<221> NAME/KEY: MISC_FEATURE
<222> LOCATION: (33)..(33)
<223> OTHER INFORMATION: X=P, Y, H, F, L, S, G or A

<400> SEQUENCE: 4

Xaa Xaa Xaa Xaa Xaa Xaa Thr Xaa Xaa Xaa Gly Xaa Leu Xaa Xaa Xaa
1               5                   10                  15

Xaa Xaa Xaa Xaa Xaa Thr Xaa Pro Xaa Thr Xaa Xaa Gly Xaa Xaa Xaa
            20                  25                  30

Xaa

<210> SEQ ID NO 5
<211> LENGTH: 37
<212> TYPE: PRT
<213> ORGANISM: Homo sapiens
```

```
<400> SEQUENCE: 5

Lys Cys Asn Thr Ala Thr Cys Ala Thr Gln Arg Leu Ala Asn Phe Leu
1               5                   10                  15

Val His Ser Ser Asn Asn Phe Gly Ala Ile Leu Ser Ser Thr Asn Val
            20                  25                  30

Gly Ser Asn Thr Tyr
        35

<210> SEQ ID NO 6
<211> LENGTH: 37
<212> TYPE: PRT
<213> ORGANISM: Artificial Sequence
<220> FEATURE:
<223> OTHER INFORMATION: synthetic

<400> SEQUENCE: 6

Lys Cys Asn Thr Ala Thr Cys Ala Thr Gln Arg Leu Ala Asn Phe Leu
1               5                   10                  15

Val His Ser Ser Asn Asn Phe Gly Pro Ile Leu Pro Pro Thr Asn Val
            20                  25                  30

Gly Ser Asn Thr Tyr
        35

<210> SEQ ID NO 7
<211> LENGTH: 32
<212> TYPE: PRT
<213> ORGANISM: Artificial Sequence
<220> FEATURE:
<223> OTHER INFORMATION: synthetic

<400> SEQUENCE: 7

Cys Ser Asn Leu Ser Thr Cys Val Leu Gly Lys Leu Ser Gln Glu Leu
1               5                   10                  15

His Lys Leu Gln Thr Tyr Pro Arg Thr Asn Thr Gly Ser Gly Thr Pro
            20                  25                  30

<210> SEQ ID NO 8
<211> LENGTH: 32
<212> TYPE: PRT
<213> ORGANISM: Homo sapiens

<400> SEQUENCE: 8

Cys Gly Asn Leu Ser Thr Cys Met Leu Gly Thr Tyr Thr Gln Asp Phe
1               5                   10                  15

Asn Lys Phe His Thr Phe Pro Gln Thr Ala Ile Gly Val Gly Ala Pro
            20                  25                  30

<210> SEQ ID NO 9
<211> LENGTH: 33
<212> TYPE: PRT
<213> ORGANISM: Artificial Sequence
<220> FEATURE:
<223> OTHER INFORMATION: synthetic

<400> SEQUENCE: 9

Glu Ala Ser Glu Ile Ser Thr Ala Ala Leu Gly Arg Leu Ser Ala Glu
1               5                   10                  15

Leu His Glu Leu Ala Thr Leu Pro Arg Thr Glu Thr Gly Pro Glu Ser
            20                  25                  30

Pro
```

```
<210> SEQ ID NO 10
<211> LENGTH: 33
<212> TYPE: PRT
<213> ORGANISM: Artificial Sequence
<220> FEATURE:
<223> OTHER INFORMATION: synthetic

<400> SEQUENCE: 10

Glu Ala Ser Glu Leu Ser Thr Ala Val Leu Gly Arg Leu Ser Ala Glu
1               5                   10                  15

Leu His Glu Leu Ala Thr Leu Pro Arg Thr Glu Thr Gly Pro Glu Ser
            20                  25                  30

Pro

<210> SEQ ID NO 11
<211> LENGTH: 33
<212> TYPE: PRT
<213> ORGANISM: Artificial Sequence
<220> FEATURE:
<223> OTHER INFORMATION: synthetic

<400> SEQUENCE: 11

Glu Ala Ser Glu Leu Ser Thr Ala Ile Leu Gly Arg Leu Ser Ala Glu
1               5                   10                  15

Leu His Glu Leu Ala Thr Leu Pro Arg Thr Glu Thr Gly Pro Glu Ser
            20                  25                  30

Pro

<210> SEQ ID NO 12
<211> LENGTH: 33
<212> TYPE: PRT
<213> ORGANISM: Artificial Sequence
<220> FEATURE:
<223> OTHER INFORMATION: synthetic

<400> SEQUENCE: 12

Glu Ala Ser Glu Leu Ser Thr Ala Ala Leu Gly Arg Leu Ser Ala Glu
1               5                   10                  15

Ile His Glu Leu Ala Thr Leu Pro Arg Thr Glu Thr Gly Pro Glu Ser
            20                  25                  30

Pro

<210> SEQ ID NO 13
<211> LENGTH: 33
<212> TYPE: PRT
<213> ORGANISM: Artificial Sequence
<220> FEATURE:
<223> OTHER INFORMATION: synthetic

<400> SEQUENCE: 13

Glu Ala Ser Glu Leu Ser Thr Ala Ala Leu Gly Arg Leu Ser Ala Glu
1               5                   10                  15

Leu His Glu Ile Ala Thr Leu Pro Arg Thr Glu Thr Gly Pro Glu Ser
            20                  25                  30

Pro

<210> SEQ ID NO 14
<211> LENGTH: 33
<212> TYPE: PRT
<213> ORGANISM: Artificial Sequence
<220> FEATURE:
<223> OTHER INFORMATION: synthetic
```

```
<400> SEQUENCE: 14

Glu Ala Ser Glu Leu Ser Thr Ala Ala Leu Gly Arg Leu Ser Ala Glu
1               5                   10                  15

Leu Ala Glu Leu Ala Thr Leu Pro Arg Thr Glu Thr Gly Pro Glu Ser
            20                  25                  30

Pro

<210> SEQ ID NO 15
<211> LENGTH: 33
<212> TYPE: PRT
<213> ORGANISM: Artificial Sequence
<220> FEATURE:
<223> OTHER INFORMATION: synthetic

<400> SEQUENCE: 15

Glu Ala Ser Glu Leu Ser Thr Ala Leu Leu Gly Arg Leu Ser Ala Glu
1               5                   10                  15

Leu His Glu Leu Ala Thr Leu Pro Arg Thr Glu Thr Gly Pro Glu Ser
            20                  25                  30

Pro

<210> SEQ ID NO 16
<211> LENGTH: 33
<212> TYPE: PRT
<213> ORGANISM: Artificial Sequence
<220> FEATURE:
<223> OTHER INFORMATION: synthetic

<400> SEQUENCE: 16

Glu Ala Ser Glu Leu Ser Thr Leu Ala Leu Gly Arg Leu Ser Ala Glu
1               5                   10                  15

Leu His Glu Leu Ala Thr Leu Pro Arg Thr Glu Thr Gly Pro Glu Ser
            20                  25                  30

Pro

<210> SEQ ID NO 17
<211> LENGTH: 33
<212> TYPE: PRT
<213> ORGANISM: Artificial Sequence
<220> FEATURE:
<223> OTHER INFORMATION: synthetic

<400> SEQUENCE: 17

Glu Ala Ser Glu Leu His Thr Ala Ala Leu Gly Arg Leu Ser Ala Glu
1               5                   10                  15

Leu His Glu Leu Ala Thr Leu Pro Arg Thr Glu Thr Gly Pro Glu Ser
            20                  25                  30

Pro

<210> SEQ ID NO 18
<211> LENGTH: 33
<212> TYPE: PRT
<213> ORGANISM: Artificial Sequence
<220> FEATURE:
<223> OTHER INFORMATION: synthetic
```

```
<400> SEQUENCE: 18

Glu Ala Ser Glu His Ser Thr Ala Ala Leu Gly Arg Leu Ser Ala Glu
1               5                   10                  15

Leu His Glu Leu Ala Thr Leu Pro Arg Thr Glu Thr Gly Pro Glu Ser
            20                  25                  30

Pro

<210> SEQ ID NO 19
<211> LENGTH: 33
<212> TYPE: PRT
<213> ORGANISM: Artificial Sequence
<220> FEATURE:
<223> OTHER INFORMATION: synthetic

<400> SEQUENCE: 19

Glu Ala Ser Glu Leu Ser Thr Ala Ala Leu Gly Arg Leu Ser Ala Glu
1               5                   10                  15

Leu His Glu Leu Ala Thr Leu Pro Arg Thr Glu Thr Gly Pro Glu His
            20                  25                  30

Pro

<210> SEQ ID NO 20
<211> LENGTH: 32
<212> TYPE: PRT
<213> ORGANISM: Artificial Sequence
<220> FEATURE:
<223> OTHER INFORMATION: synthetic

<400> SEQUENCE: 20

Ala Ser Glu Leu Ser Thr Ala Ala Leu Gly Arg Leu Ser Ala Glu Leu
1               5                   10                  15

His Glu Leu Ala Thr Leu Pro Arg Thr Glu Thr Gly Pro Glu Ser Pro
            20                  25                  30

<210> SEQ ID NO 21
<211> LENGTH: 33
<212> TYPE: PRT
<213> ORGANISM: Artificial Sequence
<220> FEATURE:
<223> OTHER INFORMATION: synthetic

<400> SEQUENCE: 21

Glu Ala Ser Glu Leu Ser Thr Ala Ala Leu Gly Arg Leu Ser Ala Glu
1               5                   10                  15

Leu His Glu Leu Ala Thr Tyr Pro Arg Thr Glu Thr Gly Pro Glu Ser
            20                  25                  30

Pro

<210> SEQ ID NO 22
<211> LENGTH: 33
<212> TYPE: PRT
<213> ORGANISM: Artificial Sequence
<220> FEATURE:
<223> OTHER INFORMATION: synthetic

<400> SEQUENCE: 22

Glu Ala Ser Glu Leu Ser Thr Ala Ala Leu Gly Arg Leu Ser Ala Glu
1               5                   10                  15

Leu His Glu Leu Ala Thr Leu Pro Arg Thr Glu Thr Gly Ser Gly Ser
            20                  25                  30

Pro
```

<210> SEQ ID NO 23
<211> LENGTH: 33
<212> TYPE: PRT
<213> ORGANISM: Artificial Sequence
<220> FEATURE:
<223> OTHER INFORMATION: synthetic

<400> SEQUENCE: 23

Glu Ala Ser Glu Leu Ser Thr Ala Ala Leu Gly Arg Leu Ser Ala Glu
1               5                   10                  15

Leu His Glu Leu Ala Thr Leu Pro Arg Thr Glu Thr Gly Ser Gly Ser
            20                  25                  30

Pro

<210> SEQ ID NO 24
<211> LENGTH: 32
<212> TYPE: PRT
<213> ORGANISM: Artificial Sequence
<220> FEATURE:
<223> OTHER INFORMATION: synthetic

<400> SEQUENCE: 24

Ala Ser Glu Leu Ser Thr Ala Ala Leu Gly Arg Leu Ser Ala Glu Leu
1               5                   10                  15

His Glu Leu Ala Thr Leu Pro Arg Thr Glu Thr Gly Ser Glu Ser Pro
            20                  25                  30

<210> SEQ ID NO 25
<211> LENGTH: 33
<212> TYPE: PRT
<213> ORGANISM: Artificial Sequence
<220> FEATURE:
<223> OTHER INFORMATION: synthetic

<400> SEQUENCE: 25

Glu Ala Ser Glu Val Ser Thr Ala Val Leu Gly Arg Leu Ser Ala Glu
1               5                   10                  15

Leu His Glu Leu Ala Thr Leu Pro Arg Thr Glu Thr Gly Pro Glu Ser
            20                  25                  30

Pro

<210> SEQ ID NO 26
<211> LENGTH: 33
<212> TYPE: PRT
<213> ORGANISM: Artificial Sequence
<220> FEATURE:
<223> OTHER INFORMATION: synthetic

<400> SEQUENCE: 26

Glu Ala Ser Glu Ile Ser Thr Ala Ile Leu Gly Arg Leu Ser Ala Glu
1               5                   10                  15

Leu His Glu Leu Ala Thr Leu Pro Arg Thr Glu Thr Gly Pro Glu Ser
            20                  25                  30

Pro

<210> SEQ ID NO 27
<211> LENGTH: 33
<212> TYPE: PRT
<213> ORGANISM: Artificial Sequence
<220> FEATURE:
<223> OTHER INFORMATION: synthetic

```
<400> SEQUENCE: 27

Glu Ala Ser Glu Leu Ser Thr Ala Val Ile Gly Arg Leu Ser Ala Glu
1               5                   10                  15

Leu His Glu Leu Ala Thr Leu Pro Arg Thr Glu Thr Gly Pro Glu Ser
            20                  25                  30

Pro

<210> SEQ ID NO 28
<211> LENGTH: 33
<212> TYPE: PRT
<213> ORGANISM: Artificial Sequence
<220> FEATURE:
<223> OTHER INFORMATION: synthetic

<400> SEQUENCE: 28

Glu Ala Ser Glu Leu Ser Thr Ala Leu Ala Gly Arg Leu Ser Ala Glu
1               5                   10                  15

Leu His Glu Leu Ala Thr Leu Pro Arg Thr Glu Thr Gly Pro Glu Ser
            20                  25                  30

Pro

<210> SEQ ID NO 29
<211> LENGTH: 33
<212> TYPE: PRT
<213> ORGANISM: Artificial Sequence
<220> FEATURE:
<223> OTHER INFORMATION: synthetic

<400> SEQUENCE: 29

Glu Pro Ser Glu Leu Ser Thr Ala Val Leu Gly Arg Leu Ser Ala Glu
1               5                   10                  15

Leu His Glu Leu Ala Thr Leu Pro Arg Thr Glu Thr Gly Pro Glu Ser
            20                  25                  30

Pro

<210> SEQ ID NO 30
<211> LENGTH: 33
<212> TYPE: PRT
<213> ORGANISM: Artificial Sequence
<220> FEATURE:
<223> OTHER INFORMATION: synthetic

<400> SEQUENCE: 30

Glu Ala Pro Glu Leu Ser Thr Ala Val Leu Gly Arg Leu Ser Ala Glu
1               5                   10                  15

Leu His Glu Leu Ala Thr Leu Pro Arg Thr Glu Thr Gly Pro Glu Ser
            20                  25                  30

Pro

<210> SEQ ID NO 31
<211> LENGTH: 33
<212> TYPE: PRT
<213> ORGANISM: Artificial Sequence
<220> FEATURE:
<223> OTHER INFORMATION: synthetic
```

```
<400> SEQUENCE: 31

Glu Ala Ser Pro Leu Ser Thr Ala Val Leu Gly Arg Leu Ser Ala Glu
1               5                   10                  15

Leu His Glu Leu Ala Thr Leu Pro Arg Thr Gly Thr Gly Pro Glu Ser
            20                  25                  30

Pro

<210> SEQ ID NO 32
<211> LENGTH: 33
<212> TYPE: PRT
<213> ORGANISM: Artificial Sequence
<220> FEATURE:
<223> OTHER INFORMATION: synthetic

<400> SEQUENCE: 32

Glu Ala Ser Glu Leu Ser Thr Ala Val Leu Gly Arg Leu Ser Ala Glu
1               5                   10                  15

Leu His Glu Leu Ala Thr Leu Pro Pro Thr Glu Thr Gly Pro Glu Ser
            20                  25                  30

Pro

<210> SEQ ID NO 33
<211> LENGTH: 33
<212> TYPE: PRT
<213> ORGANISM: Artificial Sequence
<220> FEATURE:
<223> OTHER INFORMATION: synthetic

<400> SEQUENCE: 33

Glu Ala Ser Glu Leu Ser Thr Ala Val Leu Gly Arg Leu Ser Ala Glu
1               5                   10                  15

Leu His Glu Leu Ala Thr Leu Pro Arg Thr Glu Pro Gly Pro Glu Ser
            20                  25                  30

Pro

<210> SEQ ID NO 34
<211> LENGTH: 33
<212> TYPE: PRT
<213> ORGANISM: Artificial Sequence
<220> FEATURE:
<223> OTHER INFORMATION: synthetic

<400> SEQUENCE: 34

Glu Ala Ser Glu Leu Ser Thr Ala Val Leu Gly Arg Leu Ser Ala Glu
1               5                   10                  15

Leu Ala Glu Leu Ala Thr Leu Pro Arg Thr Glu Thr Gly Pro Glu Ser
            20                  25                  30

Pro

<210> SEQ ID NO 35
<211> LENGTH: 33
<212> TYPE: PRT
<213> ORGANISM: Artificial Sequence
<220> FEATURE:
<223> OTHER INFORMATION: synthetic
```

```
<400> SEQUENCE: 35

Glu Ala Ser Glu Leu Ser Thr Ala Ala Leu Gly Arg Leu Ser Ala Glu
1               5                   10                  15

Leu His Glu Leu Ala Thr Tyr Pro Arg Thr Glu Thr Gly Ser Gly Ser
            20                  25                  30

Pro

<210> SEQ ID NO 36
<211> LENGTH: 32
<212> TYPE: PRT
<213> ORGANISM: Artificial Sequence
<220> FEATURE:
<223> OTHER INFORMATION: synthetic

<400> SEQUENCE: 36

Ala Ser Glu Leu Ser Thr Ala Ala Leu Gly Arg Leu Ser Ala Glu Leu
1               5                   10                  15

His Glu Leu Ala Thr Leu Pro Arg Thr Glu Thr Gly Ser Pro Ser Pro
            20                  25                  30

<210> SEQ ID NO 37
<211> LENGTH: 33
<212> TYPE: PRT
<213> ORGANISM: Artificial Sequence
<220> FEATURE:
<223> OTHER INFORMATION: synthetic

<400> SEQUENCE: 37

Glu Ala Ser Glu Val Ser Thr Ala Val Leu Gly Arg Leu Ser Ala Glu
1               5                   10                  15

Leu His Glu Val Ala Thr Leu Pro Arg Thr Glu Thr Gly Pro Glu Ser
            20                  25                  30

Pro

<210> SEQ ID NO 38
<211> LENGTH: 33
<212> TYPE: PRT
<213> ORGANISM: Artificial Sequence
<220> FEATURE:
<223> OTHER INFORMATION: synthetic

<400> SEQUENCE: 38

Glu Ala Ser Glu Ile Ser Thr Ala Ile Ile Gly Arg Leu Ser Ala Glu
1               5                   10                  15

Leu His Glu Leu Ala Thr Leu Pro Arg Thr Glu Thr Gly Pro Glu Ser
            20                  25                  30

Pro

<210> SEQ ID NO 39
<211> LENGTH: 33
<212> TYPE: PRT
<213> ORGANISM: Artificial Sequence
<220> FEATURE:
<223> OTHER INFORMATION: synthetic

<400> SEQUENCE: 39

Glu Ala Pro Pro Leu Ser Thr Ala Val Leu Gly Arg Leu Ser Ala Glu
1               5                   10                  15

Leu His Glu Leu Ala Thr Leu Pro Arg Thr Glu Thr Gly Pro Glu Ser
            20                  25                  30

Pro
```

```
<210> SEQ ID NO 40
<211> LENGTH: 33
<212> TYPE: PRT
<213> ORGANISM: Artificial Sequence
<220> FEATURE:
<223> OTHER INFORMATION: synthetic

<400> SEQUENCE: 40

Glu Ala Ser Glu Leu Ser Thr Ala Val Leu Gly Lys Leu Ser Ala Glu
1               5                   10                  15
Leu His Glu Leu Ala Thr Leu Pro Lys Thr Glu Thr Gly Pro Glu Ser
            20                  25                  30
Pro

<210> SEQ ID NO 41
<211> LENGTH: 32
<212> TYPE: PRT
<213> ORGANISM: Artificial Sequence
<220> FEATURE:
<223> OTHER INFORMATION: synthetic

<400> SEQUENCE: 41

Ala Ser Glu Leu Ser Thr Ala Ala Leu Gly Arg Leu Ser Ala Glu Leu
1               5                   10                  15
His Glu Leu Ala Thr Leu Pro Arg Thr Glu Thr Gly Ser Gly Ser Pro
            20                  25                  30

<210> SEQ ID NO 42
<211> LENGTH: 32
<212> TYPE: PRT
<213> ORGANISM: Artificial Sequence
<220> FEATURE:
<223> OTHER INFORMATION: synthetic

<400> SEQUENCE: 42

Ala Ser Lys Leu Ser Thr Ala Ala Leu Gly Arg Leu Ser Ala Glu Leu
1               5                   10                  15
His Glu Leu Ala Thr Leu Pro Arg Thr Glu Thr Gly Ser Gly Ser Pro
            20                  25                  30

<210> SEQ ID NO 43
<211> LENGTH: 32
<212> TYPE: PRT
<213> ORGANISM: Artificial Sequence
<220> FEATURE:
<223> OTHER INFORMATION: synthetic

<400> SEQUENCE: 43

Ala Ser Glu Leu Ser Thr Ala Ala Leu Gly Arg Leu Ser Ala Lys Leu
1               5                   10                  15
His Glu Leu Ala Thr Leu Pro Arg Thr Glu Thr Gly Ser Gly Ser Pro
            20                  25                  30

<210> SEQ ID NO 44
<211> LENGTH: 32
<212> TYPE: PRT
<213> ORGANISM: Artificial Sequence
<220> FEATURE:
<223> OTHER INFORMATION: synthetic
```

```
<400> SEQUENCE: 44

Ala Ser Glu Leu Ser Thr Ala Ala Leu Gly Arg Leu Ser Ala Glu Leu
1               5                   10                  15

His Lys Leu Ala Thr Leu Pro Arg Thr Glu Thr Gly Ser Gly Ser Pro
            20                  25                  30

<210> SEQ ID NO 45
<211> LENGTH: 32
<212> TYPE: PRT
<213> ORGANISM: Artificial Sequence
<220> FEATURE:
<223> OTHER INFORMATION: synthetic

<400> SEQUENCE: 45

Ala Ser Glu Leu Ser Thr Ala Ala Leu Gly Arg Leu Ser Ala Glu Leu
1               5                   10                  15

His Glu Leu Ala Thr Leu Pro Arg Thr Lys Thr Gly Ser Gly Ser Pro
            20                  25                  30

<210> SEQ ID NO 46
<211> LENGTH: 32
<212> TYPE: PRT
<213> ORGANISM: Artificial Sequence
<220> FEATURE:
<223> OTHER INFORMATION: synthetic

<400> SEQUENCE: 46

Ala Ser Glu Leu Ser Thr Ala Ala Leu Gly Arg Leu Ser Ala Glu Leu
1               5                   10                  15

His Glu Leu Ala Thr Tyr Pro Arg Thr Glu Thr Gly Ser Gly Ser Pro
            20                  25                  30

<210> SEQ ID NO 47
<211> LENGTH: 33
<212> TYPE: PRT
<213> ORGANISM: Artificial Sequence
<220> FEATURE:
<223> OTHER INFORMATION: synthetic

<400> SEQUENCE: 47

Ala Ala Ser Glu Leu Ser Thr Ala Ala Leu Gly Arg Leu Ser Ala Glu
1               5                   10                  15

Leu His Glu Leu Ala Thr Tyr Pro Arg Thr Glu Thr Gly Ser Gly Ser
            20                  25                  30

Tyr

<210> SEQ ID NO 48
<211> LENGTH: 32
<212> TYPE: PRT
<213> ORGANISM: Artificial Sequence
<220> FEATURE:
<223> OTHER INFORMATION: synthetic

<400> SEQUENCE: 48

Ala Ser Glu Leu Ser Thr Ala Ala Leu Gly Arg Leu Ser Ala Glu Leu
1               5                   10                  15

His Glu Leu Ala Thr Leu Pro Arg Thr Glu Thr Gly Ser Gly Ser Tyr
            20                  25                  30

<210> SEQ ID NO 49
<211> LENGTH: 32
<212> TYPE: PRT
<213> ORGANISM: Artificial Sequence
```

```
<220> FEATURE:
<223> OTHER INFORMATION: synthetic

<400> SEQUENCE: 49

Ala Ser Glu Leu Ser Thr Ala Ala Leu Gly Arg Leu Ser Ala Glu Leu
1               5                   10                  15

His Glu Leu Ala Thr Leu Pro Arg Thr Glu Thr Gly Ser Gly Ser His
            20                  25                  30

<210> SEQ ID NO 50
<211> LENGTH: 32
<212> TYPE: PRT
<213> ORGANISM: Artificial Sequence
<220> FEATURE:
<223> OTHER INFORMATION: synthetic

<400> SEQUENCE: 50

Ala Ser Glu Leu Ser Thr Ala Ala Leu Gly Arg Leu Ser Ala Glu Leu
1               5                   10                  15

His Glu Leu Ala Thr Leu Pro Arg Thr Glu Thr Gly Ser Gly Ser Phe
            20                  25                  30

<210> SEQ ID NO 51
<211> LENGTH: 32
<212> TYPE: PRT
<213> ORGANISM: Artificial Sequence
<220> FEATURE:
<223> OTHER INFORMATION: synthetic

<400> SEQUENCE: 51

Ala Ser Glu Leu Ser Thr Ala Ala Leu Gly Arg Leu Ser Ala Glu Leu
1               5                   10                  15

His Glu Leu Ala Thr Leu Pro Arg Thr Glu Thr Gly Ser Gly Ser Leu
            20                  25                  30

<210> SEQ ID NO 52
<211> LENGTH: 32
<212> TYPE: PRT
<213> ORGANISM: Artificial Sequence
<220> FEATURE:
<223> OTHER INFORMATION: synthetic

<400> SEQUENCE: 52

Ala Ser Glu Leu Ser Thr Ala Ala Leu Gly Arg Leu Ser Ala Glu Leu
1               5                   10                  15

His Glu Leu Ala Thr Leu Pro Arg Thr Glu Thr Gly Ser Gly Ser Ser
            20                  25                  30

<210> SEQ ID NO 53
<211> LENGTH: 32
<212> TYPE: PRT
<213> ORGANISM: Artificial Sequence
<220> FEATURE:
<223> OTHER INFORMATION: synthetic

<400> SEQUENCE: 53

Ala Ser Glu Leu Ser Thr Ala Ala Leu Gly Arg Leu Ser Ala Glu Leu
1               5                   10                  15

His Glu Leu Ala Thr Leu Pro Arg Thr Glu Thr Gly Ser Gly Ser Gly
            20                  25                  30
```

```
<210> SEQ ID NO 54
<211> LENGTH: 32
<212> TYPE: PRT
<213> ORGANISM: Artificial Sequence
<220> FEATURE:
<223> OTHER INFORMATION: synthetic

<400> SEQUENCE: 54

Ala Ser Glu Leu Ser Thr Ala Ala Leu Gly Arg Leu Ser Ala Glu Leu
1               5                   10                  15

His Glu Leu Ala Thr Leu Pro Arg Thr Glu Thr Gly Ser Gly Ser Ala
            20                  25                  30

<210> SEQ ID NO 55
<211> LENGTH: 32
<212> TYPE: PRT
<213> ORGANISM: Artificial Sequence
<220> FEATURE:
<223> OTHER INFORMATION: synthetic

<400> SEQUENCE: 55

Ala Ser Glu Leu Ser Thr Ala Ala Leu Gly Arg Leu Ser Glu Glu Leu
1               5                   10                  15

His Glu Leu Ala Thr Leu Pro Arg Thr Glu Thr Gly Ser Gly Ser Pro
            20                  25                  30

<210> SEQ ID NO 56
<211> LENGTH: 32
<212> TYPE: PRT
<213> ORGANISM: Artificial Sequence
<220> FEATURE:
<223> OTHER INFORMATION: synthetic

<400> SEQUENCE: 56

Ala Ser Glu Leu Ser Thr Ala Ala Leu Gly Arg Leu Ser Glu Glu Leu
1               5                   10                  15

His Glu Leu Ala Thr Leu Pro Arg Thr Glu Thr Gly Ser Gly Ser Pro
            20                  25                  30

<210> SEQ ID NO 57
<211> LENGTH: 32
<212> TYPE: PRT
<213> ORGANISM: Artificial Sequence
<220> FEATURE:
<223> OTHER INFORMATION: synthetic

<400> SEQUENCE: 57

Ala Ser Glu Leu Ser Thr Ala Ala Leu Gly His Leu Ser Ala Glu Leu
1               5                   10                  15

His Glu Leu Ala Thr Leu Pro Arg Thr Glu Thr Gly Ser Gly Ser Pro
            20                  25                  30

<210> SEQ ID NO 58
<211> LENGTH: 32
<212> TYPE: PRT
<213> ORGANISM: Artificial Sequence
<220> FEATURE:
<223> OTHER INFORMATION: synthetic

<400> SEQUENCE: 58

Ala Ser Glu Leu Ser Thr Ala Ala Leu Gly Arg Leu Ser Ala Glu Leu
1               5                   10                  15

His Glu Leu Ala Thr Leu Pro His Thr Glu Thr Gly Ser Gly Ser Pro
            20                  25                  30
```

```
<210> SEQ ID NO 59
<211> LENGTH: 32
<212> TYPE: PRT
<213> ORGANISM: Artificial Sequence
<220> FEATURE:
<223> OTHER INFORMATION: synthetic

<400> SEQUENCE: 59

Ala Ser Glu Leu Ser Thr Ala Ala Leu Gly Arg Leu Ser Ala Glu Leu
1               5                   10                  15

His Glu Leu Ala Thr Leu Pro Arg Thr Glu Thr Gly Thr Gly Thr Pro
            20                  25                  30

<210> SEQ ID NO 60
<211> LENGTH: 32
<212> TYPE: PRT
<213> ORGANISM: Artificial Sequence
<220> FEATURE:
<223> OTHER INFORMATION: synthetic

<400> SEQUENCE: 60

Ala Ser Glu Leu Ser Thr Ala Ala Leu Gly Arg Leu Ser Ala Glu Leu
1               5                   10                  15

His Glu Leu Ala Thr Leu Pro Arg Thr Glu Thr Gly Ser Gly Pro Pro
            20                  25                  30

<210> SEQ ID NO 61
<211> LENGTH: 32
<212> TYPE: PRT
<213> ORGANISM: Artificial Sequence
<220> FEATURE:
<223> OTHER INFORMATION: synthetic

<400> SEQUENCE: 61

Ala Ser Glu Leu Ser Thr Ala Val Leu Gly Arg Leu Ser Ala Glu Leu
1               5                   10                  15

His Glu Leu Ala Thr Leu Pro Arg Thr Glu Thr Gly Ser Gly Ser Pro
            20                  25                  30

<210> SEQ ID NO 62
<211> LENGTH: 33
<212> TYPE: PRT
<213> ORGANISM: Artificial Sequence
<220> FEATURE:
<223> OTHER INFORMATION: synthetic

<400> SEQUENCE: 62

Glu Ala Ser Glu Ile Ser Thr Ala Ile Ile Gly Arg Leu Ser Ala Glu
1               5                   10                  15

Leu His Glu Ile Ala Thr Leu Pro Arg Thr Glu Thr Gly Pro Glu Ser
            20                  25                  30

Pro

<210> SEQ ID NO 63
<211> LENGTH: 32
<212> TYPE: PRT
<213> ORGANISM: Artificial Sequence
<220> FEATURE:
<223> OTHER INFORMATION: synthetic
```

```
<400> SEQUENCE: 63

Ala Ser Gln Leu Ser Thr Ala Ala Leu Gly Arg Leu Ser Ala Glu Leu
1               5                   10                  15

His Glu Leu Ala Thr Leu Pro Arg Thr Glu Thr Gly Ser Gly Ser Pro
            20                  25                  30

<210> SEQ ID NO 64
<211> LENGTH: 32
<212> TYPE: PRT
<213> ORGANISM: Artificial Sequence
<220> FEATURE:
<223> OTHER INFORMATION: synthetic

<400> SEQUENCE: 64

Ala Ser Gly Leu Ser Thr Ala Ala Leu Gly Arg Leu Ser Ala Glu Leu
1               5                   10                  15

His Glu Leu Ala Thr Tyr Pro Arg Thr Glu Thr Gly Ser Gly Ser Pro
            20                  25                  30

<210> SEQ ID NO 65
<211> LENGTH: 32
<212> TYPE: PRT
<213> ORGANISM: Artificial Sequence
<220> FEATURE:
<223> OTHER INFORMATION: synthetic

<400> SEQUENCE: 65

Ala Ser Glu Leu Ser Thr Ala Ala Leu Gly Arg Leu Ser Ala Glu Leu
1               5                   10                  15

His Glu Leu Ala Thr Tyr Pro Arg Thr Glu Thr Gly Ser Gly Ser Tyr
            20                  25                  30

<210> SEQ ID NO 66
<211> LENGTH: 32
<212> TYPE: PRT
<213> ORGANISM: Artificial Sequence
<220> FEATURE:
<223> OTHER INFORMATION: synthetic

<400> SEQUENCE: 66

Ala Ser Glu Leu Ser Thr Ala Ala Leu Gly Arg Leu Ser Ala Glu Leu
1               5                   10                  15

His Glu Leu Ala Thr Tyr Pro Arg Thr Glu Thr Gly Ser Gly Ala Pro
            20                  25                  30

<210> SEQ ID NO 67
<211> LENGTH: 32
<212> TYPE: PRT
<213> ORGANISM: Artificial Sequence
<220> FEATURE:
<223> OTHER INFORMATION: synthetic

<400> SEQUENCE: 67

Ala Ser Glu Leu Ser Thr Ala Ala Leu Gly Arg Leu Ser Ala Glu Leu
1               5                   10                  15

His Glu Leu Ser Thr Tyr Pro Arg Thr Glu Thr Gly Ser Gly Ser Pro
            20                  25                  30

<210> SEQ ID NO 68
<211> LENGTH: 34
<212> TYPE: PRT
<213> ORGANISM: Artificial Sequence
<220> FEATURE:
<223> OTHER INFORMATION: synthetic
```

```
<400> SEQUENCE: 68

Glu Ala Ala Ser Glu Leu Ser Thr Ala Ala Leu Gly Arg Leu Ser Ala
1               5                   10                  15

Glu Leu His Glu Leu Ala Thr Tyr Pro Arg Thr Glu Thr Gly Ser Gly
            20                  25                  30

Ser Pro

<210> SEQ ID NO 69
<211> LENGTH: 32
<212> TYPE: PRT
<213> ORGANISM: Artificial Sequence
<220> FEATURE:
<223> OTHER INFORMATION: synthetic

<400> SEQUENCE: 69

Ala Ser Glu Leu Ser Thr Ala Ala Leu Gly His Leu Ser Ala Glu Leu
1               5                   10                  15

His Glu Leu Ala Thr Leu Pro His Thr Glu Thr Gly Ser Gly Ser Pro
            20                  25                  30

<210> SEQ ID NO 70
<211> LENGTH: 32
<212> TYPE: PRT
<213> ORGANISM: Artificial Sequence
<220> FEATURE:
<223> OTHER INFORMATION: synthetic

<400> SEQUENCE: 70

Ala Ser Glu Leu Thr Thr Ala Val Leu Gly Arg Leu Ser Ala Glu Leu
1               5                   10                  15

His Glu Leu Ala Thr Leu Pro Arg Thr Glu Thr Gly Ser Gly Ser Pro
            20                  25                  30

<210> SEQ ID NO 71
<211> LENGTH: 32
<212> TYPE: PRT
<213> ORGANISM: Artificial Sequence
<220> FEATURE:
<223> OTHER INFORMATION: synthetic

<400> SEQUENCE: 71

Ala Ser Glu Val Ser Thr Ala Val Leu Gly Arg Leu Ser Ala Glu Leu
1               5                   10                  15

His Glu Leu Ala Thr Leu Pro Arg Thr Glu Thr Gly Ser Gly Ser Pro
            20                  25                  30

<210> SEQ ID NO 72
<211> LENGTH: 32
<212> TYPE: PRT
<213> ORGANISM: Artificial Sequence
<220> FEATURE:
<223> OTHER INFORMATION: synthetic

<400> SEQUENCE: 72

Ala Ser Gln Leu Ser Thr Ala Ala Leu Gly Arg Leu Ser Ala Gln Leu
1               5                   10                  15

His Glu Leu Ala Thr Leu Pro Arg Thr Glu Thr Gly Ser Gly Ser Pro
            20                  25                  30

<210> SEQ ID NO 73
<211> LENGTH: 32
<212> TYPE: PRT
<213> ORGANISM: Artificial Sequence
```

```
<220> FEATURE:
<223> OTHER INFORMATION: synthetic

<400> SEQUENCE: 73

Ala Ser Glu Leu Ser Thr Ala Ala Leu Gly Arg Leu Ser Ala Glu Leu
1               5                   10                  15

His Glu Leu Ala Thr Tyr Pro Arg Thr Glu Thr Gly Ser Gly Ser Tyr
            20                  25                  30

<210> SEQ ID NO 74
<211> LENGTH: 33
<212> TYPE: PRT
<213> ORGANISM: Artificial Sequence
<220> FEATURE:
<223> OTHER INFORMATION: synthetic

<400> SEQUENCE: 74

Ala Ser Glu Leu Ser Thr Ala Ala Leu Gly Arg Leu Ser Ala Glu Leu
1               5                   10                  15

His Glu Leu Ala Thr Tyr Pro Arg Thr Glu Thr Gly Ser Gly Ser Pro
            20                  25                  30

Gly

<210> SEQ ID NO 75
<211> LENGTH: 33
<212> TYPE: PRT
<213> ORGANISM: Artificial Sequence
<220> FEATURE:
<223> OTHER INFORMATION: synthetic

<400> SEQUENCE: 75

Ala Ser Glu Leu Ser Thr Ala Ala Leu Gly Arg Leu Ser Ala Glu Leu
1               5                   10                  15

His Glu Leu Ala Thr Tyr Pro Arg Thr Glu Thr Gly Ser Gly Ser Pro
            20                  25                  30

Lys

<210> SEQ ID NO 76
<211> LENGTH: 32
<212> TYPE: PRT
<213> ORGANISM: Artificial Sequence
<220> FEATURE:
<223> OTHER INFORMATION: synthetic

<400> SEQUENCE: 76

Ala Ser Glu Leu Ser Thr Ala Ser Leu Gly Arg Leu Ser Ala Glu Leu
1               5                   10                  15

His Glu Leu Ala Thr Tyr Pro Arg Thr Glu Thr Gly Ser Gly Ser Tyr
            20                  25                  30

<210> SEQ ID NO 77
<211> LENGTH: 32
<212> TYPE: PRT
<213> ORGANISM: Artificial Sequence
<220> FEATURE:
<223> OTHER INFORMATION: synthetic

<400> SEQUENCE: 77

Ala Ser Glu Leu Ser Thr Ala Thr Leu Gly Arg Leu Ser Ala Glu Leu
1               5                   10                  15

His Glu Leu Ser Thr Tyr Pro Arg Thr Glu Thr Gly Ser Gly Ser Pro
            20                  25                  30
```

```
<210> SEQ ID NO 78
<211> LENGTH: 32
<212> TYPE: PRT
<213> ORGANISM: Artificial Sequence
<220> FEATURE:
<223> OTHER INFORMATION: synthetic

<400> SEQUENCE: 78

Ala Ser Glu Leu Ser Thr Ala Ala Leu Gly His Leu Ser Ala Glu Leu
1               5                   10                  15

His Glu Leu Ala Thr Leu Pro His Thr Glu Thr Gly Thr Gly Thr Pro
            20                  25                  30

<210> SEQ ID NO 79
<211> LENGTH: 32
<212> TYPE: PRT
<213> ORGANISM: Artificial Sequence
<220> FEATURE:
<223> OTHER INFORMATION: synthetic

<400> SEQUENCE: 79

Ala Ser Glu Leu Thr Thr Ala Val Leu Gly Arg Leu Ser Ala Glu Leu
1               5                   10                  15

His Glu Leu Ala Thr Leu Pro Arg Thr Glu Thr Gly Ser Gly Thr Pro
            20                  25                  30

<210> SEQ ID NO 80
<211> LENGTH: 32
<212> TYPE: PRT
<213> ORGANISM: Artificial Sequence
<220> FEATURE:
<223> OTHER INFORMATION: synthetic

<400> SEQUENCE: 80

Ala Ser Glu Leu Thr Thr Ala Val Leu Gly Arg Leu Ser Ala Glu Leu
1               5                   10                  15

His Glu Leu Ala Thr Leu Pro Arg Thr Glu Thr Gly Thr Gly Thr Pro
            20                  25                  30

<210> SEQ ID NO 81
<211> LENGTH: 32
<212> TYPE: PRT
<213> ORGANISM: Artificial Sequence
<220> FEATURE:
<223> OTHER INFORMATION: synthetic

<400> SEQUENCE: 81

Ala Ser Glu Val Ser Thr Ala Val Val Gly Arg Leu Ser Ala Glu Leu
1               5                   10                  15

His Glu Leu Ala Thr Leu Pro Arg Thr Glu Thr Gly Ser Gly Ser Pro
            20                  25                  30

<210> SEQ ID NO 82
<211> LENGTH: 32
<212> TYPE: PRT
<213> ORGANISM: Artificial Sequence
<220> FEATURE:
<223> OTHER INFORMATION: synthetic

<400> SEQUENCE: 82

Ala Ser Glu Leu Ser Thr Ala Ala Leu Gly Arg Leu Ser Ala Glu Leu
1               5                   10                  15

His Glu Leu Ser Thr Tyr Pro Arg Thr Glu Thr Gly Ser Gly Ser Tyr
            20                  25                  30
```

```
<210> SEQ ID NO 83
<211> LENGTH: 32
<212> TYPE: PRT
<213> ORGANISM: Artificial Sequence
<220> FEATURE:
<223> OTHER INFORMATION: synthetic

<400> SEQUENCE: 83

Ala Ser Gly Leu Ser Thr Ala Val Leu Gly Arg Leu Ser Ala Glu Leu
1               5                   10                  15
His Glu Leu Ala Thr Tyr Pro Arg Thr Glu Thr Gly Ser Gly Thr Pro
            20                  25                  30

<210> SEQ ID NO 84
<211> LENGTH: 32
<212> TYPE: PRT
<213> ORGANISM: Artificial Sequence
<220> FEATURE:
<223> OTHER INFORMATION: synthetic

<400> SEQUENCE: 84

Ala Ser Glu Leu Ser Thr Ala Thr Leu Gly Arg Leu Ser Ala Glu Leu
1               5                   10                  15
His Glu Leu Ser Thr Tyr Pro Arg Thr Glu Thr Gly Ser Gly Ser Pro
            20                  25                  30

<210> SEQ ID NO 85
<211> LENGTH: 32
<212> TYPE: PRT
<213> ORGANISM: Artificial Sequence
<220> FEATURE:
<223> OTHER INFORMATION: synthetic

<400> SEQUENCE: 85

Ala Ser Glu Leu Ser Thr Ala Ser Leu Gly Arg Leu Ser Ala Glu Leu
1               5                   10                  15
His Glu Leu Ser Thr Tyr Pro Arg Thr Glu Thr Gly Ser Gly Ser Tyr
            20                  25                  30

<210> SEQ ID NO 86
<211> LENGTH: 32
<212> TYPE: PRT
<213> ORGANISM: Artificial Sequence
<220> FEATURE:
<223> OTHER INFORMATION: synthetic

<400> SEQUENCE: 86

Ala Ser Glu Leu Ser Thr Ala Ala Leu Gly Lys Leu Ser Ala Glu Leu
1               5                   10                  15
His Glu Leu Ala Thr Tyr Pro Lys Thr Glu Thr Gly Ser Gly Ser Tyr
            20                  25                  30

<210> SEQ ID NO 87
<211> LENGTH: 32
<212> TYPE: PRT
<213> ORGANISM: Artificial Sequence
<220> FEATURE:
<223> OTHER INFORMATION: synthetic

<400> SEQUENCE: 87

Ala Ser Glu Val Ser Thr Ala Val Val Gly Arg Leu Ser Ala Glu Leu
1               5                   10                  15
His Glu Val Ala Thr Leu Pro Arg Thr Glu Thr Gly Ser Gly Ser Pro
            20                  25                  30
```

```
<210> SEQ ID NO 88
<211> LENGTH: 33
<212> TYPE: PRT
<213> ORGANISM: Artificial Sequence
<220> FEATURE:
<223> OTHER INFORMATION: synthetic

<400> SEQUENCE: 88
```

Glu Ala Ser Gly Leu Ser Thr Ala Ala Leu Gly Arg Leu Ser Gln Glu
1               5                   10                  15

Leu His Glu Leu Gln Thr Tyr Pro Arg Thr Glu Thr Gly Ser Gly Thr
            20                  25                  30

Tyr

```
<210> SEQ ID NO 89
<211> LENGTH: 32
<212> TYPE: PRT
<213> ORGANISM: Artificial Sequence
<220> FEATURE:
<223> OTHER INFORMATION: synthetic

<400> SEQUENCE: 89
```

Ala Ser Gly Leu Ser Thr Ala Val Leu Gly Arg Leu Ser Ala Glu Leu
1               5                   10                  15

His Glu Leu Ala Thr Tyr Pro Arg Thr Glu Thr Gly Ser Gly Thr Tyr
            20                  25                  30

```
<210> SEQ ID NO 90
<211> LENGTH: 32
<212> TYPE: PRT
<213> ORGANISM: Artificial Sequence
<220> FEATURE:
<223> OTHER INFORMATION: synthetic

<400> SEQUENCE: 90
```

Ala Ser Glu Leu Thr Thr Ala Val Leu Gly Arg Leu Thr Ala Glu Leu
1               5                   10                  15

His Glu Leu Glu Thr Leu Pro Arg Thr Glu Thr Gly Thr Gly Thr Pro
            20                  25                  30

```
<210> SEQ ID NO 91
<211> LENGTH: 32
<212> TYPE: PRT
<213> ORGANISM: Artificial Sequence
<220> FEATURE:
<223> OTHER INFORMATION: synthetic

<400> SEQUENCE: 91
```

Ala Ser Glu Leu Thr Thr Ala Val Leu Gly Arg Leu Glu Ala Glu Leu
1               5                   10                  15

His Glu Leu Thr Thr Leu Pro Arg Thr Glu Thr Gly Thr Gly Thr Pro
            20                  25                  30

```
<210> SEQ ID NO 92
<211> LENGTH: 32
<212> TYPE: PRT
<213> ORGANISM: Artificial Sequence
<220> FEATURE:
<223> OTHER INFORMATION: synthetic
```

```
<400> SEQUENCE: 92

Ala Ser Gly Leu Ser Thr Ala Ala Leu Gly Arg Leu Ser Gln Glu Leu
1               5                   10                  15

His Glu Leu Gln Thr Tyr Pro Arg Thr Glu Thr Gly Ser Lys Thr Tyr
            20                  25                  30

<210> SEQ ID NO 93
<211> LENGTH: 32
<212> TYPE: PRT
<213> ORGANISM: Artificial Sequence
<220> FEATURE:
<223> OTHER INFORMATION: synthetic

<400> SEQUENCE: 93

Ala Ser Gly Leu Ser Thr Ala Ala Leu Gly Arg Leu Ser Gln Glu Leu
1               5                   10                  15

His Glu Leu Glu Thr Tyr Pro Arg Thr Glu Thr Gly Ser Gly Thr Tyr
            20                  25                  30

<210> SEQ ID NO 94
<211> LENGTH: 32
<212> TYPE: PRT
<213> ORGANISM: Artificial Sequence
<220> FEATURE:
<223> OTHER INFORMATION: synthetic

<400> SEQUENCE: 94

Ala Ser Gly Leu Ser Thr Ala Ala Leu Gly Arg Leu Ser Gln Glu Leu
1               5                   10                  15

His Glu Leu Gln Thr Tyr Pro Arg Thr Glu Thr Gly Ser Gln Thr Tyr
            20                  25                  30

<210> SEQ ID NO 95
<211> LENGTH: 32
<212> TYPE: PRT
<213> ORGANISM: Artificial Sequence
<220> FEATURE:
<223> OTHER INFORMATION: synthetic

<400> SEQUENCE: 95

Ala Ser Gly Leu Ser Thr Ala Ala Leu Gly Arg Leu Ser Gln Glu Leu
1               5                   10                  15

His Glu Leu Gln Thr Tyr Pro Arg Thr Glu Thr Gly Ser Gly Thr Tyr
            20                  25                  30

<210> SEQ ID NO 96
<211> LENGTH: 32
<212> TYPE: PRT
<213> ORGANISM: Artificial Sequence
<220> FEATURE:
<223> OTHER INFORMATION: synthetic

<400> SEQUENCE: 96

Ala Ser Gly Leu Ser Thr Ala Ala Leu Gly Arg Leu Ser Gln Glu Leu
1               5                   10                  15

His Glu Leu Gln Thr Tyr Pro Arg Thr Glu Thr Gly Ser Gly Thr Tyr
            20                  25                  30

<210> SEQ ID NO 97
<211> LENGTH: 32
<212> TYPE: PRT
<213> ORGANISM: Artificial Sequence
<220> FEATURE:
<223> OTHER INFORMATION: synthetic
```

<400> SEQUENCE: 97

Ala Ser Gly Leu Ser Thr Ala Ala Leu Gly Arg Leu Ser Thr Glu Leu
1               5                   10                  15

His Glu Leu Glu Thr Tyr Pro Arg Thr Glu Thr Gly Ser Gly Thr Tyr
            20                  25                  30

<210> SEQ ID NO 98
<211> LENGTH: 32
<212> TYPE: PRT
<213> ORGANISM: Artificial Sequence
<220> FEATURE:
<223> OTHER INFORMATION: synthetic

<400> SEQUENCE: 98

Ala Ser Gly Leu Ser Thr Ala Ala Leu Gly Arg Leu Ser Glu Glu Leu
1               5                   10                  15

His Glu Leu Gln Thr Tyr Pro Arg Thr Glu Thr Gly Ser Gly Thr Tyr
            20                  25                  30

<210> SEQ ID NO 99
<211> LENGTH: 32
<212> TYPE: PRT
<213> ORGANISM: Artificial Sequence
<220> FEATURE:
<223> OTHER INFORMATION: synthetic

<400> SEQUENCE: 99

Ala Ser Glu Leu Ser Thr Ala Val Leu Gly Arg Leu Ser Gln Glu Leu
1               5                   10                  15

His Glu Leu Gln Thr Tyr Pro Arg Thr Glu Thr Gly Ser Gly Thr Tyr
            20                  25                  30

<210> SEQ ID NO 100
<211> LENGTH: 33
<212> TYPE: PRT
<213> ORGANISM: Artificial Sequence
<220> FEATURE:
<223> OTHER INFORMATION: synthetic

<400> SEQUENCE: 100

Glu Ala Ser Gln Leu Ser Thr Ala Val Leu Gly Arg Leu Ser Gln Glu
1               5                   10                  15

Leu His Glu Leu Gln Thr Tyr Pro Arg Thr Gly Thr Gly Ser Gly Thr
            20                  25                  30

Tyr

<210> SEQ ID NO 101
<211> LENGTH: 32
<212> TYPE: PRT
<213> ORGANISM: Artificial Sequence
<220> FEATURE:
<223> OTHER INFORMATION: synthetic

<400> SEQUENCE: 101

Ala Ser Gln Leu Ser Thr Ala Val Leu Gly Arg Leu Ser Gln Glu Leu
1               5                   10                  15

His Glu Leu Gln Thr Tyr Pro Arg Thr Glu Thr Gly Ser Gln Thr Tyr
            20                  25                  30

<210> SEQ ID NO 102
<211> LENGTH: 32
<212> TYPE: PRT
<213> ORGANISM: Artificial Sequence

```
<220> FEATURE:
<223> OTHER INFORMATION: synthetic

<400> SEQUENCE: 102

Ala Ser Gly Leu Ser Thr Ala Ala Leu Gly Arg Leu Ser Gln Glu Leu
1               5                   10                  15
His Glu Leu Gln Thr Tyr Pro His Thr Glu Thr Gly Ser Gly Thr Tyr
            20                  25                  30

<210> SEQ ID NO 103
<211> LENGTH: 32
<212> TYPE: PRT
<213> ORGANISM: Artificial Sequence
<220> FEATURE:
<223> OTHER INFORMATION: synthetic

<400> SEQUENCE: 103

Ala Ser Gly Leu Ser Thr Ala Val Leu Gly Arg Leu Ser Gln Glu Leu
1               5                   10                  15
His Glu Leu Gln Thr Tyr Pro Arg Thr Glu Thr Gly Ser Gly Thr Tyr
            20                  25                  30

<210> SEQ ID NO 104
<211> LENGTH: 32
<212> TYPE: PRT
<213> ORGANISM: Artificial Sequence
<220> FEATURE:
<223> OTHER INFORMATION: synthetic

<400> SEQUENCE: 104

Ala Ser Gly Leu Ser Thr Ala Val Leu Gly Arg Leu Ser Gln Glu Leu
1               5                   10                  15
His Glu Leu Gln Thr Tyr Pro Arg Thr Glu Thr Gly Ser Gln Thr Tyr
            20                  25                  30

<210> SEQ ID NO 105
<211> LENGTH: 32
<212> TYPE: PRT
<213> ORGANISM: Artificial Sequence
<220> FEATURE:
<223> OTHER INFORMATION: synthetic

<400> SEQUENCE: 105

Ala Ser Gly Leu Ser Thr Ala Val Leu Gly Arg Leu Ser Gln Glu Leu
1               5                   10                  15
His Glu Leu Gln Thr Tyr Pro Arg Thr Glu Thr Gly Ser Gly Thr Tyr
            20                  25                  30

<210> SEQ ID NO 106
<211> LENGTH: 32
<212> TYPE: PRT
<213> ORGANISM: Artificial Sequence
<220> FEATURE:
<223> OTHER INFORMATION: synthetic

<400> SEQUENCE: 106

Ala Ser Gly Leu Ser Thr Ala Val Leu Gly Arg Leu Ser Gln Glu Leu
1               5                   10                  15
His Glu Leu Gln Thr Tyr Pro Arg Thr Glu Thr Gly Ser Gly Thr Tyr
            20                  25                  30
```

```
<210> SEQ ID NO 107
<211> LENGTH: 32
<212> TYPE: PRT
<213> ORGANISM: Artificial Sequence
<220> FEATURE:
<223> OTHER INFORMATION: synthetic

<400> SEQUENCE: 107

Ala Ser Gly Leu Ser Thr Ala Val Leu Gly Arg Leu Ser Gln Glu Leu
1               5                   10                  15
His Glu Leu Gln Thr Tyr Pro Arg Thr Glu Thr Gly Ser Ala Thr Tyr
            20                  25                  30

<210> SEQ ID NO 108
<211> LENGTH: 32
<212> TYPE: PRT
<213> ORGANISM: Artificial Sequence
<220> FEATURE:
<223> OTHER INFORMATION: synthetic

<400> SEQUENCE: 108

Leu Ser Gly Leu Ser Thr Ala Val Leu Gly Arg Leu Ser Ala Glu Leu
1               5                   10                  15
His Glu Leu Ser Thr Tyr Pro Arg Thr Glu Thr Gly Ser Gly Thr Tyr
            20                  25                  30

<210> SEQ ID NO 109
<211> LENGTH: 32
<212> TYPE: PRT
<213> ORGANISM: Artificial Sequence
<220> FEATURE:
<223> OTHER INFORMATION: synthetic

<400> SEQUENCE: 109

Ala Ser Gly Leu Ser Thr Ala Thr Leu Gly Arg Leu Ser Gln Glu Leu
1               5                   10                  15
His Glu Leu Gln Thr Tyr Pro Arg Thr Glu Thr Gly Ser Gly Thr Tyr
            20                  25                  30

<210> SEQ ID NO 110
<211> LENGTH: 32
<212> TYPE: PRT
<213> ORGANISM: Artificial Sequence
<220> FEATURE:
<223> OTHER INFORMATION: synthetic

<400> SEQUENCE: 110

Ala Ser Gly Leu Ser Thr Ala Val Leu Gly Arg Leu Ser Gln Glu Leu
1               5                   10                  15
His Glu Leu Gln Thr Tyr Pro Pro Thr Glu Thr Gly Ser Gln Thr Tyr
            20                  25                  30

<210> SEQ ID NO 111
<211> LENGTH: 32
<212> TYPE: PRT
<213> ORGANISM: Artificial Sequence
<220> FEATURE:
<223> OTHER INFORMATION: synthetic

<400> SEQUENCE: 111

Ala Ser Gly Leu Ser Thr Leu Val Leu Gly Arg Leu Ser Gln Glu Leu
1               5                   10                  15
His Glu Leu Gln Thr Tyr Pro Arg Thr Glu Thr Gly Ser Gln Thr Tyr
            20                  25                  30
```

```
<210> SEQ ID NO 112
<211> LENGTH: 32
<212> TYPE: PRT
<213> ORGANISM: Artificial Sequence
<220> FEATURE:
<223> OTHER INFORMATION: synthetic

<400> SEQUENCE: 112

Leu Ser Gly Leu Ser Thr Ala Val Leu Gly Arg Leu Ser Gln Glu Leu
1               5                   10                  15

His Glu Leu Gln Thr Tyr Pro Arg Thr Glu Thr Gly Ser Gln Thr Tyr
            20                  25                  30

<210> SEQ ID NO 113
<211> LENGTH: 32
<212> TYPE: PRT
<213> ORGANISM: Artificial Sequence
<220> FEATURE:
<223> OTHER INFORMATION: synthetic

<400> SEQUENCE: 113

Ala Ser Gly Leu Ser Thr Ala Thr Leu Gly Arg Leu Ser Gln Glu Leu
1               5                   10                  15

His Glu Leu Gln Thr Tyr Pro Pro Thr Glu Thr Gly Ser Gly Thr Tyr
            20                  25                  30

<210> SEQ ID NO 114
<211> LENGTH: 33
<212> TYPE: PRT
<213> ORGANISM: Artificial Sequence
<220> FEATURE:
<223> OTHER INFORMATION: synthetic

<400> SEQUENCE: 114

Glu Leu Ser Gly Leu Ser Thr Leu Val Leu Gly Arg Leu Ser Gln Glu
1               5                   10                  15

Leu His Glu Leu Gln Thr Tyr Pro Arg Thr Gly Thr Gly Ser Gly Thr
            20                  25                  30

Tyr

<210> SEQ ID NO 115
<211> LENGTH: 32
<212> TYPE: PRT
<213> ORGANISM: Artificial Sequence
<220> FEATURE:
<223> OTHER INFORMATION: synthetic

<400> SEQUENCE: 115

Ala Ser Gly Leu Ser Thr Ala Val Leu Gly Arg Leu Ser Gln Glu Leu
1               5                   10                  15

His Glu Leu Gln Thr Tyr Pro Arg Thr Glu Thr Gly Ser Gln Thr Tyr
            20                  25                  30

<210> SEQ ID NO 116
<211> LENGTH: 32
<212> TYPE: PRT
<213> ORGANISM: Artificial Sequence
<220> FEATURE:
<223> OTHER INFORMATION: synthetic
```

```
<400> SEQUENCE: 116

Ala Ser Gly Leu Ser Thr Ala Val Leu Gly Lys Leu Ser Gln Glu Leu
1               5                   10                  15

His Glu Leu Gln Thr Tyr Pro Pro Thr Glu Thr Gly Ser Gly Thr Tyr
            20                  25                  30

<210> SEQ ID NO 117
<211> LENGTH: 32
<212> TYPE: PRT
<213> ORGANISM: Artificial Sequence
<220> FEATURE:
<223> OTHER INFORMATION: synthetic

<400> SEQUENCE: 117

Ala Ser Gln Leu Ser Thr Ala Val Leu Gly Arg Leu Ser Gln Arg Leu
1               5                   10                  15

His Arg Leu Gln Thr Tyr Pro Arg Thr Gln Thr Gly Ser Gln Thr Tyr
            20                  25                  30

<210> SEQ ID NO 118
<211> LENGTH: 32
<212> TYPE: PRT
<213> ORGANISM: Artificial Sequence
<220> FEATURE:
<223> OTHER INFORMATION: synthetic

<400> SEQUENCE: 118

Leu Ser Gln Leu Ser Thr Leu Val Leu Gly Arg Leu Ser Gln Arg Leu
1               5                   10                  15

His Arg Leu Gln Thr Tyr Pro Arg Thr Gln Thr Gly Ser Gln Thr Tyr
            20                  25                  30

<210> SEQ ID NO 119
<211> LENGTH: 35
<212> TYPE: PRT
<213> ORGANISM: Artificial Sequence
<220> FEATURE:
<223> OTHER INFORMATION: synthetic

<400> SEQUENCE: 119

Ala Ser Gly Leu Ser Thr Ala Val Leu Gly Arg Leu Ser Gln Glu Leu
1               5                   10                  15

His Glu Leu Gln Thr Leu Gln Thr Tyr Pro Arg Thr Glu Thr Gly Ser
            20                  25                  30

Gln Thr Tyr
        35
```

AMYLIN AND CALCITONIN RECEPTOR AGONIST

CROSS-REFERENCE TO RELATED APPLICATIONS

This application is a continuation of U.S. application Ser. No. 15/151,093, filed May 10, 2016 (now U.S. Pat. No. 9,593,149, issued Mar. 14, 2017), which is a continuation of International Application PCT/EP2015/069996 (WO 2016/034604), filed Sep. 2, 2015, which claims priority to European Patent Application EP 14183551.2, filed Sep. 4, 2014; the contents of all above-named applications are incorporated herein by reference.

SEQUENCE LISTING

The instant application contains a Sequence Listing which has been submitted in ASCII format via EFS-Web and is hereby incorporated by reference in its entirety. Said ASCII copy, created on Jan. 20, 2017, is named 140030US03_SeqList.txt and is 51 kilobytes in size.

TECHNICAL FIELD

The present invention relates to peptides comprising an amino acid sequence SEQ ID NO: 1 (EASELSTAALGRLSAELHELATLPRTETGPESP).

BACKGROUND

It has been known for a long time that when traditional insulin is used to treat diabetes, it is associated with an increase in body weight. Insulin has to be injected subcutaneously up to several times per day. Thus, an antidiabetic therapeutic approach should not only lower fasting and postprandial blood glucose levels but optimally also induce weight loss. Type 2 diabetes is generally treated in the early phases with diet and exercise. As the condition progresses, various oral anti-diabetic agents are added. Novel hormone-based therapies for type 2 diabetes are now emerging resembling an endogenous mode of action, such as glucagon like peptide (GLP)-1 and amylin analogues. These agents do not only improve glucose homeostasis but also very promisingly exert beneficial effects on body weight. In obese individuals, fasting amylin concentrations are elevated in conjunction with hyperinsulinemia and in patients with type 2 diabetes, amylin, like insulin, is relatively deficient depending on the severity of β-cell secretory failure. Amylin receptor agonists are useful in reducing food intake and treating obesity. Human amylin is a 37 amino acid long polypeptide which has physico-chemical properties that make its use as a drug troublesome. In particular, it has a tendency for fibrillogenesis, i.e. the formation of fibrils, in vitro and/or ex vivo and becomes ineffective due to precipitation. Pramlintide is a drug product marketed by Amylin Pharmaceuticals as Symlin® and a human amylin analogue and receptor agonist used in the treatment of diabetes as an add-on to insulin. Pramlintide is chemically unstable at neutral pH and it is therefore provided in an acidic solution.

The calcitonin receptor is found in many tissues throughout the body and it is believed to be involved in regulation of bone metabolism. Salmon calcitonin is currently sold under the tradename Miacalcic®. The product is used against hypercalcaemia, osteoporosis (including post-menopausal osteoporosis and glucocorticoid-related osteoporosis), ostitis deformans (Pagets disease) and is administered once daily either by injection or nasally. The calcitonin is bound to specific receptors in the membrane of the skeleton, the kidneys and in the central nervous system (CNS). Calcitonin is chemically unstable at neutral pH and it is therefore provided in an acidic solution.

Polypeptides with activity at both the amylin and calcitonin receptor and the amylin receptor may be advantageous; however increased half-life of amylin and calcitonin receptor agonists would highly increase the usability and convenience for the use as a medicament in treating the above mentioned diseases. A further drawback of the currently known pool of calcitonin and amylin peptides is that they are only chemically stable in solution when handled in a narrow acidic pH range, which makes them bothersome to handle under circumstances were a broader range of pH is desired. Thus polypeptides which are amylin and/or calcitonin receptor agonists with more flexible solubility profiles would increase the usability in medicinal products.

SUMMARY

The invention relates to peptides comprising an amino acid sequence SEQ ID NO: 1 (EASELSTAALGRLSAELHELATLPRTETGPESP), analogues and derivatives thereof and pharmaceutical compositions comprising SEQ ID NO: 1, analogues or derivatives thereof.

Further this invention relates to derivatives, pharmaceutical formulations, co-formulations and co-treatments of such mimylin peptides or derivatives in combination with GLP-1 compounds and the use thereof as medicaments in the treatment of diabetes, overweight, obesity or neuropathic pain.

In some embodiments the present invention relates to a mimylin peptide comprising a sequence having at least 66% sequence identity to SEQ ID NO: 1. In some embodiments a mimylin peptide according to the present invention comprises up to 11 amino acid modifications relative to SEQ ID NO: 1. In some embodiments a mimylin peptide according to the present invention comprises up to 11 amino acid modifications in one or more of the positions 1, 2, 3, 4, 5, 6, 8, 9, 10, 12, 14, 15, 16, 17, 18, 19, 20, 21, 23, 24, 25, 27, 28, 30, 31, 32 relative to SEQ ID NO: 1, wherein the amino acid numbering corresponds to SEQ ID NO: 1.

In some embodiments the present invention relates to a mimylin peptide comprising a sequence having at least 66% sequence identity to SEQ ID NO: 1 and c-terminal amide group.

In some embodiments the present invention relates to a mimylin peptide comprising a sequence having at least 66% sequence identity to SEQ ID NO: 1 and no disulfide bridge. In some embodiments the present invention relates to a mimylin peptide comprising a sequence having at least 66% sequence identity to SEQ ID NO: 1 and comprises no cysteins in certain positions, preferably no cysteins in position 2 and/or 8, wherein the amino acid numbering corresponds to SEQ ID NO: 1.

In some embodiments the mimylin peptides of the present invention have less than 60% sequence identity to known amylin and calcitonin receptor agonists. However, the inventors surprisingly found that mimylin peptides are agonists to the amylin and calcitonin receptors and show a favourable solubility profile throughout the complete pH scale, especially at neutral pH and above, i.e. from about pH 6.0 and above, preferably from about pH 7.0 and above. Further the peptides of the present invention are very stable peptides and thus potentially very useful for use in medicaments. Furthermore mimylin has a low Immunogenicity Risk Score (IRS). It was surprisingly found that the mimylin compounds of this invention are able to be combined with GLP-1 compounds in co-formulations wherein both remain stable. It was surprisingly found that the mimylin compounds of this invention are able to be combined with GLP-1 compounds in formulations at pH between about 7.0 and 8.5 wherein both remain stable. It was further surprisingly found that co-administration in DIO rats of a compound according to this invention and liraglutatide enhanced the weight-loss achieved by the liraglutide treatment alone, surpassing an add-on effect. Further studies are ongoing. It was surprisingly found that compounds of this invention do not affect the PK profile of liraglutide, and liraglutide does surprisingly not affect the PK profile of compounds of this invention when administered as co-formulations to LYD pigs. It was surprisingly found that Ex. compound 2 or 46 of this invention do not affect the PK profile of liraglutide and liraglutide does surprisingly not affect the PK profile of Ex. compound 2 or 46 of this invention when administered as co-formulations to LYD pigs.

The invention may also solve further problems that will be apparent from the disclosure of the exemplary embodiments and aspects.

BRIEF DESCRIPTION OF THE DRAWINGS

FIG. 1 shows relative body weight (% of initial) in DIO rats during the treatment period with liraglutide (QD) and Compound of Ex. #2. Data are mean±SEM, n=10.

DESCRIPTION

The invention relates to mimylin peptides comprising an amino acid sequence which is a mimylin analogue (EASELSTAALGRLSAELHELATLPRTETGPESP) or analogues or derivatives thereof which all show agonist effects on the amylin receptor. Further this invention relates to derivatives, pharmaceutical compositions comprising of such mimylin peptides and the use of such mimylin peptides as medicaments.

In some embodiments the mimylin peptides of the present invention are agonists to the calcitonin receptor. In some embodiments the mimylin peptide of the present invention agonises the human amylin and human calcitonin receptors and shows solubility throughout the complete pH scale, preferably neutral pH and above.

In some embodiments a mimylin peptide according to the present invention comprises up to 11 amino acid modifications relative to SEQ ID NO: 1. In some embodiments a mimylin peptide according to the present invention comprises up to 11 amino acid modifications relative to SEQ ID NO: 1, wherein in one or more of the positions 1, 2, 3, 4, 5, 6, 8, 9, 10, 12, 14, 15, 16, 17, 18, 19, 20, 21, 23, 24, 25, 27, 28, 30, 31, 32, wherein the amino acid numbering corresponds to SEQ ID NO: 1.

In some embodiments the present invention relates to a mimylin peptide comprising a sequence having at least 66% sequence identity to SEQ ID NO: 1 and a c-terminal amide group.

In some embodiments the present invention relates to a mimylin peptide comprising a sequence having at least 66% sequence identity to SEQ ID NO: 1 and no disulfide bridge. In some embodiments the present invention relates to a mimylin peptide comprising a sequence having at least 66% sequence identity to SEQ ID NO: 1 and comprises no cysteins, preferably in position 2 and/or 8, wherein the amino acid numbering corresponds to SEQ ID NO: 1.

In some embodiments a mimylin peptide according to the present invention has an $EC_{50}$ in a human amylin receptor functional assay (tested as disclosed in Assay IIb) of about 50 pM or less. In some embodiments a mimylin peptide according to the present invention has an $EC_{50}$ in a human amylin receptor functional assay (tested as disclosed in Assay IIb) of about 20 pM or less. In some embodiments a mimylin peptide according to the present invention has an $EC_{50}$ in a human amylin receptor functional assay (tested as disclosed in Assay IIb) of about 19 pM or less. In some embodiments a mimylin peptide according to the present invention has an $EC_{50}$ in a human amylin receptor functional assay (tested as disclosed in Assay IIb) of about 18 pM or less. In some embodiments a mimylin peptide according to the present invention has an $EC_{50}$ in a human amylin receptor functional assay (tested as disclosed in Assay IIb) of about 17 pM or less. In some embodiments a mimylin peptide according to the present invention has an $EC_{50}$ in a human amylin receptor functional assay (tested as disclosed in Assay IIb) of about 16 pM or less. In some embodiments a mimylin peptide according to the present invention has an $EC_{50}$ in a human amylin receptor functional assay (tested as disclosed in Assay IIb) of about 15 pM or less. In some embodiments a mimylin peptide according to the present invention has an $EC_{50}$ in a human amylin receptor functional assay (tested as disclosed in Assay IIb) of about 14 pM or less. In some embodiments a mimylin peptide according to the present invention has an $EC_{50}$ in a human amylin receptor functional assay (tested as disclosed in Assay IIb) of about 13 pM or less. In some embodiments a mimylin peptide according to the present invention has an $EC_{50}$ in a human amylin receptor functional assay (tested as disclosed in Assay IIb) of about 12 pM or less. In some embodiments a mimylin peptide according to the present invention has an $EC_{50}$ in a human amylin receptor functional assay (tested as disclosed in Assay IIb) of about 11 pM or less. In some embodiments a mimylin peptide according to the present invention has an $EC_{50}$ in a human amylin receptor functional assay (tested as disclosed in Assay IIb) of about 10 pM or less. In some embodiments a mimylin peptide according to the present invention has an $EC_{50}$ in a human amylin receptor functional assay (tested as disclosed in Assay IIb) of about 5 pM or less.

In some embodiments a mimylin peptide according to the present invention is a peptide comprising SEQ ID NO: 2; X(-1)-X1-X2-X3-X4-X5-X6-X7-X8-X9-X10-X11-X12-X13-X14-X15-X16-X17-X18-X19-X20-X21-X22-X23-X24-X25-X26-X27-X28-X29-X30-X31-X32-X33-X34 (SEQ ID NO: 2),
wherein X represents amino acids and wherein
X(-1) is E or no amino acid,
X1 is selected from the group consisting of E or A or no amino acid,
X2 is selected from the group consisting of L, A or P,
X3 is selected from the group consisting of S or P
X4 is selected from the group consisting of E, P, K, Q or G
X5 is selected from the group consisting of L, V, or I,
X6 is 5, T or H,
X7 is T,
X8 is selected from the group consisting of L or A,
X9 is selected from the group consisting of A, V, I, S or T,
X10 is selected from the group consisting of L, A, I, H or V,
X11 is G,
X12 is selected from the group consisting of R, H or K,
X13 is L,
X14 is selected from the group consisting of S, T or E, X15 is selected from the group consisting of A, Q, E, e or T,
X16 is selected from the group consisting of R, E, K or Q,
X17 is selected from the group consisting of L or I,
X18 is selected from the group consisting of H or A,
X19 is selected from the group consisting of E, R or K,
X20 is selected from the group consisting of L, I or V,
X21 is selected from the group consisting of A, Q, S, E or T,
X22 is T,
X23 is selected from the group consisting of T, Y or L,
X24 is P,
X25 is selected from the group consisting of R, P, H or K,
X26 is T,
X27 is selected from the group consisting of E, Q, G or K,
X28 is selected from the group consisting of T or P,
X29 is G,
X30 is selected from the group consisting of P, S or T,
X31 is selected from the group consisting of E, Q, G, A, P or K,
X32 is selected from the group consisting of T, S, H, P or A and
X33 is P, Y, H, F, L, S, G or A and
X34 is G or no amino acid In some embodiments a mimylin peptide according to the present invention is a peptide comprising SEQ ID NO: 3;
X1-X2-X3-X4-X5-X6-X7-X8-X9-X10-X11-X12-X13-X14-X15-X16-X17-X18-X19-X20-X21-X22-X23-X24-X25-X26-X27-X28-X29-X30-X31-X32-X33-X34-X35-X36 (SEQ ID NO: 3)
wherein X represents amino acids and wherein
X1 is selected from the group consisting of E or A or no amino acid,
X2 is selected from the group consisting of L, A or P,
X3 is selected from the group consisting of S or P
X4 is selected from the group consisting of E, P, K, Q or G
X5 is selected from the group consisting of L, V, or I,
X6 is S, T or H,
X7 is T,
X8 is selected from the group consisting of L or A,
X9 is selected from the group consisting of A, V, I, S or T,
X10 is selected from the group consisting of L, A, I, H or V,
X11 is G,
X12 is selected from the group consisting of R, H or K,
X13 is L,
X14 is selected from the group consisting of S, T or E,
X15 is selected from the group consisting of A, Q, E, e or T,
X16 is selected from the group consisting of R, E, K or Q,
X17 is selected from the group consisting of L or I,
X18 is selected from the group consisting of H or A,
X19 is selected from the group consisting of E, R or K,
X20 is selected from the group consisting of L, I or V,
X21 is selected from the group consisting of A, Q, S, E or T,
X22 is T,
X23 is selected from the group consisting of T, Y or L,
X24 is P,
X25 is selected from the group consisting of R, P, H or K,
X26 is T,
X27 is selected from the group consisting of E, Q, G or K,
X28 is selected from the group consisting of T or P,
X29 is G,
X30 is selected from the group consisting of P, S or T,
X31 is selected from the group consisting of E, Q, G, A, P or K,
X32 is selected from the group consisting of T, S, H, P or A,
X33 is P, Y, H, F, L, S, G or A
X34 is G or no amino acid
X35 is T or no amino acid and
X36 is Y or no amino acid.

In some embodiments a mimylin peptide according to the present invention is a peptide comprising SEQ ID NO: 4;
X1-X2-X3-X4-X5-X6-T-X8-X9-X10-G-X12-L-X14-X15-X16-X17-X18-X19-X20-X21-T-X23-P-X25-T-X27-X28-G-X30-X31-X32-X33 (SEQ ID NO: 4),
wherein X represents amino acids and wherein
X1 is selected from the group consisting of E or A or no amino acid,
X2 is selected from the group consisting of L, A or P,
X3 is selected from the group consisting of S or P
X4 is selected from the group consisting of E, P, K, Q or G
X5 is selected from the group consisting of L, V, or I,
X6 is S, T or H,
X8 is selected from the group consisting of L or A,
X9 is selected from the group consisting of A, V, I, S or T,
X10 is selected from the group consisting of L, A, I, H or V,
X12 is selected from the group consisting of R, H or K,
X14 is selected from the group consisting of S, T or E,
X15 is selected from the group consisting of A, Q, E, e or T,
X16 is selected from the group consisting of R, E, K or Q,
X17 is selected from the group consisting of L or I,
X18 is selected from the group consisting of H or A,
X19 is selected from the group consisting of E, R or K,
X20 is selected from the group consisting of L, I or V,
X21 is selected from the group consisting of A, Q, S, E or T,
X23 is selected from the group consisting of T, Y or L,
X25 is selected from the group consisting of R, P, H or K,
X27 is selected from the group consisting of E, Q, G or K,
X28 is selected from the group consisting of T or P,
X30 is selected from the group consisting of P, S or T,
X31 is selected from the group consisting of E, Q, G, A, P or K,
X32 is selected from the group consisting of T, S, H, P or A and
X33 is P, Y, H, F, L, S, G or A.

In some embodiments a mimylin peptide according to this invention can be a peptide SEQ ID NO: 2, 3 or 4, wherein an additional amino acid is added to the N-terminal. In some embodiments a mimylin peptide according to this invention can be a peptide SEQ ID NO: 2, 3 or 4, wherein an additional amino acid is added to the N-terminal, wherein said additional amino acid is E.

In some embodiments a mimylin peptide according to this invention can be described according to any one of the SEQ ID NO: 2, 3 or 4, wherein said mimylin peptide is derivatised with a side chain in the alpha amino group of the N-terminal amino acid, wherein said side chain comprises a protracting moiety as defined in the present invention and optionally comprises a linker.

For some embodiments, the mimylin peptide has a substituent on one amino acid residue, which amino acid residue is either the amino acid residue in the N-terminal residue or the amino acid residue is a Lysine, wherein said lysine can be at any of the positions 1-33 according to the numbering of SEQ ID NO: 1.

For some embodiments, the mimylin peptide has a substituent on the N-terminal amino acid residue bound via the α(alpha)-amino group of the N-terminal amino acid residue.

For some embodiments, the N-terminal amino acid residue is Lysine and the mimylin peptide has a substituent on the N-terminal amino acid residue bound via the ε(epsilon)-amino group of the lysine amino residue.

For some embodiments, the mimylin peptide is extended by addition of a Lysine residue at the N-terminal and the mimylin peptide has a substituent on the N-terminal amino acid residue bound via the s-amino group of the lysine amino residue.

For some embodiments, the mimylin peptide is extended by addition of a Glutamic acid residue at the N-terminal and the mimylin peptide has a substituent on the N-terminal amino acid residue bound via the α-amino group of the lysine amino residue.

For some embodiments, the mimylin peptide is extended by addition of an amino acid residue at the N-terminal and the mimylin peptide has a substituent on the N-terminal amino acid residue bound via the α-amino group of the N-terminal amino acid residue.

In some embodiments an amylin derivative is produced by derivatising a mimylin peptide with a side chain attached in the N-terminal of said mimylin peptide. In some embodiments an amylin derivative is produced by derivatising a mimylin peptide with a side chain attached at a K (Lys) within the sequence of said mimylin peptide. In some embodiments such attachment at a K (Lys) can be in position 4, 12, 16, 23, 18, 27 or 34.

In some embodiments SEQ ID NO: 2, 3 or 4 are analogues of SEQ ID NO: 1.

In some embodiments a mimylin peptide according to the present invention comprises a sequence according to SEQ ID NO: 2, 3 or 4, wherein the sequence is up to 11 amino acids different from SEQ ID NO: 1. In some embodiments a mimylin peptide according to the present invention comprises a sequence according to SEQ ID NO: 2, 3 or 4, wherein the sequence is up to 11, 10, 9, 8, 7, 6, 5, 4, 3, 2 or 1, preferably 1, 2 or 3, more preferably 4, 3 or 5 amino acids different from SEQ ID NO: 1. In some embodiments a mimylin peptide according to the present invention comprises a sequence according to SEQ ID NO: 2, 3 or 4, wherein the sequence is up to 5 amino acids different from SEQ ID NO: 1. In some embodiments a mimylin peptide according to the present invention comprises a sequence according to SEQ ID NO: 2, 3 or 4, wherein the sequence is up to 4 amino acids different from SEQ ID NO: 1. In some embodiments a mimylin peptide according to the present invention comprises a sequence according to SEQ ID NO: 2, 3 or 4, wherein the sequence is up to 3 amino acids different from SEQ ID NO: 1. In some embodiments a mimylin peptide according to the present invention comprises a sequence according to SEQ ID NO: 2, 3 or 4, wherein the sequence is up to 2 amino acids different from SEQ ID NO: 1. In some embodiments a mimylin peptide according to the present invention comprises a sequence according to SEQ ID NO: 2, 3 or 4, wherein the sequence is 1 amino acid different from SEQ ID NO: 1.

In some embodiments a mimylin peptide according to the present invention comprises a sequence according to SEQ ID NO: 2, 3 or 4, wherein the sequence is at least 22 amino acids identical with SEQ ID NO: 1.

In some embodiments a mimylin peptide according to the present invention comprises a sequence according to SEQ ID NO: 2, 3 or 4, wherein the sequence is at least 23 amino acids identical with SEQ ID NO: 1. In some embodiments a mimylin peptide according to the present invention comprises a sequence according to SEQ ID NO: 2, 3 or 4, wherein the sequence is at least 24 amino acids identical with SEQ ID NO: 1. In some embodiments a mimylin peptide according to the present invention comprises a sequence according to SEQ ID NO: 2, 3 or 4, wherein the sequence is at least 25 amino acids identical with SEQ ID NO: 1.

In some embodiments a mimylin peptide according to the present invention comprises a sequence according to SEQ ID NO: 2, 3 or 4, wherein the sequence is at least 26 amino acids identical with SEQ ID NO: 1.

In some embodiments a mimylin peptide according to the present invention comprises a sequence according to SEQ ID NO: 2, 3 or 4, wherein the sequence is at least 27 amino acids identical with SEQ ID NO: 1. In some embodiments a mimylin peptide according to the present invention comprises a sequence according to SEQ ID NO: 2, 3 or 4, wherein the sequence is at least 28 amino acids identical with SEQ ID NO: 1.

In some embodiments a mimylin peptide according to the present invention comprises a sequence according to SEQ ID NO: 2, 3 or 4, wherein the sequence is at least 29 amino acids identical with SEQ ID NO: 1. In some embodiments a mimylin peptide according to the present invention comprises a sequence according to SEQ ID NO: 2, 3 or 4, wherein the sequence is at least 30 amino acids identical with SEQ ID NO: 1. In some embodiments a mimylin peptide according to the present invention comprises a sequence according to SEQ ID NO: 2, 3 or 4, wherein the sequence is at least 31 amino acids identical with SEQ ID NO:

In some embodiments a mimylin peptide according to the present invention comprises a sequence according to SEQ ID NO: 2, 3 or 4, wherein the sequence is at least 32 amino acids identical with SEQ ID NO: 1.

In some embodiments a mimylin peptide according to the present invention comprises a sequence according to SEQ ID NO: 2, 3 or 4 and a c-terminal amide group. In some embodiments a mimylin peptide according to the present invention comprises a sequence according to SEQ ID NO: 2, 3 or 4, wherein X1 is E. In some embodiments a mimylin peptide according to the present invention comprises a sequence according to SEQ ID NO: 2, 3 or 4, wherein X1 is E and the mimylin peptide is derivatised with a side chain attached to the mimylin peptide at the N-terminal. In some embodiments a mimylin peptide according to the present invention comprises a sequence according to SEQ ID NO: 2, 3 or 4, wherein X1 is E and the mimylin peptide is derivatised with a side chain attached to the mimylin peptide at the N-terminal, wherein said side chain comprises a protracting moiety and a linker. In some embodiments a mimylin peptide according to the present invention comprises a sequence according to SEQ ID NO: 2, 3 or 4, wherein X1 is E and the mimylin peptide is derivatised with a side chain attached to the mimylin peptide at the N-terminal, wherein said side chain comprises a protracting moiety and no linker.

In some embodiments a mimylin peptide according to the present invention comprises a sequence according to SEQ ID NO: 2, 3 or 4, wherein X1 is A. In some embodiments a mimylin peptide according to the present invention comprises a sequence according to SEQ ID NO: 2, 3 or 4, wherein X1 is A and the mimylin peptide is derivatised with a side chain attached to the mimylin peptide at the N-terminal. In some embodiments a mimylin peptide according to the present invention comprises a sequence according to SEQ ID NO: 2, 3 or 4, wherein X1 is A and the mimylin peptide is derivatised with a side chain attached to the mimylin peptide at the N-terminal, wherein said side chain comprises a protracting moiety and a linker.

In some embodiments a mimylin peptide according to the present invention comprises a sequence according to SEQ ID NO: 2, 3 or 4, wherein X1 is any amino acid except E. In some embodiments a mimylin peptide according to the present invention comprises a sequence according to SEQ ID NO: 2, 3 or 4, wherein X1 is any amino acid except E and the mimylin peptide is derivatised with a side chain attached to the mimylin peptide at the N-terminal. In some embodiments a mimylin peptide according to the present invention comprises a sequence according to SEQ ID NO: 2, 3 or 4, wherein X1 is any amino acid except E and the mimylin peptide is derivatised with a side chain attached to the mimylin peptide at the N-terminal, wherein said side chain comprises a protracting moiety and a linker. In particular embodiments, the side chain and/or the protracting moiety are lipophilic, and/or negatively charged at physiological pH (pH about 7.4).

In some embodiments a mimylin peptide according to the present invention comprises a sequence according to SEQ ID NO: 2, 3 or 4, wherein X2 is L. In some embodiments a mimylin peptide according to the present invention comprises a sequence according to SEQ ID NO: 2, 3 or 4, wherein X2 is A. In some embodiments a mimylin peptide according to the present invention comprises a sequence according to SEQ ID NO: 2, 3 or 4, wherein X2 is P.

In some embodiments a mimylin peptide according to the present invention comprises a sequence according to SEQ ID NO: 2, 3 or 4, wherein X3 is S. In some embodiments a mimylin peptide according to the present invention comprises a sequence according to SEQ ID NO: 2, 3 or 4, wherein X3 is P.

In some embodiments a mimylin peptide according to the present invention comprises a sequence according to SEQ ID NO: 2, 3 or 4, wherein X4 is L. In some embodiments a mimylin peptide according to the present invention comprises a sequence according to SEQ ID NO: 2, 3 or 4, wherein X4 is A.

In some embodiments a mimylin peptide according to the present invention comprises a sequence according to SEQ ID NO: 2, 3 or 4, wherein X5 is L. In some embodiments a mimylin peptide according to the present invention comprises a sequence according to SEQ ID NO: 2, 3 or 4, wherein X5 is I. In some embodiments a mimylin peptide according to the present invention comprises a sequence according to SEQ ID NO: 2, 3 or 4, wherein X5 is V.

In some embodiments a mimylin peptide according to the present invention comprises a sequence according to SEQ ID NO: 2, 3 or 4, wherein X7 is T.

In some embodiments a mimylin peptide according to the present invention comprises a sequence according to SEQ ID NO: 2, 3 or 4, wherein X8 is L. In some embodiments a mimylin peptide according to the present invention comprises a sequence according to SEQ ID NO: 2, 3 or 4, wherein X8 is A.

In some embodiments a mimylin peptide according to the present invention comprises a sequence according to SEQ ID NO: 2, 3 or 4, wherein X9 is A. In some embodiments a mimylin peptide according to the present invention comprises a sequence according to SEQ ID NO: 2, 3 or 4, wherein X9 is V. In some embodiments a mimylin peptide according to the present invention comprises a sequence according to SEQ ID NO: 2, 3 or 4, wherein X9 is I. In some embodiments a mimylin peptide according to the present invention comprises a sequence according to SEQ ID NO: 2, 3 or 4, wherein X9 is S. In some embodiments a mimylin peptide according to the present invention comprises a sequence according to SEQ ID NO: 2, 3 or 4, wherein X9 is T. In some embodiments a mimylin peptide according to the present invention comprises a sequence according to SEQ ID NO: 2, 3 or 4, wherein X9 is L.

In some embodiments a mimylin peptide according to the present invention comprises a sequence according to SEQ ID NO: 2, 3 or 4, wherein X10 is L. In some embodiments a mimylin peptide according to the present invention comprises a sequence according to SEQ ID NO: 2, 3 or 4, wherein X10 is A. In some embodiments a mimylin peptide according to the present invention comprises a sequence according to SEQ ID NO: 2, 3 or 4, wherein X10 is V. In some embodiments a mimylin peptide according to the present invention comprises a sequence according to SEQ ID NO: 2, 3 or 4, wherein X10 is I.

In some embodiments a mimylin peptide according to the present invention comprises a sequence according to SEQ ID NO: 2, 3 or 4, wherein X12 is R. In some embodiments a mimylin peptide according to the present invention comprises a sequence according to SEQ ID NO: 2, 3 or 4, wherein X12 is H. In some embodiments a mimylin peptide according to the present invention comprises a sequence according to SEQ ID NO: 2, 3 or 4, wherein X12 is K.

In some embodiments a mimylin peptide according to the present invention comprises a sequence according to SEQ ID NO: 2, 3 or 4, wherein X15 is A. In some embodiments a mimylin peptide according to the present invention comprises a sequence according to SEQ ID NO: 2, 3 or 4, wherein X15 is Q. In some embodiments a mimylin peptide according to the present invention comprises a sequence according to SEQ ID NO: 2, 3 or 4, wherein X15 is E. In some embodiments a mimylin peptide according to the present invention comprises a sequence according to SEQ ID NO: 2, 3 or 4, wherein X15 is e, wherein e is the d-isoform of Glutamic acid. In some embodiments a mimylin peptide according to the present invention comprises a sequence according to SEQ ID NO: 2, 3 or 4, wherein X15 is T.

In some embodiments a mimylin peptide according to the present invention comprises a sequence according to SEQ ID NO: 2, 3 or 4, wherein X19 is E. In some embodiments a mimylin peptide according to the present invention comprises a sequence according to SEQ ID NO: 2, 3 or 4, wherein X19 is R. In some embodiments a mimylin peptide according to the present invention comprises a sequence according to SEQ ID NO: 2, 3 or 4, wherein X19 is K.

In some embodiments a mimylin peptide according to the present invention comprises a sequence according to SEQ ID NO: 2, 3 or 4, wherein X20 is L. In some embodiments a mimylin peptide according to the present invention comprises a sequence according to SEQ ID NO: 2, 3 or 4, wherein X20 is I. In some embodiments a mimylin peptide according to the present invention comprises a sequence according to SEQ ID NO: 2, 3 or 4, wherein X20 is V.

In some embodiments a mimylin peptide according to the present invention comprises a sequence according to SEQ ID NO: 2, 3 or 4, wherein X21 is A. In some embodiments a mimylin peptide according to the present invention comprises a sequence according to SEQ ID NO: 2, 3 or 4, wherein X21 is Q. In some embodiments a mimylin peptide according to the present invention comprises a sequence according to SEQ ID NO: 2, 3 or 4, wherein X21 is S. In some embodiments a mimylin peptide according to the present invention comprises a sequence according to SEQ ID NO: 2, 3 or 4, wherein X21 is S. In some embodiments a mimylin peptide according to the present invention comprises a sequence according to SEQ ID NO: 2, 3 or 4, wherein X21 is E. In some embodiments a mimylin peptide according to the present invention comprises a sequence according to SEQ ID NO: 2, 3 or 4, wherein X21 is T.

In some embodiments a mimylin peptide according to the present invention comprises a sequence according to SEQ ID NO: 2, 3 or 4, wherein X23 is Y. In some embodiments a mimylin peptide according to the present invention comprises a sequence according to SEQ ID NO: 2, 3 or 4, wherein X23 is L.

In some embodiments a mimylin peptide according to the present invention comprises a sequence according to SEQ ID NO: 2, 3 or 4, wherein X27 is E. In some embodiments a mimylin peptide according to the present invention comprises a sequence according to SEQ ID NO: 2, 3 or 4, wherein X27 is Q. In some embodiments a mimylin peptide according to the present invention comprises a sequence according to SEQ ID NO: 2, 3 or 4, wherein X27 is G. In some embodiments a mimylin peptide according to the present invention comprises a sequence according to SEQ ID NO: 2, 3 or 4, wherein X27 is K.

In some embodiments a mimylin peptide according to the present invention comprises a sequence according to SEQ ID NO: 2, 3 or 4, wherein X30 is P. In some embodiments a mimylin peptide according to the present invention comprises a sequence according to SEQ ID NO: 2, 3 or 4, wherein X20 is S. In some embodiments a mimylin peptide according to the present invention comprises a sequence according to SEQ ID NO: 2, 3 or 4, wherein X30 is T.

In some embodiments a mimylin peptide according to the present invention comprises a sequence according to SEQ ID NO: 2, 3 or 4, wherein X31 is E. In some embodiments a mimylin peptide according to the present invention comprises a sequence according to SEQ ID NO: 2, 3 or 4, wherein X31 is Q. In some embodiments a mimylin peptide according to the present invention comprises a sequence according to SEQ ID NO: 2, 3 or 4, wherein X31 is G. In some embodiments a mimylin peptide according to the present invention comprises a sequence according to SEQ ID NO: 2, 3 or 4, wherein X31 is A. In some embodiments a mimylin peptide according to the present invention comprises a sequence according to SEQ ID NO: 2, 3 or 4, wherein X31 is P. In some embodiments a mimylin peptide according to the present invention comprises a sequence according to SEQ ID NO: 2, 3 or 4, wherein X31 is K.

In some embodiments a mimylin peptide according to the present invention comprises a sequence according to SEQ ID NO: 2, 3 or 4, wherein X32 is T. In some embodiments a mimylin peptide according to the present invention comprises a sequence according to SEQ ID NO: 2, 3 or 4, wherein X32 is S. In some embodiments a mimylin peptide according to the present invention comprises a sequence according to SEQ ID NO: 2, 3 or 4, wherein X32 is H. In some embodiments a mimylin peptide according to the present invention comprises a sequence according to SEQ ID NO: 2, 3 or 4, wherein X32 is P. In some embodiments a mimylin peptide according to the present invention comprises a sequence according to SEQ ID NO: 2, 3 or 4, wherein X32 is A.

In some embodiments a mimylin peptide according to the present invention comprises a sequence according to SEQ ID NO: 2, 3 or 4, wherein X33 is Y. In some embodiments a mimylin peptide according to the present invention comprises a sequence according to SEQ ID NO: 2, 3 or 4, wherein X33 is S. In some embodiments a mimylin peptide according to the present invention comprises a sequence according to SEQ ID NO: 2, 3 or 4, wherein X16 is H. In some embodiments a mimylin peptide according to the present invention comprises a sequence according to SEQ ID NO: 2, 3 or 4, wherein X33 is F. In some embodiments a mimylin peptide according to the present invention comprises a sequence according to SEQ ID NO: 2, 3 or 4, wherein X16 is L. In some embodiments a mimylin peptide according to the present invention comprises a sequence according to SEQ ID NO: 2, 3 or 4, wherein X33 is S. In some embodiments a mimylin peptide according to the present invention comprises a sequence according to SEQ ID NO: 2, 3 or 4, wherein X33 is G. In some embodiments a mimylin peptide according to the present invention comprises a sequence according to SEQ ID NO: 2, 3 or 4, wherein X33 is A.

In some embodiments a mimylin peptide according to the present invention comprises a sequence according to SEQ ID NO: 2 or 3, wherein X34 is R. In some embodiments a mimylin peptide according to the present invention comprises a sequence according to SEQ ID NO: 2 or 3, wherein X34 is deleted.

In some embodiments the mimylin peptide according to the present invention comprises a sequence according to SEQ ID NO: 2, 3 or 4, wherein one or all of X5, X10, X13, X17, X20 and X23 are L. In some embodiments the mimylin peptide according to the present invention comprises a sequence according to SEQ ID NO: 2, 3 or 4, wherein at least four of X5, X10, X13, X17, X20 and X23 are L. In some embodiments the mimylin peptide according to the present invention comprises a sequence according to SEQ ID NO: 2, 3 or 4, wherein at least three of X5, X10, X13, X17, X20 and X23 are L.

In some embodiments the mimylin peptide according to the present invention comprises a sequence according to SEQ ID NO: 2, 3 or 4, wherein X12 and/or X25 is R. In some embodiments the mimylin peptide according to the present invention comprises a sequence according to SEQ ID NO: 2, 3 or 4, wherein one or all of X5, X10, X13, X17, X20 and X23 are L and wherein X12 and/or X25 is R.

In some embodiments a mimylin peptide according to the present invention comprises a sequence according to SEQ ID NO: 2, 3 or 4, which does not comprise any N. In some embodiments a mimylin peptide according to the present invention comprises a sequence according to SEQ ID NO: 2, 3 or 4, which does not comprise any Q. In some embodiments a mimylin peptide according to the present invention comprises a sequence according to SEQ ID NO: 2, 3 or 4, which does not comprise any C. In some embodiments a mimylin peptide according to the present invention comprises a sequence according to SEQ ID NO: 2, 3 or 4, which does not comprise any disulfide bridges.

In some embodiments a mimylin derivative according to this invention is represented by the compounds listed in Table 1. The compound names as used herein are listed in Table 1 indicating the modifications relative to SEQ ID NO: 1 (also designated mimylin herein) and the side chain as well as the site of attachment of the side chain to the mimylin peptide. Table 1 discloses the compound number (EX. #) and the compound name. Table 2 indicates the modifications relative to mimylin in the mimylin peptides, i.e. the mimylin peptides, which are derivatised with a side chain to the mimylin derivatives listed in Table 1. Ex. #1 in Table 1 is SEQ ID NO: 1 and is not derivatised as also indicated by the name.

TABLE 1 mimylin derivatives (Example compounds)

| Ex. # | Compound name |
|---|---|
| 1 | mimylin |
| 2 | [N-terminal(C18 diacid)]mimylin |
| 3 | [N-terminal(C16 diacid)]mimylin |
| 4 | [N-terminal(C14 diacid)]mimylin |
| 5 | [N-terminal(C14 diacid-2xgGlu-4xOEG)]mimylin |
| 6 | [N-terminal(C12 diacid)]mimylin |
| 7 | [N-terminal(C16)]mimylin |
| 8 | [N-terminal(C18 diacid), 5I]mimylin |
| 9 | [N-terminal(C18 diacid), 9V]mimylin |
| 10 | [N-terminal(C18 diacid), 9I]mimylin |
| 11 | [N-terminal(C18 diacid), 17I]mimylin |
| 12 | [N-terminal(C18 diacid), 20I]mimylin |
| 13 | [N-terminal(C18 diacid), 18A]mimylin |
| 14 | [N-terminal(C18 diacid), 9L]mitnylin |
| 15 | [N-terminal(C18 diacid), 8L]mimylin |
| 16 | [N-terminal(C18 diacid), 6H]mimylin |
| 17 | [N-terminal(C18 diacid), 5H]mimylin |
| 18 | [N-terminal(C18 diacid), 32H]mimylin |
| 19 | [N-terminal(C14 diacid-gGlu), des1]mimylin |
| 20 | [N-terminal(C18 diacid), 23Y]mimylin |
| 21 | [N-terminal(C18 diacid), 30S, 31G]mimylin |
| 22 | [N-terminal(C20 diacid), 30S, 31G]mimylin |
| 23 | [N-terminal(C18 diacid-gGlu), des1, 30S]mimylin |
| 24 | [N-terminal(C18 diacid), 5V, 9V]mimylin |
| 25 | [N-terminal(C18 diacid), 5I, 9I]mimylin |
| 26 | [N-terminal(C18 diacid), 9V, 10I]mimylin |
| 27 | [N-terminal(C18 diacid), 9L, 10A]mimylin |
| 28 | [N-terminal(C18 diacid), 2P, 9V]mimylin |
| 29 | [N-terminal(C18 diacid), 3P, 9V]mimylin |
| 30 | [N-terminal(C18 diacid), 4P, 9V]mimylin |
| 31 | [N-terminal(C18 diacid), 9V, 25P]mimylin |
| 32 | [N-terminal(C18 diacid), 9V, 28P]mimylin |
| 33 | [N-terminal(C18 diacid), 9V, 18A]mimylin |
| 34 | [N-terminal(C20 diacid-gGlu), 23Y, 30S, 31G]mimylin |
| 35 | [N-terminal(C18 diacid-gGlu), des1, 30S, 31P]mimylin |
| 36 | [N-terminal(C18 diacid), 5V, 9V, 20V]mimylin |
| 37 | [N-terminal(C18 diacid), 5I, 9I, 10I]mimylin |
| 38 | [N-terminal(C18 diacid), 3P, 4P, 9V]mimylin |
| 39 | [N-terminal(C18 diacid), 9V, 12K, 25K]mimylin |
| 40 | [N-terminal(C20 diacid-gGlu), des1, 30S, 31G]mimylin |
| 41 | [N-terminal(C20 diacid-gGlu-OEG), des1, 30S, 31G]mimylin |
| 42 | [N-terminal(C20 diacid-gGlu-2xOEG), des1, 30S, 31G]mimylin |
| 43 | [N-terminal(C20 diacid-gGlu-3xOEG), des1, 30S, 31G]mimylin |
| 44 | [N-terminal(C20 diacid-gGlu-4xOEG), des1, 30S, 31G]mimylin |
| 45 | [N-terminal(C20 diacid-gGlu-5xOEG), des1, 30S, 31G]mimylin |
| 46 | [N-terminal(C18 diacid-gGlu), des1, 30S, 31G]mimylin |
| 47 | [N-terminal(C16 diacid-gGlu), des1, 30S, 31G]mimylin |
| 48 | [N-terminal(C18 diacid), des1, 30S, 31G]mimylin |
| 49 | [N-terminal(C16 diacid), des1, 30S, 31G]mimylin |
| 50 | [N-terminal(C14 diacid-gGlu), des1, 30S, 31G]mimylin |
| 51 | [N-terminal(C14 diacid), des1, 30S, 31G]mimylin |
| 52 | [des1, 4K(C20 diacid-gGlu), 30S, 31G]mimylin |
| 53 | [des1, 16K(C20 diacid-gGlu), 30S, 31G]mimylin |
| 54 | [des1, 19K(C20 diacid-gGlu), 30S, 31G]mimylin |
| 55 | [des1, 27K(C20 diacid-gGlu), 30S, 31G]mimylin |
| 56 | [N-terminal(C20 diacid-gGlu), des1, 23Y, 30S, 31G]mimylin |
| 57 | [N-terminal(C20 diacid-gGlu), 1A, 23Y, 30S, 31G]mimylin |
| 58 | [N-terminal(C18 diacid-gGlu), des1, 23Y, 30S, 31G]mimylin |
| 59 | [N-terminal(C20 diacid-gGlu), des1, 30S, 31G, 33Y]mimylin |
| 60 | [N-terminal(C20 diacid-gGlu), des1, 30S, 31G, 33H]mimylin |
| 61 | [N-terminal(C20 diacid-gGlu), des1, 30S, 31G, 33F]mimylin |
| 62 | [N-terminal(C20 diacid-gGlu), des1, 30S, 31G, 33L]mimylin |
| 63 | [N-terminal(C20 diacid-gGlu), des1, 30S, 31G, 33S]mimylin |
| 64 | [N-terminal(C20 diacid-gGlu), des1, 30S, 31G, 33G]mimylin |
| 65 | [N-terminal(C20 diacid-gGlu), des1, 30S, 31G, 33A]mimylin |
| 66 | [N-terminal(C20 diacid-gGlu), des1, 15E, 30S, 31G]mimylin |
| 67 | [N-terminal(C20 diacid-gGlu), des1, 15e, 30S, 31G]mimylin |
| 68 | [N-terminal(acetyl), des1, 4K(C20 diacid-gGlu), 30S, 31G]mimylin |
| 69 | [N-terminal(acetyl), des1, 16K(C20 diacid-gGlu), 30S, 31G]mimylin |
| 70 | [N-terminal(acetyl), des1, 19K(C20 diacid-gGlu), 30S, 31G]mimylin |
| 71 | [N-terminal(acetyl), des1, 27K(C20 diacid-gGlu), 30S, 31G]mimylin |
| 72 | [N-terminal(C20 diacid-gGlu), des1, 12H, 30S, 31G]mimylin |
| 73 | [N-terminal(C20 diacid-gGlu), des1, 25H, 30S, 31G]mimylin |
| 74 | [N-terminal(C20 diacid-gGlu), des1, 30T, 31G, 32T]mimylin |

TABLE 1-continued mimylin derivatives (Example compounds)

| Ex. # | Compound name |
|---|---|
| 75 | [N-terminal(C18 diacid-gGlu), des1, 30S, 31G, 32P]mimylin |
| 76 | [N-terminal(C18 diacid-gGlu), des1, 9V, 30S, 31G]mimylin |
| 77 | [N-terminal(C18 diacid), 5I, 9I, 10I, 20I]mimylin |
| 78 | [N-terminal(C18 diacid-gGlu), des1, 4Q, 30S, 31G]mimylin |
| 79 | [N-terminal(C20 diacid-gGlu), des1, 4G, 23Y, 30S, 31G]mimylin |
| 80 | [N-terminal(C20 diacid-gGlu), des1, 23Y, 30S, 31G, 33Y]mimylin |
| 81 | [N-terminal(C20 diacid-gGlu), des1, 23Y, 30S, 31G, 32A]mimylin |
| 82 | [N-terminal(C20 diacid-gGlu), des1, 21S, 23Y, 30S, 31G]mimylin |
| 83 | [N-terminal(C20 diacid-gGlu), -1E, 1A, 23Y, 30S, 31G]mimylin |
| 84 | [N-terminal(C20 diacid-gGlu), des1, 12H, 25H, 30S, 31G]mimylin |
| 85 | [N-terminal(C18 diacid-gGlu), des1, 6T, 9V, 30S, 31G]mimylin |
| 86 | [N-terminal(C18 diacid-gGlu), des1, 5V, 9V, 30S, 31G]mimylin |
| 87 | [N-terminal(C18 diacid-gGlu), des1, 4Q, 16Q, 30S, 31G]mimylin |
| 88 | [N-terminal(C20 diacid-gGlu), des1, 23Y, 30S, 31G, 33Y, C-terminal(-)]mimylin |
| 89 | [N-terminal(C20 diacid-gGlu), des1, 23Y, 30S, 31G, 34G, C-terminal(-)]mimylin |
| 90 | [N-terminal(C20 diacid-gGlu), des1, 23Y, 30S, 31G, 34K, C-terminal(-)]mimylin |
| 91 | [N-terminal(C20 diacid-gGlu), des1, 9S, 23Y, 30S, 31G, 33Y]mimylin |
| 92 | [N-terminal(C20 diacid-gGlu), des1, 9T, 21S, 23Y, 30S, 31G]mimylin |
| 93 | [N-terminal(C20 diacid-gGlu), des1, 12H, 25H, 30T, 31G, 32T]mimylin |
| 94 | [N-terminal(C18 diacid-gGlu), des1, 6T, 9V, 30S, 31G, 32T]mimylin |
| 95 | [N-terminal(C18 diacid-gGlu), des1, 6T, 9V, 30T, 31G, 32T]mimylin |
| 96 | [N-terminal(C18 diacid-gGlu), des1, 5V, 9V, 10V, 30S, 31G]mimylin |
| 97 | [N-terminal(C20 diacid-gGlu), des1, 21S, 23Y, 30S, 31G, 33Y]mimylin |
| 98 | [N-terminal(C20 diacid-gGlu), des1, 4G, 9V, 23Y, 30S, 31G, 32T]mimylin |
| 99 | [N-terminal(C20 diacid-gGlu), des1, 9T, 21S, 23Y, 30S, 31G, 33Y]mimylin |
| 100 | [N-terminal(C20 diacid-gGlu), des1, 9S, 21S, 23Y, 30S, 31G, 33Y]mimylin |
| 101 | [N-terminal(C20 diacid-gGlu), des1, 12K, 23Y, 25K, 30S, 31G, 33Y]mimylin |
| 102 | [N-terminal(C18 diacid-gGlu), des1, 5V, 9V, 10V, 20V, 30S, 31G]mimylin |
| 103 | [N-terminal(C20 diacid-gGlu), 4G, 15Q, 21Q, 23Y, 30S, 31G, 32T, 33Y]mimylin |
| 104 | [N-terminal(C20 diacid-gGlu), des1, 4G, 9V, 23Y, 30S, 31G, 32T, 33Y]mimylin |
| 105 | [N-terminal(C18 diacid-gGlu), des1, 6T, 9V, 14T, 21E, 30T, 31G, 32T]mimylin |
| 106 | [N-terminal(C18 diacid-gGlu), des1, 6T, 9V, 14E, 21T, 30T, 31G, 32T]mimylin |
| 107 | [des1, 4G, 15Q, 21Q, 23Y, 30S, 31K(C20 diacid-gGlu), 32T, 33Y]mimylin |
| 108 | [N-terminal(C20 diacid-gGlu), des1, 4G, 15Q, 21E, 23Y, 30S, 31G, 32T, 33Y]mimylin |
| 109 | [N-terminal(C20 diacid-gGlu), des1, 4G, 15Q, 21Q, 23Y, 30S, 31G, 32T, 33Y]mimylin |
| 110 | [N-terminal(C18 diacid-gGlu), des1, 4G, 15Q, 21Q, 23Y, 30S, 31G, 32T, 33Y]mimylin |
| 111 | [N-terminal(C20 diacid), des1, 4G, 15Q, 21Q, 23Y, 30S, 31G, 32T, 33Y]mimylin |
| 112 | [N-terminal(C20 diacid-gGlu), des1, 4G, 15T, 21E, 23Y, 30S, 31G, 32T, 33Y]mimylin |
| 113 | [N-terminal(C20 diacid-gGlu), des1, 4G, 15E, 21Q, 23Y, 30S, 31G, 32T, 33Y]mimylin |
| 114 | [N-terminal(C20 diacid-gGlu), des1, 9V, 15Q, 21Q, 23Y, 30S, 31G, 32T, 33Y]mimylin |
| 115 | [N-terminal(C20 diacid-gGlu), 4Q, 9V, 15Q, 21Q, 23Y, 27G, 30S, 31G, 32T, 33Y]mimylin |
| 116 | [N-terminal(C20 diacid-gGlu), des1, 4Q, 9V, 15Q, 21Q, 23Y, 30S, 31Q, 32T, 33Y]mimylin |
| 117 | [N-terminal(C20 diacid-gGlu), des1, 4G, 15Q, 21Q, 23Y, 25H, 30S, 31G, 32T, 33Y]mimylin |
| 118 | [N-terminal(C20 diacid-gGlu), des1, 4G, 9V, 15Q, 21Q, 23Y, 30S, 31G, 32T, 33Y]mimylin |
| 119 | [N-terminal(C20 diacid-gGlu), des1, 4G, 9V, 15Q, 21Q, 23Y, 30S, 31Q, 32T, 33Y]mimylin |
| 120 | [N-terminal(C20 diacid-gGlu-2xOEG), des1, 4G, 9V, 15Q, 21Q, 23Y, 30S, 31G, 32T, 33Y]mimylin |
| 121 | [N-terminal(C18 diacid-gGlu-2xOEG), des1, 4G, 9V, 15Q, 21Q, 23Y, 30S, 31G, 32T, 33Y]mimylin |
| 122 | [N-terminal(C20 diacid-gGlu), des1, 4G, 9V, 15Q, 21Q, 23Y, 30S, 31A, 32T, 33Y]mimylin |
| 123 | [N-terminal(C20 diacid-gGlu), des1, 2L, 4G, 9V, 21S, 23Y, 30S, 31G, 32T, 33Y]mimylin |
| 124 | [N-terminal(C20 diacid-gGlu), des1, 4G, 9T, 15Q, 21Q, 23Y, 30S, 31G, 32T, 33Y]mimylin |
| 125 | [N-terminal(C20 diacid-gGlu), des1, 4G, 9V, 15Q, 21Q, 23Y, 25P, 30S, 31Q, 32T, 33Y]mimylin |
| 126 | [N-terminal(C20 diacid-gGlu), des1, 4G, 8L, 9V, 15Q, 21Q, 23Y, 30S, 31Q, 32T, 33Y]mimylin |
| 127 | [N-terminal(C20 diacid-gGlu), des1, 2L, 4G, 9V, 15Q, 21Q, 23Y, 30S, 31Q, 32T, 33Y]mimylin |
| 128 | [N-terminal(C20 diacid-gGlu), des1, 4G, 9T, 15Q, 21Q, 23Y, 25P, 30S, 31G, 32T, 33Y]mimylin |
| 129 | [N-terminal(C20 diacid-gGlu), 2L, 4G, 8L, 9V, 15Q, 21Q, 23Y, 27G, 30S, 31G, 32T, 33Y]mimylin |
| 130 | [N-terminal(C20 diacid-gGlu), des1, 4G, 9V, 15Q, 21Q, 23aQ, 23bT, 23cY, 30S, 31Q, 32T, 33Y]mimylin |
| 131 | [N-terminal(C20 diacid-gGlu), des1, 4G, 9V, 12K, 15Q, 21Q, 23Y, 25P, 30S, 31G, 32T, 33Y]mimylin |
| 132 | [N-terminal(C20 diacid-gGlu), des1, 4Q, 9V, 15Q, 16R, 19R, 21Q, 23Y, 27Q, 30S, 31Q, 32T, 33Y]mimylin |
| 133 | [N-terminal(C20 diacid-gGlu), des1, 2L, 4Q, 8L, 9V, 15Q, 16R, 19R, 21Q, 23Y, 27Q, 30S, 31Q, 32T, 33Y]mimylin |
| 134 | [N-terminal(C18 diacid), C-terminal(-)]mimylin |
| 135 | [C-terminal(-)]mimylin |

In some embodiments a mimylin peptide according to this invention is represented by the compounds listed in Table 2, wherein Table 2 indicates the amino acid modifications relative to SEQ ID NO: 1, also designated mimylin. Table 2 indicates the modifications relative to mimylin in the mimylin peptides, i.e. the mimylin peptides, which are derivatised with a side chain to form the mimylin derivatives listed in Table 1. Table 2 represents the mimylin analogues which have been derivatised, resulting in the corresponding mimylin derivative represented in Table 1. Thus the compound in EX. #8 in Table 1 or 3, respectively is a derivative of a mimylin analogue which has been modified with the amino acids as indicated in Table 2 or 4 as Ex. #8bb

TABLE 2 mimylin peptides (backbones)

| Ex. # | Amino acid modifications relative to mimylin (SEQ ID NO: 1) |
|---|---|
| 1bb | N/A |
| 2bb | N/A |
| 3bb | N/A |
| 4bb | N/A |
| 5bb | N/A |
| 6bb | N/A |
| 7bb | N/A |
| 8bb | 5I |
| 9bb | 9V |
| 10bb | 9I |
| 11bb | 17I |
| 12bb | 20I |
| 13bb | 18A |
| 14bb | 9L |
| 15bb | 8L |
| 16bb | 6H |
| 17bb | 5H |
| 18bb | 32H |
| 19bb | des1 |
| 20bb | 23Y |
| 21bb | 30S, 31G |
| 22bb | 30S, 31G |
| 23bb | des1, 30S |
| 24bb | 5V, 9V |
| 25bb | 5I, 9I |
| 26bb | 9V, 10I |
| 27bb | 9L, 10A |
| 28bb | 2P, 9V |
| 29bb | 3P, 9V |
| 30bb | 4P, 9V |
| 31bb | 9V, 25P |
| 32bb | 9V, 28P |
| 33bb | 9V, 18A |
| 34bb | 23Y, 30S, 31G |
| 35bb | des1, 30S, 31P |
| 36bb | 5V, 9V, 20V |
| 37bb | 5I, 9I, 10I |
| 38bb | 3P, 4P, 9V |
| 39bb | 9V, 12K, 25K |
| 40bb | des1, 30S, 31G |
| 41bb | des1, 30S, 31G |
| 42bb | des1, 30S, 31G |
| 43bb | des1, 30S, 31G |
| 44bb | des1, 30S, 31G |
| 45bb | des1, 30S, 31G |
| 46bb | des1, 30S, 31G |
| 47bb | des1, 30S, 31G |
| 48bb | des1, 30S, 31G |
| 49bb | des1, 30S, 31G |
| 50bb | des1, 30S, 31G |
| 51bb | des1, 30S, 31G |
| 52bb | des1, 4K, 30S, 31G |
| 53bb | des1, 16K, 30S, 31G |
| 54bb | des1, 19K, 30S, 31G |
| 55bb | des1, 27K, 30S, 31G |
| 56bb | des1, 23Y, 30S, 31G |
| 57bb | 1A, 23Y, 30S, 31G |
| 58bb | des1, 23Y, 30S, 31G |
| 59bb | des1, 30S, 31G, 33Y |
| 60bb | des1, 30S, 31G, 33H |
| 61bb | des1, 30S, 31G, 33F |
| 62bb | des1, 30S, 31G, 33L |
| 63bb | des1, 30S, 31G, 33S |
| 64bb | des1, 30S, 31G, 33G |
| 65bb | des1, 30S, 31G, 33A |
| 66bb | des1, 15E, 30S, 31G |
| 67bb | des1, 15e, 30S, 31G |
| 68bb | des1, 4K, 30S, 31G |
| 69bb | des1, 16K, 30S, 31G |
| 70bb | des1, 19K, 30S, 31G |
| 71bb | des1, 27K, 30S, 31G |
| 72bb | des1, 12H, 30S, 31G |
| 73bb | des1, 25H, 30S, 31G |
| 74bb | des1, 30T, 31G, 32T |
| 75bb | des1, 30S, 31G, 32P |
| 76bb | des1, 9V, 30S, 31G |
| 77bb | 5I, 9I, 10I, 20I |
| 78bb | des1, 4Q, 30S, 31G |
| 79bb | des1, 4G, 23Y, 30S, 31G |
| 80bb | des1, 23Y, 30S, 31G, 33Y |
| 81bb | des1, 23Y, 30S, 31G, 32A |
| 82bb | des1, 21S, 23Y, 30S, 31G |
| 83bb | −1E, 1A, 23Y, 30S, 31G |
| 84bb | des1, 12H, 25H, 30S, 31G |
| 85bb | des1, 6T, 9V, 30S, 31G |
| 86bb | des1, 5V, 9V, 30S, 31G |
| 87bb | des1, 4Q, 16Q, 30S, 31G |
| 88bb | des1, 23Y, 30S, 31G, 33Y |
| 89bb | des1, 23Y, 30S, 31G, 34G |
| 90bb | des1, 23Y, 30S, 31G, 34K |
| 91bb | des1, 9S, 23Y, 30S, 31G, 33Y |
| 92bb | des1, 9T, 21S, 23Y, 30S, 31G |
| 93bb | des1, 12H, 25H, 30T, 31G, 32T |
| 94bb | des1, 6T, 9V, 30S, 31G, 32T |
| 95bb | des1, 6T, 9V, 30T, 31G, 32T |
| 96bb | des1, 5V, 9V, 10V, 30S, 31G |
| 97bb | des1, 21S, 23Y, 30S, 31G, 33Y |
| 98bb | des1, 4G, 9V, 23Y, 30S, 31G, 32T |
| 99bb | des1, 9T, 21S, 23Y, 30S, 31G, 33Y |
| 100bb | des1, 9S, 21S, 23Y, 30S, 31G, 33Y |
| 101bb | des1, 12K, 23Y, 25K, 30S, 31G, 33Y |
| 102bb | des1, 5V, 9V, 10V, 20V, 30S, 31G |
| 103bb | 4G, 15Q 21Q, 23Y 30S, 31G, 32T, 33Y |
| 104bb | des1, 4G, 9V, 23Y, 30S, 31G, 32T, 33Y |
| 104bb | des1, 4G, 9V, 23Y, 30S, 31G, 32T, 33Y |
| 105bb | des1, 6T, 9V, 14T, 21E, 30T, 31G, 32T |
| 106bb | des1, 6T, 9V, 14E, 21T, 30T, 31G, 32T |
| 107bb | des1, 4G, 15Q, 21Q, 23Y, 30S, 31K, 32T, 33Y |
| 108bb | des1, 4G, 15Q, 21E, 23Y, 30S, 31G, 32T, 33Y |
| 109bb | des1, 4G, 15Q, 21Q, 23Y, 30S, 31G, 32T, 33Y |
| 110bb | des1, 4G, 15Q, 21Q, 23Y, 30S, 31G, 32T, 33Y |
| 111bb | des1, 4G, 15Q, 21Q, 23Y, 30S, 31G, 32T, 33Y |
| 112bb | des1, 4G, 15T, 21E, 23Y, 30S, 31G, 32T, 33Y |
| 113bb | des1, 4G, 15E, 21Q, 23Y, 30S, 31G, 32T, 33Y |
| 114bb | des1, 9V, 15Q, 21Q, 23Y, 30S, 31G, 32T, 33Y |
| 115bb | 4Q, 9V, 15Q, 21Q, 23Y, 27G, 30S, 31G, 32T, 33Y |
| 116bb | des1, 4Q, 9V, 15Q, 21Q, 23Y, 30S, 31Q, 32T, 33Y |
| 117bb | des1, 4G, 15Q, 21Q, 23Y, 25H, 30S, 31Q, 32T, 33Y |
| 118bb | des1, 4G, 9V, 15Q, 21Q, 23Y, 30S, 31G, 32T, 33Y |
| 119bb | des1, 4G, 9V, 15Q, 21Q, 23Y, 30S, 31Q, 32T, 33Y |
| 120bb | des1, 4G, 9V, 15Q, 21Q, 23Y, 30S, 31G, 32T, 33Y |
| 121bb | des1, 4G, 9V, 15Q, 21Q, 23Y, 30S, 31G, 32T, 33Y |
| 122bb | des1, 4G, 9V, 15Q, 21Q, 23Y, 30S, 31A, 32T, 33Y |
| 123bb | des1, 2L, 4G, 9V, 21S, 23Y, 30S, 31G, 32T, 33Y |
| 124bb | des1, 4G, 9T, 15Q, 21Q, 23Y, 30S, 31G, 32T, 33Y |
| 125bb | des1, 4G, 9V, 15Q, 21Q, 23Y, 25P, 30S, 31Q, 32T, 33Y |
| 126bb | des1, 4G, 8L, 9V, 15Q, 21Q, 23Y, 30S, 31Q, 32T, 33Y |
| 127bb | des1, 2L, 4G, 9V, 15Q, 21Q, 23Y, 30S, 31Q, 32T, 33Y |
| 128bb | des1, 4G, 9T, 15Q, 21Q, 23Y, 25P, 30S, 31Q, 32T, 33Y |
| 129bb | 2L, 4G, 8L, 9V, 15Q, 21Q, 23Y, 27G, 30S, 31G, 32T, 33Y |

TABLE 2-continued mimylin peptides (backbones)

| Ex. # | Amino acid modifications relative to mimylin (SEQ ID NO: 1) |
|---|---|
| 130bb | des1, 4G, 9V, 15Q, 21Q, 23aQ, 23bT, 23cY, 30S, 31Q, 32T, 33Y |
| 131bb | des1, 4G, 9V, 12K, 15Q, 21Q, 23Y, 25P, 30S, 31G, 32T, 33Y |
| 132bb | des1, 4Q, 9V, 15Q, 16R, 19R, 21Q, 23Y, 27Q, 30S, 31Q, 32T, 33Y |
| 133bb | des1, 2L, 4Q, 8L, 9V, 15Q, 16R, 19R, 21Q, 23Y, 27Q, 30S, 31Q, 32T, 33Y |

In some embodiments a mimylin derivative comprising a mimylin peptide with up to 11 amino acid modifications relative to SEQ ID NO: 1 (mimylin) according to this invention is represented by the compounds listed in Table 3. Table 2 and 4 respectively, represent the mimylin analogues which have been derivatised, resulting in the corresponding mimylin derivative represented in Table 1 or 3 respectively. Thus the compound in EX. #8 in Table 1 or 3, respectively is a derivative of a mimylin analogue which has been modified with the amino acids as indicated in Table 2 or 4 as Ex. #8bb.

TABLE 3 mimylin derivatives (mimylin compounds) comprising mimylin backbones with up to 11 amino acid modifications relative to SEQ ID NO: 1
Ex. #

| 1 | 19 | 37 | 55 | 73 | 91 | 109 |
| 2 | 20 | 38 | 56 | 74 | 92 | 110 |
| 3 | 21 | 39 | 57 | 75 | 93 | 111 |
| 4 | 22 | 40 | 58 | 76 | 94 | 112 |
| 5 | 23 | 41 | 59 | 77 | 95 | 113 |
| 6 | 24 | 42 | 60 | 78 | 96 | 114 |
| 7 | 25 | 43 | 61 | 79 | 97 | 115 |
| 8 | 26 | 44 | 62 | 80 | 98 | 116 |
| 9 | 27 | 45 | 63 | 81 | 99 | 117 |
| 10 | 28 | 46 | 64 | 82 | 100 | 118 |
| 11 | 29 | 47 | 65 | 83 | 101 | 119 |
| 12 | 30 | 48 | 66 | 84 | 102 | 120 |

TABLE 3-continued mimylin derivatives (mimylin compounds) comprising mimylin backbones with up to 11 amino acid modifications relative to SEQ ID NO: 1
Ex. #

| 13 | 31 | 49 | 67 | 85 | 103 | 121 |
| 14 | 32 | 50 | 68 | 86 | 104 | 122 |
| 15 | 33 | 51 | 69 | 87 | 105 | 123 |
| 16 | 34 | 52 | 70 | 88 | 106 | 124 |
| 17 | 35 | 53 | 71 | 89 | 107 | — |
| 18 | 36 | 54 | 72 | 90 | 108 | — |

In some embodiments a mimylin peptide with up to 11 amino acid modifications relative to SEQ ID NO: 1 (mimylin) according to this invention is represented by the compounds listed in Table 4. Thus the compound in Ex. #8 in Table 1 or 3, respectively is a derivative of a mimylin analogue which has been modified with the amino acids as indicated in Table 2 or 4 as Ex. #8bb.

TABLE 4 mimylin peptides (backbones (bb)) with up to 11 amino acid modifications relative to SEQ ID NO: 1
Ex. #

| 1bb | 18bb | 35bb | 52bb | 69bb | 86bb | 103bb | 120bb |
| 2bb | 19bb | 36bb | 53bb | 70bb | 87bb | 104bb | 121bb |
| 3bb | 20bb | 37bb | 54bb | 71bb | 88bb | 105bb | 122bb |
| 4bb | 21bb | 38bb | 55bb | 72bb | 89bb | 106bb | 123bb |
| 5bb | 22bb | 39bb | 56bb | 73bb | 90bb | 107bb | 124bb |
| 6bb | 23bb | 40bb | 57bb | 74bb | 91bb | 108bb | 125bb |
| 7bb | 24bb | 41bb | 58bb | 75bb | 92bb | 109bb | 126bb |
| 8bb | 25bb | 42bb | 59bb | 76bb | 93bb | 110bb | 127bb |
| 9bb | 26bb | 43bb | 60bb | 77bb | 94bb | 111bb | — |
| 10bb | 27bb | 44bb | 61bb | 78bb | 95bb | 112bb | — |
| 11bb | 28bb | 45bb | 62bb | 79bb | 96bb | 113bb | — |
| 12bb | 29bb | 46bb | 63bb | 80bb | 97bb | 114bb | — |
| 13bb | 30bb | 47bb | 64bb | 81bb | 98bb | 115bb | — |
| 14bb | 31bb | 48bb | 65bb | 82bb | 99bb | 116bb | — |
| 15bb | 32bb | 49bb | 66bb | 83bb | 100bb | 117bb | — |
| 16bb | 33bb | 50bb | 67bb | 84bb | 101bb | 118bb | — |
| 17bb | 34bb | 51bb | 68bb | 85bb | 102bb | 119bb | — |

I one embodiment the mimylin derivatives of this invention can be presented by their structure formula as presented in Table 5.

TABLE 5
Structure formulas of mimylin derivatives (mimylin compounds)
| Ex # | Structure of compound |
|---|---|
| 1 | H—E A S E L S T A A L G R L S A E L H E L A T L P R T E T G P E S P—NH$_2$ (SEQ ID NO: 1) |
| 2 | 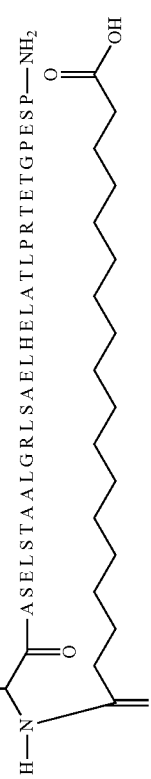 (SEQ ID NO: 1) |
| 3 | 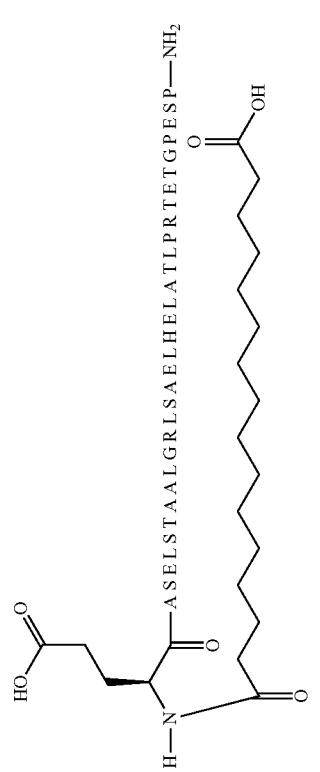 (SEQ ID NO: 1) |

TABLE 5-continued
Structure formulas of mimylin derivatives (mimylin compounds)
| Ex # | Structure of compound |
|---|---|
| 4 | 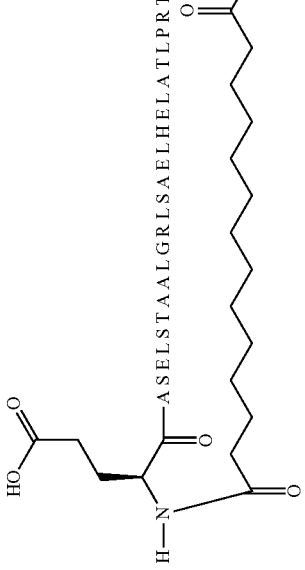 (SEQ ID NO: 1) |
| 5 | 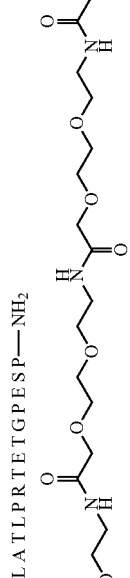 (SEQ ID NO: 1) |
| 6 | 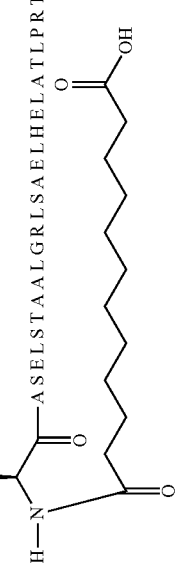 (SEQ ID NO: 1) |

TABLE 5-continued
Structure formulas of mimylin derivatives (mimylin compounds)
| Ex # | Structure of compound |
|---|---|
| 7 | 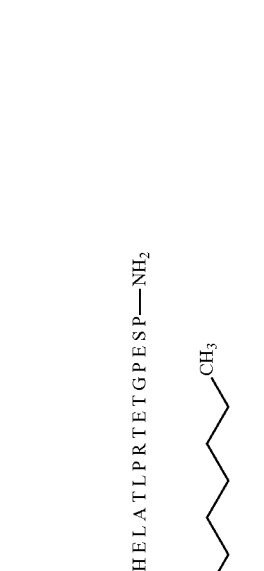 (SEQ ID NO: 1) |
| 8 | 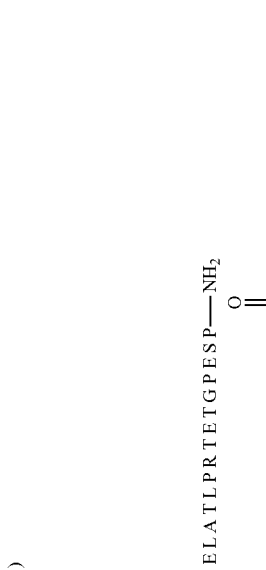 (SEQ ID NO: 9) |
| 9 | 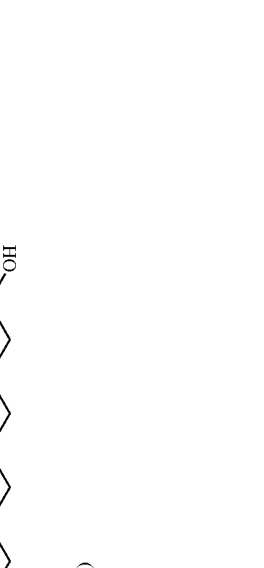 (SEQ ID NO: 10) |

TABLE 5-continued

Structure formulas of mimylin derivatives (mimylin compounds)

| Ex # | Structure of compound |
|---|---|
| 10 | HOOC-CH(NH-H)-C(=O)-ASELSTAILGRLSAELHELATLPRTETGPESP-NH$_2$, with side chain -(CH$_2$)$_n$-COOH (SEQ ID NO: 11) |
| 11 | HOOC-CH(NH-H)-C(=O)-ASELSTAALGRLSAEIHELATLPRTETGPESP-NH$_2$, with side chain -(CH$_2$)$_n$-COOH (SEQ ID NO: 12) |

TABLE 5-continued

Structure formulas of mimylin derivatives (mimylin compounds)

| Ex # | Structure of compound |
|---|---|
| 12 | ASELSTAALGRLSAELHEIATLPRTETGPESP-NH2 (SEQ ID NO: 13) |
| 13 | ASELSTAALGRLSAELAELATLPRTETGPESP-NH2 (SEQ ID NO: 14) |
| 14 | ASELSTALLGRLSAELHELATLPRTETGPESP-NH2 (SEQ ID NO: 15) |

TABLE 5-continued

Structure formulas of mimylin derivatives (mimylin compounds)

| Ex # | Structure of compound |
|---|---|
| 15 | ASELSTLALGRLSAELHELATLPRTETGPESP—NH$_2$ with glutamic acid-linked C10 diacid side chain (SEQ ID NO: 16) |
| 16 | ASELHTAALGRLSAELHELATLPRTETGPESP—NH$_2$ with glutamic acid-linked C10 diacid side chain (SEQ ID NO: 17) |

TABLE 5-continued

Structure formulas of mimylin derivatives (mimylin compounds)

| Ex # | Structure of compound |
|---|---|
| 17 | ASEHSTAALGRLSAELHELATLPRTETGPESP—NH₂ (with E side chain linked via amide to long alkyl chain terminating in —COOH) (SEQ ID NO: 18) |
| 18 | ASELSTAALGRLSAELHELATLPRTETGPEHP—NH₂ (with E side chain linked via amide to long alkyl chain terminating in —COOH) (SEQ ID NO: 19) |
| 19 | SELSTAALGRLSAELHELATLPRTETGPESP—NH₂ (N-terminally modified with Ala-γGlu-(CH₂)ₙ-COOH moiety) (SEQ ID NO: 20) |

TABLE 5-continued
Structure formulas of mimylin derivatives (mimylin compounds)
| Ex # | Structure of compound |
|---|---|
| 20 | 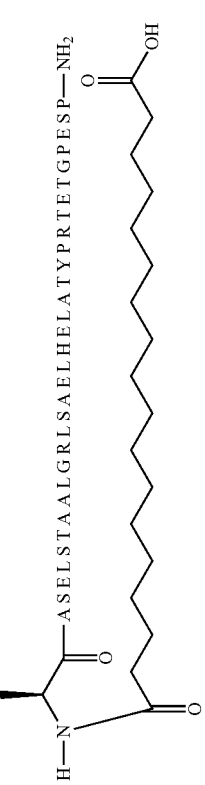 ASELSTAALGRLSAELHELATYPRTETGPESP—NH₂ (SEQ ID NO: 21) |
| 21 | 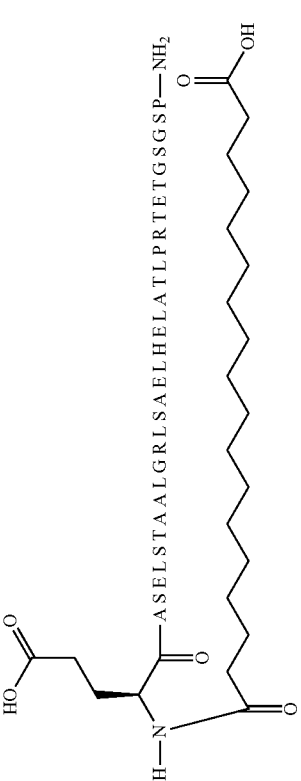 ASELSTAALGRLSAELHELATLPRTETGSGSP—NH₂ (SEQ ID NO: 22) |
| 22 | 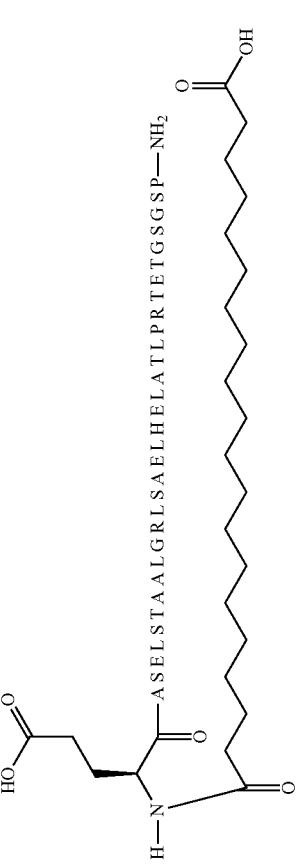 ASELSTAALGRLSAELHELATLPRTETGSGSP—NH₂ (SEQ ID NO: 23) |

TABLE 5-continued

Structure formulas of mimylin derivatives (mimylin compounds)

| Ex # | Structure of compound |
|---|---|
| 23 | H₃C-CH(NH-CO-(CH₂)₈-CO-NH-CH(COOH)-CO-NH)-SELSTAALGRLSAELHELATLPRTETGSESP—NH₂ (SEQ ID NO: 24) |
| 24 | HOOC-CH₂-CH₂-CH(NH₂)-CO-(long alkyl chain)-CO-NH-ASEVSTAVLGRLSAELHELATLPRTETGPESP—NH₂ (SEQ ID NO: 25) |
| 25 | HOOC-CH₂-CH₂-CH(NH₂)-CO-(long alkyl chain)-CO-NH-ASEISTAILGRLSAELHELATLPRTETGPESP—NH₂ (SEQ ID NO: 26) |

TABLE 5-continued

Structure formulas of mimylin derivatives (mimylin compounds)

| Ex # | Structure of compound |
|---|---|
| 26 | ASELSTAVIGRLSAELHELATLPRTETGPESP—NH$_2$ (with Glu-linked fatty acid chain terminating in COOH) (SEQ ID NO: 27) |
| 27 | ASELSTALAGRLSAELHELATLPRTETGPESP—NH$_2$ (with Glu-linked fatty acid chain terminating in COOH) (SEQ ID NO: 28) |
| 28 | PSELSTAVLGRLSAELHELATLPRTETGPESP—NH$_2$ (with Glu-linked fatty acid chain terminating in COOH) (SEQ ID NO: 29) |

TABLE 5-continued

Structure formulas of mimylin derivatives (mimylin compounds)

| Ex # | Structure of compound |
|---|---|
| 29 | APELSTAVLGRLSAELHELATLPRTETGPESP—NH₂ with glutamic acid and C12 fatty diacid linker (SEQ ID NO: 30) |
| 30 | ASPLSTAVLGRLSAELHELATLPRTETGPESP—NH₂ with glutamic acid and C12 fatty diacid linker (SEQ ID NO: 31) |

TABLE 5-continued

Structure formulas of mimylin derivatives (mimylin compounds)

| Ex # | Structure of compound |
|---|---|
| 31 | HOOC-CH(NH-)-CO-ASELSTAVLGRLSAELHELATLPPTETGPESP-NH₂, with N-acyl C₁₆ diacid chain terminating in COOH (SEQ ID NO: 32) |
| 32 | HOOC-CH(NH-)-CO-ASELSTAVLGRLSAELHELATLPRTEPGPESP-NH₂, with N-acyl C₁₆ diacid chain terminating in COOH (SEQ ID NO: 33) |
| 33 | HOOC-CH(NH-)-CO-ASELSTAVLGRLSAELAELATLPRTETGPESP-NH₂, with N-acyl C₁₆ diacid chain terminating in COOH (SEQ ID NO: 34) |

TABLE 5-continued

Structure formulas of mimylin derivatives (mimylin compounds)

| Ex # | Structure of compound |
|---|---|
| 34 | ASELSTAALGRLSAELHELATYPRTETGSGSP—NH₂ (SEQ ID NO: 35) |
| 35 | SELSTAALGRLSAELHELATLPRTETGSGSP—NH₂ (SEQ ID NO: 36) |
| 36 | ASEVSTAVLGRLSAELHEVATLPRTETGPESP—NH₂ (SEQ ID NO: 37) |

TABLE 5-continued

Structure formulas of mimylin derivatives (mimylin compounds)

| Ex # | Structure of compound |
|---|---|
| 37 | HOOC-CH(NH-H)-CO-ASEISTAIIGRLSAELHELATLPRTETGPESP-NH₂ ; CO-(CH₂)ₙ-COOH (SEQ ID NO: 38) |
| 38 | HOOC-CH(NH-H)-CO-APPLSTAVLGRLSAELHELATLPRTETGPESP-NH₂ ; CO-(CH₂)ₙ-COOH (SEQ ID NO: 39) |
| 39 | HOOC-CH(NH-H)-CO-ASELSTAVLGKLSAELHELATLPKTETGPESP-NH₂ ; CO-(CH₂)ₙ-COOH (SEQ ID NO: 40) |

TABLE 5-continued

Structure formulas of mimylin derivatives (mimylin compounds)

| Ex # | Structure of compound |
|---|---|
| 40 | SELSTAALGRLSAELHELATLPRTETGSGSP—NH$_2$ with modified N-terminus (SEQ ID NO: 41) |
| 41 | SELSTAALGRLSAELHELATLPRTETGPGSP—NH$_2$ with modified N-terminus (SEQ ID NO: 41) |
| 42 | SELSTAALGRLSAELHELATLPRTETGPGSP—NH$_2$ with modified N-terminus (SEQ ID NO: 41) |
| 43 | SELSTAALGRLSAELHELATLPRTETGPGSP—NH$_2$ with modified N-terminus (SEQ ID NO: 41) |

TABLE 5-continued

Structure formulas of mimylin derivatives (mimylin compounds)

| Ex # | Structure of compound |
|---|---|
| 44 | H-SELSTAALGRLSAELHELATLPRTETGPGSP-NH₂ with N-terminal CH₃-Ala and PEG-linker conjugated to glutamic acid bearing a C10 dicarboxylic acid (SEQ ID NO: 41) |
| 45 | H-SELSTAALGRLSAELHELATLPRTETGPGSP-NH₂ with N-terminal CH₃-Ala and PEG-linker conjugated to glutamic acid bearing a C18 fatty diacid (SEQ ID NO: 41) |
| 46 | H-SELSTAALGRLSAELHELATLPRTETGSGSP-NH₂ with N-terminal Ala modified by γ-Glu conjugated to a C18 dicarboxylic acid (SEQ ID NO: 41) |

TABLE 5-continued

Structure formulas of mimylin derivatives (mimylin compounds)

| Ex # | Structure of compound |
|---|---|
| 47 | SELSTAALGRLSAELHELATLPRTETGSGSP—NH$_2$ (SEQ ID NO: 41) |
| 48 | SELSTAALGRLSAELHELATLPRTETGSGSP—NH$_2$ (SEQ ID NO: 41) |
| 49 | SELSTAALGRLSAELHELATLPRTETGSGSP—NH$_2$ (SEQ ID NO: 41) |

TABLE 5-continued
Structure formulas of mimylin derivatives (mimylin compounds)
| Ex # | Structure of compound |
|---|---|
| 50 | 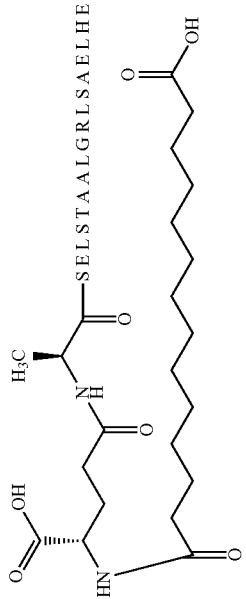  (SEQ ID NO: 41) |
| 51 | 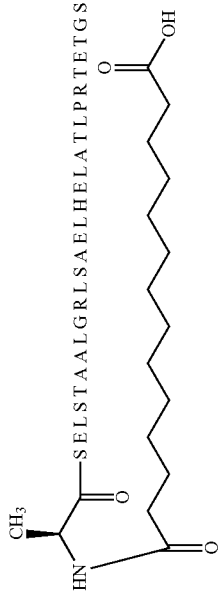  (SEQ ID NO: 41) |
| 52 | 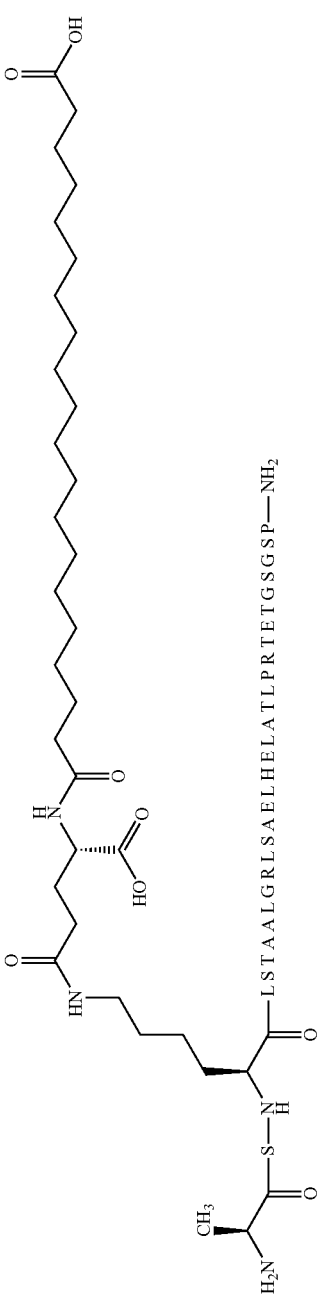  (SEQ ID NO: 42) |

TABLE 5-continued

Structure formulas of mimylin derivatives (mimylin compounds)

| Ex # | Structure of compound |
|---|---|
| 53 | CH₃-CH(NH₂)-CO-SELSTAALGRLSA-NH-CH(COOH)-(CH₂)₄-NH-CO-(CH₂)₂-CH(NH-CO-(CH₂)ₙ-COOH)(COOH) ... LHELATLPRTETGSGSP-NH₂ (SEQ ID NO: 42) |
| 54 | CH₃-CH(NH₂)-CO-SELSTAALGRLSAELH-NH-CH(CO-LATLPRTETGSGSP-NH₂)-(CH₂)₄-NH-CO-(CH₂)₂-CH(NH-CO-(CH₂)ₙ-COOH)(COOH) (SEQ ID NO: 44) |

TABLE 5-continued

Structure formulas of mimylin derivatives (mimylin compounds)

| Ex # | Structure of compound |
|---|---|
| 55 | S E L S T A A L G R L S A E L H E L A T L P R T — T G S G S P — NH₂ (SEQ ID NO: 43) |
| 56 | S E L S T A A L G R L S A E L H E L A T Y P R T E T G S G S P — NH₂ (SEQ ID NO: 45) |
| 57 | A S E L S T A A L G R L S A E L H E L A T Y P R T E T G S G S P — NH₂ (SEQ ID NO: 46) |

TABLE 5-continued

Structure formulas of mimylin derivatives (mimylin compounds)

| Ex # | Structure of compound |
|---|---|
| 58 | SELSTAALGRLSAELHELATYPRTETGSGSP—NH$_2$ (with Glu and dodecanedioic acid modification on N-terminal Ala) (SEQ ID NO: 44) |
| 59 | SELSTAALGRLSAELHELATLPRTETGSGSY—NH$_2$ (with Glu and tetradecanedioic acid modification on N-terminal Ala) (SEQ ID NO: 48) |
| 60 | SELSTAALGRLSAELHELATLPRTETGSGSH—NH$_2$ (with Glu and hexadecanedioic acid modification on N-terminal Ala) (SEQ ID NO: 49) |

TABLE 5-continued

Structure formulas of mimylin derivatives (mimylin compounds)

| Ex # | Structure of compound |
|---|---|
| 61 | SELSTAALGRLSAELHELATLPRTETGSGSF—NH₂ (SEQ ID NO: 50) |
| 62 | SELSTAALGRLSAELHELATLPRTETGSGSL—NH₂ (SEQ ID NO: 51) |
| 63 | SELSTAALGRLSAELHELATLPRTETGSGSS—NH₂ (SEQ ID NO: 52) |

TABLE 5-continued

Structure formulas of mimylin derivatives (mimylin compounds)

| Ex # | Structure of compound |
|---|---|
| 64 | SELSTAALGRLSAELHELATLPRTETGSGSG—NH₂ (SEQ ID NO: 53) |
| 65 | SELSTAALGRLSAELHELATLPRTETGSGSA—NH₂ (SEQ ID NO: 39) |
| 66 | SELSTAALGRLSEELHELATLPRTETGSGSP—NH₂ (SEQ ID NO: 40) |

TABLE 5-continued

Structure formulas of mimylin derivatives (mimylin compounds)

| Ex # | Structure of compound |
|---|---|
| 67 | SELSTAALGRLS—ELHELATLPRTETGSGSP—NH₂ with Glu side chain linker to fatty diacid (SEQ ID NO: 41) |
| 68 | LSTAALGRLSAELHELATLPRTETGSGSP—NH₂ with acetyl-Ala-S-Lys(γGlu-C16 diacid) modification (SEQ ID NO: 42) |

TABLE 5-continued

Structure formulas of mimylin derivatives (mimylin compounds)

| Ex # | Structure of compound |
|---|---|
| 69 | [Structure with C18 diacid linked via Glu to Lys side chain, peptide: SELSTAALGRLSA-[Lys]-LHELATLPRTETGSGSP-NH₂, N-terminal Ac-Ala] (SEQ ID NO: 54) |
| 70 | [Structure with C18 diacid linked via Glu to Lys side chain, peptide: SELSTAALGRLSAELH-[Lys]-LATLPRTETGSGSP-NH₂, N-terminal Ac-Ala] (SEQ ID NO: 55) |

TABLE 5-continued

Structure formulas of mimylin derivatives (mimylin compounds)

| Ex # | Structure of compound |
|---|---|
| 71 | SELSTAALGRLSAELHELATLPRT-TGSGSP-NH2 (SEQ ID NO: 56) |
| 72 | SELSTAALGHLSAELHELATLPRTETGSGSP-NH2 (SEQ ID NO: 57) |
| 73 | SELSTAALGRLSAELHELATLPHTETGSGSP-NH2 (SEQ ID NO: 58) |

TABLE 5-continued

Structure formulas of mimylin derivatives (mimylin compounds)

| Ex # | Structure of compound |
|---|---|
| 74 | SELSTAALGRLSAELHELATLPRTETGTGTP—NH$_2$ (SEQ ID NO: 59) |
| 75 | SELSTAALGRLSAELHELATLPRTETGSGPP—NH$_2$ (SEQ ID NO: 60) |
| 76 | SELSTAVLGRLSAELHELATLPRTETGSGSP—NH$_2$ (SEQ ID NO: 61) |

TABLE 5-continued
Structure formulas of mimylin derivatives (mimylin compounds)
| Ex # | Structure of compound |
|---|---|
| 77 | 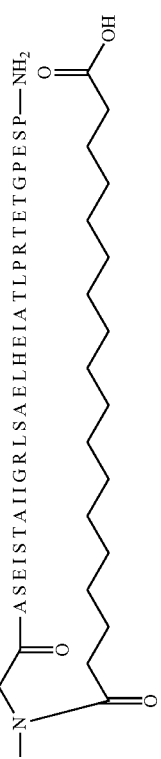/ASEISTAIIGRLSAELHEIATLPRTETGPESP—NH₂ (SEQ ID NO: 62) |
| 78 | 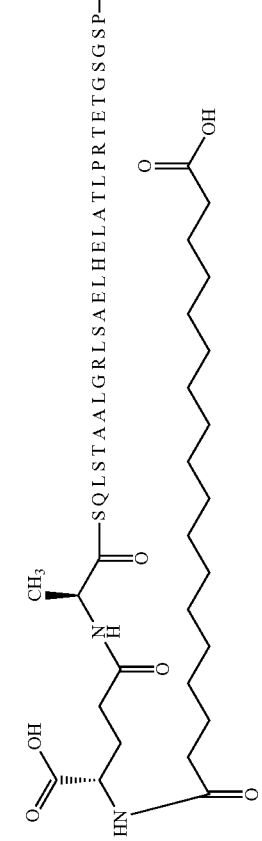 SQLSTAALGRLSAELHELATLPRTETGSGSP—NH₂ (SEQ ID NO: 63) |
| 79 | 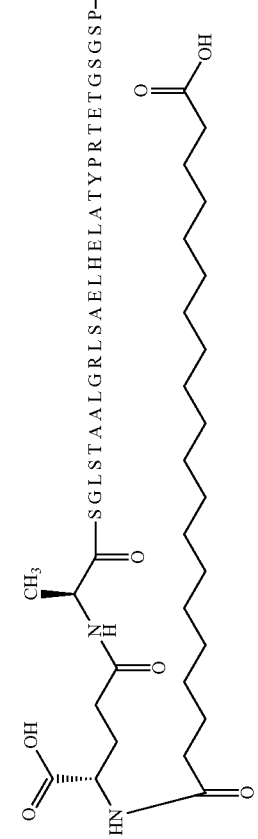 SGLSTAALGRLSAELHELATYPRTETGSGSP—NH₂ (SEQ ID NO: 64) |

TABLE 5-continued

Structure formulas of mimylin derivatives (mimylin compounds)

| Ex # | Structure of compound |
|---|---|
| 80 | SELSTAALGRLSAELHELATYPRTETGSGSY—NH$_2$ (SEQ ID NO: 65) |
| 81 | SELSTAALGRLSAELHELATYPRTETGSGAP—NH$_2$ (SEQ ID NO: 66) |
| 82 | SELSTAALGRLSAELHELSTYPRTETGSGSP—NH$_2$ (SEQ ID NO: 67) |

TABLE 5-continued
Structure formulas of mimylin derivatives (mimylin compounds)
| Ex # | Structure of compound |
|---|---|
| 83 | 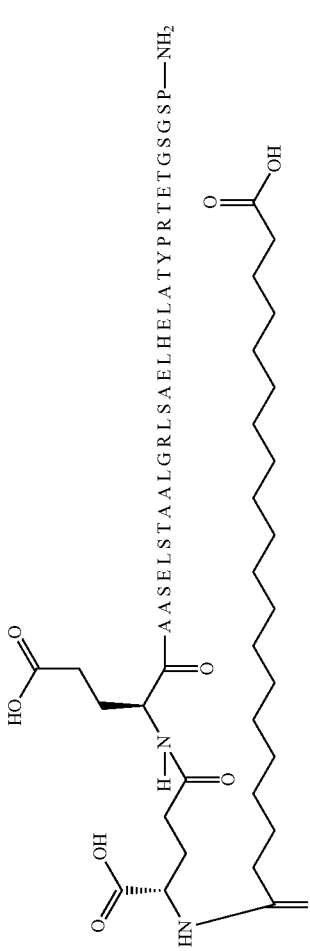 (SEQ ID NO: 68) |
| 84 | 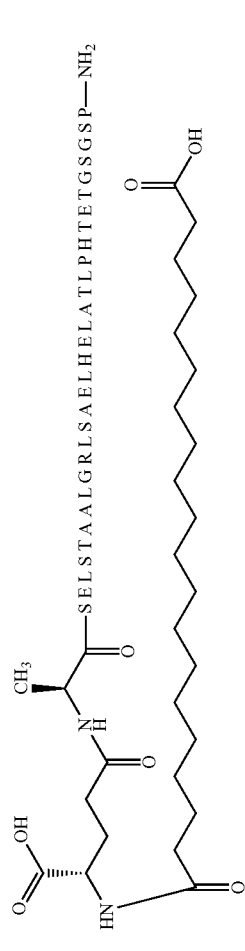 (SEQ ID NO: 69) |
| 85 | 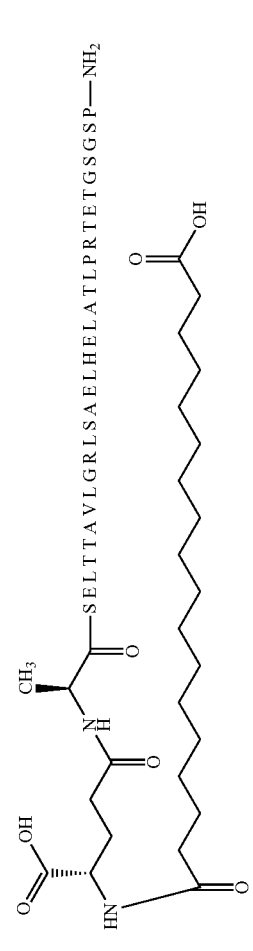 (SEQ ID NO: 70) |

TABLE 5-continued

Structure formulas of mimylin derivatives (mimylin compounds)

| Ex # | Structure of compound |
|---|---|
| 86 | SEVSTAVLGRLSAELHELATLPRTETGSGSP—NH₂ (with modified N-terminal alanine linked via glutamic acid to a fatty acid chain terminating in —COOH) (SEQ ID NO: 71) |
| 87 | SQLSTAALGRLSAQLHELATLPRTETGSGSP—NH₂ (with modified N-terminal alanine linked via glutamic acid to a fatty acid chain terminating in —COOH) (SEQ ID NO: 72) |
| 88 | SELSTAALGRLSAQLHELATYPRTETGSGSY—OH (with modified N-terminal alanine linked via glutamic acid to a longer fatty acid chain terminating in —COOH) (SEQ ID NO: 73) |

TABLE 5-continued

Structure formulas of mimylin derivatives (mimylin compounds)

| Ex # | Structure of compound |
|---|---|
| 89 | SELSTAALGRLSAELHELATYPRTETGSGSPG—OH (with Glu side chain linked via amide to a long alkyl diacid chain terminating in —OH) (SEQ ID NO: 74) |
| 90 | SELSTAALGRLSAELHELATYPRTETGSGSPK—OH (with Glu side chain linked via amide to a long alkyl diacid chain terminating in —OH) (SEQ ID NO: 75) |
| 91 | SELSTASLGRLSAELHELATYPRTETGSGSY—OH (with Glu side chain linked via amide to a long alkyl diacid chain terminating in —OH) (SEQ ID NO: 76) |

TABLE 5-continued
Structure formulas of mimylin derivatives (mimylin compounds)
| Ex # | Structure of compound |
|---|---|
| 92 | 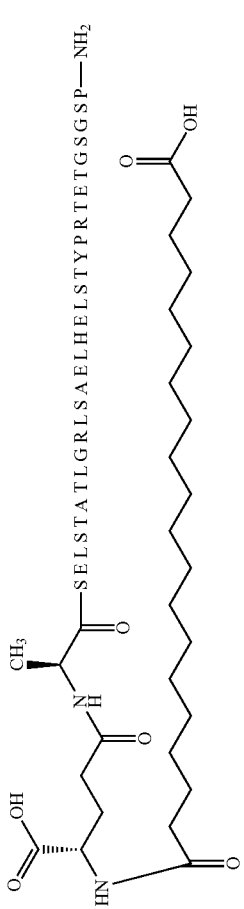 (SEQ ID NO: 77) |
| 93 | 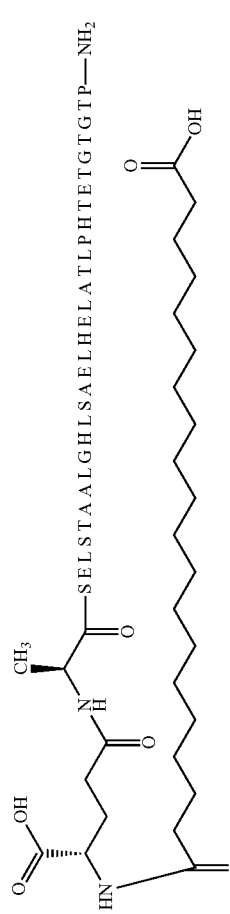 (SEQ ID NO: 78) |
| 94 | 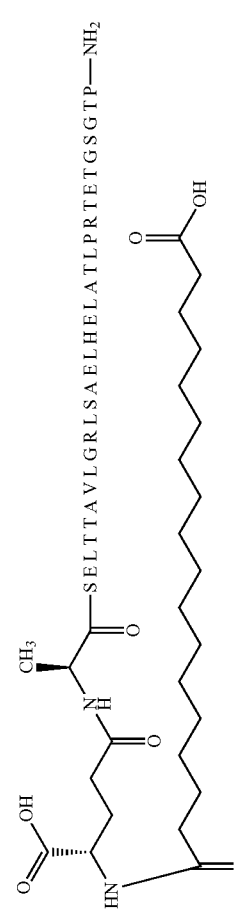 (SEQ ID NO: 79) |

TABLE 5-continued

Structure formulas of mimylin derivatives (mimylin compounds)

| Ex # | Structure of compound |
|---|---|
| 95 | SELTTAVLGRLSAELHELATLPRTETGTGTP—NH₂ (with modified residue bearing CH₃-CH(NH-)-C(O)- group, side chain -CH(COOH)-NH-C(O)-(CH₂)₁₀-COOH) (SEQ ID NO: 80) |
| 96 | SEVSTAVVGRLSAELHELATLPRTETGSGSP—NH₂ (with modified residue bearing CH₃-CH(NH-)-C(O)- group, side chain -CH(COOH)-NH-C(O)-(CH₂)₁₀-COOH) (SEQ ID NO: 81) |
| 97 | SELSTAALGRLSAELHELSTYPRTETGSGSY—NH₂ (with modified residue bearing CH₃-CH(NH-)-C(O)- group, side chain -CH(COOH)-NH-C(O)-(CH₂)₁₂-COOH) (SEQ ID NO: 82) |

TABLE 5-continued

Structure formulas of mimylin derivatives (mimylin compounds)

| Ex # | Structure of compound |
|---|---|
| 98 | ...SGLSTAVLGRLSAELHELATYPRTETGSGTP—NH₂ (SEQ ID NO: 83) |
| 99 | ...SELSTATLGRLSAELHELSTYPRTETGSGSY—NH₂ (SEQ ID NO: 84) |
| 100 | ...SELSTASLGRLSAELHELSTYPRTETGSGSY—NH₂ (SEQ ID NO: 85) |

TABLE 5-continued
Structure formulas of mimylin derivatives (mimylin compounds)
| Ex # | Structure of compound |
|---|---|
| 101 | 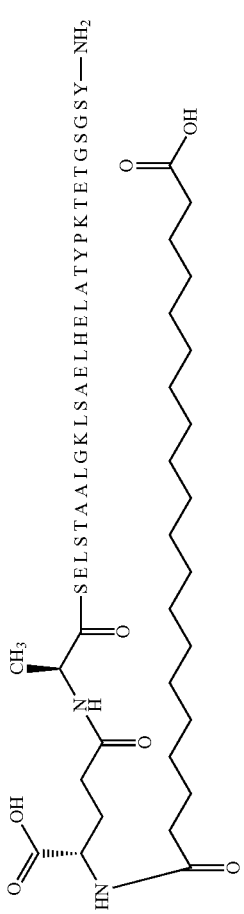 SELSTAALGKLSAELHELATYPKTETGSGSY—NH$_2$ (SEQ ID NO: 86) |
| 102 | 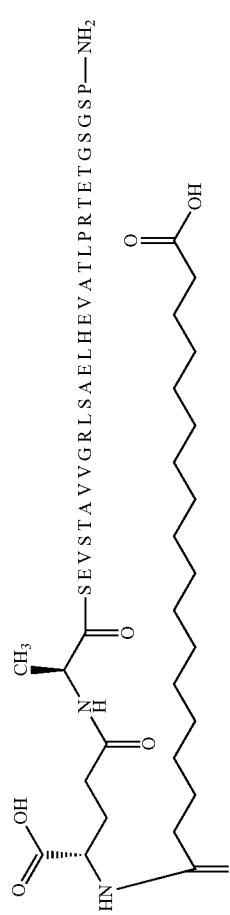 SEVSTAVVGRLSAELHEVATLPRTETGSGSP—NH$_2$ (SEQ ID NO: 87) |
| 103 | 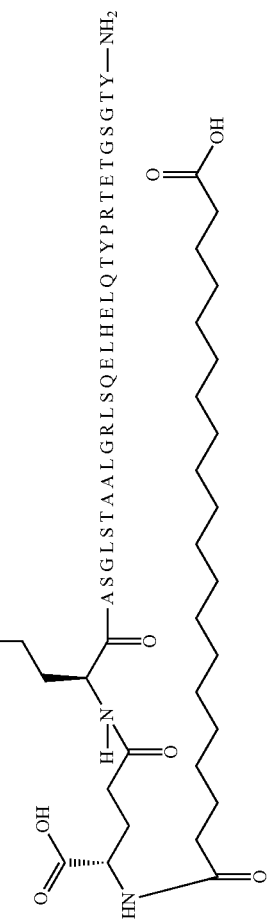 ASGLSTAALGRLSQELHELQTYPRTETGSGTY—NH$_2$ (SEQ ID NO: 88) |

TABLE 5-continued

Structure formulas of mimylin derivatives (mimylin compounds)

| Ex # | Structure of compound |
|---|---|
| 104 | SGLSTAVLGRLSAELHELATYPRTETGSGTY—NH₂ (with modified N-terminus bearing Ala-CH₃, glutamic acid residue with free α-COOH, linked via amide to a long-chain dicarboxylic acid terminating in —COOH) (SEQ ID NO: 89) |
| 105 | SELTTAVLGRLTAELHELETLPRTETGTGTP—NH₂ (with modified N-terminus bearing Ala-CH₃, glutamic acid residue with free α-COOH, linked via amide to a long-chain dicarboxylic acid terminating in —COOH) (SEQ ID NO: 90) |
| 106 | SELTTAVLGRLEAELHELTTLPRTETGTGTP—NH₂ (with modified N-terminus bearing Ala-CH₃, glutamic acid residue with free α-COOH, linked via amide to a long-chain dicarboxylic acid terminating in —COOH) (SEQ ID NO: 91) |

TABLE 5-continued

Structure formulas of mimylin derivatives (mimylin compounds)

| Ex # | Structure of compound |
|---|---|
| 107 | H-A-SGLSTAALGRLSQELHELQTYPRTETGS-K(γE-C17diacid)-TY-NH$_2$ (SEQ ID NO: 92) |
| 108 | H-A-SGLSTAALGRLSQELHELETYPRTETGSGTY-NH$_2$ with γE-C17diacid modification (SEQ ID NO: 93) |
| 109 | H-A-SGLSTAALGRLSQELHELQTYPRTETGSQTY-NH$_2$ with γE-C17diacid modification (SEQ ID NO: 94) |

TABLE 5-continued
Structure formulas of mimylin derivatives (mimylin compounds)
| Ex # | Structure of compound |
|---|---|
| 110 | 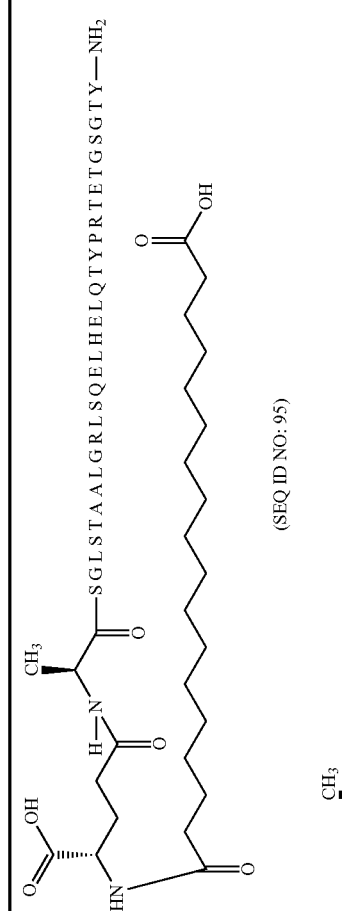<br>(SEQ ID NO: 95) |
| 111 | 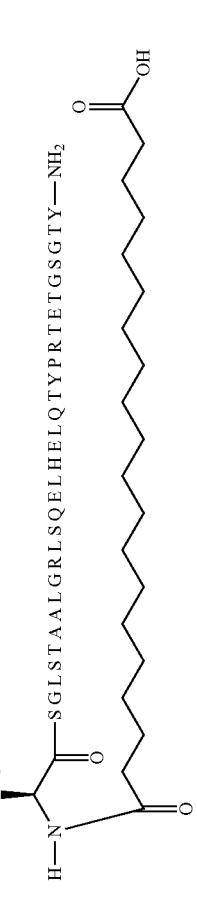<br>(SEQ ID NO: 96) |
| 112 | 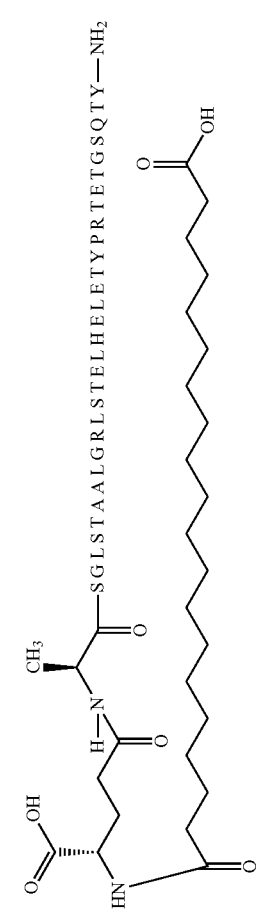<br>(SEQ ID NO: 97) |

TABLE 5-continued

Structure formulas of mimylin derivatives (mimylin compounds)

| Ex # | Structure of compound |
|---|---|
| 113 | ...SGLSTAALGRLSEELHELQTYPRTETGSGTY—NH₂ (SEQ ID NO: 98) |
| 114 | ...SELSTAVLGRLSQELHELQTYPRTETGSGTY—NH₂ (SEQ ID NO: 99) |
| 115 | ...ASQLSTAVLGRLSQELHELQTYPRTGTGSGTY—NH₂ (SEQ ID NO: 100) |

TABLE 5-continued

Structure formulas of mimylin derivatives (mimylin compounds)

| Ex # | Structure of compound |
|---|---|
| 116 | ...SQLSTAVLGRLSQELHELQTYPRTETGSQTY—NH$_2$ (SEQ ID NO: 101) |
| 117 | ...SGLSTAALGRLSQELHELQTYPHTETGSGTY—NH$_2$ (SEQ ID NO: 102) |
| 118 | ...SGLSTAVLGRLSQELHELQTYPRTETGSGTY—NH$_2$ (SEQ ID NO: 103) |

TABLE 5-continued

Structure formulas of mimylin derivatives (mimylin compounds)

| Ex # | Structure of compound |
|---|---|
| 119 | SGLSTAVLGRLSQELHELQTYPRTETGSQTY—NH₂ with modified N-terminus bearing alanine and glutamic acid residues linked to a long-chain fatty diacid (terminal —COOH) (SEQ ID NO: 104) |
| 120 | SGLSTAVLGRLSQELHELQTYPRTETGSGTY—NH₂ with N-terminal alanine linked via a PEG-like spacer (—O—CH₂—CH₂—O—CH₂—C(O)—NH—) to a glutamic acid, whose side chain is acylated with a long-chain fatty diacid (terminal —COOH) (SEQ ID NO: 105) |
| 121 | SGLSTAVLGRLSQELHELQTYPRTETGSGTY—NH₂ with N-terminal alanine linked via a PEG-like spacer (—O—CH₂—CH₂—O—CH₂—C(O)—NH—) to a glutamic acid, whose side chain is acylated with a long-chain fatty diacid (terminal —COOH) (SEQ ID NO: 106) |

TABLE 5-continued

Structure formulas of mimylin derivatives (mimylin compounds)

| Ex # | Structure of compound |
|---|---|
| 122 | SGLSTAVLGRLSQELHELQTYPRTETGSATY—NH2 (SEQ ID NO: 107) |
| 123 | SGLSTAVLGRLSAELHELSTYPRTETGSGTY—NH2 (SEQ ID NO: 108) |
| 124 | SGLSTATLGRLSQELHELQTYPRTETGSGTY—NH2 (SEQ ID NO: 109) |

TABLE 5-continued
Structure formulas of mimylin derivatives (mimylin compounds)
| Ex # | Structure of compound |
|---|---|
| 125 | 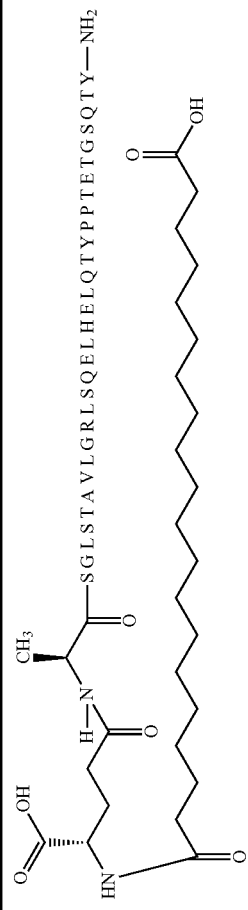 SGLSTAVLGRLSQELHELQTYPPTETGSQTY—NH₂ (SEQ ID NO: 110) |
| 126 | 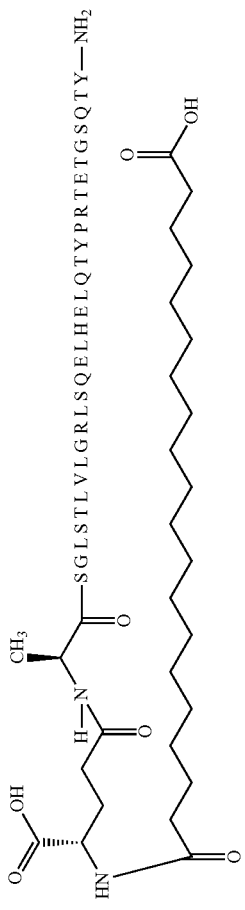 SGLSTLVLGRLSQELHELQTYPRTETGSQTY—NH₂ (SEQ ID NO: 111) |
| 127 | 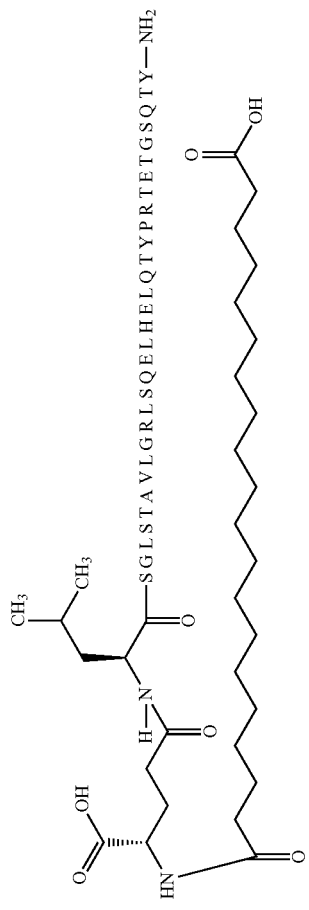 SGLSTAVLGRLSQELHELQTYPRTETGSQTY—NH₂ (SEQ ID NO: 112) |

TABLE 5-continued

Structure formulas of mimylin derivatives (mimylin compounds)

| Ex # | Structure of compound |
|---|---|
| 128 | SGLSTATLGRLSQELHELQTYPPTETGSGTY—NH$_2$ (SEQ ID NO: 113) |
| 129 | LSGLSTLVLGRLSQELHELQTYPRTGTGSGTY—NH$_2$ (SEQ ID NO: 114) |
| 130 | SGLSTAVLGRLSQELHELQTLQTYPRTETGSQTY—NH$_2$ (SEQ ID NO: 115) |

TABLE 5-continued

Structure formulas of mimylin derivatives (mimylin compounds)

| Ex # | Structure of compound |
|---|---|
| 131 | —SGLSTAVLGKLSQELHELQTYPPTETGSGTY—NH₂ (SEQ ID NO: 116) |
| 132 | —SQLSTAVLGRLSQRLHRLQTYPRTQTGSQTY—NH₂ (SEQ ID NO: 117) |
| 133 | —SQLSTLVLGRLSQRLHRLQTYPRTQTGSQTY—NH₂ (SEQ ID NO: 118) |
| 72 bb | H—ASELSTAALGHLSAELHELATLPRTETGSGSP—NH₂ (SEQ ID NO: 57) |
| 95 bb | H—ASELTTAVLGRLSAELHELATLPRTETGTGTP—NH₂ (SEQ ID NO: 80) |

TABLE 5-continued

Structure formulas of mimylin derivatives (mimylin compounds)

| Ex # | Structure of compound |
|---|---|
| 134 | [Structure: Glutamic acid residue linked via amide to a long alkyl chain terminating in carboxylic acid, attached to peptide ASELSTAALGRLSAELHELATLPRTETGPESP—OH] (SEQ ID NO: 1) |
| 127 bb | H—LSGLSTAVLGRLSQELHELQTYPRTETGSQTY—NH₂ (SEQ ID NO: 112) |
| 22 bb | H—EASELSTAALGRLSAELHELATLPRTETGSGSP—NH₂ (SEQ ID NO: 23) |
| 86 bb | H—ASEVSTAVLGRLSAELHELATLPRTETGSGSP—NH₂ (SEQ ID NO: 71) |
| 106 bb | H—ASELTTAVLGRLEAELHELTTLPRTETGTGTP—NH₂ (SEQ ID NO: 91) |
| 135 | H—EASELSTAALGRLSAELHELATLPRTETGPES—N[proline residue]—OH (SEQ ID NO: 1) |

TABLE 6 side chain names and structure

| Side chain name | Side chain structure |
|---|---|
| C18diacid | |
| C16diacid | |
| C14diacid | |
| C14diacid-2xgGlu-4xOEG | |
| C12diacid | |
| C16 | |
| C14diacid-gGlu | |
| C20diacid | |
| C18diacid-gGlu | |
| C20diacid-gGlu | |

TABLE 6-continued side chain names and structure

| Side chain name | Side chain structure |
|---|---|
| C20diacid-gGlu-OEG | |
| C20diacid-gGlu-2xOEG | |
| C20diacid-gGlu-3xOEG | |
| C20diacid-gGlu-4xOEG | |
| C20diacid-gGlu-5xOEG | |
| C16diacid-gGlu | |

In some embodiments the invention relates to a method for weight management making use of a mimylin peptide or derivative a pharmaceutical formulation, co-formulation or co-treatment of any one of the non-limiting numbered aspects of this invention. In some embodiments the invention relates to a method for reduction of appetite making use of a mimylin peptide or derivative a pharmaceutical formulation, co-formulation or co-treatment of any one of the non-limiting numbered aspects of this invention. In some embodiments the invention relates to a method for reduction of food intake making use of a mimylin peptide or derivative a pharmaceutical formulation, co-formulation or co-treatment of any one of the non-limiting numbered aspects of this invention.

In some embodiments the invention relates to a method for treatment or prevention of obesity making use of a mimylin peptide or derivative a pharmaceutical formulation, co-formulation or co-treatment of any one of the non-limiting numbered aspects of this invention. In some embodiments the invention relates to use of a mimylin peptide or derivative or a pharmaceutical formulation, co-formulation or co-treatment according to the non-limiting numbered aspects of this invention for treatment or prevention of obesity. In some embodiments the subject suffering from obesity is human, such as an adult human or a paediatric human (including infants, children, and adolescents). A human subject suffering from obesity may have a BMI of ≥30; this subject may also be referred to as obese. In some embodiments the human subject suffering from obesity may have a BMI of ≥35 or a BMI in the range of ≥30 to <40. In some embodiments the obesity is severe obesity or morbid obesity, wherein the human subject may have a BMI of ≥40.

In some embodiments the invention relates to a method for treatment or prevention of overweight making use of a mimylin peptide or derivative a pharmaceutical formulation, co-formulation or co-treatment of any one of the non-limiting numbered aspects of this invention, optionally in the presence of at least one weight-related comorbidity. In some embodiments the invention relates to use of the a mimylin peptide or derivative or a pharmaceutical formulations, co-formulation or co-treatment according to the non-limiting numbered aspects of this invention for treatment or prevention of overweight, optionally in the presence of at least one weight-related comorbidity. In some embodiments the subject suffering from overweight is human, such as an adult human or a paediatric human (including infants, children, and adolescents). In some embodiments a human subject suffering from overweight may have a BMI of ≥25, such as a BMI of ≥27. In some embodiments a human subject suffering from overweight has a BMI in the range of 25 to <30 or in the range of 27 to <30. In some embodiments the weight-related comorbidity is selected from the group consisting of hypertension, diabetes (such as type 2 diabetes), dyslipidaemia, high cholesterol, and obstructive sleep apnea.

In some embodiments the invention relates to a method for reduction of body weight making use of a mimylin peptide or derivative a pharmaceutical formulation, co-formulation or co-treatment of any one of the non-limiting numbered aspects of this invention. In some embodiments the invention relates to use of a mimylin peptide or derivative or a pharmaceutical formulations according to the non-limiting numbered aspects of this invention for reduction of body weight. A human to be subjected to reduction of body weight according to the present invention may have a BMI of ≥25, such as a BMI of ≥27 or a BMI of ≥30. In some embodiments the human to be subjected to reduction of body weight according to the present invention may have a BMI of ≥35 or a BMI of ≥40. The term "reduction of body weight" may include treatment or prevention of obesity and/or overweight.

Non-Limiting Aspect of the Invention

1. A mimylin peptide comprising a sequence with at least 54% sequence identity to SEQ ID NO: 1;
   EASELSTAALGRLSAELHELATLPRTETGPESP (SEQ ID NO: 1)
2. A mimylin peptide having at least 66% sequence identity to SEQ ID NO: 1;
3. The mimylin peptide according to any one of the preceding aspects, wherein said mimylin peptide more than about 66% sequence identity to SEQ ID NO:1;
4. The mimylin peptide according to any one of the preceding aspects, wherein said mimylin peptide has at least about 69% sequence identity to SEQ ID NO:1;
5. The mimylin peptide according to any one of the preceding aspects, wherein said mimylin peptide has at least about 72% sequence identity to SEQ ID NO:1;
6. The mimylin peptide according to any one of the preceding aspects, wherein said mimylin peptide has at least about 75% sequence identity to SEQ ID NO:1;
7. The mimylin peptide according to any one of the preceding aspects, wherein said mimylin peptide has at least about 78% sequence identity to SEQ ID NO:1;
8. The mimylin peptide according to any one of the preceding aspects, wherein said mimylin peptide has at least about 81% sequence identity to SEQ ID NO:1;
9. The mimylin peptide according to any one of the preceding aspects, wherein said mimylin peptide has at least about 84% sequence identity to SEQ ID NO:1;
10. The mimylin peptide according to any one of the preceding aspects, wherein said mimylin peptide has at least about 87% sequence identity to SEQ ID NO:1;
11. The mimylin peptide according to any one of the preceding aspects, wherein said mimylin peptide has at least about 90% sequence identity to SEQ ID NO:1;
12. The mimylin peptide according to any one of the preceding aspects, wherein said mimylin peptide has at least about 93% sequence identity to SEQ ID NO:1;
13. The mimylin peptide according to any one of the preceding aspects, wherein said mimylin peptide has at least about 96% sequence identity to SEQ ID NO:1;
14. The mimylin peptide according to any one of the preceding aspects, having ≤ about 70% sequence identity with salmon calcitonin;
15. The mimylin peptide according to any one of the preceding aspects, having ≤ about 70% sequence identity with eel calcitonin;
16. The mimylin peptide according to any one of the preceding aspects, having ≤ about 70% sequence identity with any calcitonin variant;
17. The mimylin peptide according to any one of the preceding aspects, having ≤ about 66% sequence identity with salmon calcitonin;
18. The mimylin peptide according to any one of the preceding aspects, having ≤ about 66% sequence identity with eel calcitonin;
19. The mimylin peptide according to any one of the preceding aspects, having ≤ about 66% sequence identity with any calcitonin variant;
20. The mimylin peptide according to any one of the preceding aspects, having ≤ about 60% sequence identity with salmon calcitonin;
21. The mimylin peptide according to any one of the preceding aspects, having ≤ about 60% sequence identity with eel calcitonin;
22. The mimylin peptide according to any one of the preceding aspects, having ≤ about 60% sequence identity with any calcitonin variant;
23. The mimylin peptide according to any one of the preceding aspects wherein up to 11 amino acids have been modified by means of substitutions or deletions of one or more of amino acids relative to SEQ ID NO: 1;
24. The mimylin peptide according to any one of the preceding aspects wherein up to 10 amino acids have been modified by means of substitutions or deletions of one or more of amino acids relative to SEQ ID NO: 1;
25. The mimylin peptide according to any one of the preceding aspects wherein up to 9 amino acids have been modified by means of substitutions or deletions of one or more of amino acids relative to SEQ ID NO: 1;
26. The mimylin peptide according to any one of the preceding aspects wherein up to 8 amino acids have been modified by means of substitutions or deletions of one or more of amino acids relative to SEQ ID NO: 1;
27. The mimylin peptide according to any one of the preceding aspects wherein up to 7 amino acids have been modified by means of substitutions or deletions of one or more of amino acids relative to SEQ ID NO: 1;
28. The mimylin peptide according to any one of the preceding aspects wherein up to 6 amino acids have been modified by means of substitutions or deletions of one or more of amino acids relative to SEQ ID NO: 1;
29. The mimylin peptide according to any one of the preceding aspects wherein up to 5 amino acids have been modified by means of substitutions or deletions of one or more of amino acids relative to SEQ ID NO: 1;

30. The mimylin peptide according to any one of the preceding aspects wherein up to 4 amino acids have been modified by means of substitutions or deletions of one or more of amino acids relative to SEQ ID NO: 1;
31. The mimylin peptide according to any one of the preceding aspects wherein up to 3 amino acids have been modified by means of substitutions or deletions of one or more of amino acids relative to SEQ ID NO: 1;
32. The mimylin peptide according to any one of the preceding aspects wherein up to 2 amino acids have been modified by means of substitutions or deletions of one or more of amino acids relative to SEQ ID NO: 1;
33. The mimylin peptide according to any one of the preceding aspects wherein 1 amino acid has been modified by means of substitution or deletion of one amino acid relative to SEQ ID NO: 1;
34. A mimylin peptide according to any one of the preceding aspects, wherein said mimylin peptide comprises a c-terminal amide group;
35. A mimylin peptide according to any one of the preceding aspects, wherein said mimylin peptide comprises an amide group in its c-terminal;
36. A mimylin peptide according to any one of the preceding aspects, wherein said mimylin peptide comprises a c-terminal acid;
37. A mimylin peptide according to any one of the preceding aspects, wherein said mimylin peptide does not comprise a c-terminal acid;
38. The mimylin peptide according to any one of the preceding aspects, wherein said mimylin peptide does not comprise any disulfide bridge;
39. The mimylin peptide according to any one of the preceding aspects, wherein said mimylin peptide does not comprise a disulfide bridge between the amino acids in positions 2 and 8, wherein the amino acid numbering corresponds to SEQ ID NO: 1
40. The mimylin peptide according to any one of the preceding aspects, wherein said mimylin peptide does not comprise cystein residues in one or both positions 2 and 8, wherein the amino acid numbering corresponds to SEQ ID NO: 1;
41. The mimylin peptide according to any one of the preceding aspects, wherein said mimylin peptide comprises up to one cystein residue;
42. The mimylin peptide according to any one of the preceding aspects, wherein said mimylin peptide does not comprise any cysteins;
43. The mimylin peptide according to any one of the preceding aspects, wherein said mimylin peptide comprises L in one, more or all of the positions selected from 5, 10, 13, 17, 20 and 23, wherein the amino acid numbering corresponds to SEQ ID NO: 1;
44. The mimylin peptide according to any one of the preceding aspects, wherein said mimylin peptide comprises L in positions 5, 10 and 13, wherein the amino acid numbering corresponds to SEQ ID NO: 1;
45. The mimylin peptide according to any one of the preceding aspects, wherein said mimylin peptide comprises L in positions 5, 10, 13 and 17, wherein the amino acid numbering corresponds to SEQ ID NO: 1;
46. The mimylin peptide according to any one of the preceding aspects, wherein said mimylin peptide comprises L in positions 5, 10, 13, 17 and 20, wherein the amino acid numbering corresponds to SEQ ID NO: 1;
47. The mimylin peptide according to any one of the preceding aspects, wherein said mimylin peptide comprises L in positions 10, 13, 17 and 20, wherein the amino acid numbering corresponds to SEQ ID NO: 1;
48. The mimylin peptide according to any one of the preceding aspects, wherein said mimylin peptide comprises L in positions 10, 13, 17, 20 and 23, wherein the amino acid numbering corresponds to SEQ ID NO: 1;
49. The mimylin peptide according to any one of the preceding aspects, wherein said mimylin peptide comprises L in positions 5, 10, 13, 17, 20 and 23, wherein the amino acid numbering corresponds to SEQ ID NO: 1;
50. The mimylin peptide according to any one of the preceding aspects, wherein said mimylin peptide comprises R in one or more of the positions 12 or 25, wherein the amino acid numbering corresponds to SEQ ID NO: 1;
51. The mimylin peptide according to any one of the preceding aspects, wherein said mimylin peptide comprises R in both positions 12 and 25, wherein the amino acid numbering corresponds to SEQ ID NO: 1;
52. The mimylin peptide according to any one of the preceding aspects 35-41 further comprising R in one or both of the positions 12 or 25, wherein the amino acid numbering corresponds to SEQ ID NO: 1;
53. The mimylin peptide according to any one of the aspects 35-41 further comprising R in both positions 12 and 25, wherein the amino acid numbering corresponds to SEQ ID NO: 1;
54. The mimylin peptide according to any one of the preceding aspects, wherein said mimylin peptide comprises a P, Y, H, F, L, S, G or A in position 33, wherein the amino acid numbering corresponds to SEQ ID NO: 1;
55. The mimylin peptide according to any one of the preceding aspects, wherein said mimylin peptide comprises a P, Y, H, F, L, S or A in position 33, wherein the amino acid numbering corresponds to SEQ ID NO: 1;
56. The mimylin peptide according to any one of the preceding aspects, wherein said mimylin peptide comprises a P, Y, H or F in position 33, wherein the amino acid numbering corresponds to SEQ ID NO: 1;
57. The mimylin peptide according to any one of the preceding aspects, wherein said mimylin peptide comprises a P, Y or F in position 33, wherein the amino acid numbering corresponds to SEQ ID NO: 1;
58. The mimylin peptide according to any one of the preceding aspects, wherein said mimylin peptide comprises a P or Y in position 33, wherein the amino acid numbering corresponds to SEQ ID NO: 1;
59. The mimylin peptide according to any one of the preceding aspects, wherein said mimylin peptide comprises a P or in position 33, wherein the amino acid numbering corresponds to SEQ ID NO: 1;
60. The mimylin peptide according to any one of the preceding aspects, wherein said peptide does not comprise any N;
61. The mimylin peptide according to any one of the preceding aspects, wherein said peptide does not comprise N in position 4 or position 27
62. The mimylin peptide according to any one of the preceding aspects, wherein said peptide does not comprise any Q;
63. The mimylin peptide according to any one of the preceding aspects, wherein said peptide only comprises one Q;
64. The mimylin peptide according to any one of the preceding aspects, wherein said peptide only comprises up to 2 Q; The mimylin peptide according to any one of the preceding aspects, wherein said peptide does not comprise any K;

65. The mimylin peptide according to any one of the preceding aspects, wherein said peptide does not comprises one or more K;
66. The mimylin peptide according to any one of the preceding aspects, wherein said mimylin peptide does not comprise any aromatic amino acids;
67. The mimylin peptide according to any one of the preceding aspects 1-65, wherein said mimylin peptide comprises at least one of the following amino acids or modifications relative to SEQ ID NO: 1:
   a. E or no amino acid in position −1,
   b. E, A or no amino acid in position 1,
   c. A, L or P in position 2,
   d. S or P in position 3,
   e. E, P, K, Q or G in position 4,
   f. L, V, I or H in position 5,
   g. S, T or H in position 6,
   h. T in position 7,
   i. L or A in position 8,
   j. A, V, I, S or T in position 9,
   k. L, A, I, H or V in position 10,
   l. G in position 11,
   m. R, H or K in position 12,
   n. L in position 13,
   o. S, T or E in position 14,
   p. A, Q, E, e or T in position 15,
   q. E, R, K or Q in position 16,
   r. L or I in position 17,
   s. H or A in position 18,
   t. E, R or K in position 19,
   u. L, I or V in position 20,
   v. A, Q, S, E or T in position 21,
   w. T in position 22,
   x. L or Y in position 23,
   y. P in position 24,
   z. R, P, H or K in position 25,
   aa. T in position 26,
   bb. E, Q, G or K in position 27,
   cc. T or P in position 28,
   dd. G in position 29,
   ee. P, S or T in position 30,
   ff. E, Q, G, A, P or K in position 31,
   gg. T, S, H, P or A in position 32,
   hh. P, Y, H, F, L, S, G or A in position 33,
   ii. G or K in position 34.
68. The mimylin peptide according to any one of the preceding aspects 1-67, wherein said mimylin peptide comprises at least one of the following amino acids or modifications relative to SEQ ID NO: 1:
   a. E or no amino acid in position −1,
   b. E, A or no amino acid in position 1,
   c. L, A or P in position 2,
   d. P in position 3,
   e. E, Q, G or P in position 4,
   f. V, I or H in position 5,
   g. T or H in position 6,
   h. T in position 7,
   i. L or A in position 8,
   j. A, I, S or T in position 9,
   k. A, I, H or V in position 10,
   l. R, H in position 12,
   m. T or E in position 14,
   n. A, E, e or T in position 15,
   o. R, K or Q in position 16,
   p. I in position 17,
   q. A in position 18,
   r. E or R in position 19,
   s. A, S, E or T in position 21,
   t. L in position 23,
   u. R, P, H or K in position 25,
   v. E, Q, G or K in position 27,
   w. P in position 28,
   x. P, S or T in position 30,
   y. E, Q, G, A, P or K in position 31,
   z. S, H, P or A in position 32,
   aa. Y, H, F, L, S, G or A in position 33,
   bb. G or K in position 34.
69. The mimylin peptide according to any one of the preceding aspects 1-67, wherein said mimylin peptide comprises at least one of the following amino acids or modifications relative to SEQ ID NO: 1:
   a. E or no amino acid in position −1,
   b. E, A or no amino acid in position 1,
   c. L, A or P in position 2,
   d. S or P in position 3,
   e. E, Q, G or P in position 4,
   f. L, V, I or H in position 5,
   g. S, T or H in position 6,
   h. T in position 7,
   i. L or A in position 8,
   j. A, I, S or T in position 9,
   k. R, H in position 12,
   l. A, E, e or T in position 15,
   m. E or R in position 19,
   n. A, S, E or T in position 21,
   o. L in position 23,
   p. E, Q, G or K in position 27,
   q. P, S or T in position 30,
   r. E, Q, G, A, P or K in position 31,
   s. S, H, P or A in position 32,
   t. Y, H, F, L, S, G or A in position 33,
   u. G or K in position 34.
70. The mimylin peptide according to any one of the preceding aspects 1-67, wherein said mimylin peptide comprises any one of the following amino acids or modifications relative to SEQ ID NO: 1:
   a. E or no amino acid in position −1,
   b. E, A or no amino acid in position 1,
   c. L, A or P in position 2,
   d. S or P in position 3,
   e. E, Q, G or P in position 4,
   f. V, I or H in position 5,
   g. S, T or H in position 6,
   h. T in position 7,
   i. L or A in position 8,
   j. A, V, I, S or T in position 9,
   k. L, A, I, H or V in position 10,
   l. G in position 11,
   m. R, H or K in position 12,
   n. L in position 13,
   o. S, T or E in position 14,
   p. A, Q, E, e or T in position 15,
   q. R, E, K or Q in position 16,
   r. L or I in position 17,
   s. H or A in position 18,
   t. E, R or K in position 19,
   u. L, I or V in position 20,
   v. A, Q, S, E or T in position 21,
   w. T in position 22,
   x. Y or L in position 23,
   y. P in position 24,
   z. R, P, H or K in position 25,
   aa. T in position 26,
   bb. E, Q, G or K in position 27, cc. T or P in position 28,
dd. G in position 29,
ee. P, S or T in position 30,
ff. E, Q, G, A, P or K in position 31,
gg. T, S, H, P or A in position 32,
hh. P, Y, H, F, L, S, G or A in position 33,
ii. G or K in position 34.
71. The mimylin peptide according to any one of the preceding aspects 1-67, wherein said mimylin peptide comprises any one of the following amino acids or modifications relative to SEQ ID NO: 1:
a. E or no amino acid in position −1,
b. E, A or no amino acid in position 1,
c. L, A or P in position 2,
d. P in position 3,
e. E, Q, G or P in position 4,
f. V, I or H in position 5,
g. T or H in position 6,
h. T in position 7,
i. L or A in position 8,
j. A, I, S or T in position 9,
k. A, I, H or V in position 10,
l. R or H in position 12,
m. T or E in position 14,
n. A, E, e or T in position 15,
o. R, K or Q in position 16,
p. I in position 17,
q. A in position 18,
r. E or R in position 19,
s. A, S, E or T in position 21,
t. L in position 23,
u. R, P, H or K in position 25,
v. E, Q, G or K in position 27,
w. P in position 28,
x. P, S or T in position 30,
y. E, Q, G, A, P or K in position 31,
z. S, H, P or A in position 32,
aa. Y, H, F, L, S, G or A in position 33,
bb. G or K in position 34.
72. The mimylin peptide according to any one of the preceding aspects 1-67, wherein said mimylin peptide comprises any one of the following amino acids or modifications relative to SEQ ID NO: 1:
a. E or no amino acid in position −1,
b. E, A or no amino acid in position 1,
c. L, A or P in position 2,
d. S or P in position 3,
e. E, Q, G or P in position 4,
f. L, V, I or H in position 5,
g. S, T or H in position 6,
h. T in position 7,
i. L or A in position 8,
j. A, I, S or T in position 9,
k. R or H in position 12,
l. A, E, e or T in position 15,
m. E or R in position 19,
n. A, S, E or T in position 21,
o. L in position 23,
p. E, Q, G or K in position 27,
q. P, S or T in position 30,
r. E, Q, G, A, P or K in position 31,
s. S, H, P or A in position 32,
t. Y, H, F, L, S, G or A in position 33,
u. G or K in position 34.
73. The mimylin peptide according to any one of the preceding aspects 1-67, wherein said mimylin peptide comprises 1, 2, 3, 4, 5, 6, 7, 8, 9, 10 or 11, most preferably 1 2, 3, 4 or 5 of the following amino acids or modifications relative to SEQ ID NO: 1:
a. E or no amino acid in position −1,
b. E, A or no amino acid in position 1,
c. L, A or P in position 2,
d. S or P in position 3,
e. E, Q, G or P in position 4,
f. V, I or H in position 5,
g. S, T or H in position 6,
h. T in position 7,
i. L or A in position 8,
j. A, V, I, S or T in position 9,
k. L, A, I, H or V in position 10,
l. G in position 11,
m. R, H or K in position 12,
n. L in position 13,
o. S, T or E in position 14,
p. A, Q, E, e or T in position 15,
q. R, E, K or Q in position 16,
r. L or I in position 17,
s. H or A in position 18,
t. E, R or K in position 19,
u. L, I or V in position 20,
v. A, Q, S, E or T in position 21,
w. T in position 22,
x. Y or L in position 23,
y. P in position 24,
z. R, P, H or K in position 25,
aa. T in position 26,
bb. E, Q, G or K in position 27,
cc. T or P in position 28,
dd. G in position 29,
ee. P, S or T in position 30,
ff. E, Q, G, A, P or K in position 31,
gg. T, S, H, P or A in position 32,
hh. P, Y, H, F, L, S, G or A in position 33,
ii. G or K in position 34.
74. The mimylin peptide according to any one of the preceding aspects 1-67, wherein said mimylin peptide comprises 1, 2, 3, 4, 5, 6, 7, 8, 9, 10 or 11, most preferably 1, 2, 3, 4 or 5 of the following amino acids or modifications relative to SEQ ID NO: 1:
a. E or no amino acid in position −1,
b. E, A or no amino acid in position 1,
c. L, A or P in position 2,
d. P in position 3,
e. E, Q, G or P in position 4,
f. V, I or H in position 5,
g. T or H in position 6,
h. T in position 7,
i. L or A in position 8,
j. A, I, S or T in position 9,
k. A, I, H or V in position 10,
l. R or H in position 12,
m. T or E in position 14,
n. A, E, e or T in position 15,
o. R, K or Q in position 16,
p. I in position 17,
q. A in position 18,
r. E or R in position 19,
s. A, S, E or T in position 21,
t. L in position 23,
u. R, P, H or K in position 25,
v. E, Q, G or K in position 27, w. P in position 28,
x. P, S or T in position 30,
y. E, Q, G, A, P or K in position 31,
z. S, H, P or A in position 32,
aa. Y, H, F, L, S, G or A in position 33,
bb. G or K in position 34.

75. The mimylin peptide according to any one of the preceding aspects 1-67, wherein said mimylin peptide comprises 1, 2, 3, 4, 5, 6, 7, 8, 9, 10 or 11, most preferably 1, 2, 3, 4 or 5 of the following amino acids or modifications relative to SEQ ID NO: 1:
   a. E or no amino acid in position −1,
   b. E, A or no amino acid in position 1,
   c. L, A or P in position 2,
   d. S or P in position 3,
   e. E, Q, G or P in position 4,
   f. L, V, I or H in position 5,
   g. S, T or H in position 6,
   h. T in position 7,
   i. L or A in position 8,
   j. A, I, S or T in position 9,
   k. R or H in position 12,
   l. A, E, e or T in position 15,
   m. E or R in position 19,
   n. A, S, E or T in position 21,
   o. L in position 23,
   p. E, Q, G or K in position 27,
   q. P, S or T in position 30,
   r. E, Q, G, A, P or K in position 31,
   s. S, H, P or A in position 32,
   t. Y, H, F, L, S, G or A in position 33,
   u. G or K in position 34.

76. The mimylin peptide according to any one of the preceding aspects 1-67, wherein said mimylin peptide comprises 1, 2, 3, 4, 5, 6, 7, 8, 9, 10 or 11, most preferably 1 2, 3, 4 or 5 of the following amino acids or modifications relative to SEQ ID NO: 1:
   a. E or no amino acid in position −1,
   b. E, A or no amino acid in position 1, preferably E,
   c. A, L or P in position 2,
   d. S or P in position 3,
   e. E, P, K, Q or G in position 4,
   f. L, V, I or H in position 5,
   g. S, T or H in position 6, preferably S,
   h. T in position 7,
   i. L or A in position 8, preferably A,
   j. A, V, I, S or T in position 9, preferably A or V or I,
   k. L, A, I, H or V in position 10, preferably L or I,
   l. G in position 11,
   m. R, H or K in position 12,
   n. L in position 13,
   o. S, T or E in position 14,
   p. A, Q, E, e or T in position 15, preferably A,
   q. E, R, K or Q in position 16, preferably E,
   r. L or I in position 17,
   s. H or A in position 18,
   t. E, R or K in position 19, preferably E,
   u. L, I or V in position 20, preferably L,
   v. A, Q, S, E or T in position 21, preferably A,
   w. T in position 22,
   x. L or Y in position 23,
   y. P in position 24,
   z. R, P, H or K in position 25, preferably R,
   aa. T in position 26,
   bb. E, Q, G or K in position 27, preferably E,
   cc. T or P in position 28,
   dd. G in position 29,
   ee. P, S or T in position 30,
   ff. E, Q, G, A, P or K in position 31, preferably E or G,
   gg. T, S, H, P or A in position 32, preferably S or T,
   hh. P, Y, H, F, L, S, G or A in position 33 preferably P or Y,
   ii. G or K in position 34, preferably P or Y.

77. The mimylin peptide according to any one of the preceding aspects 1-67, wherein said mimylin peptide comprises 1, 2, 3, 4, 5, 6, 7, 8, 9, 10 or 11, most preferably 1 2, 3, 4 or 5 of the following amino acids or modifications relative to SEQ ID NO: 1:
   a. E or no amino acid in position −1,
   b. E, A or no amino acid in position 1, preferably E,
   c. L, A or P in position 2,
   d. P in position 3,
   e. E, Q, G or P in position 4,
   f. V, I or H in position 5,
   g. T or H in position 6,
   h. T in position 7,
   i. L or A in position 8, preferably A,
   j. A, I, S or T in position 9, preferably A or I,
   k. A, I, H or V in position 10, preferably I,
   l. R, H in position 12,
   m. T or E in position 14,
   n. A, E, e or T in position 15, preferably A,
   o. R, K or Q in position 16,
   p. I in position 17,
   q. A in position 18,
   r. E or R in position 19, preferably E,
   s. A, S, E or T in position 21,
   t. L in position 23,
   u. R, P, H or K in position 25, preferably R,
   v. E, Q, G or K in position 27, preferably E,
   w. P in position 28,
   x. P, S or T in position 30,
   y. E, Q, G, A, P or K in position 31, preferably E or G,
   z. S, H, P or A in position 32 preferably S,
   aa. Y, H, F, L, S, G or A in position 33, preferably Y,
   bb. G or K in position 34.

78. The mimylin peptide according to any one of the preceding aspects 1-67, wherein said mimylin peptide comprises 1, 2, 3, 4, 5, 6, 7, 8, 9, 10 or 11, most preferably 1 2, 3, 4 or 5 of the following amino acids or modifications relative to SEQ ID NO: 1:
   a. E or no amino acid in position −1,
   b. E, A or no amino acid in position 1, preferably E,
   c. L, A or P in position 2,
   d. S or P in position 3,
   e. E, Q, G or P in position 4,
   f. L, V, I or H in position 5,
   g. S, T or H in position 6, preferably S,
   h. T in position 7,
   i. L or A in position 8, preferably A,
   j. A, I, S or T in position 9, preferably A or V or I,
   k. R, H in position 12,
   l. A, E, e or T in position 15, preferably A,
   m. E or R in position 19, preferably E,
   n. A, S, E or T in position 21, preferably E,
   o. L in position 23,
   p. E, Q, G or K in position 27, preferably E,
   q. P, S or T in position 30,
   r. E, Q, G, A, P or K in position 31, preferably E or G,
   s. S, H, P or A in position 32, preferably S or G,
   t. Y, H, F, L, S, G or A in position 33, preferably P or Y,
   u. G or K in position 34.

79. The mimylin peptide according to any one of the preceding aspects 1-67, wherein said mimylin peptide comprises 1, 2, 3, 4, 5, 6, 7, 8, 9, 10 or 11, most preferably 1 2, 3, 4 or 5 of the following amino acids or modifications relative to SEQ ID NO: 1:
  a. E or no amino acid in position −1,
  b. E, A or no amino acid in position 1, preferably E,
  c. A, L or P in position 2,
  d. S or P in position 3,
  e. E, P, K, Q or G in position 4,
  f. L, V, I or H in position 5,
  g. S, T or H in position 6, preferably S,
  h. T in position 7,
  i. L or A in position 8, preferably A,
  j. A, V, I, S or T in position 9, preferably A or V or I,
  k. L, A, I, H or V in position 10, preferably L or I,
  l. G in position 11,
  m. R, H or K in position 12,
  n. L in position 13,
  o. S, T or E in position 14,
  p. A, Q, E, e or T in position 15, preferably A,
  q. E, R, K or Q in position 16, preferably E,
  r. L or I in position 17,
  s. H or A in position 18,
  t. E, R or K in position 19, preferably E,
  u. L, I or V in position 20, preferably L,
  v. A, Q, S, E or T in position 21, preferably A,
  w. T in position 22,
  x. L or Y in position 23,
  y. P in position 24,
  z. R, P, H or K in position 25, preferably R,
  aa. T in position 26,
  bb. E, Q, G or K in position 27, preferably E,
  cc. T or P in position 28,
  dd. G in position 29,
  ee. P, S or T in position 30,
  ff. E, Q, G, A, P or K in position 31, preferably E or G,
  gg. T, S, H, P or A in position 32, preferably S or T,
  hh. P, Y, H, F, L, S, G or A in position 33 preferably P or Y,
  ii. G or K in position 34, preferably P or Y.
80. The mimylin peptide according to any one of the preceding aspects 1-67, wherein said mimylin peptide comprises 1, 2, 3, 4, 5, 6, 7, 8, 9, 10 or 11, most preferably 1, 2, 3, 4 or 5 of the following amino acids or modifications relative to SEQ ID NO: 1:
  a. E or no amino acid in position −1,
  b. E, A or no amino acid in position 1, preferably E,
  c. L, A or P in position 2,
  d. P in position 3,
  e. E, Q, G or P in position 4,
  f. V, I or H in position 5,
  g. T or H in position 6,
  h. T in position 7,
  i. L or A in position 8, preferably A,
  j. A, I, S or T in position 9, preferably A or I,
  k. A, I, H or V in position 10, preferably I,
  l. R, H in position 12,
  m. T or E in position 14,
  n. A, E, e or T in position 15, preferably A,
  o. R, K or Q in position 16,
  p. I in position 17,
  q. A in position 18,
  r. E or R in position 19, preferably E,
  s. A, S, E or T in position 21,
  t. L in position 23,
  u. R, P, H or K in position 25, preferably R,
  v. E, Q, G or K in position 27, preferably E,
  w. P in position 28,
  x. P, S or T in position 30,
  y. E, Q, G, A, P or K in position 31, preferably E or G,
  z. S, H, P or A in position 32 preferably S,
  aa. Y, H, F, L, S, G or A in position 33, preferably Y,
  bb. G or K in position 34.
81. The mimylin peptide according to any one of the preceding aspects 65, wherein said mimylin peptide comprises 1, 2, 3, 4, 5, 6, 7, 8, 9, 10 or 11, most preferably 1, 2, 3, 4 or 5 of the following amino acids or modifications relative to SEQ ID NO: 1:
  a. E or no amino acid in position −1,
  b. E, A or no amino acid in position 1,
  c. L, A or P in position 2,
  d. S or P in position 3,
  e. E, Q, G or P in position 4,
  f. L, V, I or H in position 5,
  g. S, T or H in position 6,
  h. T in position 7,
  i. L or A in position 8,
  j. A, I, S or T in position 9,
  k. R or H in position 12,
  l. A, E, e or T in position 15,
  m. E or R in position 19,
  n. A, S, E or T in position 21,
  o. L in position 23,
  p. E, Q, G or K in position 27,
  q. P, S or T in position 30,
  r. E, Q, G, A, P or K in position 31,
  s. S, H, P or A in position 32,
  t. Y, H, F, L, S, G or A in position 33,
  u. G or K in position 34.
82. The mimylin peptide according to any one of the preceding aspects, wherein said mimylin peptide comprises T in position 7, G in position 11, L in position 13, T in position 22, P in position 24, T in position 26 and G in position 29, wherein the amino acid numbering corresponds to SEQ ID NO: 1.
83. The mimylin peptide according to any one of the preceding aspects, wherein said mimylin peptide comprises T in position 7, G in position 11, L in position 13, T in position 22, P in position 24, T in position 26 and G in position 29, wherein position 33 remains P or is modified to Y, F, H, S, G or A, wherein the amino acid numbering corresponds to SEQ ID NO: 1.
84. The mimylin peptide according to any one of the preceding aspects, wherein said mimylin peptide comprises T in position 7, G in position 11, L in position 13, T in position 22, P in position 24, T in position 26 and G in position 29, wherein position 33 remains P, Y or F, wherein the amino acid numbering corresponds to SEQ ID NO: 1.
85. The mimylin peptide according to any one of the preceding, wherein said mimylin peptide comprises T in position 7, G in position 11, L in position 13, T in position 22, P in position 24, T in position 26 and G in position 29, wherein the amino acid numbering corresponds to SEQ ID NO: 1.
86. The mimylin peptide according to any one of the any one of the preceding, wherein said mimylin peptide comprises T in position 7, G in position 11, L in position 13, T in position 22, P in position 24, T in position 26 and G in position 29, wherein position 33 remains P, Y, F, H, S, G or A, wherein the amino acid numbering corresponds to SEQ ID NO: 1.

87. The mimylin peptide according to any one of the any one of the preceding, wherein said mimylin peptide comprises T in position 7, G in position 11, L in position 13, T in position 22, P in position 24, T in position 26 and G in position 29, wherein position 33 remains P, Y or F, wherein the amino acid numbering corresponds to SEQ ID NO: 1.

88. The mimylin peptide according to any one of the preceding aspects wherein an E is added in the position −1, wherein the amino acid numbering corresponds to SEQ ID NO: 1.

89. The mimylin peptide according to any one of the preceding aspects, wherein said mimylin peptide has been modified in one or more of the positions 1, 2, 3, 4, 5, 6, 8, 9, 10, 12, 14, 15, 16, 17, 18, 19, 20, 21, 23, 24, 25, 27, 28, 30, 31, 32 of SEQ ID NO: 1, wherein the amino acid numbering corresponds to SEQ ID NO: 1.

90. The mimylin peptide according to any one of the preceding aspects, wherein said mimylin peptide has been modified in up to 11, up to 10, up to 9, up to 8, up to 7, up to 6, preferably up to 5, up to 4, up to 3, up to 2 or 1 of the positions selected from the group consisting of: 1, 2, 3, 4, 5, 6, 8, 9, 10, 12, 14, 15, 16, 17, 18, 19, 20, 21, 23, 24, 25, 27, 28, 30, 31, 32 of SEQ ID NO: 1, wherein the amino acid numbering corresponds to SEQ ID NO: 1.

91. The mimylin peptide according to any one of the preceding aspects, wherein said mimylin peptide has been modified in one or more of the positions 1, 2, 4, 8, 9, 15, 21, 23, 25, 30, 31, 32, 33 of SEQ ID NO: 1, wherein the amino acid numbering corresponds to SEQ ID NO: 1.

92. The mimylin peptide according to any one of the preceding aspects, wherein said mimylin peptide has been modified in up to 11 of the positions 1, 2, 4, 8, 9, 15, 21, 23, 25, 27, 30, 31, 32, 33 of SEQ ID NO: 1, wherein the amino acid numbering corresponds to SEQ ID NO: 1.

93. The mimylin peptide according to any one of the preceding aspects, wherein said mimylin peptide has been modified in 11 of the positions 1, 2, 4, 8, 9, 15, 21, 23, 25, 30, 31, 32, 33 of SEQ ID NO: 1, wherein the amino acid numbering corresponds to SEQ ID NO: 1.

94. The mimylin peptide according to any one of the preceding aspects, wherein said mimylin peptide has been modified in one or more of the positions 1, 2, 4, 8, 9, 15, 21, 23, 25, 30, 31, 32, 33 of SEQ ID NO: 1, wherein the amino acid numbering corresponds to SEQ ID NO: 1, wherein said one or more modifications are selected from the list consisting of:
E in said position 1 is absent,
position 2 can be modified to L,
position 4 can be modified to G,
position 8 can be modified to L,
position 9 can be modified to V or T,
position 15 can be modified to Q,
position 21 can be modified to Q,
position 23 can be modified to Y,
position 25 can be modified to P,
position 30 can be modified to S,
position 31 can be modified to G or Q,
position 32 can be modified to T,
position 33 can be modified to Y, H, F, L, S, G or A, preferably Y.

95. The mimylin peptide according to any one of the preceding aspects, wherein said mimylin peptide has been modified in one or more of the positions 1, 4, 9, 15, 21, 23, 25, 27, 30, 31, 32, 33 of SEQ ID NO: 1, wherein the amino acid numbering corresponds to SEQ ID NO: 1.

96. The mimylin peptide according to any one of the preceding aspects, wherein said mimylin peptide has been modified up to 10 of the positions 1, 4, 9, 15, 21, 23, 25, 27, 30, 31, 32, 33 of SEQ ID NO: 1, wherein the amino acid numbering corresponds to SEQ ID NO: 1.

97. The mimylin peptide according to any one of the preceding aspects, wherein said mimylin peptide has been modified in 10 of the positions 1, 4, 9, 15, 21, 23, 25, 27, 30, 31, 32, 33 of SEQ ID NO: 1, wherein the amino acid numbering corresponds to SEQ ID NO: 1.

98. The mimylin peptide according to any one of the preceding aspects, wherein said mimylin peptide has been modified in one or more of the 1, 4, 9, 15, 21, 23, 25, 27, 30, 31, 32, 33 of SEQ ID NO: 1, wherein the amino acid numbering corresponds to SEQ ID NO: 1, wherein said one or more modifications are selected from the list consisting of:
E in said position 1 is absent,
position 4 can be modified to G or Q,
position 9 can be modified to V or T,
position 15 can be modified to Q,
position 21 can be modified to Q,
position 23 can be modified to Y,
position 25 can be modified to H or P,
position 27 can be modified to G,
position 30 can be modified to S,
position 31 can be modified to G, Q or A,
position 32 can be modified to T,
position 33 can be modified to Y.

99. The mimylin peptide according to any one of the preceding aspects, wherein said mimylin peptide has been modified in one or more of the positions 1, 4, 15, 21, 23, 30, 32, 32 or 33 of SEQ ID NO: 1, wherein the amino acid numbering corresponds to SEQ ID NO: 1

100. The mimylin peptide according to any one of the preceding aspects, wherein said mimylin peptide has been modified up to 9 of the positions 1, 4, 15, 21, 23, 30, 32, 32 and 33 of SEQ ID NO: 1, wherein the amino acid numbering corresponds to SEQ ID NO: 1

101. The mimylin peptide according to any one of the preceding aspects, wherein said mimylin peptide has been modified in 9 of the positions 1, 4, 15, 21, 23, 30, 32, 32 and 33 of SEQ ID NO: 1, wherein the amino acid numbering corresponds to SEQ ID NO: 1

102. The mimylin peptide according to any one of the preceding aspects, wherein said mimylin peptide has been modified in one or more of the 1, 4, 15, 21, 23, 30, 32, 32 or 33 of SEQ ID NO: 1, wherein the amino acid numbering corresponds to SEQ ID NO: 1, wherein said one or more modifications are selected from the list consisting of:
E in said position 1 is absent,
position 4 can be modified to G,
position 9 can be modified to V,
position 15 can be modified to Q, T or E,
position 21 can be modified to Q or E,
position 23 can be modified to Y,
position 30 can be modified to S,
position 31 can be modified to G, Q or K,
position 32 can be modified to T,
position 33 can be modified to Y.

103. The mimylin peptide according to any one of the preceding aspects, wherein said mimylin peptide has been modified in one or more of the positions 1, 4, 6, 9, 14, 15, 21, 23, 30, 31, 32 or 33 of SEQ ID NO: 1, wherein the amino acid numbering corresponds to SEQ ID NO: 1.

104. The mimylin peptide according to any one of the preceding aspects, wherein said mimylin peptide has been modified up to 8 of the positions 1, 4, 6, 9, 14, 15, 21, 23, 30, 31, 32 and 33 of SEQ ID NO: 1, wherein the amino acid numbering corresponds to SEQ ID NO: 1.

105. The mimylin peptide according to any one of the preceding aspects, wherein said mimylin peptide has been modified in 8 of the positions 1, 4, 6, 9, 14, 15, 21, 23, 30, 31, 32 and 33 of SEQ ID NO: 1, wherein the amino acid numbering corresponds to SEQ ID NO: 1.

106. The mimylin peptide according to any one of the preceding aspects, wherein said mimylin peptide has been modified in one or more of the positions 1, 4, 6, 9, 14, 15, 21, 23, 30, 31, 32 or 33 of SEQ ID NO: 1, wherein the amino acid numbering corresponds to SEQ ID NO: 1, wherein said one or more modifications are selected from the list consisting of:
E in said position 1 is absent,
position 4 can be modified to G,
position 6 can be modified to T,
position 9 can be modified to V,
position 14 can be modified to T or S,
position 15 can be modified to Q,
position 21 can be modified to Q, T or E,
position 23 can be modified to Y,
position 30 can be modified to S or T,
position 31 can be modified to G,
position 32 can be modified to T,
position 33 can be modified to Y.

107. The mimylin peptide according to any one of the preceding aspects, wherein said mimylin peptide has been modified in one or more of the positions 1, 4, 5, 6, 9, 10, 12, 20, 21, 23, 25, 30, 31, 32 or 33 of SEQ ID NO: 1, wherein the amino acid numbering corresponds to SEQ ID NO: 1.

108. The mimylin peptide according to any one of the preceding aspects, wherein said mimylin peptide has been modified up to 7 of the positions 1, 4, 5, 6, 9, 10, 12, 20, 21, 23, 25, 30, 31, 32 and 33 of SEQ ID NO: 1, wherein the amino acid numbering corresponds to SEQ ID NO: 1.

109. The mimylin peptide according to any one of the preceding aspects, wherein said mimylin peptide has been modified in 7 of the positions 1, 4, 5, 6, 9, 10, 12, 20, 21, 23, 25, 30, 31, 32 and 33 of SEQ ID NO: 1, wherein the amino acid numbering corresponds to SEQ ID NO: 1.

110. The mimylin peptide according to any one of the preceding aspects, wherein said mimylin peptide has been modified in one or more of the positions 1, 4, 5, 6, 9, 10, 12, 20, 21, 23, 25, 30, 31, 21 or 33 of SEQ ID NO: 1, wherein the amino acid numbering corresponds to SEQ ID NO: 1, wherein said one or more modifications are selected from the list consisting of:
E in said position 1 is absent,
position 4 can be modified to G,
position 5 can be modified to V,
position 6 can be modified to T,
position 9 can be modified to V, T or S,
position 10 can be modified to V,
position 12 can be modified to K,
position 20 can be modified to V,
position 21 can be modified to S,
position 23 can be modified to Y,
position 25 can be modified to K,
position 30 can be modified to S,
position 31 can be modified to G,
position 32 can be modified to S,
position 33 can be modified to Y.

111. The mimylin peptide according to aspect 107 does not comprise K.

112. The mimylin peptide according to any one of the preceding aspects, wherein said mimylin peptide has been modified in one or more of the positions 1, 5, 6, 9, 10, 21, 23, 30, 31, 32 or 33 of SEQ ID NO: 1, wherein the amino acid numbering corresponds to SEQ ID NO: 1.

113. The mimylin peptide according to any one of the preceding aspects, wherein said mimylin peptide has been modified up to 6 of the positions 1, 5, 6, 9, 10, 21, 23, 30, 31, 32 and 33 of SEQ ID NO: 1, wherein the amino acid numbering corresponds to SEQ ID NO: 1.

114. The mimylin peptide according to any one of the preceding aspects, wherein said mimylin peptide has been modified in 6 of the positions 1, 5, 6, 9, 10, 21, 23, 30, 31, 32 and 33 of SEQ ID NO: 1, wherein the amino acid numbering corresponds to SEQ ID NO: 1.

115. The mimylin peptide according to any one of the preceding aspects, wherein said mimylin peptide has been modified in one or more of the 1, 5, 6, 9, 10, 21, 23, 30, 31, 32 or 33 of SEQ ID NO: 1, wherein the amino acid numbering corresponds to SEQ ID NO: 1, wherein said one or more modifications are selected from the list consisting of:
E in said position 1 is absent,
position 5 can be modified to V,
position 6 can be modified to T,
position 9 can be modified to V, T or S,
position 10 can be modified to V,
position 21 can be modified to S,
position 23 can be modified to Y,
position 30 can be modified to S or T,
position 31 can be modified to G,
position 32 can be modified to T and position 33 can be modified to Y.

116. The mimylin peptide according to any one of the preceding aspects, wherein said mimylin peptide has been modified in one or more of the positions −1, 1, 4, 5, 6, 9, 12, 16, 21, 23, 25, 30, 31, 32, 33 or 34 of SEQ ID NO: 1, wherein the amino acid numbering corresponds to SEQ ID NO: 1.

117. The mimylin peptide according to any one of the preceding aspects, wherein said mimylin peptide has been modified up to 5 of the positions −1, 1, 4, 5, 6, 9, 12, 16, 21, 23, 25, 30, 31, 32, 33 and 34 of SEQ ID NO: 1, wherein the amino acid numbering corresponds to SEQ ID NO: 1.

118. The mimylin peptide according to any one of the preceding aspects, wherein said mimylin peptide has been modified in 5 of the positions −1, 1, 4, 5, 6, 9, 12, 16, 21, 23, 25, 30, 31, 32, 33 and 34 of SEQ ID NO: 1, wherein the amino acid numbering corresponds to SEQ ID NO: 1.

119. The mimylin peptide according to any one of the preceding aspects, wherein said mimylin peptide has been modified in one or more of the positions −1, 1, 4, 5, 6, 9, 12, 16, 21, 23, 25, 30, 31, 32, 33 or 34 of SEQ ID NO: 1, wherein the amino acid numbering corresponds to SEQ ID NO: 1, wherein said one or more modifications are selected from the list consisting of:
position −1 can be modified to E or is absent
position 1 can be modified to A or deleted,
position 4 can be modified to G,
position 5 can be modified to V,
position 6 can be modified to T,
position 9 can be modified to V,
position 12 can be modified to H,
position 21 can be modified to S, position 23 can be modified to Y,
position 25 can be modified to H,
position 30 can be modified to S,
position 31 can be modified to G,
position 32 can be modified to A,
position 33 can be modified to Y and
position 34 can be modified to K.
120. The mimylin peptide according to any one of the preceding aspects, wherein said mimylin peptide has been modified in one or more of the positions 1, 4, 5, 9, 12, 15, 16, 19, 20, 23, 25, 27, 30, 31, 32 or 33 of SEQ ID NO: 1, wherein the amino acid numbering corresponds to SEQ ID NO: 1.
121. The mimylin peptide according to any one of the preceding aspects, wherein said mimylin peptide has been modified up to 4 of the positions 1, 4, 5, 9, 12, 15, 16, 19, 20, 23, 25, 27, 30, 31, 32 and 33 of SEQ ID NO: 1, wherein the amino acid numbering corresponds to SEQ ID NO: 1.
122. The mimylin peptide according to any one of the preceding aspects, wherein said mimylin peptide has been modified in 4 of the positions 1, 4, 5, 9, 12, 15, 16, 19, 20, 23, 25, 27, 30, 31, 32 and 33 of SEQ ID NO: 1, wherein the amino acid numbering corresponds to SEQ ID NO: 1.
123. The mimylin peptide according to any one of the preceding aspects, wherein said mimylin peptide has been modified in one or more of the positions 1, 4, 5, 9, 10 12, 15, 16, 19, 20, 23, 25, 27, 30, 31, 32 or 33 of SEQ ID NO: 1, wherein the amino acid numbering corresponds to SEQ ID NO: 1, wherein said one or more modifications are selected from the list consisting of:
position 1 can be modified to A or deleted,
position 4 can be modified to K or Q,
position 5 can be modified to I,
position 9 can be modified to V or I,
position 10 can be modified to I,
position 12 can be modified to H,
position 15 can be modified to E or e,
position 20 can be modified to I,
position 23 can be modified to Y,
position 25 can be modified to H,
position 27 can be modified to K
position 30 can be modified to S,
position 31 can be modified to G,
position 32 can be modified to T or P, and position 33 can be modified Y, H, F, L, S, A or G, preferably Y.
124. The mimylin peptide according to any one of the preceding aspects, wherein said mimylin peptide has been modified in one or more of the positions 1, 3, 4, 5, 9, 10, 12, 20, 23, 25, 30 or 31 of SEQ ID NO: 1, wherein the amino acid numbering corresponds to SEQ ID NO: 1.
125. The mimylin peptide according to any one of the preceding aspects, wherein said mimylin peptide has been modified up to 3 of the positions 1, 3, 4, 5, 9, 10, 12, 20, 23, 25, 30 and 31, wherein the amino acid numbering corresponds to SEQ ID NO: 1.
126. The mimylin peptide according to any one of the preceding aspects, wherein said mimylin peptide has been modified in 3 of the positions 1, 3, 4, 5, 9, 10, 12, 20, 23, 25, 30 and 31, wherein the amino acid numbering corresponds to SEQ ID NO: 1.
127. The mimylin peptide according to any one of the preceding aspects, wherein said mimylin peptide has been modified in one or more of the positions 1, 3, 4, 5, 9, 10, 12, 20, 23, 25, 30 and 31 of SEQ ID NO: 1, wherein the amino acid numbering corresponds to SEQ ID NO: 1, wherein said one or more modifications are selected from the list consisting of:
position 1 can be deleted,
position 3 can be modified to P,
position 4 can be modified to P,
position 5 can be modified to I,
position 9 can be modified to V or I,
position 10 can be modified to I,
position 12 can be modified to K,
position 20 can be modified to V,
position 23 can be modified to Y,
position 25 can be modified to K,
position 30 can be modified to S, and
position 31 can be modified to G.
128. The mimylin peptide according to any one of the preceding aspects, wherein said mimylin peptide has been modified in one or more of the positions 1, 2, 3, 4, 5, 9, 10, 18, 25, 28, 30 or 31 of SEQ ID NO: 1, wherein the amino acid numbering corresponds to SEQ ID NO: 1.
129. The mimylin peptide according to any one of the preceding aspects, wherein said mimylin peptide has been modified up to 2 of the positions 1, 2, 3, 4, 5, 9, 10, 18 25, 28, 30 and 31 of SEQ ID NO: 1, wherein the amino acid numbering corresponds to SEQ ID NO: 1.
130. The mimylin peptide according to any one of the preceding aspects, wherein said mimylin peptide has been modified in 2 of the positions 1, 2, 3, 4, 5, 9, 10, 18 25, 28, 30 and 31 of SEQ ID NO: 1, wherein the amino acid numbering corresponds to SEQ ID NO: 1.
131. The mimylin peptide according to any one of the preceding aspects, wherein said mimylin peptide has been modified in one or more of the positions 1, 2, 3, 4, 5, 9, 10, 18, 25, 28, 30 and 31 of SEQ ID NO: 1, wherein the amino acid numbering corresponds to SEQ ID NO: 1, wherein said one or more modifications are selected from the list consisting of:
position 1 can be deleted,
position 2 can be modified to P,
position 3 can be modified to P,
position 4 can be modified to P,
position 5 can be modified to I or V,
position 9 can be modified to V or I,
position 10 can be modified to I,
position 18 can be modified to A,
position 25 can be modified to P,
position 28 can be modified with P,
position 30 can be modified to S, and
position 31 can be modified to G.
132. The mimylin peptide according to any one of the preceding aspects, wherein said mimylin peptide has been modified in one of the positions 1, 5, 6, 8, 9, 17, 20, 23 or 32 of SEQ ID NO: 1, wherein the amino acid numbering corresponds to SEQ ID NO: 1.
133. The mimylin peptide according to any one of the preceding aspects, wherein said mimylin peptide has been modified in one or more of the positions 1, 5, 6, 8, 9, 17, 20, 23 and 32 of SEQ ID NO: 1, wherein the amino acid numbering corresponds to SEQ ID NO: 1, wherein said one or more modifications are selected from the list consisting of:
position 1 can be deleted,
position 5 can be modified to H,
position 6 can be modified to H,
position 8 can be modified to L,
position 9 can be modified to L, V or I,
position 17 can be modified to I, position 20 can be modified to I,
position 23 can be modified to Y,
position 28 can be modified with P, and position 32 can be modified to H.

134. The mimylin peptide according to any one of the preceding aspects, wherein said mimylin peptide comprises an E in position 1, wherein the amino acid numbering corresponds to SEQ ID NO: 1.

135. The mimylin peptide according to any one of the preceding aspects, wherein positions 10, 13, 17 and 20 are L, wherein the amino acid numbering corresponds to SEQ ID NO: 1.

136. The mimylin peptide according to any one of the preceding aspects, wherein position 23 in L, wherein the amino acid numbering corresponds to SEQ ID NO: 1.

137. The mimylin peptide according to any one of the preceding aspects, wherein position 9 is V, wherein the amino acid numbering corresponds to SEQ ID NO: 1.

138. The mimylin peptide according to any one of the preceding aspects, wherein position 30 is S and/or position 31 is G, wherein the amino acid numbering corresponds to SEQ ID NO: 1.

139. The mimylin peptide according to any one of the preceding aspects, wherein a G is added in position 34 and the amino acid numbering corresponds to SEQ ID NO: 1.

140. The mimylin peptide according to any one of the preceding aspects, wherein a G is added in position 34 and the amino acid numbering corresponds to SEQ ID NO: 1.

141. The mimylin peptide according to any one of the preceding aspects comprising the sequence EASELSTAALGRLSAELHELATLPRTETGPESP (SEQ ID NO: 1).

142. The mimylin peptide according to any one of the preceding aspects comprising the sequence EASELSTAALGRLSAELHELATLPRTETGSGSP (SEQ ID NO: 22).

143. The mimylin peptide according to any one of the preceding aspects comprising the sequence selected from the group consisting of the compounds listed in Table 2.

144. The mimylin peptide according to any one of the preceding aspects comprising the sequence selected from the group consisting of the compounds listed in Table 4.

145. The mimylin peptide according to any one of the preceding aspects having the sequence EASELSTAALGRLSAELHELATLPRTETGPESP (SEQ ID NO: 1).

146. The mimylin peptide according to any one of the preceding aspects having the sequence EASELSTAALGRLSAELHELATLPRTETGSGSP (SEQ ID NO: 22).

147. The mimylin peptide according to any one of the preceding aspects having the sequence selected from the group consisting of the compounds listed in Table 4.

148. The mimylin peptide according to any one of the preceding aspects, comprising a sequence selected from the group consisting of EX. #1bb to EX. #7bb.

149. The mimylin peptide according to any one of the preceding aspects, comprising a sequence selected from the group consisting of EX. #8bb to EX. #20bb.

150. The mimylin peptide according to any one of the preceding aspects, comprising a sequence selected from the group consisting of EX. #21bb to EX. #33bb 151. The mimylin peptide according to any one of the preceding aspects, comprising a sequence selected from the group consisting of EX. #34bb to EX. #51bb 152. The mimylin peptide according to any one of the preceding aspects, comprising a sequence selected from the group consisting of EX. #52bb to EX. #55bb and EX. #68bb to EX. #72bb.

153. The mimylin peptide according to any one of the preceding aspects, comprising a sequence selected from the group consisting of EX. #56bb to EX. #67bb and EX. #72bb to EX. #78bb and EX. #107bb.

154. The mimylin peptide according to any one of the preceding aspects, comprising a sequence selected from the group consisting of EX. #79bb to EX. #90bb.

155. The mimylin peptide according to any one of the preceding aspects, comprising a sequence selected from the group consisting of EX. #91bb to EX. #97bb.

156. The mimylin peptide according to any one of the preceding aspects, comprising a sequence selected from the group consisting of EX. #98bb to EX. #102bb.

157. The mimylin peptide according to any one of the preceding aspects, comprising a sequence selected from the group consisting of EX. #103bb to EX. #106bb.

158. The mimylin peptide according to any one of the preceding aspects, comprising a sequence selected from the group consisting of EX. #8bb to EX. #20bb.

159. The mimylin peptide according to any one of the preceding aspects, comprising a sequence selected from the group consisting of EX. #107bb to EX. #114bb.

160. The mimylin peptide according to any one of the preceding aspects, comprising a sequence selected from the group consisting of EX. #115bb to EX. #124bb.

161. The mimylin peptide according to any one of the preceding aspects, comprising a sequence selected from the group consisting of EX. #125bb to EX. #127bb.

162. The mimylin peptide according to any one of the preceding aspects, comprising a sequence selected from the group consisting of EX. #128bb to EX. #133bb.

163. The mimylin peptide according to any one of the preceding aspects 1-162, comprising sequence: mimylin.

164. The mimylin peptide according to any one of the preceding aspects 1-162, comprising sequence: [9V] mimylin.

165. The mimylin peptide according to any one of the preceding aspects 1-162, comprising sequence: [5I]mimylin.

166. The mimylin peptide according to any one of the preceding aspects 1-162, comprising sequence: [9I]mimylin.

167. The mimylin peptide according to any one of the preceding aspects 1-162, comprising sequence: [17I]mimylin.

168. The mimylin peptide according to any one of the preceding aspects 1-162, comprising sequence: [20I]mimylin.

169. The mimylin peptide according to any one of the preceding aspects 1-162, comprising sequence: [18A] mimylin.

170. The mimylin peptide according to any one of the preceding aspects 1-162, comprising sequence: [9L] mimylin.

171. The mimylin peptide according to any one of the preceding aspects 1-162, comprising sequence: [8L] mimylin.

172. The mimylin peptide according to any one of the preceding aspects 1-162, comprising sequence: [6H] mimylin.

173. The mimylin peptide according to any one of the preceding aspects 1-162, comprising sequence: [5H] mimylin.

174. The mimylin peptide according to any one of the preceding aspects 1-162, comprising sequence: [32H] mimylin.

175. The mimylin peptide according to any one of the preceding aspects 1-162, comprising sequence: [des1] mimylin.
176. The mimylin peptide according to any one of the preceding aspects 1-162, comprising sequence: [23Y] mimylin.
177. The mimylin peptide according to any one of the preceding aspects 1-162, comprising sequence: [30S, 31G]mimylin.
178. The mimylin peptide according to any one of the preceding aspects 1-162, comprising sequence: [30S, 31G]mimylin.
179. The mimylin peptide according to any one of the preceding aspects 1-162, comprising sequence: [des1, 30S]mimylin.
180. The mimylin peptide according to any one of the preceding aspects 1-162, comprising sequence: [5V, 9V]mimylin.
181. The mimylin peptide according to any one of the preceding aspects 1-162, comprising sequence: [5I, 9I]mimylin.
182. The mimylin peptide according to any one of the preceding aspects 1-162, comprising sequence: [9V, 10I] mimylin.
183. The mimylin peptide according to any one of the preceding aspects 1-162, comprising sequence: [9L, 10A] mimylin.
184. The mimylin peptide according to any one of the preceding aspects 1-162, comprising sequence: [2P, 9V]mimylin.
185. The mimylin peptide according to any one of the preceding aspects 1-162, comprising sequence: [3P, 9V]mimylin.
186. The mimylin peptide according to any one of the preceding aspects, comprising sequence: [4P, 9V]mimylin.
187. The mimylin peptide according to any one of the preceding aspects 1-162, comprising sequence: [9V, 25P] mimylin.
188. The mimylin peptide according to any one of the preceding aspects 1-162, comprising sequence: [9V, 28P] mimylin.
189. The mimylin peptide according to any one of the preceding aspects 1-162, comprising sequence: [9V, 18A] mimylin.
190. The mimylin peptide according to any one of the preceding aspects 1-162, comprising sequence: [23Y, 30S, 31G]mimylin.
191. The mimylin peptide according to any one of the preceding aspects 1-162, comprising sequence: [des1, 30S, 31P]mimylin.
192. The mimylin peptide according to any one of the preceding aspects 1-162, comprising sequence: [5V, 9V, 20V]mimylin.
193. The mimylin peptide according to any one of the preceding aspects 1-162, comprising sequence: [5I, 9I, 10I]mimylin.
194. The mimylin peptide according to any one of the preceding aspects 1-162, comprising sequence: [3P, 4P, 9V]mimylin.
195. The mimylin peptide according to any one of the preceding aspects 1-162, comprising sequence: [9V, 12K, 25K]mimylin.
196. The mimylin peptide according to any one of the preceding aspects 1-162, comprising sequence: [des1, 30S, 31G]mimylin.
197. The mimylin peptide according to any one of the preceding aspects 1-162, comprising sequence: [des1, 30S, 31G]mimylin.
198. The mimylin peptide according to any one of the preceding aspects 1-162, comprising sequence: [des1, 30S, 31G]mimylin.
199. The mimylin peptide according to any one of the preceding aspects 1-162, comprising sequence: [des1, 30S, 31G]mimylin.
200. The mimylin peptide according to any one of the preceding aspects 1-162, comprising sequence: [des1, 30S, 31G]mimylin.
201. The mimylin peptide according to any one of the preceding aspects 1-162, comprising sequence: [des1, 30S, 31G]mimylin.
202. The mimylin peptide according to any one of the preceding aspects 1-162, comprising sequence: [des1, 30S, 31G]mimylin.
203. The mimylin peptide according to any one of the preceding aspects 1-162, comprising sequence: [des1, 30S, 31G]mimylin.
204. The mimylin peptide according to any one of the preceding aspects 1-162, comprising sequence: [des1, 30S, 31G]mimylin.
205. The mimylin peptide according to any one of the preceding aspects, comprising sequence: [des1, 30S, 31G] mimylin.
206. The mimylin peptide according to any one of the preceding aspects 1-162, comprising sequence: [des1, 30S, 31G]mimylin.
207. The mimylin peptide according to any one of the preceding aspects, comprising sequence: [des1, 30S, 31G] mimylin.
208. The mimylin peptide according to any one of the preceding aspects 1-162, comprising sequence: [des1, 4K, 30S, 31G]mimylin.
209. The mimylin peptide according to any one of the preceding aspects 1-162, comprising sequence: [des1, 16K, 30S, 31G]mimylin.
210. The mimylin peptide according to any one of the preceding aspects 1-162, comprising sequence: [des1, 19K, 30S, 31G]mimylin.
211. The mimylin peptide according to any one of the preceding aspects 1-162, comprising sequence: [des1, 27K, 30S, 31G]mimylin.
212. The mimylin peptide according to any one of the preceding aspects 1-162, comprising sequence: [des1, 23Y, 30S, 31G]mimylin.
213. The mimylin peptide according to any one of the preceding aspects 1-162, comprising sequence: [1A, 23Y, 30S, 31G]mimylin.
214. The mimylin peptide according to any one of the preceding aspects, comprising sequence: [des1, 23Y, 30S, 31G]mimylin.
215. The mimylin peptide according to any one of the preceding aspects 1-162, comprising sequence: [des1, 30S, 31G, 33Y]mimylin.
216. The mimylin peptide according to any one of the preceding aspects 1-162, comprising sequence: [des1, 30S, 31G, 33H]mimylin.
217. The mimylin peptide according to any one of the preceding aspects 1-162, comprising sequence: [des1, 30S, 31G, 33F]mimylin.
218. The mimylin peptide according to any one of the preceding aspects, comprising sequence: [des1, 30S, 31G, 33L]mimylin.

219. The mimylin peptide according to any one of the preceding aspects 1-162, comprising sequence: [des1, 30S, 31G, 33S]mimylin.
220. The mimylin peptide according to any one of the preceding aspects 1-162, comprising sequence: [des1, 30S, 31G, 33G]mimylin.
221. The mimylin peptide according to any one of the preceding aspects 1-162, comprising sequence: [des1, 30S, 31G, 33A]mimylin.
222. The mimylin peptide according to any one of the preceding aspects 1-162, comprising sequence: [des1, 15E, 30S, 31G]mimylin.
223. The mimylin peptide according to any one of the preceding aspects 1-162, comprising sequence: [des1, 15e, 30S, 31G]mimylin.
224. The mimylin peptide according to any one of the preceding aspects 1-162, comprising sequence: [des1, 4K, 30S, 31G]mimylin.
225. The mimylin peptide according to any one of the preceding aspects 1-162, comprising sequence: [des1, 16K, 30S, 31G]mimylin.
226. The mimylin peptide according to any one of the preceding aspects 1-162, comprising sequence: [des1, 19K, 30S, 31G]mimylin.
227. The mimylin peptide according to any one of the preceding aspects 1-162, comprising sequence: [des1, 27K, 30S, 31G]mimylin.
228. The mimylin peptide according to any one of the preceding aspects 1-162, comprising sequence: [des1, 12H, 30S, 31G]mimylin.
229. The mimylin peptide according to any one of the preceding aspects 1-162, comprising sequence: [des1, 25H, 30S, 31G]mimylin.
230. The mimylin peptide according to any one of the preceding aspects 1-162, comprising sequence: [des1, 30T, 31G, 32T]mimylin.
231. The mimylin peptide according to any one of the preceding aspects 1-162, comprising sequence: [des1, 30S, 31G, 32P]mimylin.
232. The mimylin peptide according to any one of the preceding aspects 1-162, comprising sequence: [des1, 9V, 30S, 31G]mimylin.
233. The mimylin peptide according to any one of the preceding aspects 1-162, comprising sequence: [5I, 9I, 10I, 20I]mimylin.
234. The mimylin peptide according to any one of the preceding aspects 1-162, comprising sequence: [des1, 4Q, 30S, 31G]mimylin.
235. The mimylin peptide according to any one of the preceding aspects 1-162, comprising sequence: [des1, 4G, 23Y, 30S, 31G]mimylin.
236. The mimylin peptide according to any one of the preceding aspects 1-162, comprising sequence: [des1, 23Y, 30S, 31G, 33Y]mimylin.
237. The mimylin peptide according to any one of the preceding aspects, comprising sequence: [des1, 23Y, 30S, 31G, 32A]mimylin.
238. The mimylin peptide according to any one of the preceding aspects 1-162, comprising sequence: [des1, 21S, 23Y, 30S, 31G]mimylin.
239. The mimylin peptide according to any one of the preceding aspects 1-162, comprising sequence: [−1E, 1A, 23Y, 30S, 31G]mimylin.
240. The mimylin peptide according to any one of the preceding aspects 1-162, comprising sequence: [des1, 12H, 25H, 30S, 31G]mimylin.
241. The mimylin peptide according to any one of the preceding aspects 1-162, comprising sequence: [des1, 6T, 9V, 30S, 31G]mimylin.
242. The mimylin peptide according to any one of the preceding aspects 1-162, comprising sequence: [des1, 5V, 9V, 30S, 31G]mimylin.
243. The mimylin peptide according to any one of the preceding aspects 1-162, comprising sequence: [des1, 4Q, 16Q, 30S, 31G]mimylin.
244. The mimylin peptide according to any one of the preceding aspects 1-162, comprising sequence: [des1, 23Y, 30S, 31G, 33Y]mimylin.
245. The mimylin peptide according to any one of the preceding aspects 1-162, comprising sequence: [des1, 23Y, 30S, 31G, 34G]mimylin.
246. The mimylin peptide according to any one of the preceding aspects 1-162, comprising sequence: [des1, 23Y, 30S, 31G, 34K]mimylin.
247. The mimylin peptide according to any one of the preceding aspects 1-162, comprising sequence: [des1, 9S, 23Y, 30S, 31G, 33Y]mimylin.
248. The mimylin peptide according to any one of the preceding aspects 1-162, comprising sequence: [des1, 9T, 21S, 23Y, 30S, 31G]mimylin.
249. The mimylin peptide according to any one of the preceding aspects 1-162, comprising sequence: [des1, 12H, 25H, 30T, 31G, 32T]mimylin.
250. The mimylin peptide according to any one of the preceding aspects 1-162, comprising sequence: [des1, 6T, 9V, 30S, 31G, 32T]mimylin.
251. The mimylin peptide according to any one of the preceding aspects 1-162, comprising sequence: [des1, 6T, 9V, 30T, 31G, 32T]mimylin.
252. The mimylin peptide according to any one of the preceding aspects 1-162, comprising sequence: [des1, 5V, 9V, 10V, 30S, 31G]mimylin.
253. The mimylin peptide according to any one of the preceding aspects 1-162, comprising sequence: [des1, 21S, 23Y, 30S, 31G, 33Y]mimylin.
254. The mimylin peptide according to any one of the preceding aspects 1-162, comprising sequence: [des1, 4G, 9V, 23Y, 30S, 31G, 32T]mimylin.
255. The mimylin peptide according to any one of the preceding aspects 1-162, comprising sequence: [des1, 9T, 21S, 23Y, 30S, 31G, 33Y]mimylin.
256. The mimylin peptide according to any one of the preceding aspects 1-162, comprising sequence: [des1, 9S, 21S, 23Y, 30S, 31G, 33Y]mimylin.
257. The mimylin peptide according to any one of the preceding aspects 1-162, comprising sequence: [des1, 12K, 23Y, 25K, 30S, 31G, 33Y]mimylin.
258. The mimylin peptide according to any one of the preceding aspects 1-162, comprising sequence: [des1, 5V, 9V, 10V, 20V, 30S, 31G]mimylin.
259. The mimylin peptide according to any one of the preceding aspects 1-162, comprising sequence: [4G, 15Q, 21Q, 23Y, 30S, 31G, 32T, 33Y]mimylin.
260. The mimylin peptide according to any one of the preceding aspects 1-162, comprising sequence: [des1, 4G, 9V, 23Y, 30S, 31G, 32T, 33Y]mimylin.
261. The mimylin peptide according to any one of the preceding aspects 1-162, comprising sequence: [des1, 6T, 9V, 14T, 21E, 30T, 31G, 32T]mimylin.
262. The mimylin peptide according to any one of the preceding aspects 1-162, comprising sequence: [des1, 6T, 9V, 14E, 21T, 30T, 31G, 32T]mimylin.

263. The mimylin peptide according to any one of the preceding aspects 1-162, comprising sequence: [des1, 4G, 15Q, 21Q, 23Y, 30S, 31K, 32T, 33Y]mimylin.
264. The mimylin peptide according to any one of the preceding aspects 1-162, comprising sequence: [des1, 4G, 15Q, 21E, 23Y, 30S, 31G, 32T, 33Y]mimylin.
265. The mimylin peptide according to any one of the preceding aspects 1-162, comprising sequence: [des1, 4G, 15Q, 21Q, 23Y, 30S, 31Q, 32T, 33Y]mimylin.
266. The mimylin peptide according to any one of the preceding aspects 1-162, comprising sequence: [des1, 4G, 15Q, 21Q, 23Y, 30S, 31G, 32T, 33Y]mimylin.
267. The mimylin peptide according to any one of the preceding aspects 1-162, comprising sequence: [des1, 4G, 15Q, 21Q, 23Y, 30S, 31G, 32T, 33Y]mimylin.
268. The mimylin peptide according to any one of the preceding aspects, comprising sequence: [des1, 4G, 15T, 21E, 23Y, 30S, 31G, 32T, 33Y]mimylin.
269. The mimylin peptide according to any one of the preceding aspects 1-162, comprising sequence: [des1, 4G, 15E, 21Q, 23Y, 30S, 31G, 32T, 33Y]mimylin.
270. The mimylin peptide according to any one of the preceding aspects, comprising sequence: [des1, 9V, 15Q, 21Q, 23Y, 30S, 31G, 32T, 33Y]mimylin.
271. The mimylin peptide according to any one of the preceding aspects 1-162, comprising sequence: [4Q, 9V, 15Q, 21Q, 23Y, 27G, 30S, 31G, 32T, 33Y]mimylin.
272. The mimylin peptide according to any one of the preceding aspects, comprising sequence: [des1, 4Q, 9V, 15Q, 21Q, 23Y, 30S, 31Q, 32T, 33Y]mimylin.
273. The mimylin peptide according to any one of the preceding aspects 1-162, comprising sequence: [des1, 4G, 15Q, 21Q, 23Y, 25H, 30S, 31G, 32T, 33Y]mimylin.
274. The mimylin peptide according to any one of the preceding aspects 1-162, comprising sequence: [des1, 4G, 9V, 15Q, 21Q, 23Y, 30S, 31G, 32T, 33Y]mimylin.
275. The mimylin peptide according to any one of the preceding aspects, comprising sequence: [des1, 4G, 9V, 15Q, 21Q, 23Y, 30S, 31G, 32T, 33Y]mimylin.
276. The mimylin peptide according to any one of the preceding aspects 1-162, comprising sequence: [des1, 4G, 9V, 15Q, 21Q, 23Y, 30S, 31G, 32T, 33Y]mimylin.
277. The mimylin peptide according to any one of the preceding aspects, comprising sequence: [des1, 4G, 9V, 15Q, 21Q, 23Y, 30S, 31G, 32T, 33Y]mimylin.
278. The mimylin peptide according to any one of the preceding aspects 1-162, comprising sequence: [des1, 4G, 9V, 15Q, 21Q, 23Y, 30S, 31A, 32T, 33Y]mimylin.
279. The mimylin peptide according to any one of the preceding aspects, comprising sequence: [des1, 2L, 4G, 9V, 21S, 23Y, 30S, 31G, 32T, 33Y]mimylin.
280. The mimylin peptide according to any one of the preceding aspects 1-162, comprising sequence: [des1, 4G, 9T, 15Q, 21Q, 23Y, 30S, 31G, 32T, 33Y]mimylin.
281. The mimylin peptide according to any one of the preceding aspects 1-162, comprising sequence: [des1, 4G, 9V, 15Q, 21Q, 23Y, 25P, 30S, 31Q, 32T, 33Y]mimylin.
282. The mimylin peptide according to any one of the preceding aspects 1-162, comprising sequence: [des1, 4G, 8L, 9V, 15Q, 21Q, 23Y, 30S, 31Q, 32T, 33Y]mimylin.
283. The mimylin peptide according to any one of the preceding aspects 1-162, comprising sequence: [des1, 2L, 4G, 9V, 15Q, 21Q, 23Y, 30S, 31Q, 32T, 33Y]mimylin.
284. The mimylin peptide according to any one of the preceding aspects 1-162, comprising sequence: [des1, 4G, 9T, 15Q, 21Q, 23Y, 25P, 30S, 31Q, 32T, 33Y]mimylin.
285. The mimylin peptide according to any one of the preceding aspects 1-162, comprising sequence: [2L, 4G, 8L, 9V, 15Q, 21Q, 23Y, 27G, 30S, 31G, 32T, 33Y]mimylin.
286. The mimylin peptide according to any one of the preceding aspects 1-162, comprising sequence: [des1, 4G, 9V, 15Q, 21Q, 23aQ, 23bT, 23cY, 30S, 31Q, 32T, 33Y]mimylin.
287. The mimylin peptide according to any one of the preceding aspects 1-162, comprising sequence: [des1, 4G, 9V, 12K, 15Q, 21Q, 23Y, 25P, 30S, 31G, 32T, 33Y]mimylin.
288. The mimylin peptide according to any one of the preceding aspects 1-162, comprising sequence: [des1, 4Q, 9V, 15Q, 16R, 19R, 21Q, 23Y, 27Q, 30S, 31Q, 32T, 33Y]mimylin.
289. The mimylin peptide according to any one of the preceding aspects 1-162, comprising sequence: [des1, 2L, 4Q, 8L, 9V, 15Q, 16R, 19R, 21Q, 23Y, 27Q, 30S, 31Q, 32T, 33Y]mimylin.
290. The mimylin peptide according to any one of the preceding aspects 1-162, comprising sequence: [N-terminal(C18 diacid),C-terminal(−)]mimylin.
291. A mimylin derivative, wherein a mimylin peptide according to any one of the preceding aspects 1-162 is derivatised with a side chain.
292. The mimylin derivative according to aspect 280, wherein said mimylin peptide according to any one of the aspects 1-162 is derivatised by bonding, in particular covalent bonding of a side chain to said mimylin peptide.
293. The mimylin derivative according to any one of the preceding aspects 163-292, wherein said derivatisation is performed by acylation chemistry.
294. The mimylin derivative according to any one of the preceding aspects 163-293, wherein a mimylin peptide is derivatised in the N-terminal.
295. The mimylin derivative according to any one of the preceding aspects 163-295, wherein a mimylin peptide is derivatised in the alpha-amino group of the N-terminal amino acid.
296. The mimylin derivative according to any one of the preceding aspects 163-296, wherein said fatty acid or diacid is directly attached to the N-terminal, wherein the N-terminal amino acid is E in position 1, wherein the amino acid numbering corresponds to SEQ ID NO: 1.
297. The mimylin derivative according to any one of the preceding aspects 163-297, wherein said mimylin peptide is derivatised at E in position 1, wherein the amino acid numbering corresponds to SEQ ID NO: 1.
298. The mimylin derivative according to any one of the preceding aspects 163-298, wherein said mimylin peptide is derivatised at any K in the mimylin peptide sequence of any one of the mimylin peptides according to aspect 1-163.
299. The mimylin derivative according to aspect 298, wherein such K can be in position, 4, 12, 16, 23, 18, 27 or 34, wherein the amino acid numbering is relative to SEQ ID NO: 1.
300. The mimylin derivative according to any one of the preceding aspects 163-299, wherein said fatty acid or diacid is covalently bonded to the alpha-amino group of the N-terminal amino residue, wherein the N-terminal amino acid is E in position 1 and wherein the amino acid numbering is relative to SEQ ID NO: 1.
301. The mimylin derivative according to any one of the preceding aspects 163-300, wherein said fatty acid or diacid is covalently bonded to the alpha-amino group of the N-terminal amino residue, wherein any amino acid in position 1 is not an E and wherein the amino acid numbering is relative to SEQ ID NO: 1.
302. The mimylin derivative according to any one of the preceding aspects 163-301, wherein said fatty acid or diacid is covalently bonded to the alpha-amino group of the N-terminal amino residue, wherein any amino acid in position 1 is any other amino acid than E and wherein the amino acid numbering is relative to SEQ ID NO: 1.
303. The mimylin derivative according to any one of the preceding aspects 163-302, wherein said fatty acid or diacid is covalently bonded to the alpha-amino group of the N-terminal amino residue, wherein any amino acid in position 1 is any other amino acid than E, Q and/or N and wherein the amino acid numbering is relative to SEQ ID NO: 1.
304. The mimylin derivative according to any one of the aspects 163-303, comprising a side chain, wherein said side chain comprises a protracting moiety.
305. The mimylin derivative according to any one of the aspects 163-304, comprising a side chain, wherein said side chain comprises a protracting moiety which is a fatty acid or diacid.
306. The mimylin derivative according to any one of the aspects 163-305, aspects comprising a protracting moiety which is a fatty diacid.
307. The mimylin derivative according to any one of the aspects 163-306, wherein said fatty diacid comprises 14-20 carbon atoms.
308. The mimylin derivative according to any one of the aspects 163-307, wherein said fatty diacid comprises 14, 16, 18 or 20 carbon atoms.
309. The mimylin derivative according to any one of the aspects 163-308, wherein said fatty diacid comprises 18 carbon atoms.
310. The mimylin derivative according to any one of the aspects 163-309, wherein said fatty diacid comprises 20 carbon atoms.
311. The mimylin derivative according to any one of the aspects 163-310, wherein said fatty acid or diacid is directly attached to the N-terminal.
312. The mimylin derivative according to any one of the aspects 163-311, wherein said fatty acid or diacid is covalently bonded to the alpha-amino group of the N-terminal amino residue.
313. The mimylin derivative according to any one of the aspects 163-312, wherein said fatty acid or diacid is directly attached to the N-terminal, wherein any amino acid in position 1 is not an E and wherein said diacid comprises 20 carbon acids.
314. The mimylin derivative according to any one of the aspects 163-313, wherein said fatty acid or diacid is directly attached to the N-terminal, wherein any amino acid in position 1 is an amino acid is different from Q, N and/or E and wherein said diacid comprises 20 carbon acids.
315. The mimylin derivative according to any one of the aspects 163-314, wherein a mimylin peptide is derivatised at E in position 1, wherein the amino acid numbering corresponds to SEQ ID NO: 1.
316. The mimylin derivative according to any one of the aspects 163-315, wherein a mimylin peptide is derivatised at E in said mimylin peptides in position −1, wherein the amino acid numbering corresponds to SEQ ID NO: 1.
317. The mimylin derivative according to any one of the aspects 163-316, wherein a mimylin peptide is derivatised at E in position 2, wherein the amino acid numbering corresponds to SEQ ID NO: 1.
318. The mimylin derivative according to any one of the preceding aspects 163-317-, wherein a mimylin peptide is derivatised with a side chain comprising a protracting moiety and a linker.
319. The mimylin derivative according to any one of the preceding aspects 163-318, wherein a mimylin peptide is derivatised in the N-terminal and wherein said mimylin peptide is derivatised with a side chain comprising a protracting moiety and a linker.
320. The mimylin derivative according to any one of the preceding aspects 163-319, wherein a mimylin peptide is derivatised in the N-terminal and wherein said mimylin peptide is derivatised with a side chain comprising a protracting moiety and no linker.
321. The mimylin derivative according to any one of the preceding aspects 163-320, wherein a mimylin peptide is derivatised in the N-terminal and wherein said mimylin peptide is derivatised with a side chain without a linker.
322. The mimylin derivative according to any one of the preceding aspects 163-321, wherein said fatty acid or diacid is attached to the N-terminal or E in position 1 via a linker and wherein the amino acid numbering is relative to SEQ ID NO: 1.
323. The mimylin derivative according to any one of the preceding aspects 163-322, wherein a mimylin peptide is derivatised at any K present in the sequence, preferably in any one of the position selected from positions 4K, 16K, 19K and 27K.
324. A mimylin derivative according to any one of the aspects 163-323, wherein said mimylin derivative is a mimylin peptide according to any one of the aspects 1-162 which is derivatised with a side chain comprising fatty acid or diacid and a linker.
325. The mimylin derivative according aspect to any one of the aspects 163-324, wherein said linker is an gGlu, gGlu-OEG, gGlu-OEG-OEG, gGlu-OEG-OEG-OEG, gGlu-OEG-OEG-OEG-OEG, gGlu-OEG-OEG-OEG-OEG-OEG.
326. The mimylin derivative according to aspect 325, wherein said linker is a gGlu.
327. The mimylin derivative according to aspect 325, wherein said linker is a gGlu-OEG.
328. The mimylin derivative according to aspect 325, wherein said linker is a gGlu-OEG-OEG.
329. The mimylin derivative according to aspect 325, wherein said linker is a gGlu-OEG-OEG-OEG.
330. The mimylin derivative according to aspect 325, wherein said linker is a gGlu-OEG-OEG-OEG-OEG.
331. The mimylin derivative according to aspect 325, wherein said linker is a gGlu-OEG-OEG-OEG-OEG.
332. The mimylin derivative according to aspect 331, wherein the side chain is selected from Table 6.
333. The mimylin derivative according to any one of the preceding aspects 163-332, increasing the half-life of more than 3 hours, preferably more than 6 hours, most preferably more than 12 hours after intravenous treatment in rats when measured with Assay (X).
334. The mimylin derivative according to any one of the preceding aspects 163-333, increasing the half-life of more than 3 hours, preferably more than 13 hours after subcutaneous treatment in rats when measured with Assay (X).
335. The mimylin derivative according to any one of the preceding aspects 163-334, increasing the half-life of the mimylin peptide in mini pig relative to the corresponding mimylin peptide without a side chain according to any one of the aspects 1-162, measured according to Assay (IX).

336. The mimylin derivative according to any one of the preceding aspects 163-335, with a T½ of about 1-200 hours longer than the T½ of compound of Ex. #1 or salmon calcitonin measured according to Assay (IX).

337. The mimylin derivative according to any one of the preceding aspects 163-336, with a T½ of about 1-200 hours, preferably ≥ about 1 hour, ≥ about 2 hour, ≥ about 17, ≥ about 32, ≥ about 86, ≥ about 87, ≥ about 88, ≥ about 90, ≥ about 108, about ≥118, ≥ about 171 hours measured according to Assay (IX).

338. The mimylin derivative according to any one of the preceding aspects 163-337, with a T½ of about 85 hours measured according to Assay (IX).

339. The mimylin derivative according to any one of the preceding aspects 163-338, with a T½ of about 50-70 in LYD-pigs, preferably about 64 hours intravenously and has a subcutaneous bioavailability of about 80-100%, preferably about 99%, measured according to Assay (XVI).

340. The mimylin derivative according to any one of the preceding aspects 163-339, with a T½ of about 80-110 in Beagle dogs, preferably about 95 hours intravenously and a subcutaneous bioavailability of about 80-100%, preferably about 99%, measured according to Assay (XVII).

341. The mimylin derivative according to any one of the preceding aspects 163-340, increasing the half-life of the mimylin peptide in human relative to the corresponding mimylin peptide without a side chain according to any one of the aspects 1-162.

342. The mimylin derivative according to any one of the preceding aspects 163-341, comprising a G in position 34, wherein said G in position 34 is converted in such a way that the resulting mimylin peptide comprises an amino acid in position 33 with a c-terminal amide and wherein the amino acid numbering corresponds to SEQ ID NO: 1.

343. The mimylin derivative according to any one of the preceding aspects 163-342, comprising a G in position 34, wherein said G in position 34 is converted with PAM enzymes in such a way that the resulting mimylin peptide comprises an amino acid in position 33 with a c-terminal amide and wherein the amino acid numbering corresponds to SEQ ID NO: 1.

344. The mimylin derivative according to any one of the preceding aspects 163-343 comprising V in position 9, wherein the amino acid numbering corresponds to SEQ ID NO: 1.

345. The mimylin derivative according to any one of the preceding aspects 163-344, comprising S in position 30 and/or G in position 31, wherein the amino acid numbering corresponds to SEQ ID NO: 1.

346. The mimylin derivative according to any one of the preceding aspects 163-345, wherein said mimylin derivative has a calculated pI value of between about 3.5 to about 5.5.

347. The mimylin derivative according to any one of the preceding aspects 163-346, wherein said mimylin peptide has a pI value of between about 3.5 to about 5.5, wherein the calculated pI is estimated by solving the equation Q(pI)=0, with Q designation the net charge found by summing the protonation fraction of all ionizable sites in the molecule, wherein natural amino acid residues tabulated pKa-values are used for free terminals and ionizable sites in the side chains, wherein pKa-values for non-natural amino acid residues are estimated by ACD/Labs Software ver. 12 package, wherein compounds with more than 255 atoms and comprising residues containing pseudo atoms should not have their pI estimated according to this method.

348. The mimylin derivative according to any one of the preceding aspects 163-347, wherein said mimylin peptide has a calculated pI value of about 4 to about 5.

349. The mimylin derivative according to any one of the preceding aspects 163-348, wherein said mimylin peptide has a calculated pI value of 4, 5 plus or minus 1 pI value.

350. The mimylin derivative according to any one of the preceding aspects 163-349, wherein said mimylin peptide has a calculated pI value of 4, 5 plus or minus 1 pH value.

351. The mimylin derivative according to any one of the preceding aspects 163-350, wherein said mimylin peptide is soluble in the complete pH range, preferably in the pH range about 6.0 to about 8.0.

352. The mimylin derivative according to any one of the preceding aspects 163-351, wherein said mimylin peptide is completely soluble in the complete pH range, preferably in the pH range about 6.0 to about 8.0, wherein completely soluble means that the solubility score is of ≥μ200 μM tested in Assay IV.

353. The mimylin derivative according to any one of the preceding aspects 163-352, wherein said mimylin peptide is highly soluble in the complete pH range, preferably in the pH range about 6.0 to about 8.0, wherein highly soluble means that the solubility score is of ≥μ100 μM tested in Assay IV.

354. The mimylin derivative according to any one of the preceding aspects 163-353, wherein said mimylin derivative is soluble in the pH ranges below about pH 3 and above about 5, when tested at a concentration of 200 μM in Assay IV.

355. The mimylin derivative according to any one of the preceding aspects 163-354, wherein said mimylin peptide is soluble in the pH ranges below about 3 and above about 6.

356. The mimylin derivative according to any one of the preceding aspects 163-355, wherein said mimylin peptide is soluble in the pH ranges below about 3 and above about 6.5.

357. The mimylin derivative according to any one of the preceding aspects 163-356, wherein said mimylin peptide is soluble above pH about 4.

358. The mimylin derivative according to any one of the preceding aspects 163-357, wherein said mimylin peptide is soluble above pH about 5.

359. The mimylin derivative according to any one of the preceding aspects 163-358, wherein said mimylin peptide is soluble at pH about 3, 4, 5, 6 7, 8 and 9.

360. The mimylin derivative according to any one of the preceding aspects 163-359, wherein said mimylin peptide is soluble at pH about 3, 4, 7, 8 and 9.

361. The mimylin derivative according to any one of the preceding aspects 163-360, wherein said mimylin peptide is soluble at pH about 3, 6, 7, 8 and 9.

362. The mimylin derivative according to any one of the aspects 163-361, wherein said mimylin derivative is soluble in the complete pH range or soluble in the complete pH range, preferably between about 6.0 to about 8.0 and decreasing in solubility in the pH range around the said mimylin peptides pI.

363. The mimylin derivative according to any one of the aspects 163-362, wherein said mimylin derivative is soluble in the complete pH range or soluble in the complete pH range, preferably in the pH range about 6.0 to about 8.0 and decreasing in solubility in the pH range in the pH range plus or minus 1 pH value from said mimylin peptides pI.

364. The mimylin derivative according to any one of the aspects 163-363, wherein said mimylin derivative is soluble in the complete pH range or soluble in the complete pH range and not soluble in the pH range around the said mimylin peptides pI.

365. The mimylin derivative according to any one of the aspects 163-364, wherein said mimylin derivative is soluble in the complete pH range or soluble in the complete pH range and not soluble in the pH range in the pH range plus or minus 1 pH value from said mimylin peptides pI.

366. The mimyin derivative according to any one of the preceding aspects 163-365, selected from the compounds listed in table 16.

367. The mimyin derivative according to any one of the preceding aspects 163-366, wherein said derivative has a solubility of ≥200 μM in the complete pH range tested, preferably in the range between pH 6.0 to about 8.0, tested in Assay IV selected from the compounds listed in Table 16, preferably Ex #2-19, 21-85, 87-88, 91-99, 101-106, 108-110, 112-114, 116-117, 119-125, 126-128, 130-131, most preferably Ex #2-19, 21-85, 87-88, 91-99, 101-106, 108-110, 112-114, 116-117, 119-125, 126-127.

368. The mimylin derivative according to any one of the preceding aspects 163-367, which is selected from the group consisting of any one of the example compounds of Ex #2 to Ex #7.

369. The mimylin derivative according to any one of the preceding aspects 163-368, which is selected from the group consisting of any one of the example compounds Ex #8 to Ex #19.

370. The mimylin derivative according to any one of the preceding aspects 163-369, which is selected from the group consisting of any one of the example compounds Ex #21 to Ex #33.

371. The mimylin derivative according to any one of the preceding aspects 163-370, which is selected from the group consisting of any one of the example compounds Ex #34 to Ex #1.

372. The mimylin derivative according to any one of the preceding aspects 163-371, which is selected from the group consisting of any one of the example compounds Ex #52 to Ex #55 and Ex #68 to Ex #72.

373. The mimylin derivative according to any one of the preceding aspects 162-372, which is selected from the group consisting of any one of the example compounds Ex #56 to Ex #67 and Ex #72 to Ex #78 and Ex #107.

374. The mimylin derivative according to any one of the preceding aspects 163-373, which is selected from the group consisting of any one of the example compounds Ex #79 to Ex #90.

The mimylin derivative according to any one of the preceding aspects 163-374, which is selected from the group consisting of any one of the example compounds Ex #91 to Ex #97.

375. The mimylin derivative according to any one of the preceding aspects 163-374, which is selected from the group consisting of any one of the example compounds Ex #103 to Ex #106.

376. The mimylin derivative according to any one of the preceding aspects 163-375, which is selected from the group consisting of any one of the example compounds Ex #108 to Ex #114.

377. The mimylin derivative according to any one of the preceding aspects 163-376, which is selected from the group consisting of any one of the example compounds Ex #115 to Ex #124.

378. The derivatised mimylin peptide or mimylin derivative according to any one of the preceding aspects 163-376, which is selected from the group consisting of any one of the example compounds Ex #125 to Ex #127.

379. The derivatised mimylin peptide or mimylin derivative according to any one of the preceding aspects 163-378, which is selected from the group consisting of any one of the example compounds Ex #2 to Ex #33.

380. The mimylin derivative according to any one of the preceding aspects 163-379, which is which is a derivatised mimylin peptide selected from the group consisting of any one of the example compounds Ex #2 to Ex #131.

381. The mimylin derivative according to any one of the preceding aspects 163-380, which is a derivatised mimylin peptide selected from the group consisting of any one of the example compounds Ex #2 to Ex #127.

382. The derivative according to any one of the preceding aspects 163-381, comprising the sequence selected from the group consisting of the compounds listed in Table 1.

383. The mimylin derivative according to any one of the preceding aspects 163-382, comprising the sequence selected from the group consisting of the compounds listed in Table 3.

384. The mimylin derivative according to any one of the preceding aspects 163-384, comprising the sequence selected from the group consisting of the compounds listed in Table 5.

385. The mimylin derivative according to any one of the preceding aspects 163-384, having the compound name [N-terminal(C18 diacid)]mimylin.

386. The mimylin derivative according to any one of the preceding aspects 163-385, having the compound name [N-terminal(C16 diacid)]mimylin.

387. The mimylin derivative according to any one of the preceding aspects 163-386, having the compound name [N-terminal(C14 diacid)]mimylin.

388. The mimylin derivative according to any one of the preceding aspects 163-387, having the compound name [N-terminal(C14 diacid-2×gGlu-4×OEG)]mimylin.

389. The mimylin derivative according to any one of the preceding aspects 163-388, having the compound name [N-terminal(C12 diacid)]mimylin.

390. The mimylin derivative according to any one of the preceding aspects 163-389, having the compound name [N-terminal(C16)]mimylin.

391. The mimylin derivative according to any one of the preceding aspects 163-390, having the compound name [N-terminal(C18 diacid), 5I]mimylin.

392. The mimylin derivative according to any one of the preceding aspects 163-391, having the compound name [N-terminal(C18 diacid), 9V]mimylin.

393. The mimylin derivative according to any one of the preceding aspects 163-392, having the compound name [N-terminal(C18 diacid), 9I]mimylin.

394. The mimylin derivative according to any one of the preceding aspects 163-393, having the compound name [N-terminal(C18 diacid), 17I]mimylin.

395. The mimylin derivative according to any one of the preceding aspects 163-394, having the compound name [N-terminal(C18 diacid), 20I]mimylin.

396. The mimylin derivative according to any one of the preceding aspects 163-395, having the compound name [N-terminal(C18 diacid), 18A]mimylin.

397. The mimylin derivative according to any one of the preceding aspects 163-396, having the compound name [N-terminal(C18 diacid), 9L]mimylin.
398. The mimylin derivative according to any one of the preceding aspects 163-397, having the compound name [N-terminal(C18 diacid), 8L]mimylin.
399. The mimylin derivative according to any one of the preceding aspects 163-398, having the compound name [N-terminal(C18 diacid), 6H]mimylin.
400. The mimylin derivative according to any one of the preceding aspects 163-399, having the compound name [N-terminal(C18 diacid), 5H]mimylin.
401. The mimylin derivative according to any one of the preceding aspects 163-400, having the compound name [N-terminal(C18 diacid), 32H]mimylin.
402. The mimylin derivative according to any one of the preceding aspects 163-401, having the compound name [N-terminal(C14 diacid-gGlu), des1]mimylin.
403. The mimylin derivative according to any one of the preceding aspects 163-402, having the compound name [N-terminal(C18 diacid), 23Y]mimylin.
404. The mimylin derivative according to any one of the preceding aspects 163-403, having the compound name [N-terminal(C18 diacid), 30S, 31G]mimylin.
405. The mimylin derivative according to any one of the preceding aspects 163-404, having the compound name [N-terminal(C20 diacid), 30S, 31G]mimylin.
406. The mimylin derivative according to any one of the preceding aspects 163-405, having the compound name [N-terminal(C18 diacid-gGlu), des1, 30S]mimylin.
407. The mimylin derivative according to any one of the preceding aspects 163-406, having the compound name [N-terminal(C18 diacid), 5V, 9V]mimylin.
408. The mimylin derivative according to any one of the preceding aspects 163-407, having the compound name [N-terminal(C18 diacid), 5I, 9I]mimylin.
409. The mimylin derivative according to any one of the preceding aspects 163-408, having the compound name [N-terminal(C18 diacid), 9V, 10I]mimylin.
410. The mimylin derivative according to any one of the preceding aspects 163-409, having the compound name [N-terminal(C18 diacid), 9L, 10A]mimylin.
411. The mimylin derivative according to any one of the preceding aspects 163-410, having the compound name [N-terminal(C18 diacid), 2P, 9V]mimylin.
412. The mimylin derivative according to any one of the preceding aspects 163-411, having the compound name [N-terminal(C18 diacid), 3P, 9V]mimylin.
413. The mimylin derivative according to any one of the preceding aspects 163-412, having the compound name [N-terminal(C18 diacid), 4P, 9V]mimylin.
414. The mimylin derivative according to any one of the preceding aspects 163-413, having the compound name [N-terminal(C18 diacid), 9V, 25P]mimylin.
415. The mimylin derivative according to any one of the preceding aspects 163-414, having the compound name [N-terminal(C18 diacid), 9V, 28P]mimylin.
416. The mimylin derivative according to any one of the preceding aspects 163-415, having the compound name [N-terminal(C18 diacid), 9V, 18A]mimylin.
417. The mimylin derivative according to any one of the preceding aspects 163-416, having the compound name [N-terminal(C20 diacid-gGlu), 23Y, 30S, 31G]mimylin.
418. The mimylin derivative according to any one of the preceding aspects 163-417, having the compound name [N-terminal(C18 diacid-gGlu), des1, 31P]mimylin.
419. The mimylin derivative according to any one of the preceding aspects 163-418, having the compound name [N-terminal(C18 diacid), 5V, 9V, 20V]mimylin.
420. The mimylin derivative according to any one of the preceding aspects 163-419, having the compound name [N-terminal(C18 diacid), 5I, 9I, 10I]mimylin.
421. The mimylin derivative according to any one of the preceding aspects 163-420, having the compound name [N-terminal(C18 diacid), 3P, 4P, 9V]mimylin.
422. The mimylin derivative according to any one of the preceding aspects 163-421, having the compound name [N-terminal(C18 diacid), 9V, 12K, 25K]mimylin.
423. The mimylin derivative according to any one of the preceding aspects 163-422, having the compound name [N-terminal(C20 diacid-gGlu), des1, 30S, 31G]mimylin.
424. The mimylin derivative according to any one of the preceding aspects 163-423, having the compound name [N-terminal(C20 diacid-gGlu-OEG), des1, 30S, 31G]mimylin.
425. The mimylin derivative according to any one of the preceding aspects 163-424, having the compound name [N-terminal(C20 diacid-gGlu-2×OEG), des1, 30S, 31G]mimylin.
426. The mimylin derivative according to any one of the preceding aspects 163-425, having the compound name [N-terminal(C20 diacid-gGlu-3×OEG), des1, 30S, 31G]mimylin.
427. The mimylin derivative according to any one of the preceding aspects 163-426, having the compound name [N-terminal(C20 diacid-gGlu-4×OEG), des1, 30S, 31G]mimylin.
428. The mimylin derivative according to any one of the preceding aspects 163-427, having the compound name [N-terminal(C20 diacid-gGlu-5×OEG), des1, 30S, 31G]mimylin.
429. The mimylin derivative according to any one of the preceding aspects 163-428, having the compound name [N-terminal(C18 diacid-gGlu), des1, 30S, 31G]mimylin.
430. The mimylin derivative according to any one of the preceding aspects 163-429, having the compound name [N-terminal(C16 diacid-gGlu), des1, 30S, 31G]mimylin.
431. The mimylin derivative according to any one of the preceding aspects 163-430, having the compound name [N-terminal(C18 diacid), des1, 30S, 31G]mimylin.
432. The mimylin derivative according to any one of the preceding aspects 163-431, having the compound name [N-terminal(C16 diacid), des1, 30S, 31G]mimylin.
433. The mimylin derivative according to any one of the preceding aspects 163-432, having the compound name [N-terminal(C14 diacid-gGlu), des1, 30S, 31G]mimylin.
434. The mimylin derivative according to any one of the preceding aspects 163-433, having the compound name [N-terminal(C14 diacid), des1, 30S, 31G]mimylin.
435. The mimylin derivative according to any one of the preceding aspects 163-434, having the compound name [des1, 4K(C20 diacid-gGlu), 30S, 31G]mimylin.
436. The mimylin derivative according to any one of the preceding aspects 163-435, having the compound name [des1, 16K(C20 diacid-gGlu), 30S, 31G]mimylin.
437. The mimylin derivative according to any one of the preceding aspects 163-436, having the compound name [des1, 19K(C20 diacid-gGlu), 30S, 31G]mimylin.
438. The mimylin derivative according to any one of the preceding aspects 163-437, having the compound name [des1, 27K(C20 diacid-gGlu), 30S, 31G]mimylin.

439. The mimylin derivative according to any one of the preceding aspects 163-438, having the compound name [N-terminal(C20 diacid-gGlu), des1, 23Y, 30S, 31G]mimylin.
440. The mimylin derivative according to any one of the preceding aspects 163-439, having the compound name [N-terminal(C20 diacid-gGlu), 1A, 23Y, 30S, 31G]mimylin.
441. The mimylin derivative according to any one of the preceding aspects 163-440, having the compound name [N-terminal(C18 diacid-gGlu), des1, 23Y, 30S, 31G]mimylin.
442. The mimylin derivative according to any one of the preceding aspects 163-441, having the compound name [N-terminal(C20 diacid-gGlu), des1, 30S, 31G, 33Y]mimylin.
443. The mimylin derivative according to any one of the preceding aspects 163-442, having the compound name [N-terminal(C20 diacid-gGlu), des1, 30S, 31G, 33H]mimylin.
444. The mimylin derivative according to any one of the preceding aspects 163-443, having the compound name [N-terminal(C20 diacid-gGlu), des1, 30S, 31G, 33F]mimylin.
445. The mimylin derivative according to any one of the preceding aspects 163-444, having the compound name [N-terminal(C20 diacid-gGlu), des1, 30S, 31G, 33L]mimylin.
446. The mimylin derivative according to any one of the preceding aspects 163-445, having the compound name [N-terminal(C20 diacid-gGlu), des1, 30S, 31G, 33S]mimylin.
447. The mimylin derivative according to any one of the preceding aspects 163-446, having the compound name [N-terminal(C20 diacid-gGlu), des1, 30S, 31G, 33G]mimylin.
448. The mimylin derivative according to any one of the preceding aspects 163-447, having the compound name [N-terminal(C20 diacid-gGlu), des1, 30S, 31G, 33A]mimylin.
449. The mimylin derivative according to any one of the preceding aspects 163-448, having the compound name [N-terminal(C20 diacid-gGlu), des1, 15E, 30S, 31G]mimylin.
450. The mimylin derivative according to any one of the preceding aspects 163-449, having the compound name [N-terminal(C20 diacid-gGlu), des1, 15e, 30S, 31G]mimylin.
451. The mimylin derivative according to any one of the preceding aspects 163-450, having the compound name [N-terminal(acetyl), des1, 4K(C20 diacid-gGlu), 30S, 31G]mimylin.
452. The mimylin derivative according to any one of the preceding aspects 163-451, having the compound name [N-terminal(acetyl), des1, 16K(C20 diacid-gGlu), 30S, 31G]mimylin.
453. The mimylin derivative according to any one of the preceding aspects 163-452, having the compound name [N-terminal(acetyl), des1, 19K(C20 diacid-gGlu), 30S, 31G]mimylin.
454. The mimylin derivative according to any one of the preceding aspects 163-553, having the compound name [N-terminal(acetyl), des1, 27K(C20 diacid-gGlu), 30S, 31G]mimylin.
455. The mimylin derivative according to any one of the preceding aspects 163-454, having the compound name [N-terminal(C20 diacid-gGlu), des1, 12H, 30S, 31G]mimylin.
456. The mimylin derivative according to any one of the preceding aspects 163-455, having the compound name [N-terminal(C20 diacid-gGlu), des1, 25H, 30S, 31G]mimylin.
457. The mimylin derivative according to any one of the preceding aspects 163-456, having the compound name [N-terminal(C20 diacid-gGlu), des1, 30T, 31G, 32T]mimylin.
458. The mimylin derivative according to any one of the preceding aspects 163-457, having the compound name [N-terminal(C18 diacid-gGlu), des1, 30S, 31G, 32P]mimylin.
459. The mimylin derivative according to any one of the preceding aspects 163-458, having the compound name [N-terminal(C18 diacid-gGlu), des1, 9V, 30S, 31G]mimylin.
460. The mimylin derivative according to any one of the preceding aspects 163-459, having the compound name [N-terminal(C18 diacid), 5I, 9I, 10I, 20I]mimylin.
461. The mimylin derivative according to any one of the preceding aspects 163-460, having the compound name [N-terminal(C18 diacid-gGlu), des1, 4Q, 30S, 31G]mimylin.
462. The mimylin derivative according to any one of the preceding aspects 163-461, having the compound name [N-terminal(C20 diacid-gGlu), des1, 4G, 23Y, 30S, 31G]mimylin.
463. The mimylin derivative according to any one of the preceding aspects 163-462, having the compound name [N-terminal(C20 diacid-gGlu), des1, 23Y, 30S, 31G, 33Y]mimylin.
464. The mimylin derivative according to any one of the preceding aspects 163-463, having the compound name [N-terminal(C20 diacid-gGlu), des1, 23Y, 30S, 31G, 32A]mimylin.
465. The mimylin derivative according to any one of the preceding aspects 163-464, having the compound name [N-terminal(C20 diacid-gGlu), des1, 21S, 23Y, 30S, 31G]mimylin.
466. The mimylin derivative according to any one of the preceding aspects 163-465, having the compound name [N-terminal(C20 diacid-gGlu), -1E, 1A, 23Y, 30S, 31G]mimylin.
467. The mimylin derivative according to any one of the preceding aspects 163-466, having the compound name [N-terminal(C20 diacid-gGlu), des1, 12H, 25H, 30S, 31G]mimylin.
468. The mimylin derivative according to any one of the preceding aspects 163-467, having the compound name [N-terminal(C18 diacid-gGlu), des1, 6T, 9V, 30S, 31G]mimylin.
469. The mimylin derivative according to any one of the preceding aspects 163-468, having the compound name [N-terminal(C18 diacid-gGlu), des1, 5V, 9V, 30S, 31G]mimylin.
470. The mimylin derivative according to any one of the preceding aspects 163-469, having the compound name [N-terminal(C18 diacid-gGlu), des1, 4Q, 16Q, 30S, 31G]mimylin.
471. The mimylin derivative according to any one of the preceding aspects 163-470, having the compound name [N-terminal(C20 diacid-gGlu), des1, 23Y, 30S, 31G, 33Y, C-terminal(-)]mimylin.

472. The mimylin derivative according to any one of the preceding aspects 163-471, having the compound name [N-terminal(C20 diacid-gGlu), des1, 23Y, 30S, 31G, 34G, C-terminal(–)]mimylin.
473. The mimylin derivative according to any one of the preceding aspects 163-472, having the compound name [N-terminal(C20 diacid-gGlu), des1, 23Y, 30S, 31G, 34K, C-terminal(–)]mimylin.
474. The mimylin derivative according to any one of the preceding aspects 163-473, having the compound name [N-terminal(C20 diacid-gGlu), des1, 9S, 23Y, 30S, 31G, 33Y]mimylin.
475. The mimylin derivative according to any one of the preceding aspects 163-474, having the compound name [N-terminal(C20 diacid-gGlu), des1, 9T, 21S, 23Y, 30S, 31G]mimylin.
476. The mimylin derivative according to any one of the preceding aspects 163-475, having the compound name [N-terminal(C20 diacid-gGlu), des1, 12H, 25H, 30T, 31G, 32T]mimylin.
477. The mimylin derivative according to any one of the preceding aspects 163-476, having the compound name [N-terminal(C18 diacid-gGlu), des1, 6T, 9V, 30S, 31G, 32T]mimylin.
478. The mimylin derivative according to any one of the preceding aspects 163-477, having the compound name [N-terminal(C18 diacid-gGlu), des1, 6T, 9V, 30T, 31G, 32T]mimylin.
479. The mimylin derivative according to any one of the preceding aspects 163-478, having the compound name [N-terminal(C18 diacid-gGlu), des1, 5V, 9V, 10V, 30S, 31G]mimylin.
480. The mimylin derivative according to any one of the preceding aspects 163-479, having the compound name [N-terminal(C20 diacid-gGlu), des1, 21S, 23Y, 30S, 31G, 33Y]mimylin.
481. The mimylin derivative according to any one of the preceding aspects 163-480, having the compound name [N-terminal(C20 diacid-gGlu), des1, 4G, 9V, 23Y, 30S, 31G, 32T]mimylin.
482. The mimylin derivative according to any one of the preceding aspects 163-481, having the compound name [N-terminal(C20 diacid-gGlu), des1, 9T, 21S, 23Y, 30S, 31G, 33Y]mimylin.
483. The mimylin derivative according to any one of the preceding aspects 163-482, having the compound name [N-terminal(C20 diacid-gGlu), des1, 9S, 21S, 23Y, 30S, 31G, 33Y]mimylin.
484. The mimylin derivative according to any one of the preceding aspects 163-483, having the compound name [N-terminal(C20 diacid-gGlu), des1, 12K, 23Y, 25K, 30S, 31G, 33Y]mimylin.
485. The mimylin derivative according to any one of the preceding aspects 163-484, having the compound name [N-terminal(C18 diacid-gGlu), des1, 5V, 9V, 10V, 20V, 30S, 31G]mimylin.
486. The mimylin derivative according to any one of the preceding aspects 163-485, having the compound name [N-terminal(C20 diacid-gGlu), 4G, 15Q, 21Q, 23Y, 30S, 31G, 32T, 33Y]mimylin.
487. The mimylin derivative according to any one of the preceding aspects 163-486, having the compound name [N-terminal(C20 diacid-gGlu), des1, 4G, 9V, 23Y, 30S, 31G, 32T, 33Y]mimylin.
488. The mimylin derivative according to any one of the preceding aspects 163-487, having the compound name [N-terminal(C18 diacid-gGlu), des1, 6T, 9V, 14T, 21E, 30T, 31G, 32T]mimylin.
489. The mimylin derivative according to any one of the preceding aspects 163-488, having the compound name [N-terminal(C18 diacid-gGlu), des1, 6T, 9V, 14E, 21T, 30T, 31G, 32T]mimylin.
490. The mimylin derivative according to any one of the preceding aspects 163-489, having the compound name [des1, 4G, 15Q, 21Q, 23Y, 30S, 31K(C20 diacid-gGlu), 32T, 33Y]mimylin.
491. The mimylin derivative according to any one of the preceding aspects 163-490, having the compound name [N-terminal(C20 diacid-gGlu), des1, 4G, 15Q, 21E, 23Y, 30S, 31G, 32T, 33Y]mimylin.
492. The mimylin derivative according to any one of the preceding aspects 163-491, having the compound name [N-terminal(C20 diacid-gGlu), des1, 4G, 15Q, 21Q, 23Y, 30S, 31Q, 32T, 33Y]mimylin.
493. The mimylin derivative according to any one of the preceding aspects 163-492, having the compound name [N-terminal(C18 diacid-gGlu), des1, 4G, 15Q, 21Q, 23Y, 30S, 31G, 32T, 33Y]mimylin.
494. The mimylin derivative according to any one of the preceding aspects 163-493, having the compound name [N-terminal(C20 diacid), des1, 4G, 15Q, 21Q, 23Y, 30S, 31G, 32T, 33Y]mimylin.
495. The mimylin derivative according to any one of the preceding aspects 163-494, having the compound name [N-terminal(C20 diacid-gGlu), des1, 4G, 15T, 21E, 23Y, 30S, 31G, 32T, 33Y]mimylin.
496. The mimylin derivative according to any one of the preceding aspects 163-495, having the compound name [N-terminal(C20 diacid-gGlu), des1, 4G, 15E, 21Q, 23Y, 30S, 31G, 32T, 33Y]mimylin.
497. The mimylin derivative according to any one of the preceding aspects 163-496, having the compound name [N-terminal(C20 diacid-gGlu), des1, 9V, 15Q, 21Q, 23Y, 30S, 31G, 32T, 33Y]mimylin.
498. The mimylin derivative according to any one of the preceding aspects 163-497, having the compound name [N-terminal(C20 diacid-gGlu), 4Q, 9V, 15Q, 21Q, 23Y, 27G, 30S, 31G, 32T, 33Y]mimylin.
499. The mimylin derivative according to any one of the preceding aspects 163-498, having the compound name [N-terminal(C20 diacid-gGlu), des1, 4Q, 9V, 15Q, 21Q, 23Y, 30S, 31Q, 32T, 33Y]mimylin.
500. The mimylin derivative according to any one of the preceding aspects 163-499, having the compound name [N-terminal(C20 diacid-gGlu), des1, 4G, 15Q, 21Q, 23Y, 25H, 30S, 31G, 32T, 33Y]mimylin.
501. The mimylin derivative according to any one of the preceding aspects 163-500, having the compound name [N-terminal(C20 diacid-gGlu), des1, 4G, 9V, 15Q, 21Q, 23Y, 30S, 31G, 32T, 33Y]mimylin.
502. The mimylin derivative according to any one of the preceding aspects 163-501, having the compound name [N-terminal(C20 diacid-gGlu), des1, 4G, 9V, 15Q, 21Q, 23Y, 30S, 31Q, 32T, 33Y]mimylin.
503. The mimylin derivative according to any one of the preceding aspects 163-502, having the compound name [N-terminal(C20 diacid-gGlu-2×OEG), des1, 4G, 9V, 15Q, 21Q, 23Y, 30S, 31G, 32T, 33Y]mimylin.
504. The mimylin derivative according to any one of the preceding aspects 163-503, having the compound name

[N-terminal(C18 diacid-gGlu-2×OEG), des1, 4G, 9V, 15Q, 21Q, 23Y, 30S, 31G, 32T, 33Y]mimylin.

505. The mimylin derivative according to any one of the preceding aspects 163-504, having the compound name [N-terminal(C20 diacid-gGlu), des1, 4G, 9V, 15Q, 21Q, 23Y, 30S, 31A, 32T, 33Y]mimylin.

506. The mimylin derivative according to any one of the preceding aspects 163-505, having the compound name [N-terminal(C20 diacid-gGlu), des1, 2L, 4G, 9V, 21S, 23Y, 30S, 31G, 32T, 33Y]mimylin.

507. The mimylin derivative according to any one of the preceding aspects 163-506, having the compound name [N-terminal(C20 diacid-gGlu), des1, 4G, 9T, 15Q, 21Q, 23Y, 30S, 31G, 32T, 33Y]mimylin.

508. The mimylin derivative according to any one of the preceding aspects 163-507, having the compound name [N-terminal(C20 diacid-gGlu), des1, 4G, 9V, 15Q, 21Q, 23Y, 25P, 30S, 31Q, 32T, 33Y]mimylin.

509. The mimylin derivative according to any one of the preceding aspects 163-508, having the compound name [N-terminal(C20 diacid-gGlu), des1, 4G, 8L, 9V, 15Q, 21Q, 23Y, 30S, 31Q, 32T, 33Y]mimylin.

510. The mimylin derivative according to any one of the preceding aspects 163-509, having the compound name [N-terminal(C20 diacid-gGlu), des1, 2L, 4G, 9V, 15Q, 21Q, 23Y, 30S, 31Q, 32T, 33Y]mimylin.

511. The mimylin derivative according to any one of the preceding aspects 163-510, having the compound name [N-terminal(C20 diacid-gGlu), des1, 4G, 9T, 15Q, 21Q, 23Y, 25P, 30S, 31Q, 32T, 33Y]mimylin.

512. The mimylin derivative according to any one of the preceding aspects 163-511, having the compound name [N-terminal(C20 diacid-gGlu), 2L, 4G, 8L, 9V, 15Q, 21Q, 23Y, 27G, 30S, 31G, 32T, 33Y]mimylin.

513. The mimylin derivative according to any one of the preceding aspects 163-512, having the compound name [N-terminal(C20 diacid-gGlu), des1, 4G, 9V, 15Q, 21Q, 23aQ, 23bT, 23cY, 30S, 31Q, 32T, 33Y]mimylin.

514. The mimylin derivative according to any one of the preceding aspects 163-513, having the compound name [N-terminal(C20 diacid-gGlu), des1, 4G, 9V, 12K, 15Q, 21Q, 23Y, 25P, 30S, 31G, 32T, 33Y]mimylin.

515. The mimylin derivative according to any one of the preceding aspects 163-514, having the compound name [N-terminal(C20 diacid-gGlu), des1, 4Q, 9V, 15Q, 16R, 19R, 21Q, 23Y, 27Q, 30S, 31Q, 32T, 33Y]mimylin.

516. The mimylin derivative according to any one of the preceding aspects 163-515, having the compound name [N-terminal(C20 diacid-gGlu), des1, 2L, 4Q, 8L, 9V, 15Q, 16R, 19R, 21Q, 23Y, 27Q, 30S, 31Q, 32T, 33Y]mimylin.

517. The mimylin derivative according to any one of the preceding aspects 163-515, having an $IC_{50}$ in a human amylin receptor binding assay (Assay V) of about 1200 pM or less.

518. The mimylin derivative according to any one of the preceding aspects 163-515 having an $IC_{50}$ in a human amylin receptor binding assay (Assay V) of about 1000 pM or less.

519. The mimylin derivative according to any one of the preceding aspects 163-515 having an $IC_{50}$ in a human amylin receptor binding assay (Assay V) of about 900 pM or less.

520. The mimylin derivative according to any one of the preceding aspects 163-515, having an $IC_{50}$ in a human amylin receptor binding assay (Assay V) of about 800 pM or less.

521. The mimylin derivative according to any one of the preceding aspects 163-515, having an $IC_{50}$ in a human amylin receptor binding assay (Assay V) of about 700 pM or less.

522. The mimylin derivative according to any one of the preceding aspects 163-515 having an $IC_{50}$ in a human amylin receptor binding assay (Assay V) of about 600 pM or less.

523. The mimylin derivative according to any one of the preceding aspects 163-515 having an $IC_{50}$ in a human amylin receptor binding assay (Assay V) of about 500 pM or less.

524. The mimylin derivative according to any one of the preceding aspects 163-515 having an $IC_{50}$ in a human amylin receptor binding assay (Assay V) of about 400 pM or less.

525. The mimylin derivative according to any one of the preceding aspects v having an $IC_{50}$ in a human amylin receptor binding assay (Assay V) of about 300 pM or less.

526. The mimylin derivative according to any one of the preceding aspects 163-515, having an $IC_{50}$ in a human amylin receptor binding assay (Assay V) of about 200 pM or less.

527. The mimylin derivative according to any one of the preceding aspects 163-515 having an $IC_{50}$ in a human amylin receptor binding assay (Assay V) of about 100 pM or less.

528. The mimylin derivative according to any one of the preceding aspects 163-515 having an $IC_{50}$ in a human amylin receptor binding assay (Assay V) of about 90 pM or less.

529. The mimylin derivative according to any one of the preceding aspects 163-515 having an $IC_{50}$ in a human amylin receptor binding assay (Assay V) of about 80 pM or less.

530. The mimylin derivative according to any one of the preceding aspects 163-515, having an $IC_{50}$ in a human amylin receptor binding assay (Assay V) of about 70 pM or less.

531. The mimylin derivative according to any one of the preceding aspects 163-515 having an $IC_{50}$ in a human amylin receptor binding assay (Assay V) of about 60 pM or less.

532. The mimylin derivative according to any one of the preceding aspects 163-515, having an $IC_{50}$ in a human amylin receptor binding assay (Assay V) of about 50 pM or less.

533. The mimylin derivative according to any one of the preceding aspects 163-515, having an $IC_{50}$ in a human amylin receptor binding assay (Assay V) of about 40 pM or less.

534. The mimylin derivative according to any one of the preceding aspects 163-515, having an $IC_{50}$ in a human amylin receptor binding assay (Assay V) of about 30 pM or less.

535. The mimylin derivative according to any one of the preceding aspects 163-515 having an $IC_{50}$ in a human amylin receptor binding assay (Assay V) of about 20 pM or less.

536. The mimylin derivative according to any one of the preceding aspects 163-515 having an $IC_{50}$ in a human amylin receptor binding assay (Assay V) of about 19 pM or less.

537. The mimylin derivative according to any one of the preceding aspects 163-515, having an $IC_{50}$ in a human amylin receptor binding assay (Assay V) of about 18 pM or less.

538. The mimylin derivative according to any one of the preceding aspects 163-515 having an $IC_{50}$ in a human amylin receptor binding assay (Assay V) of about 17 pM or less.
539. The mimylin derivative according to any one of the preceding aspects 163-515, having an $IC_{50}$ in a human amylin receptor binding assay (Assay V) of about 16 pM or less.
540. The mimylin derivative according to any one of the preceding aspects 163-515 having an $IC_{50}$ in a human amylin receptor binding assay (Assay V) of about 15 pM or less.
541. The mimylin derivative according to any one of the preceding aspects 163-515, having an $IC_{50}$ in a human amylin receptor binding assay (Assay V) of about 14 pM or less.
542. The mimylin derivative according to any one of the preceding aspects 163-515 having an $IC_{50}$ in a human amylin receptor binding assay (Assay V) of about 13 pM or less 543. The mimylin derivative according to any one of the preceding aspects 163-515, having an $IC_{50}$ in a human amylin receptor binding assay (Assay V) of about 12 pM or less.
544. The mimylin derivative according to any one of the preceding aspects 163-515 having an $IC_{50}$ in a human amylin receptor binding assay (Assay V) of about 10 pM or less.
545. The mimylin derivative according to any one of the preceding aspects 163-515 having an $IC_{50}$ in a human amylin receptor binding assay (Assay V) of about 5 pM or less.
546. The mimylin derivative according to any one of the preceding aspects 163-515 having an $IC_{50}$ in a human amylin receptor binding assay (Assay V) of about 1000 pM or less.
547. The mimylin derivative according to any one of the preceding aspects 163-515 having wherein said derivative has an $EC_{50}$ in a human amylin receptor functional Assay IIb of about 1000 pM or less.
548. The mimylin derivative according to any one of the preceding aspects 163-515 $EC_{50}$ in a human amylin receptor function I Assay IIb of about 900 pM or less.
549. The mimylin derivative according to any one of the preceding aspects 163-515, wherein said derivative has an $EC_{50}$ in a human amylin receptor functional Assay IIb of about 800 pM or less.
550. The mimylin derivative according to any one of the preceding aspects 163-515 wherein said derivative has an $EC_{50}$ in a human amylin receptor functional Assay IIb of about 700 pM or less.
551. The mimylin derivative according to any one of the preceding aspects 163-515 wherein said derivative has an $EC_{50}$ in a human amylin receptor functional Assay IIb of about 600 pM or less.
552. The mimylin derivative according to any one of the preceding aspects 163-515 wherein said derivative has an $EC_{50}$ in a human amylin receptor functional Assay IIb of about 500 pM or less.
553. The mimylin derivative according to any one of the preceding aspects 151-542, wherein said derivative has an $EC_{50}$ in a human amylin receptor functional Assay IIb of about 90 pM or less.
554. The mimylin derivative according to any one of the preceding aspects 163-515, wherein said derivative has an $EC_{50}$ in a human amylin receptor functional Assay IIb of about 80 pM or less.
555. The mimylin derivative according to any one of the preceding aspects 163-515 wherein said derivative has an $EC_{50}$ in a human amylin receptor functional Assay IIb of about 70 pM or less.
556. The mimylin derivative according to any one of the preceding aspects 163-515 wherein said derivative has an $EC_{50}$ in a human amylin receptor functional Assay IIb of about 60 pM or less.
557. The mimylin derivative according to any one of the preceding aspects 163-515, wherein said derivative has an $EC_{50}$ in a human amylin receptor functional Assay IIb of about 50 pM or less.
558. The mimylin derivative according to any one of the preceding aspects 163-515 wherein said derivative has an $EC_{50}$ in a human amylin receptor functional Assay IIb of about 40 pM or less.
559. The mimylin derivative according to any one of the preceding aspects 163-515 wherein said derivative has an $EC_{50}$ in a human amylin receptor functional Assay IIb of about 30 pM or less.
560. The mimylin derivative according to any one of the preceding aspects 163-515 wherein said derivative has an $EC_{50}$ in a human amylin receptor functional Assay IIb of about 20 pM or less.
561. The mimylin derivative according to any one of the preceding aspects 163-515 wherein said derivative has an $EC_{50}$ in a human amylin receptor functional Assay IIb of about 19 pM or less.
562. The mimylin derivative according to any one of the preceding aspects 163-515 wherein said derivative has an $EC_{50}$ in a human amylin receptor functional Assay IIb of about 18 pM or less.
563. The mimylin derivative according to any one of the preceding aspects 163-515, wherein said derivative has an $EC_{50}$ in a human amylin receptor function I Assay IIb of about 17 pM or less.
564. The mimylin derivative according to any one of the preceding aspects 163-515, wherein said derivative has an $EC_{50}$ in a human amylin receptor functional Assay IIb of about 16 pM or less.
565. The mimylin derivative according to any one of the preceding aspects 163-515, wherein said derivative has an $EC_{50}$ in a human amylin receptor functional Assay IIb of about 15 pM or less.
566. The mimylin derivative according to any one of the preceding aspects 163-515 wherein said derivative has an $EC_{50}$ in a human amylin receptor functional Assay IIb of about 14 pM or less.
567. The mimylin derivative according to any one of the preceding aspects 163-515 wherein said derivative has an $EC_{50}$ in a human amylin receptor functional Assay IIb of about 13 pM or less.
568. The mimylin derivative according to any one of the preceding aspects 163-515 wherein said derivative has an $EC_{50}$ in a human amylin receptor functional Assay IIb of about 12 pM or less.
569. The mimylin derivative according to any one of the preceding aspects 163-515 wherein said derivative has an $EC_{50}$ in a human amylin receptor functional Assay IIb of about 10 pM or less.
570. The mimylin derivative according to any one of preceding aspects 163-515 wherein said derivative has an $EC_{50}$ in a human amylin receptor functional Assay IIb of about 5 pM or less.
571. The mimylin derivative according to any one of the preceding aspects 163-515, wherein said derivative is selected from table 13.

572. The mimylin derivative according to any one of the preceding aspects 163-515, wherein said derivative is selected from table 14.
573. The mimylin derivative according to any one of the preceding aspects 163-515 which is physically stable.
574. The mimylin derivative according to any one of the preceding aspects 163-515 which is physically stable when tested in Assay III as disclosed herein.
575. The mimylin derivative according to any one of the preceding aspects 163-515 which is physically stable when tested in Assay IIIa as disclosed herein.
576. The mimylin derivative according to any one of the preceding aspects 163-515, which has as high lag-time and recovery as possible when tested in Assay III as disclosed herein.
577. The mimylin derivative according to any one of the preceding aspects 163-515, which has as high lag-time and recovery as possible when tested in Assay Ma as disclosed herein.
578. The mimylin derivative according to any one of the preceding aspects 163-577, wherein said mimylin peptide or mimylin derivative reduces appetite.
579. The mimylin derivative according to any one of the preceding aspects 163-578 wherein said mimylin peptide or mimylin derivative increase appetite.
580. The mimylin derivative according to any one of the preceding aspects 163-580, wherein said mimylin peptide or mimylin derivative reduces food intake.
581. The mimylin derivative according to any one of the preceding aspects 163-581, wherein said mimylin peptide or mimylin derivative increase food intake.
582. The mimylin derivative according to any one of the preceding aspects 163-582, wherein said mimylin peptide or mimylin derivative reduces body weight.
583. The mimylin derivative according to any one of the preceding aspects 163-583, wherein said mimylin peptide or mimylin derivative increase body weight.
584. The mimylin derivative according to any one of the preceding aspects 163-583, showing show food intake reduction in rats tested according to Assay I after administration of 3 nmol/kg or 30 nmol/kg.
585. The mimylin derivative according to any one of the preceding aspects 163-583, showing food intake reduction in rats tested according to Assay I after administration of 3 nmol/kg or 30 nmol/kg.
586. The mimylin derivative according to any one of the preceding aspects 163-583, showing reduction in food intake in rats tested according to Assay I which can be seen within 0-24 hours after administration of 3 nmol/kg or 30 nmol/kg.
587. The mimylin derivative according to any one of the preceding aspects 163-583, showing reduction in food intake in rats tested according to Assay I which can be seen within 0-24 and/or 24-48 hours after administration of 3 nmol/kg or 30 nmol/kg.
588. The mimylin derivative according to any one of the preceding aspects 163-583, showing reduction in food intake by at least 10% in rats tested according to Assay I which can be seen within 0-24 hours after administration of 3 nmol/kg or 30 nmol/kg.
589. The mimylin derivative according to any one of the preceding 163-583, showing reduction in food intake by at least 10% in rats tested according to Assay I which can be seen within 24-48 hours after administration of 3 nmol/kg or 30 nmol/kg.
590. The mimylin derivative according to ant of the preceding aspects 163-583 selected form the compounds listed in Table 8.
591. The mimylin derivative according to ant of the preceding aspects 163-583 selected form the compounds listed in Table 9.
592. The mimylin derivative according to ant of the preceding aspects 163-583 selected form the compounds listed in Table 10.
593. The mimylin derivative according to ant of the preceding aspects 163-583 selected form the compounds listed in Table 11.
594. The mimylin derivative according to ant of the preceding aspects 163-583 selected form the compounds listed in Table 12.
595. The mimylin peptide according to any one of the preceding aspects 1-162 or mimylin derivative according to any one of the preceding aspects 163-583 which has low immunogenicity.
596. The mimylin peptide according to any one of the preceding aspects 1-162 or mimylin derivative according to any one of the preceding aspects 162-583 which has low immunogenicity determined by immunogenicity prediction as disclosed in Assay XI.
597. The mimylin peptide according to any one of the preceding aspects 1-162 or mimylin derivative according to any one of the preceding aspects 162-583 being an agonist of the amylin and/or calcitonin receptor.
598. A pharmaceutical formulation comprising a mimylin peptide or mimylin derivative according to any one of the aspects 1-587.
599. An aqueous pharmaceutical formulation comprising a mimylin peptide 1-162 or mimylin derivative according to any one of the preceding aspects 162-583, wherein said formulation is suitable for injection and comprises pharmaceutical acceptable ingredients.
600. The pharmaceutical formulation according to aspect 599, wherein said pharmaceutical acceptable ingredients are selected from pH buffers, tonicity agents and antimicrobial agents
601. The pharmaceutical formulation according to aspect 599-600, wherein one or more of said pharmaceutical acceptable ingredients are selected from the list consisting of: glycerol, phosphate, propylene glycol, phenol, m-cresol, or a combination of phenol and m-cresol or equivalents of said ingredients listed.
602. The pharmaceutical formulation according to aspect 599-600, wherein
  a. said phosphate is present in a range of between about 4 mM to about 12 mM,
  b. said propylene glycol about 1 mg/mL to about 30 mg/mL,
  c. m-cresol about 5 mM to about 40 mM,
  d. phenol about 5 mM to about 90 mM,
  e. said mimylin peptide concentration is selected in a concentration about 0.001 mM to about 15 mM, and
  f. said glycerol about 1 mg/mL to about 30 mg/mL.
603. The pharmaceutical formulation according to aspect 599-600, wherein
  a. said phosphate is present in a range of between about 4 mM to about 12 mM, preferably about 6 mM to about 10 mM, more preferably about 7 mM to about 9 mM, even more preferred about 8 mM,
  b. said propylene glycol about 1 mg/mL to about 30 mg/mL, preferably about 5 mg/mL to about 25 mg/mL, more preferably about 10 mg/mL to about 20 mg/mL, even more preferred about 14 mg/mL, c. m-cresol about 5 mM to about 40 mM, preferably about 10 mM to about 35 mM, more preferably about 20 mM to about 35 mM, even more preferred about 30 mM,
d. phenol about 5 mM to about 90 mM, preferably about 10 mM to about 70 mM, more preferably about 30 mM to about 65 mM, even more preferred about 58 mM,
e. said mimylin peptide concentration is selected in a concentration about 0.001 mg/mL to about 15 mg/mL, preferably about 0.01 to about 10 mg/mL, more preferably about 0.1 mg/mL to about 1 mg/mL
f. said glycerol about 1 mg/mL to about 30 mg/mL, preferably about 5 mg/mL to about 25 mg/mL, more preferably about 10 mg/mL to about 20 mg/mL, even more preferred about 16 mg/mL.

604. The pharmaceutical formulation according to any one of the aspects 599-600, wherein the concentration of antimicrobial agents, i.e. said concentration of either phenol, m-cresol, or a combination of phenol and m-cresol is selected to accommodate the Food and Drug Administration's (USA) or European Medicine Agency's (EU) requirements for antimicrobial preservation of the chosen concentration of peptide.

605. The pharmaceutical formulation according to any one of the aspects 586-589, wherein the concentration of phenol is selected to accommodate the Food and Drug Administration's (USA) or European Medicine Agency's (EU) requirements for antimicrobial preservation of the chosen concentration of peptide.

606. The pharmaceutical formulation according to aspect 599-600, wherein
a. said phosphate is about 8 mM,
b. said propylene glycol is about 14 mg/mL,
c. phenol is about 58 mM,
d. said mimylin peptide concentration is selected in a concentration about 0.001 mg/mL to about 15 mg/mL, preferably about 0.01 to about 10 mg/mL, more preferably about 0.1 mg/mL to about 1 mg/mL 607. The pharmaceutical formulation according to aspect 599-600, wherein
a. said phosphate is about 8 mM,
b. said propylene glycol is about 14 mg/mL,
c. phenol is about 58 mM, optionally said phenol can be exchanged with m-cresol or be combined with m-cresol according to any one of the preceding aspects 599-606,
d. said mimylin peptide concentration is selected in a concentration about 0.001 mg/mL to about 15 mg/mL, preferably about 0.01 to about 10 mg/mL, more preferably about 0.1 mg/mL to about 1 mg/mL 608. The pharmaceutical formulation according to any one of the aspects 599-607, wherein the pH is between about 6.6 to about 8.6, preferably between about 7.0 to about 8.4, more preferably about 7.4 to about 8.2.

609. The pharmaceutical formulation according to any one of the aspects 599-608, wherein the pH is about 7.4.

610. The pharmaceutical formulation according to aspects 599-609, wherein the pH is about 8.2.

611. The pharmaceutical formulation according to any one of the aspects 599-610, wherein the formulation comprises a compound of Ex #40 or 46 and phosphate, preferably between about 8-10 mM and
a. optionally phenol or m-cresol, between about 19-60 mM, preferably about 19 mM, about 30 mM about 50 mM or about 58 mM, and
b. further optionally propylene glycol about 10-20 mg/mL, preferably about 14 mg/mL,
c. Further optionally comprising glycerol about 10 to 100 mg/mL, preferably about 10, about 16 mg/mL,
d. further optionally comprising NaCl up to 50 mM,
e. further optionally comprising HEPES in the range between 5-15 mM, preferably 10 mM,
f. at a pH 7.4 or 8.2.

612. The pharmaceutical formulation according to any one of the embodiments 599-611 wherein the formulation comprises a compound of Ex. #40 or 46, wherein said formulation is selected from any one of the formulations selected from the group consisting of the formulations F1-F38, preferably Formulations F3, F4, F7, F8, F13, F14, F15, F16, F21, F22, F23, F24, F25, F26, F27, F28.

613. The pharmaceutical formulation according to any one of the aspects 599-612 wherein the formulation comprises a compound of Ex. #2, wherein said formulation is selected from the list consisting of the formulations: F39-120.

614. The pharmaceutical formulation according to any one of the aspects 599-613, wherein said formulation has any pH in the range pH 4 to pH 9.

615. The pharmaceutical according to any one of the aspects 599-614, wherein said formulation has a neutral pH.

616. The pharmaceutical according to any one of the aspects 599-615, wherein said formulation has a pH of about pH 6.5 to pH 8.

617. The pharmaceutical formulation according to any one of the aspects 599-616, wherein said formulation has a pH of about pH 6.5 to pH 7.

618. The pharmaceutical formulation according to any one of the aspects 599-617, wherein said formulation has a pH of about pH 7 to pH 7.5.

619. The pharmaceutical formulation according to any one of the aspects 599-618, further comprising another mimylin peptide or mimylin derivative.

620. A pharmaceutical formulation, co-formulation or co-treatment comprising a mimylin peptide according to any one of the aspects 1-162 or derivative according to any one of the aspects 162-583 and further comprising other peptides.

621. A pharmaceutical formulation, co-formulation or co-treatment comprising a mimylin peptide according to any one of the aspects 1-162 or derivative according to any one of the aspects 162-583 and further comprising other peptides, wherein said further peptides are for the treatment of obesity.

622. A pharmaceutical formulation, co-formulation or co-treatment comprising a mimylin peptide according to any one of the aspects 1-162 or derivative according to any one of the aspects 162-583 or formulations according to any one of the aspects 619-622 and further comprising other peptides for the treatment of obesity.

623. A pharmaceutical formulation, co-formulation or co-treatment according to any one of the aspects 622 or 623, wherein said further peptides for treatment of obesity are any GLP-1 peptide.

624. The pharmaceutical formulation according to aspect 623, wherein said GLP-1 peptide is a GLP-1 compound, GLP-1 analogue or GLP-1 derivative.

625. The pharmaceutical formulation, co-formulation or co-treatment according to any one of the aspects 623 or 624, wherein said GLP-1 compound, GLP-1 analogue or GLP-1 derivative is semaglutide or liraglutide.

626. The pharmaceutical formulation, co-formulation or co-treatment according to any one of the preceding aspects 620-625, wherein
a. said mimylin peptide concentration is selected in a concentration about 0.001 mg/mL to about 15 mg/mL, preferably about 0.01 to about 10 mg/mL, more preferably about 0.1 mg/mL to about 1 mg/mL
b. GLP-1 compound, GLP-1 analogue or GLP-1 derivative is semaglutide or liraglutide concentration is between about 0.5 mg/mL and about 6 mg/mL, preferably about 0.5 mg/mL, about 1 mg/mL, about 1.6 mg/mL, about 2 mg/mL, about 3 mg/mL, about 4.1 mg/mL or about 6 mg/mL 627. The pharmaceutical formulation, co-formulation or co-treatment according to any one of the preceding aspects 620-625, wherein the
a. said mimylin peptide concentration is selected in a concentration about 0.001 mg/mL to about 15 mg/mL, preferably about 0.01 to about 10 mg/mL, more preferably about 0.1 mg/mL to about 1 mg/mL
b. GLP-1 compound, GLP-1 analogue or GLP-1 derivative is semaglutide or liraglutide concentration is between about 0.5 mg/mL and about 6 mg/mL, preferably selected from the list consisting of: about 1 mg/mL, about 3 mg/mL, about 6 mg/mL,
wherein said GLP-1 compound, GLP-1 analogue or GLP-1 derivative is selected to be liraglutide 628. The pharmaceutical formulation, co-formulation or co-treatment according to any one of the preceding aspects 620-625, wherein the
a. said mimylin peptide concentration is selected in a concentration about 0.001 mg/mL to about 15 mg/mL, preferably about 0.01 to about 10 mg/mL, more preferably about 0.1 mg/mL to about 1 mg/mL
b. GLP-1 compound, GLP-1 analogue or GLP-1 derivative is semaglutide or liraglutide concentration is between about 0.5 mg/mL and about 6 mg/mL, preferably about 0.5 mg/mL, about 2 mg/mL, about 4.1 mg/mL,
wherein said GLP-1 compound, GLP-1 analogue or GLP-1 derivative is selected to be semaglutide 629. The pharmaceutical formulation, co-formulation or co-treatment according to any one of the preceding aspects 620-625, wherein
a. said phosphate is present in a range of between about 4 mM to about 12 mM, preferably about 6 mM to about 10 mM, more preferably about 7 mM to about 9 mM, even more preferred about 8 mM,
b. said propylene glycol about 1 mg/mL to about 30 mg/mL, preferably about 5 mg/mL to about 25 mg/mL, more preferably about 10 mg/mL to about 20 mg/mL, even more preferred about 14 mg/mL,
c. m-cresol about 5 mM to about 40 mM, preferably about 10 mM to about 35 mM, more preferably about 20 mM to about 35 mM, even more preferred about 30 mM,
d. phenol about 5 mM to about 90 mM, preferably about 10 mM to about 70 mM, more preferably about 30 mM to about 65 mM, even more preferred about 58 mM,
e. said mimylin peptide concentration is selected in a concentration about 0.001 mg/mL to about 15 mg/mL, preferably about 0.01 to about 10 mg/mL, more preferably about 0.1 mg/mL to about 1 mg/mL
f. GLP-1 compound, GLP-1 analogue or GLP-1 derivative is semaglutide or liraglutide in a concentration between about 0.5 mg/mL and about 6 mg/mL, preferably about 0.5 mg/mL, about 2 mg/mL, about 4.1 mg/mL,
g. said glycerol about 1 mg/mL to about 30 mg/mL, preferably about 5 mg/mL to about 25 mg/mL, more preferably about 10 mg/mL to about 20 mg/mL, even more preferred about 16 mg/mL.

630. The pharmaceutical formulation according to any one of the aspects 620-625, wherein the concentration of antimicrobial agents, i.e. said concentration of either phenol, m-cresol, or a combination of phenol and m-cresol is selected to accommodate the Food and Drug Administration's (USA) or European Medicine Agency's (EU) requirements for conservation of the chosen total antimicrobial preservation of peptides.

631. The pharmaceutical formulation according to any one of the aspects 615-618, wherein the concentration of phenol is selected to accommodate the Food and Drug Administration's (USA) or European Medicine Agency's (EU) requirements for antimicrobial preservation of the chosen total concentration of peptides.

632. The pharmaceutical formulation, co-formulation or co-treatment according to any one of the preceding aspects 620-631, wherein the pH is between about 7.2 to about 8.6.

633. The pharmaceutical formulation, co-formulation or co-treatment according to aspect 620-632, wherein the pH is between about 7.2 to about 8.6, wherein said pH is selected to be about 7.4 when the GLP-1 derivative is semaglutide and to be about 8.2 when the GLP-1 derivative is selected to be liraglutide.

634. The pharmaceutical formulation, co-formulation or co-treatment according to any one of the aspects 620-633, wherein said formulation, co-formulation or co-treatment is selected from the list consisting of: F121-150.

635. A pharmaceutical formulation, co-formulation or co-treatment according to any one of the aspects 620-634 wherein said GLP-1 compound and said mimylin peptide will not affect each others pK profile (as described for a selection of compounds in Table 20), measured according to Assay (XV).

636. A pharmaceutical formulation, co-formulation or co-treatment according to any one of the aspects 620-635 wherein said GLP-1 compound and said mimylin peptide will not affect each others pK profile, wherein said mimylin peptide is compound of Ex. #2 or Ex. #46 and said GLP-1 compound is liraglutide, measured according to Assay (XV).

637. A pharmaceutical formulation, co-formulation or co-treatment according to any one of the aspects 620-636 further comprising other peptides/polypeptides for the treatment of type 2 diabetes or other metabolic syndromes.

638. The mimylin peptide, derivative or pharmaceutical formulation, co-formulation or co-treatment according to any one of the preceding aspects, for the use as a medicament.

639. The mimylin peptide, derivative or pharmaceutical formulation, co-formulation or co-treatment according to any one of the preceding aspects, for the use in treating subjects suffering from overweight or obesity.

640. The mimylin peptide, derivative or pharmaceutical formulation, co-formulation or co-treatment according to any one of the preceding aspects, for the use in treating subjects suffering from underweight.

641. The mimylin peptide, derivative or pharmaceutical formulation, co-formulation or co-treatment according to any one of the preceding aspects, for the use in treating subjects suffering reduced appetite.

642. The mimylin peptide, derivative or pharmaceutical formulation, co-formulation or co-treatment according to aspect 639, wherein said formulation comprising a mimylin compound according to this invention induces body weight reduction in DIO rats by between about 4 to about 12%, most preferably about 10%, when measured as described by ASSAY (XIV).
643. The mimylin peptide, derivative or pharmaceutical formulation, co-formulation or co-treatment according to aspect 639, wherein said formulation comprising a mimylin compound according to this invention induces body weight reduction in DIO rats by between about 4 to about 12%, most preferably about 10%, when measured as described by ASSAY (XIV), wherein said compound is Ex compound #2 in the concentrations given in Table 36.
644. The mimylin peptide, derivative or pharmaceutical formulation, co-formulation or co-treatment according to aspect 639, wherein said co-formulation or co-treatment of mimylin peptide with a GLP-1 peptide induces body weight reduction in DIO rats by between about 5 to about 20%, preferably about 8 to about 12%, most preferably about 10%, when measured as described by ASSAY (XIV).
645. The mimylin peptide, derivative or pharmaceutical formulation, co-formulation or co-treatment according to aspect 639, wherein said co-formulation or co-treatment of mimylin peptide with a GLP-1 peptide induces body weight reduction in DIO rats by between about 5 to about 20%, preferably about 8 to about 12%, most preferably about 10%, when measured as described by ASSAY (XIV), wherein said compounds are example compound #2 and liraglutide in the concentrations given in Table 36.
646. The mimylin peptide, derivative or pharmaceutical formulation, co-formulation or co-treatment according to any one of the preceding aspects, for the use in treating obesity, wherein a human subject suffering from obesity may have a BMI of ≥30; this subject may also be referred to as obese.
647. The mimylin peptide, derivative or pharmaceutical formulation, co-formulation or co-treatment according to any one of the preceding aspects, for the use in treating obesity, wherein a human subject suffering from obesity may have a BMI of 35 or a BMI in the range of ≥30 to <40.
648. The mimylin peptide, derivative or pharmaceutical formulation, co-formulation or co-treatment according to any one of the preceding aspects, for the use in treating obesity, wherein said obesity is severe obesity or morbid obesity, wherein the human subject may have a BMI of ≥40.
649. The mimylin peptide, derivative or pharmaceutical formulation, co-formulation or co-treatment according to any one of the preceding aspects, for the use in treating overweight subjects, wherein said subjects may have a BMI of such as a BMI of ≥27.
650. The mimylin peptide, derivative, pharmaceutical formulations or co-formulations according to any one of the preceding aspects.
651. The mimylin peptide, derivative, pharmaceutical formulations or co-formulations according to any one of the preceding aspects, for the use in treating osteoporosis.
652. The mimylin peptide, derivative or pharmaceutical formulations according to any one of the preceding aspects, for the use in treating type I or II diabetes.
653. The mimylin peptide, derivative or pharmaceutical formulation, co-formulation or co-treatment according to any one of the preceding aspects, 1-625 for the use in treating neuropathic pain.
654. The use according the aspect 653, wherein said neuropathic pain is selected from the list of: spinal canal stenosis, migraine, diabetic neuropathy and complex regional pain syndrome.

Definitions

A receptor agonist may be defined as a peptide or analogue that binds to a receptor and elicits a response typical of the natural ligand. A full agonist may be defined as one that elicits a response of the same magnitude as the natural ligand (see e.g. "Principles of Biochemistry", A L Lehninger, D L Nelson, M M Cox, Second Edition, Worth Publishers, 1993, page 763).

Thus, for example, an "Amylin receptor agonist" may be defined as a compound which is capable of binding to the Amylin receptor and capable of activating it. And a "full" amylin receptor agonist may be defined as an Amylin receptor agonist which is capable of eliciting a magnitude of Amylin receptor response that is similar to native amylin. An Amylin receptor agonist will often also be a calcitonin receptor agonist. Examples of Amylin receptor agonists are human amylin, pramlintide and calcitonin.

The term "human amylin" as used herein relates to the polypeptide human amylin having the sequence
KCNTATCATQRLANFLVHSSNNFGAILSSTNVG-SNTY (SEQ ID NO: 5)
which structure can be shown as

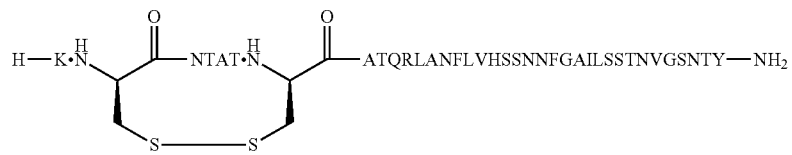

The term "pramlintide" as used herein relates to the peptide having the sequence
KCNTATCATQRLANFLVHSSNNFGPILPPTNVG-SNTY (SEQ ID NO: 6)
which structure can be shown as

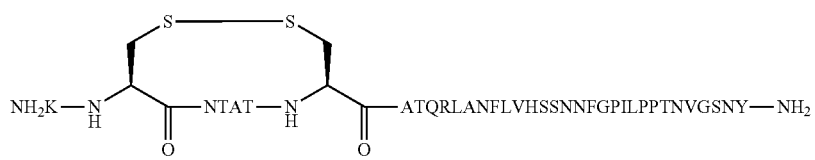

Pramlintide has a disulfide bridge between the two Cys residues and a C-terminal amide group.

The term "calcitonin" means salmon calcitonin or human calcitonin.

The term "salmon calcitonin" or "sCT" means the native protein sequence of salmon calcitonin as disclosed in Niall et al (1969), *Biochemistry* vol 64, FIG. 2. Salmon calcitonin is a polypeptide which consists of 32 amino acids and the sequence

CSNLSTCVLGKLSQELHKLQTYPRTNTGSGTP (SEQ ID NO: 7)

which structure can be shown as

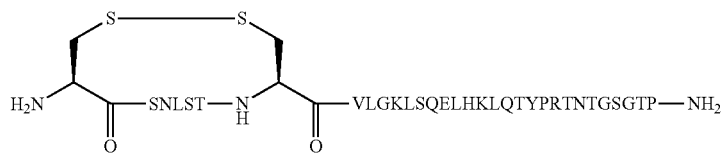

It has a disulfide bridge between the first and seventh amino acids at the amino-terminal end of the polypeptide chain and a prolinamide group at the carboxyl terminal amino acid being essential for its biological activity.

The term "human calcitonin" means the native protein sequence of human calcitonin as disclosed in Niall et al (1969), *Biochemistry* vol 64, FIG. 2. Human calcitonin is a polypeptide which consists of 32 amino acids and the sequence

CGNLSTCMLGTYTQDFNKFHTFPQTAIGVGAP (SEQ ID NO: 8)

which structure can be shown as

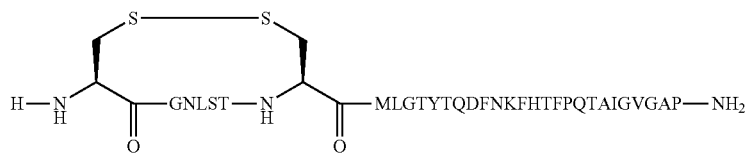

It has a disulfide bridge between the first and seventh amino acids at the amino-terminal end of the polypeptide chain, the disulfide bridge being essential for its biological activity, and a prolinamide group at the carboxyl terminal amino acid.

The term "mimylin" as used herein refers to the protein with the sequence EASELSTAALGRLSAELHELATL-PRTETGPESP (SEQ ID NO: 1)

Mimylin is a novel amylin and calcitonin receptor agonist, with less than 60% sequence identity to salmon calcitonin and has no disulfide bridges.

The term "analogue" as used herein describes a peptide comprising one or more amino acid modifications, such as but not limited to substitution and/or one or more deletion and/or one or more addition of any one of the amino acid residues for any natural or unnatural amino acid, synthetic amino acids or peptidomimetics and/or the attachment of a side chain to any one of the natural or unnatural amino acids, synthetic amino acids or peptidomimetics at any available position. The addition or deletion of amino acid residues can take place at the N-terminal of the peptide and/or at the C-terminal of the peptide.

Thus the term "mimylin analogue" or "analogue of mimylin" as used herein refers to a peptide, wherein one or more amino acids have been modified relative to SEQ ID NO: 1. The term "mimylin peptide" as used herein refers to the group of compounds comprising mimylin or an analogue thereof. The term "mimylin peptide" will thus also cover the term "backbone" and "polypeptides".

When used herein the term "natural amino acid" is an amino acid (with the usual three letter codes & one letter codes in parenthesis) selected from the group consisting of: Glycine (Gly & G), proline (Pro & P), alanine (Ala & A), valine (Val & V), leucine (Leu & L), isoleucine (Ile & I), methionine (Met & M), cysteine (Cys & C), phenylalanine (Phe & F), tyrosine (Tyr & Y), tryptophan (Trp & W), histidine (His & H), lysine (Lys & K), arginine (Arg & R), glutamine (Gln & Q), asparagine (Asn & N), glutamic acid (Glu & E), aspartic acid (Asp & D), serine (Ser & S) and threonine (Thr & T). If anywhere in this invention reference is made to a mimylin peptide, analogue or derivative or peptides according to this invention comprising or not comprising G, P, A, V, L, I, M, C, F, Y, H, K, R, Q, N, E, D, S or T, without specifying further, amino acids are meant. If not otherwise indicated amino acids indicated with a single letter code in CAPITAL letters indicate the L-isoform, if however the amino acid is indicated with a lower case letter, this amino acid is used/applied as it's D-form.

If, due to typing errors, there are deviations from the commonly used codes, the commonly used codes apply. The amino acids present in the mimylin peptides of the present invention are, preferably, amino acids which can be coded for by a nucleic acid.

If the analogue contains either more than 33 amino acid residues or less than 33 amino acid residues then the skilled person can still align that sequence with the sequence of mimylin (SEQ ID NO: 1) to determine the placement number of the corresponding, respective amino acid residue. A method for determination of "sequence identity" between two analogues the two peptides mimylin and [23Y, 30S, 31G]mimylin (i.e. EX. #24bb) are aligned. The sequence identity of the mimylin analogue relative to mimylin is given by the number of aligned identical residues minus the number of different residues divided by the total number of residues in mimylin (i.e. SEQ ID NO: 1) Accordingly, in said example the sequence identity is (33-3)/33. A suitable alignment program can be tested with a suitable alignment program is "needle", which is a Needleman-Wunsch alignment. The algorithm for this alignment program is described in Needleman, S. B. and Wunsch, C. D., (1970), Journal of Molecular Biology, 48: 443-453.

In the numbering sequence of SEQ ID NO: 1, and according to established practice in the art, the amino acid residue at the N-terminal Glutamic acid (E) is assigned no. 1 and subsequent amino acid residues are numbered consecutively, ending at the C-terminal with proline (P) assigned no. 33. Therefore, generally, any reference herein to position number of an amino acid residue provides its location in a 33 amino acid sequence; said 33 amino acid sequence being an analogue of mimylin. For example, a reference to an analogue modified at position 14 may refer to an analogue wherein the 14th amino residue out of the 33 amino acids in the analogue has been modified.

In other words, the amino acid sequence numbering of the analogue provides the position of each analogue with respect to a 33 amino acid sequence, wherein the numbering is consecutive and ascending in the direction from the N-terminal to the C-terminal.

Analogues may be described by reference to the number of the amino acid residue in mimylin (SEQ ID NO: 1) which is modified, i.e. by its position, and the nature of the modification. The following are non-limiting examples of appropriate analogue nomenclature. For example:

[I9]-mimylin designates a mimylin analogue (mimylin) wherein the change from mimylin is the substitution of A position 9 with I, such as in example compound 10. One example can also be the designation des1 in relation to an analogue of mimylin, which refers to an analogue in which the N-terminal amino acid, Glutamic acid, has been deleted. An analogue of mimylin, where the N-terminal amino acid has been deleted may also be designated des1 mimylin.

[des1, 4K, 30S, 31G]mimylin designates a mimylin analogue (mimylin), in which the E at position 1 has been deleted and E in position 4 had been substituted with K, P in position 30 with S and E in position 31 with G.

If an additional amino acid, such as Glutamic acid (E) is added to the N-terminal in the position before position 1, the amino acid change will be indicated as −1E, because no position 0 exist. In the aspects this may be described with the term that no amino acid is present in position −1, thus the term "no amino acid" as used herein is equivalent to the term "absent", which means that the position to which reference is made simply does not comprise any amino acid residue.

Thus the analogue of the derivative of compound 83 (EX. #83) is denominated as follows: [−1E, 1A, 23Y, 30S, 31G] mimylin and thus discloses a sequence in which E is added to the N-terminal amino acid, the N-terminal amino acid is modified from an E to A, P of position 30 in SEQ ID NO: 1 is substituted with S and E in position 31 of SEQ ID NO: 1 is substituted with G.

In mimylin peptides, such as EX. #130bb the indication of 23aQ, 23bT, 23cY means, that QTY has been inserted between amino acid position 23 and position 24 relative to the numbering of SEQ ID NO: 1 and the amino acid in position 23 is the original amino acid; L. The sequence of the mimylin peptide 1300bb is thus;
ASGLSTAVLGRLSQELHELQTLQTYPRTETGSQTY (SEQ ID NO: 119).

As is apparent from the above examples, amino acid residues may be identified by their full name, their one-letter code, and/or their three-letter code. These three ways are fully equivalent.

The expressions "conforms to", "corresponds to", "a position equivalent to" or "corresponding position" as used herein may be used to characterise the site of modification in an analogue of mimylin by reference to SEQ ID NO: 1. Equivalent, identical or corresponding positions are easily deduced, e.g. by simple handwriting and eyeballing; and/or a standard protein or mimylin peptide alignment program may be used, such as "needle" which is a Needleman-Wunsch alignment. The algorithm is described in Needleman, S. B. and Wunsch, C. D., (1970), Journal of Molecular Biology, 48: 443-453, and the align program by Myers and W. Miller in "Optimal Alignments in Linear Space" CABIOS (computer applications in the BioSciences) (1988) 4:11-17. For the alignment, the default scoring matrix BLOSUM62 and the default identity matrix may be used, and the penalty for the first residue in a gap may be set at −10 and the penalties for additional residues in a gap at −0.5.

Naming the derivatives herein was performed as follows: [Y(C)aa$_1$X(S)aa$_2$]P (Formula1), wherein P is the peptide (such as for example mimylin), aa1 and aa2 describe one, more or no amino acid modifications of said peptide, (S) discloses the side chain which is attached to the peptide and X describes the attachment site. X in formula 1 can thus indicate N-terminal, when the side chain (S) is attached in the N-terminal or a specific position such as K4, which then exemplified for a mimylin derivative would refer to a substitution of the amino acid E with K in position 4 corresponding to SEQ ID NO: 1, to which the side chain (S) is attached. Y(C) in formula 1 may be placed throughout the sequence, wherever relevant and indicates if additional modifications to the amino acid sequence of chemical nature are present; Y indicates the placement, so "c-terminal (−)" indicates that the chemical change is present in the c-terminal. The (−) of "c-terminal (−) means "acid", thus "c-terminal(−)" means c-terminal acid. The if "N-terminal(acetyl)" is mentioned in the naming this means that and acetyl is present at the N-terminal instead of the regular alpha amino group. If C is "c-terminal (−)" the c-terminal end of the peptide is a c-terminal acid instead of a c-terminal amide. If no indication of "c-terminal (−)" is made in the derivative name, the c-terminal of the derivatives according to the present invention are c-terminal amides.

The following are non-limiting examples of appropriate derivative nomenclature. [N-terminal(C18diacid-gGlu)] mimylin designates a mimylin derivative, wherein mimylin in the N-terminal with a side chain comprising a C18diacid as the protracting moiety and gGlu as a linker.
[N-terminal(C18diacid-gGlu) 2P, 9V]mimylin designates a mimylin derivative, wherein a mimylin analogue comprising modification 2P and 9V, relative to the numbering of SEQ ID NO: 1 is derivatised in the N-terminal with a side chain comprising a C18diacid as the protracting moiety and gGlu as a linker.

The mimylin peptide may comprise one or more side chains on one or more of the amino acid residues. Such mimylin peptides may also be called mimylin derivatives or salmon calcitonin derivatives.

The term "derivative" as used herein means a chemically modified peptide, in which one or more side chains have been covalently attached to the peptide. The term "side chain" may also be referred to as a "substituent". A derivative comprising such side chains will thus be "derivatised" peptide or "derivatised" analogue.

The term "mimylin compound" as used herein refers to the analogues and derivatives according to this invention which comprise a backbone which make reference to the mimylin backbone. Such as, but not limited to the compounds of Table 1 and 4.

In a particular embodiment, the side chain is capable of forming non-covalent aggregates with albumin and may thus also be referred to as "albumin binding moiety", thereby promoting the circulation of the derivative with the blood stream, and also having the effect of protracting the time of action of the derivative, due to the fact that the aggregate of the mimylin-derivative and albumin is only slowly disintegrated to release the active pharmaceutical ingredient. Thus, the "substituent", or "side chain", as a whole is preferably referred to as an "albumin binding moiety".

The term "albumin binding moiety" as used herein refers to any chemical group capable of non-covalent binding to albumin, i.e. has albumin binding affinity. In some embodiments the albumin binding moiety comprises an acyl group.

In another particular embodiment the side chain comprises a portion which is particularly relevant for the albumin binding and thereby the protraction, which portion may accordingly be referred to as a "protracting moiety" or "protractor". The protracting moiety may be near, preferably at, the terminal (or distal, or free) end of the albumin binding moiety, relative to its point of attachment to the peptide.

In a still further particular embodiment the side chain comprises a portion between the protracting moiety and the point of attachment to the peptide, which portion may be referred to as a "linker", "linker moiety", "spacer", or the like. The linker may be optional, and hence in that case the side chain may be identical to the protracting moiety.

The albumin binding moiety, the protracting moiety, or the linker may be covalently attached to a lysine residue of the mimylin peptide by acylation, i.e. via an amide bond formed between a carboxylic acid group thereof (of the albumin binding moiety, the protracting moiety, or the linker) and an amino group of the lysine residue or amino acid residue in the N-terminal. Additional or alternative conjugation chemistry includes alkylation, ester formation, or amide formation, or coupling to a cysteine residue, such as by maleimide or haloacetamide (such as bromo-/chloro-/iodo-) coupling.

In a preferred embodiment, an active ester of the albumin binding moiety, preferably comprising a protracting moiety and a linker, is covalently linked to an amino group of a lysine residue, preferably the epsilon amino group thereof, under formation of an amide bond, as explained above.

Unless otherwise stated, when reference is made to an acylation of a lysine residue or N-terminal amino acid, it is understood to be to the epsilon-amino group of said lysine residue or alpha-amino group of the N-terminal amino acid.

The term "epsilon amino group" or "ε-amino group", used herein in relation to lysine, refers to the amino group at the 6 position, using the IUPAC standard numbering conventions. The term "alpha amino group" or "α-amino group" refers to the amino group at the 2 position, using the IUPAC standard numbering conventions. We refer to the following structure.

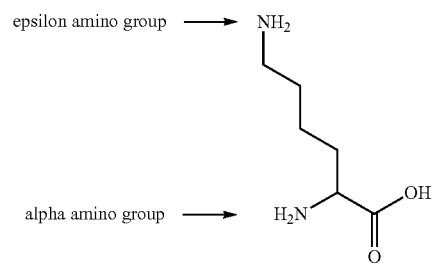

The term "linker" as used herein includes suitable side chains that can join a moiety, such as a chemical moiety, to the mimylin peptide, such as the mimylin peptide backbone. Thus, the linker and the chemical moiety become a side chain together. The moiety joined to the linker may be any suitable moiety. Examples include an albumin binding moiety.

A linker as used herein provides a bridge or link between an amino group on the mimylin peptide backbone and an acyl group on the moiety—such as an albumin binding moiety. The linker may be bound to, or near to, the N terminal amino acid residue. Preferably the linker is bound to the amino acid in position 1 of the mimylin analogue.

Another example of a linker is a combination of at least one amino acid and an amine.

The formula of another linker according to the present invention; OEG is shown below:

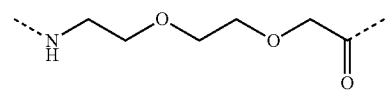

The linker can contribute to and/or enhance the binding effect of the moiety (for example the albumin binding moiety), e.g. a linker comprising γGlu can enhance the albumin binding effect of the mimylin peptide.

By using the term "γGlu" or "gGlu" or "gammaGlu" or "gamma-L-Glu" is meant an amino acid with the following structure and used interchangeably herein (also shown in FIG. 2):

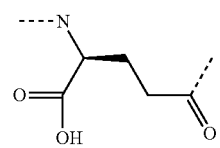

By using the term "γGlu-OEG" is meant a moiety with the following structure:

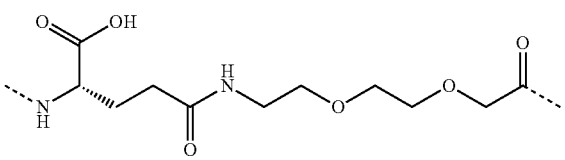

By using the term "γGlu-OEG-OEG" is meant moiety with the following structure:

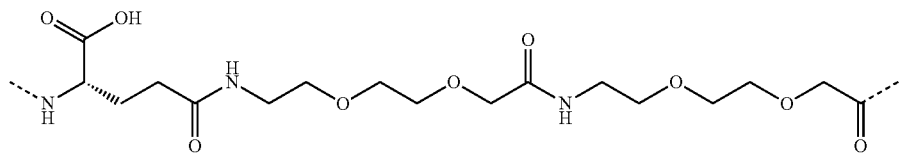

The term "fatty acid" refers to aliphatic monocarboxylic acids having from 4 to 28 carbon atoms, it is preferably un-branched, and it may be saturated or unsaturated. In the present invention fatty acids comprising 10 to 16 amino acids are preferred.

The term "fatty diacid" refers to fatty acids as defined above but with an additional carboxylic acid group in the omega position. Thus, fatty diacids are dicarboxylic acids. In the present invention fatty acids comprising 14 to 20 amino acids are preferred.

The term "substituent" or "side chain" as used herein means any suitable moiety bonded, in particular covalently bonded, to an amino acid residue, in particular to any available position on an amino acid residue. Typically, the suitable moiety is a chemical moiety.

"Albumin binding affinity" may be determined by several methods known within the art. In one method the compound to be tested is radiolabeled with e.g. $^{125}$I or $^{3}$H and incubated with immobilized albumin (Kurtzhals et. al., Biochem. J., 312, 725-731 (1995)). The binding of the compound relative to a standard is calculated. In another method a related compound is radiolabeled and its binding to albumin immobilized on e.g. SPA beads is competed by a dilution series of the compound to be tested. The $EC_{50}$ value for the competition is a measure of the affinity of the compound. In a third method, the receptor affinity or potency of a compound is tested at different concentrations of albumin, and the shift in relative affinity or potency of the compound as a function of albumin concentration reflects its affinity for albumin.

The term "disulfide bridge" can interchangeably be used for the term "disulfide bond".

The mimylin peptides of the present invention exhibit good potency. The term "potency" is used to describe the effect of a given compound in assays where a sigmoidal relationship between log concentration and the effect of a compound has been established.

Furthermore, the response should be variable from 0 to 100%. EC (effective concentration)$_{50}$ can be used to describe the concentration of a given compound yielding a response of 50% in the assay, such as in the functional assay.

The mimylin peptides of the present invention exhibit good activity. The term "activity" refers to the ability to reduce appetite and/or increase satiety. The activity can be tested by the ability to reduce appetite as e.g. described in the Assay (I) herein.

The mimylin peptides of the present invention exhibit good physical stability. The term "physical stability" of a mimylin peptide according to the invention, or a formulation thereof refers to the tendency of the mimylin peptide not to form biologically inactive and/or insoluble aggregates as a result of exposure to thermo-mechanical stresses and/or interaction with interfaces and surfaces that are destabilizing, such as hydrophobic surfaces and interfaces. Physical stability of the aqueous mimylin peptide formulations may be evaluated by means of visual inspection, ThT fibrillation assay (sometimes referred to as a ThT fibrillogenesis assay) and/or turbidity measurements as described elsewhere herein. Visual inspection of the formulations is performed in a sharp focused light with a dark background. The turbidity of the formulation is characterised by a visual score ranking the degree of turbidity for instance on a scale from 0 to 3 (a formulation showing no turbidity corresponds to a visual score 0, and a formulation showing visual turbidity in daylight corresponds to visual score 3). A formulation is classified physical unstable with respect to protein aggregation, when it shows visual turbidity in daylight. Alternatively, the turbidity of the formulation can be evaluated by simple turbidity measurements well-known to the skilled person.

The mimylin peptides of the present invention exhibit good chemical stability. The term "chemical stability" of a mimylin peptide according to the invention or of a formulation thereof refers to no chemical covalent changes in the mimylin peptide structure hence avoiding the formation of chemical degradation products with potentially less potency and/or potentially increased immunogenic properties compared to the parent (native) mimylin peptide structure. Various chemical degradation products can be formed depending on the type and nature of the parent mimylin peptide and the environment to which the mimylin peptide is exposed. Chemical degradation can most probably not be completely avoided and increasing amounts of chemical degradation products is often seen during storage and use of peptide formulations as well-known by the person skilled in the art. Most peptides are prone to deamidation, a process in which the side chain amide group in glutaminyl or asparaginyl residues is hydrolysed to form a free carboxylic acid. Other degradations pathways involves formation of high molecular weight transformation products where two or more peptide molecules are covalently bound to each other through transamidation and/or disulfide interactions leading to formation of covalently bound dimer, oligomer and polymer degradation products (*Stability of Protein Pharmaceuticals*, Ahern. T. J. & Manning M. C., Plenum Press, New York 1992). Oxidation (of for instance methionine residues) can be mentioned as another variant of chemical degradation. The chemical stability of the mimylin peptide formulation can be evaluated by measuring the amount of the chemical degradation products at various time-points after exposure to different environmental conditions (the formation of degradation products can often be accelerated by for instance increasing temperature). The amount of each individual degradation product is often determined by separation of the degradation products depending on molecule size and/or charge using various chromatography techniques (e.g. SEC-HPLC and/or RP-HPLC).

While certain features of the invention have been illustrated and described herein, many modifications, substitutions, changes, and equivalents will now occur to those of ordinary skill in the art. It is, therefore, to be understood that the appended aspects are intended to cover all such modifications and changes as fall within the true spirit of the invention.

Non-limiting examples of GLP-1 compound include a natural GLP-1, a GLP-1 analogue or a GLP-1 derivative. In its broadest sense, the term "natural GLP-1" refers to a naturally occurring molecule of the glucagon family of peptides or of the family of exendins. The glucagon family of peptides are encoded by the pre-proglucagon gene and encompasses three small peptides with a high degree of homology, i.e. glucagon (1-29), GLP-1 (1-37) and GLP-2 (1-33). The term "natural GLP-1" also refers to the human GLP-1(7-37), the sequence of which is disclosed as SEQ ID NO: 1 in WO 2006097537 and included herein by reference, and to the human GLP-1(7-36)NH2. Exendins are peptides expressed in lizards and like GLP-1, are insulinotropic. Examples of naturally occurring exendins are exendin-3 and exendin-4.

In a particular embodiment, the term "natural GLP-1" refers to glucagon (1-29), GLP-1 (1-37) and GLP-2 (1-33), the human GLP-1(7-37)), the human GLP-1(7-36)NH2, exendin-3 and exendin-4.

In a particular embodiment, the term "GLP-1 compound" does not include the human GLP-1(7-36)NH2. In a particular embodiment, the term "GLP-1 compound" does not include the human GLP-1(7-37).

In a particular embodiment, the term "GLP-1 compound" does not include glucagon.

In a particular embodiment, the term "GLP-1 compound" does not include the human GLP-1(7-36)NH2 and glucagon or does not include human GLP-1(7-36)NH2, human GLP-1(7-37) and glucagon.

In a more particular embodiment, the term "natural GLP-1" only refers to the human GLP-1(7-37).

In its broadest sense, the term "GLP-1 analogue" or "analogue of GLP-1" as used herein refers to an analogue of a natural GLP-1. It does not include a natural GLP-1 as such as defined herein. In particular, the term "GLP-1 analogue" does not include glucagon (1-29), GLP-1 (1-37) and GLP-2 (1-33), the human GLP-1(7-37)), the human GLP-1(7-36)NH2, exendin-3 and exendin-4.

In a particular embodiment, the term "GLP-1 analogue" or "analogue of GLP-1" as used herein refers to an analogue of human GLP-1(7-37) or GLP-1(7-36)NH2. Non-limiting examples of GLP-1 analogues comprise exenatide and taspoglutide.

In a particular embodiment, the "GLP-1 analogues" comprise analogues with a maximum of 17 amino acid modifications (i.e. up to 17 amino acids have been modified in total, where the changes can be amino acid substitutions, additions and/or deletions) compared to a natural GLP-1 of reference or, in particular, compared to human GLP-1-(7-36)NH2 or GLP-1(7-37).

All amino acids for which the optical isomer is not stated is to be understood to mean the L-isomer.

In embodiments of the invention a GLP-1 compound or GLP-1 analogue comprises a maximum of 17 amino acids which have been modified (substituted, deleted, added or any combination thereof) relative to a natural GLP-1 of reference or, in particular, relative to human GLP-1-(7-36)NH2 or GLP-1(7-37). In embodiments of the invention a GLP-1 compound or GLP-1 analogue comprises a maximum of 15 amino acids which have been modified. In embodiments of the invention a GLP-1 compound or GLP-1 analogue comprises a maximum of 10 amino acids which have been modified. In embodiments of the invention a GLP-1 compound or GLP-1 analogue comprises a maximum of 8 amino acids which have been modified. In embodiments of the invention a GLP-1 compound or GLP-1 analogue comprises a maximum of 7 amino acids which have been modified. In embodiments of the invention a GLP-1 compound or GLP-1 analogue comprises a maximum of 6 amino acids which have been modified. In embodiments of the invention a GLP-1 compound or GLP-1 analogue comprises a maximum of 5 amino acids which have been modified. In embodiments of the invention a GLP-1 compound or GLP-1 analogue comprises a maximum of 4 amino acids which have been modified. In embodiments of the invention a GLP-1 compound or GLP-1 analogue comprises a maximum of 3 amino acids which have been modified. In embodiments of the invention a GLP-1 compound or GLP-1 analogue comprises a maximum of 2 amino acids which have been modified. In embodiments of the invention 1 amino acid has been modified relative to a natural GLP-1 of reference or, in particular, relative to human GLP-1-(7-36)NH2 or GLP-1(7-37). In a particular embodiment, the amino acid modifications of this paragraph are relative to human GLP-1(7-37).

In a particular embodiment, the GLP-1 analogues comprise a substitution of the amino acid residue in position 34 from Lys to Arg, i.e. $Arg^{34}$, compared to GLP-1(7-37) or GLP-1-(7-36)NH2. In a particular embodiment, the GLP-1 analogues have a substitution of the amino acid residue in position 8 from Ala to Aib (alpha-amino-iso-butyric acid), i.e. $Aib^8$. In a particular embodiment, the GLP-1 analogues have the $Arg^{34}$ substitution, the $Aib^8$ substitution, or both the $Arg^{34}$ and $Aib^8$ substitutions, and possibly one more amino acid modification compared to GLP-1(7-37) or GLP-1-(7-36)NH2. In a particular embodiment, the amino acid modifications of this paragraph are relative to human GLP-1(7-37).

In its broadest sense, the term "GLP-1 derivative" or "derivative of GLP-1" as used herein refers to a derivative of a parent peptide selected from a natural GLP-1 or an analogue thereof. It does not include a natural GLP-1 as such as defined herein. In particular, the term "GLP-1 derivative" does not include glucagon (1-29), GLP-1 (1-37) and GLP-2 (1-33), the human GLP-1(7-37)), the human GLP-1(7-36) NH2, exendin-3 and exendin-4.

In a particular embodiment, the term "GLP-1 derivative" or "derivative of GLP-1" refers to a derivative of a parent peptide selected from human GLP-1(7-37) or GLP-1(7-36) NH2 or an analogue thereof.

In a particular embodiment, the term "GLP-1 derivative" or "derivative of GLP-1" as used herein refers to a derivative of a parent peptide selected from a GLP-1 analogue, where said analogue comprises a maximum of 17 amino acid modifications compared to a natural GLP-1 of reference or, in particular, compared to human GLP-1-(7-36)NH2 or GLP-1(7-37), or, in particular, compared to human GLP-1 (7-37). In one embodiment, the "GLP-1 derivative", in particular when defined in comparison to GLP-1(7-37), does not include GLP-1(7-36)NH2.

Typical modifications are amides, carbohydrates, alkyl groups, acyl groups, esters, polyethylene glycol (PEG) groups, sialylation groups, glycosylation groups and the like of a parent peptide. In one embodiment, the parent peptide is a GLP-1 analogue as defined above.

In particular embodiments, the side chain has at least 10 carbon atoms, or at least 15, 20, 25, 30, 35, or at least 40 carbon atoms. In further particular embodiments, the side chain may further include at least 5 hetero atoms, in particular O and N, for example at least 7, 9, 10, 12, 15, 17, or at least 20 hetero atoms, such as at least 1, 2, or 3 N-atoms, and/or at least 3, 6, 9, 12, or 15 O-atoms.

In one embodiment, the term "GLP-1 derivative" refers to acylated GLP-1 parent peptide. In a particular embodiment, the term "GLP-1 derivative" refers to acylated GLP-1 parent peptide where the parent peptide is selected from a GLP-1 analogue comprising a maximum of 17 amino acid modifications compared to a natural GLP-1 of reference or, in particular, compared to human GLP-1-(7-36)NH2 or GLP-1(7-37).

The side chain may be covalently attached to a lysine residue of the GLP-1 parent peptide by acylation. Additional or alternative conjugation chemistry includes alkylation, ester formation, or amide formation, or coupling to a cysteine residue, such as by maleimide or haloacetamide (such as bromo-/fluoro-/iodo-) coupling.

For the preparation, an active ester of the side chain is covalently linked to an amino group of a lysine residue, preferably the epsilon amino group thereof, under formation of an amide bond (this process being referred to as acylation).

Preferred side chains include, for example, fatty acids and fatty diacids. The term fatty acid refers to aliphatic monocarboxylic acids having from 4 to 28 carbon atoms. The fatty acid may be branched or unbranched. The fatty acid is preferably even numbered. The fatty acid may be saturated or unsaturated. The term fatty diacid refers to fatty acids as defined above but with an additional carboxylic acid group in the omega position. Thus, fatty diacids are dicarboxylic acids.

In a particular embodiment, the side chain(s) is a fatty acid having 10 to 20 carbon atoms, and preferably 14 to 20 or 16 to 18 carbon atoms, optionally with a spacer.

In a particular embodiment, the side chain(s) is a fatty acid of formula Chem. 1: $HOOC(CH_2)_mCO$, wherein m is an integer from 8 to 18, optionally with a linker. In a particular embodiment, m is an integer from 12 to 18 or from 14 to 16.

In a particular embodiment, the side chain(s) is selected from the group consisting of $HOOC(CH_2)_{14}CO-$, $HOOC(CH_2)_{16}CO-$, $HOOC(CH_2)_{22}CO-$, $CH_3(CH_2)_{14}CO-$, $CH_3(CH_2)_{16}CO-$ and $CH_3(CH_2)_{18}CO-$.

In one embodiment, the term "GLP-1 derivative" comprises or refers to monoacylated GLP-1 parent peptide, i.e. a GLP-1 parent peptide comprising only one acylation as defined above.

In a particular embodiment, the side chain is a fatty acid or a fatty diacid of which an acid group forms an amide bond with the epsilon amino group of a lysine residue in the GLP-1 compound, preferably via a spacer. In one embodiment, said lysine residue is $Lys^{26}$, especially when the parent peptide is human GLP-1(7-37), GLP-1(7-36)NH2 or a GLP-1 analogue.

In a particular embodiment, the side chain is attached to the parent peptide by means of a linker. In a particular embodiment, the linker comprises a γ-glutamic acid (γ-Glu) and/or 1, 2 or 3 OEG molecules. In γGlu the gamma carboxy group of the amino acid glutamic acid is used for connection to another linker element, or to the epsilon-amino group of lysine. An OEG molecule is also named a di-radical of 8-amino-3,6-dioxaoctanic acid, and/or it may be represented by the formula Chem. 2: $-NH-(CH2)2-O-(CH2)2-O-CH2-CO-$.

The linker may include one or more γGlu, and/or one or more OEG. More in particular, the γGlu and OEG linker elements may, independently, be used p times where p is zero or an integer in the range of 1-3. Examples of preferred linkers are γGlu, γGlu-2×OEG, and γGlu-3×OEG where in all cases the alpha-amino group of Glu forms an amide bond with the carboxy group of the protracting moiety.

In a particular embodiment, the GLP-1 derivative is a derivative of a GLP-1 analogue which comprises the $Arg^{34}$ substitution or the $Arg^{34}$ and the $Aib^8$ substitutions compared to human GLP-1(7-37), GLP-1(7-36)NH2 and which comprises a side chain attached to $Lys^{26}$. In a particular embodiment said side chain is a fatty acid as defined above, especially a fatty acid of formula Chem. 1, with m being an integer from 8 to 18, optionally with a linker being γGlu.

In one embodiment, the GLP-1 derivative is as defined in the patent applications WO 98/08871 and WO 06/097537, entirely included herein by reference. Non-limiting examples of monoacylated GLP-1 derivatives can be found in those applications.

Non-limiting examples of GLP-1 derivatives also include:

$N^{\epsilon 37}$-[2-[2-[2-[[2-[2-[2-[[(4S)-4-carboxy-4-[[4-[(19-carboxynonadecanoylamino)methyl]cyclohexanecarbonyl]amino]butanoyl]amino]ethoxy]ethoxy]acetyl]amino]ethoxy]ethoxy]acetyl]-[Imp$^7$,Glu$^{22}$,Arg$^{26}$,Arg$^{34}$,Lys$^{37}$]-GLP-1-(7-37)-peptide;

$N^{\epsilon 26}$-[2-[2-[2-[[2-[2-[2-[[(4S)-4-carboxy-4-(17-carboxyheptadecanoylamino)butanoyl]amino]ethoxy]ethoxy]acetyl]amino]ethoxy]ethoxy]acetyl]-[Aib$^8$,Arg$^{34}$]-GLP-1-(7-37)-peptide, also called semaglutide;

$N^{\epsilon 26}$-[(4S)-4-carboxy-4-(hexadecanoylamino)butanoyl]-[Arg$^{34}$]-GLP-1-(7-37)-peptide, also called liraglutide;

$N^{\epsilon 26}$-[2-[2-[2-[[2-[2-[2-[[(4S)-4-carboxy-4-[10-(4-carboxyphenoxy)decanoylamino]butanoyl]amino]ethoxy]ethoxy]acetyl]amino]ethoxy]ethoxy]acetyl],$N^{\square 37}$-[2-[2-[2-[[2-[2-[2-[[(4S)-4-carboxy-4-[10-(4-carboxyphenoxy)decanoylamino]butanoyl]amino]ethoxy]ethoxy]acetyl]amino]ethoxy]ethoxy]acetyl]-[Aib$^8$,Arg$^{34}$,Lys$^{37}$]-GLP-1-(7-37)-peptide;

$N^{\epsilon 26}$-[2-[2-[2-[[2-[2-[2-[[(4S)-4-carboxy-4-[12-(3-carboxyphenoxy)dodecanoylamino]butanoyl]amino]ethoxy]ethoxy]acetyl]amino]ethoxy]ethoxy]acetyl], $N^{\square 37}$-[2-[2-[2-[[2-[2-[2-[[(4S)-4-carboxy-4-[12-(3-carboxyphenoxy)dodecanoylamino]butanoyl]amino]ethoxy]ethoxy]acetyl]amino]ethoxy]ethoxy]acetyl]-[Aib$^8$,Arg$^{34}$,Lys$^{37}$]-GLP-1-(7-37)-peptide;

lixisenatide;
albiglutide;
dulaglutide.

In a particular embodiment, the GLP-1 derivative is liraglutide or semaglutide. The chemically modified derivatives of natural GLP-1 can be prepared for example as described in U.S. Pat. No. 6,451,762 or in Knudsen et. al. (2000) J Med Chem 43, 1664-1669.

When using terms such as "about" and "approximately" in relation to numerical values the skilled person should immediately recognise that any effect or result, which may be associated with the given values can be obtained within a certain tolerance from the particular values. The term "about" as used herein thus means in reasonable vicinity of the stated numerical value, such as plus or minus 10%.

EXAMPLES

Materials and Methods

Abbreviations

Some of the abbreviations used in the Examples are as follows:

Acm: acetamidomethyl
BHK: Baby hamster kidney
CHO: Chinese hamster ovary
HATU: (O-(7-azabenzotriazol-1-yl)-1,1,3,3-tetramethyluronium hexafluorophosphate)
HBTU: 2-(1H-Benzotriazol-1-yl-)-1,1,3,3 tetramethyluronium hexafluorophosphate
Fmoc: 9H-fluoren-9-ylmethoxycarbonyl
Boc: tert butyloxycarbonyl Mtt: 4-methyltrityl
DCM: dichloromethane
TIPS: triisopropylsilane
TFA: trifluoroacetic acid
NMP: 1-Methyl-pyrrolidin-2-one
HOAt: 1-Hydroxy-7-aza benzotriazole
DIC: Diisopropylcarbodiimide
Trt: triphenylmethyl
BHK tk'ts 13 cells: This line is a thymidine kinase deficient mutant of a ts 13, a temperature-sensitive mutant of BHK 21.

General Methods of Preparation

The production of peptides like mimylin is well known in the art.

The mimylin peptide/mimylin analogue of the invention may for instance be produced by classical peptide synthesis, e.g., solid phase peptide synthesis using t-Boc or Fmoc chemistry or other well established techniques, see, e.g., Greene and Wuts, "Protective Groups in Organic Synthesis", John Wiley & Sons, 1999, Florencio Zaragoza Dorwald, "Organic Synthesis on solid Phase", Wiley-VCH Verlag GmbH, 2000, and "Fmoc Solid Phase Peptide Synthesis", Edited by W. C. Chan and P. D. White, Oxford University Press, 2000.

Also, or alternatively, they may be produced by recombinant methods, viz. by culturing a host cell containing a DNA sequence encoding the analogue and capable of expressing the peptide in a suitable nutrient medium under conditions permitting the expression of the peptide. Non-limiting examples of host cells suitable for expression of these peptides are: *Escherichia coli, Saccharomyces cerevisiae*, as well as mammalian BHK or CHO cell lines.

Those peptides, analogues or derivatives of the invention which include non-natural amino acids and/or a covalently attached N-terminal mono- or dipeptide mimetic may e.g. be produced as described in the experimental part. Or see e.g., Hodgson et al: "The synthesis of peptides and proteins containing non-natural amino acids", Chemical Society Reviews, vol. 33, no. 7 (2004), p. 422-430; and WO 2009/083549 A1 entitled "Semi-recombinant preparation of GLP-1 analogues".

Preparations of Peptides and Derivatives

The mimylin peptide sequences were prepared according to the below-mentioned mimylin peptide synthesis and the compounds as presented in the Tables (e.g. Table 1 or Table 2) were prepared according to the below-mentioned synthesis.

One method of mimylin peptide synthesis was by Fmoc chemistry on a microwave-based Liberty peptide synthesizer (CEM Corp., North Carolina). The resin was Tentagel S RAM with a loading of about 0.25 mmol/g or PAL-ChemMatrix with a loading of about 0.43 mmol/g or PAL AM matrix with a loading of 0.5-0.75 mmol/g. The coupling chemistry was DIC/HOAt or DIC/Oxyma in NMP or DMF using amino acid solutions of 0.3 M and a molar excess of 6-8 fold. Coupling conditions was 5 minutes at up to 70° C. Deprotection was with 10% piperidine in NMP at up to 70° C. The protected amino acids used were standard Fmoc-amino acids (supplied from e.g. Anaspec or Novabiochem or Protein Technologies).

Another method of mimylin peptide synthesis was by Fmoc chemistry on a Prelude peptide synthesizer (Protein Technologies, Arizona). The resin was Tentagel S RAM with a loading of about 0.25 mmol/g or PAL-ChemMatrix with a loading of about 0.43 mmol/g or PAL AM with a loading of 0.5-0.75 mmol/g. The coupling chemistry was DIC/HOAt or DIC/Oxyma in NMP or DMF using amino acid solutions of 0.3 M and a molar excess of 6-8 fold. Coupling conditions was single or double couplings for 1 or 2 hours at room temperature. Deprotection was with 20% piperidine in NMP. The protected amino acids used were standard Fmoc-amino acids (supplied from e.g. Anaspec or Novabiochem or Protein Technologies).

N-terminal attachment of fatty acids, linkers etc. were usually performed by including the relevant building blocks in the standard peptide synthesis.

When a chemical modification of a lysine side chain was desired, the lysine was incorporated as Lys(Mtt) and the N-terminal amino acid was either incorporated into the sequence as a Boc-amino acid or, if the N-terminal amino acid was incorporated as an Fmoc-amino acid, the Fmoc group was removed and the N-terminal was protected by treatment with 6 equivalents of Boc-carbonate and 6 equivalents of DIPEA in NMP for 30 minutes. The resin was washed with NMP and DCM and the Mtt group was removed by suspending the resin in neat hexafluoroisopropanol or HFIP/DCM 3:1 for 20 minutes followed by washing with DCM and NMP. The chemical modification of the lysine was performed by adding one or more of the building blocks listed below by the same methods as used for the mimylin peptide synthesis, i.e. by one or more automated steps on the Liberty or by one or more manual coupling steps at room temperature. After synthesis the resin was washed with DCM and dried, and the mimylin peptide was cleaved from the resin by a 2 hour treatment with TFA/TIPS/water (92.5/5/2.5 or 95/2.5/2.5) followed by precipitation with 4 volumes of diethylether, further washing with diethylether and drying.

Purification: The crude mimylin peptide was purified by semipreparative HPLC on a 20 mm×250 mm column packed with either 5 um or 7 um C-18 silica. Mimylin peptide solutions were pumped onto the HPLC column and precipitated mimylin peptides were dissolved in 5 ml 50% acetic acid $H_2O$ and diluted to 20 ml with $H_2O$ and injected on the column which then was eluted with a gradient of 40-60% $CH_3CN$ in 0.1% TFA 10 ml/min during 50 min at 40° C. The mimylin peptide containing fractions were collected. The purified mimylin peptide was lyophilized after dilution of the eluate with water.

For analysis of HPLC-fractions and final product RP-HPLC analysis was performed using UV detection at 214 nm and e.g. a Vydac 218TP54 4.6 mm×250 mm 5 um C-18 silica column (The Separations Group, Hesperia, USA) and eluted at e.g. 1 ml/min at 42° C. Most often one of four different elution conditions was used:

A1: Equilibration of the column with a buffer consisting of 0.1M $(NH_4)_2SO_4$, which was adjusted to pH 2.5 with concentrated $H_2SO_4$ and elution by a gradient of 0% to 60% $CH_3CN$ in the same buffer during 50 min.

B1: Equilibration of the column with 0.1% TFA/$H_2O$ and elution by a gradient of 0% $CH_3CN$/0.1% TFA/$H_2O$ to 60% $CH_3CN$/0.1% TFA/$H_2O$ during 50 min.

B6: Equilibration of the column with 0.1% TFA/$H_2O$ and elution by a gradient of 0% $CH_3CN$/0.1% TFA/$H_2O$ to 90% $CH_3CN$/0.1% TFA/$H_2O$ during 50 min.

Alternatively the RP-HPLC analysis was performed using UV detection at 214 nm and a Symmetry 300, 3.6 mm×150 mm, 3.5 um C-18 silica column (Waters) which was eluted at 1 ml/min at 42° C.

B4: Equilibration of the column with 0.05% TFA/$H_2O$ and elution by a gradient of 5% $CH_3CN$/0.05% TFA/$H_2O$ to 95% $CH_3CN$/0.05% TFA/$H_2O$ during 15 min.

The identity of the mimylin peptide was confirmed by MALDI-MS on a Bruker Microflex.

Example Synthesis

Synthesis of Mimylin, SEQ ID NO: 1 (Example #1) an Example of a Mimylin Peptide 400 mg PAL AM resin (0.61 mmol/g) was swollen in DCM/NMP and synthesis was performed on a Prelude peptide synthesizer using 1 hour couplings in DMF as described above. After cleavage with TFA cleavage cocktail, the peptide was precipitated with ether and dried yielding 800 mg crude mimylin with a purity of about 50%. HPLC purification (as described above) gave about 200 mg mimylin with a purity of >90%

Synthesis of Compound [N-Terminal(C18 Diacid)]Mimylin (Example #2) an Example of a Mimylin Derivative 600 mg PAL ChemMatrix resin (0.43 mmol/g) was swollen in DCM/NMP and synthesis was performed on a Liberty peptide synthesizer using 5 min couplings in NMP at 70° C. as described above. As the last step of the synthesis C18-diacid-mono-t-butylester was coupled under the same conditions. After cleavage, the peptide was precipitated with ether and dried yielding 700 mg crude [N-terminal(C18 diacid)]mimylin with a purity of about 55%. HPLC purification gave about 150 mg [N-terminal(C18 diacid)]mimylin with a purity of >90%

Alternative Synthesis of Compound [N-Terminal(C18 Diacid)]Mimylin (Example #2)

Mimylin is synthesized and purified as described above, dissolved in water or a suitable mixture of water and an organic solvent such as e.g. NMP, DMF, DMSO, or acetonitrile. A solution of activated C18-diacid, e.g. C18-diacid-succinimidyl ester is added and the resulting solution of Example 2 is purified.

Observations

All references, including publications, patent applications, and patents, cited herein are hereby incorporated by reference in their entirety and to the same extent as if each reference were individually and specifically indicated to be incorporated by reference and were set forth in its entirety herein (to the maximum extent permitted by law).

All headings and sub-headings are used herein for convenience only and should not be construed as limiting the invention in any way.

The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

The citation and incorporation of patent documents herein is done for convenience only and does not reflect any view of the validity, patentability, and/or enforceability of such patent documents.

This invention includes all modifications and equivalents of the subject matter recited in the aspects appended hereto as permitted by applicable law.

In the following examples reference is made to the following Assays:

TABLE 7 list of assays

| ASSAY # | Assay Title |
|---|---|
| I | Experimental protocol for efficacy testing on appetite using an ad libitum fed rat model |
| IIa | Functional assay—Human calcitonin and amylin receptor assay with albumin |
| IIb | Functional assay—Human calcitonin and amylin receptor assay without albumin |
| IIc | Functional assay—Rat calcitonin and rat amylin receptor assays |
| III | ThT fibrillation—Determination of physical stability of protein formulations |
| IIIa | ThT fibrillation—Determination of physical stability of protein formulations |
| IV | Determination of solubility |
| V | Determination of binding to the human amylin receptor (membrane) |
| V a | Determination of binding to the human amylin receptor (whole cell) |
| VI | Determination of the binding to the rat amylin receptor |
| VII | Determination of binding to the human calcitonin receptor (membrane) |
| VIIa | Determination of binding to the human Calcitonin Receptor (whole cell) |
| VIII | Determination of binding to the rat calcitonin receptor |
| IX | pK—Determination of T½ in mini-pig |
| X | pK—Determination of T½ in rat |
| XI | Determining potential MHC Class II binding sites |
| XII | SEC-HPLC |
| XIII | Quiescent storage stability of formulations |
| XIV | Experimental protocol for testing effect on body weight using DIO rat model |
| XV | Determination subcutaneous mimylin derivative PK in LYD-pigs when co-formulated with liraglutide |
| XVI | Determination of T½ and subcutaneous bioavailability in LYD-pigs |
| XVII | Determination of T½ and subcutaneous bioavailability in Beagle dogs |

Assay (I)—Experimental Protocol for Efficacy Testing on Appetite Using an Ad Libitum Fed Rat Model Sprague Dawley (SD) rats from Taconic Europe, Denmark are used for the experiments. The rats have a body weight 200-250 g at the start of experiment. The rats arrive at least 10-14 days before start of experiment to allow acclimatisation to experimental settings. During this period the animals are handled at least 2 times. After arrival rats are housed individually for one week in a reversed light/dark phase (meaning that lights are off during daytime and on during nighttime) for two weeks. Since rats are normally active and eat their major part of their daily food intake during the dark period, rats are dosed in the morning right before lights are turned off. This set-up results in the lowest data variation and highest test sensitivity. The experiment is conducted in the rats' home cages and rats have free access to food and water throughout the acclimatization period and the experiment period. Each dose of derivative is tested in a group of 5-8 rats. A vehicle group of 6-8 rats is included in each set of testing. Rats are dosed once according to body weight with a 0.01-3 mg/kg solution administered intraperitoneally (ip), orally (po) or subcutaneously (sc). The time of dosing is recorded for each group.

After dosing, the rats are returned to their home cages, where they then have access to food and water. The food consumption is recorded individually continuously by on-line registration or manually every hour for 7 hours, and then after 24 h and sometimes 48 h. At the end of the experi-

Assay(II)a—Human Calcitonin and Amylin Receptor Assay

1. Luciferase Assay Outline

Activation of calcitonin and amylin (co-expression of calcitonin receptor and receptor activity modifying proteins (RAMP)) receptors lead to increased intracellular concentrations of cAMP. Consequently, transcription is activated by promoters containing multiple copies of the cAMP response element (CRE). It is thus possible to measure amylin activity by the use of a CRE luciferase reporter gene introduced into BHK cells also expressing calcitonin or amylin receptors.

2. Construction of Calcitonin (a)- and Amylin 3(a)-Receptor/CRE-Luc Cell Line.

A BHK570 cell line was stably transfected with the human calcitonin receptor and a CRE-responsive luciferase reporter gene. The cell line was further transfected with RAMP-3, using standard methods. This turns the calcitonin receptor into an amylin 3(a) receptor. Methotrexate, Neomycin, and Hygromycin are selection markers for luciferase, the calcitonin receptor, and RAMP-3, respectively.

3. Luciferase Assays

To perform activity assays, BHK calcitonin (a) receptor- or amylin 3(a)-receptor/CRE-luc cells were seeded in white 96 well culture plates at a density of about 20.000 cells/well. The cells were in 100 µl growth medium (DMEM with 10% FBS, 1% Pen/Strep, 1 mM Napyruvate, 250 nM Methotrexate, 500 µg/ml Neomycin, and 400 µg/ml Hygromycin). After incubation overnight at 37° C. and 5% $CO_2$, the growth medium was replaced by 50 µl/well assay medium (DMEM (without phenol red), Glutamax™, 10% FBS, and 10 mM Hepes, pH 7.4). Further, 50 µl/well of standard or sample in assay buffer were added.

After 3 hours incubation at 37° C. and 5% $CO_2$, the assay medium with standard or sample were removed and replaced by 100 µl/well PBS. Further, 100 µl/well LucLite™ was added. The plates were sealed and incubated at room temperature for 30 minutes. Finally, luminescence was tested on a TopCounter (Packard) in SPC (single photon counting) mode.

Assay(II)b—Human Calcitonin and Amylin Receptor Assay without Albumin

1. Luciferase Assay Outline

Activation of calcitonin and amylin (co-expression of calcitonin receptor and receptor activity modifying proteins (RAMP)) receptors lead to increased intracellular concentrations of cAMP. Consequently, transcription is activated by promoters containing multiple copies of the cAMP response element (CRE). It is thus possible to measure amylin activity by the use of a CRE luciferase reporter gene introduced into BHK cells also expressing calcitonin or amylin receptors.

2. Construction of Calcitonin (a)- and Amylin 3(a)-Receptor/CRE-Luc Cell Line.

A BHK570 cell line was stably transfected with the human calcitonin receptor and a CRE-responsive luciferase reporter gene (Hollex-1 cell line, obtained from ZymoGenetics described in U.S. Pat. No. 5,622,839). The cell line was further transfected with RAMP-3, using standard methods. This turns the calcitonin receptor into an amylin 3(a) receptor. Methotrexate, Neomycin, and Hygromycin are selection markers for luciferase, the calcitonin receptor, and RAMP-3, respectively. To prepare the batches of frozen cells used in the luciferase assay described in the section below, the cells were cultured in growth medium (DMEM with 10% FBS, 1% Pen/Strep and 1 mM Napyruvate). Methotrexate (250 nM) and Neomycin (500 µg/ml) were used as selection markers for the expression of the luciferase reporter and the calcitonin receptor, respectively. Cells at approximately 80-90% confluence were washed with PBS and loosened from the plates with Versene. After centrifugation (2 min, 1300 rpm, in a Centrion Scientific centriuge C2 series with a BRK 5510 rotor head), the cell pellet was dissolved in 10% DMSO, 30% FBS and 60% growth medium and frozen (−80° C.) until utilization.

3. Luciferase Assays

The day before the experiment, BHK calcitonin (a) receptor- or amylin 3(a)-receptor/CRE-luc cells were thawed, washed twice, and seeded in 40 µl growth medium on white 384 well culture plates (4.000 cells/well). On the assay day, the cells were washed 3 times in assay media (Dulbecco media W/o phenol red, 500 ml (Gibco, 11880-028); 0.1% ovalbumin; 10 mM Hepes pH 7.4; 1× Glutamin; 1% Pen/Strep). Then, 30 µl/well of sample diluted in assay buffer was added. After 3 hours of incubation at 37° C. and 5% $CO_2$, the reaction was terminated by adding 30 µl/well SteadyLite Plus™. The plates were shaken at 300 rpm for 5 min at RT. Then, the plates were sealed and incubated at room temperature for 30 minutes. Finally, luminescence was tested on a TopCounter (Packard) in SPC (single photon counting) mode.

$EC50$ values were calculated in GraphPad Prism using a nonlinear regression with hillslope=1.

Additional Comment Regarding Use of Data Retrieved Via this Method

This assay provides confirmation of biologic activity and confirms that all mimylin peptides or derivatives as described herein are amylin and calcitonin receptor agonists. Due to the presence of HSA it should be noted that mimylin derivatives with different protracting moieties should not be compared relative regarding their $EC_{50}$ value, because different side chains bind to HSA with different affinities and thus influence the $EC_{50}$ and thus shift the $EC_{50}$ towards higher values when the protracting moiety binds more efficiently to HSA. For the same reasons, measurements made in Assay IIa should not be compared in Assay IIb.

Assay (II)c—Rat Calcitonin and Rat Amylin Receptor Assays cAMP Assay Outline Activation of calcitonin and amylin (co-expression of calcitonin receptor and receptor activity modifying proteins (RAMP)) receptors lead to increased intracellular concentrations of cAMP. In order to quantify the cAMP levels in transiently transfected cells the Adenylyl Cyclase Activation FlashPlate® Assay from Perkin Elmer was used. The basic principle of the FlashPlate® Assay is a competition between radioactive and non-radioactive cAMP generated by the cells for a fixed number of binding sites.

Construction of Rat Calcitonin(a)- and Rat Amylin 3(a)-Receptor Cells.

BHK tk'ts 13 cells were transiently transfected with either rat calcitonin (a) receptor or amylin 3 (a) receptor (rat calcitonin(a) receptor+ rat RAMP3) using FuGENE® 6 (Roche), according to the manufacturers recommendations.

cAMP Assay 24 hours after transient transfection the cells (rat calcitonin(a)- or rat amylin 3(a)-receptor cells) were added (100.000 cells/well) to the 96 well FlashPlates® with samples or standard in FlashPlate stimulation buffer with IBMX and incubated for 30 min. Detection mix was created according to manufacturer's protocol and scintillation tested after 3 h of incubation on TopCounter™ (Packard).

Assay (III)—ThT Fibrillation—Determination of Physical Stability of Protein Formulations Low physical stability of a mimylin peptide may lead to amyloid fibril formation, which is observed as well-ordered, thread-like macromolecular structures in the sample eventually resulting in gel formation. This has traditionally been tested by visual inspection of the sample. However, that kind of measurement is very subjective and depending on the observer. Therefore, the application of a small molecule indicator probe is much more advantageous. Thioflavin T (ThT) is such a probe and has a distinct fluorescence signature when binding to fibrils [Naiki et al. (1989) Anal. Biochem. 177, 244-249; LeVine (1999) Methods. Enzymol. 09, 274-284].

The time course for fibril formation can be described by a sigmoidal curve with the following expression [Nielsen et al. (2001) Biochemistry 40, 6036-6046]:

$$F = f_i + m_i t + \frac{f_f + m_f t}{1 + e^{-[(t-t_0)/\tau]}} \qquad \text{Eq. (1)}$$

Here, F is the ThT fluorescence at the time t. The constant $t_0$ is the time needed to reach 50% of maximum fluorescence. The two important parameters describing fibril formation are the lag-time calculated by $t_0 - 2\tau$ and the apparent rate constant $k_{app} = 1/\tau$.

Formation of a partially folded intermediate of the mimylin peptide is suggested as a general initiating mechanism for fibrillation. Few of those intermediates nucleate to form a template onto which further intermediates may assembly and the fibrillation proceeds. The lag-time corresponds to the interval in which the critical mass of nucleus is built up and the apparent rate constant is the rate with which the fibril itself is formed.

Sample Preparation

Samples were prepared freshly before each assay. Each sample composition is described in each example. The pH of the sample was adjusted to the desired value using appropriate amounts of concentrated NaOH and HClO$_4$ or HCl. Thioflavin T was added to the samples from a stock solution in H$_2$O to a final concentration of 1 μM. Sample aliquots of 200 μl were placed in a 96 well microtiter plate (Packard OptiPlate™-96, white polystyrene). Usually, four or eight replica of each sample (corresponding to one test condition) were placed in one column of wells. The plate was sealed with Scotch Pad (Qiagen).

Incubation and Fluorescence Measurement

Incubation at given temperature, shaking and measurement of the ThT fluorescence emission were done in a Fluoroskan Ascent FL fluorescence plate reader or Varioskan plate reader (Thermo Labsystems). The temperature was adjusted to 37° C. The orbital shaking was adjusted to 960 rpm with an amplitude of 1 mm in all the presented data.

Fluorescence measurement was done using excitation through a 444 nm filter and measurement of emission through a 485 nm filter.

Each run was initiated by incubating the plate at the assay temperature for 10 min. The plate was tested every 20 minutes for a desired period of time. Between each measurement, the plate was shaken and heated as described.

Data Handling

The measurement points were saved in Microsoft Excel format for further processing and curve drawing and fitting was performed using GraphPad Prism. The background emission from ThT in the absence of fibrils was negligible. The data points are typically a mean of four or eight samples and shown with standard deviation error bars. Only data obtained in the same experiment (i.e. samples on the same plate) are presented in the same graph ensuring a relative measure of fibrillation between experiments.

The data set may be fitted to Eq. (1). However, since full sigmodial curves in this case are not always achieved during the measurement time, the degree of fibrillation is expressed as ThT fluorescence tabulated as the mean of the samples and shown with the standard deviation at various time points.

Measurement of Initial and Final Concentrations

The mimylin peptide concentration in each of the tested formulations was tested both before application in the ThT fibrillation assay ("Initial") and after completion of the ThT fibrillation ("After ThT assay"). Concentrations were determined by reverse HPLC methods using a pramlintide standard as a reference. Before measurement after completion 150 μl was collected from each of the replica and transferred to an Eppendorf tube. These were centrifuged at 30000 G for 40 mins. The supernatants were filtered through a 0.22 μm filter before application on the HPLC system.

Assay (IIIa)—ThT Fibrillation—Determination of Physical Stability of Protein Formulations Sample preparation, incubation and fluorescence measurements were done according to the principles described under ASSAY (III).

Data Handling

Fluorescence measurements for each microtiter plate well were plotted against time and the lag-time (time until an increase in ThT fluorescence was observed) was estimated based on the intercept between the linear initial lag-phase and the first part of the subsequent exponential growth phase.

Measurement of Peptide Recovery of Mimylin-Formulations

Done according to the principles described above in Assay III; however, ASSAY (XII) was used for quantification of peptide concentration before and after incubation.

Measurement of Peptide Recovery of Mimylin/GLP-1 Co-Formulations

RP-UPLC was conducted using an Acquity UPLC BEH C18 1.7 μm (2.1×30 mm) column (Eluent A: 0.1 v/v % TFA in water; Eluent B: 0.1 v/v % TFA in acetonitrile) with gradient elution (0 min: 95% A; 2 min: 20% A; 2.3 min: 20% A; 2.4 min: 95% A) in a flow rate of 0.9 ml/min and a column temperature of 30° C. UV-detection at 215 nm was used to assess the total peptide recovery (on an individual basis if separated) whereas detection at 280 nm was used to determine the recovery of the GLP-1 component (no UV-280 nm absorption from the mimylin component).

Assay (IV)—Determination of Solubility

The mimylin peptide was dissolved in water at ~500 nmol/ml and mixed 1:1 with a series of buffers (100 mM glycylglycine pH 3.0, 100 mM glycylglycine pH 4.0, 100 mM glycylglycine pH 5.0, 100 mM bistrispropane pH 6.0, 100 mM bistrispropane pH 6.5, 100 mM bistrispropane pH 7.0, 100 mM bistrispropane pH 7.5, 100 mM bistrispropane pH 8.0). After 18 hours at room temperature the samples were centrifuged and the mimylin peptide concentration determined by UPLC.

Assay (V)—Determination of Binding to the Human Amylin Receptor

The binding assay was performed using scintillation proximity assay (SPA) beads (RPNQ0001) from PerkinElmer and cell membranes from the Amylin 3(a)/CRE-luc cells (as described in Assay (II)) were used. Membranes were prepared in the following way; the cells were rinsed with PBS and incubated with Versene for approximately 5 min before harvesting. The cells were flushed with PBS and the cell-suspension was centrifuged for 5 min at 1000 rpm. Cells were homogenized (ultrathurrax) in a buffer containing 20 mM Na-HEPES and 10 mM EDTA (pH 7.4) and centrifuged at 20.000 rpm for 15 min. The resulting pellet was resuspended, homogenized and centrifuged (20.000 rpm, 15 min) in a buffer containing 20 mM Na-HEPES and 0.1 mM EDTA (pH 7.4, buffer 2). The resulting pellet was resuspended in buffer 2 and protein concentration was tested (BCA protein Assay, Pierce). The homogenate was kept cold during the whole procedure. The membranes were kept at −80° C. until use. The assay was performed in a 384 well Optiplate (PerkinElmer) in a total volume of 40 ul. Membranes were mixed with SPA beads. Final concentration of membranes 35 ng/μL final and SPA beads was 0.05 mg/well. Test-compounds were dissolved in DMSO and further diluted in assay buffer (50 mM Hepes, pH 7.4, 1 mM CaCl2, 5 mM MgCl2, 0.1% OA and 0.02% Tween20). Radioligand $^{125}$I-rat amylin (NEX448 PerkinElmer) was dissolved in assay buffer and added to the Optiplate at a final concentration of 50 pM/well (approx. 20.000 cpm/10 ul). The final mixture was incubated with shaking at 400 rpm for 120 min at 25° C. prior to centrifugation (1500 rpm, 10 min). Samples were analyzed on TopCounter™ (Packard). The $IC_{50}$ was calculated using (one site binding competition analysis) GraphPad Prism5 as a measure of receptor affinity.

Assay (Va)—Determination of Binding to the Human Amylin Receptor (Whole Cell Binding)

The binding assay was performed using a BHK tk'ts 13 cell line was stably transfected with the human calcitonin receptor, the human RAMP3 and a CRE-responsive luciferase reporter gene.

The day before the assay the cells were Seeded into Poly-D-Lysin coated 384 W Opaque White, BD BioCoat plates (10000 cells/well) and Incubated overnight at 37° C., 5% CO2, 95% humidity. Then, the cells were washed in HBSS (4° C.), and incubated overnight at 4° C. in a binding buffer containing test compounds, 50 pM [125I]-rat amylin, Dulbecco media w/o phenol red, 500 ml, 0.1% ovalbumin (5 ml 10% ovalbumin), 10 mM Hepes (5 ml 1M) 1× Glutamin (5 ml 100×) 1% P/S (5 ml 100%) Complete (1 tablet/50 ml) 0.1% Pluronic F68®. The morning after, the plates were washed three times in HBSS (4° C.), and lyzed in Lysis buffer (0.1 M NaOH (VWR #1.09136.1000), 1% SDS. Then MicroScint40 was added and the plated were shaken at 500 rpm for a short period. Then the plate was incubated at room temperature in the dark for 1 hour and Read on a TopCounter. The $IC_{50}$ was calculated using (one site binding competition analysis) GraphPad Prism5 as a measure of receptor affinity.

Assay (VI)—Determination of the Binding to the Rat Amylin Receptor (Membrane)

The assay was performed as described above (Assay (V)—Determination of binding to the human amylin receptor) with the exception that we used membranes prepared from BHK tk'ts 13 cells that were transiently transfected with the rat calcitonin receptor rat RAMP 3 at an equimolar ratio (1:2). The BHK tk'ts 13 cells were transiently transfected with rat calcitonin receptor using FuGENE® 6 (Roche), according to the manufacturer's recommendations. Cells were grown in DMEM with 10% FBS and 1% Pen/Strep. Approximately 48 hours after transfection, the cells were harvested and membranes were prepared.

Assay (VII)—Determination of Binding to the Human Calcitonin Receptor (Membrane)

The binding assay was performed using scintillation proximity assay (SPA) beads (RPNQ0001) from PerkinElmer® and cell membranes prepared from a BHK tk'ts 13 cell line was stably transfected with the human calcitonin receptor and a CRE-responsive luciferase reporter gene. Membranes were prepared in the following way; the cells were rinsed with PBS and incubated with Versene for approximately 5 min before harvesting. The cells were flushed with PBS and the cell-suspension was centrifuged for 5 min at 1000 rpm. Cells were homogenized in a buffer containing 20 mM Na-HEPES and 10 mM EDTA (pH 7.4) and centrifuged at 20.000 rpm for 15 min. The resulting pellet was resuspended, homogenized and centrifuged (20.000 rpm, 15 min) in a buffer containing 20 mM Na-HEPES and 0.1 mM EDTA (pH 7.4, buffer 2). The resulting pellet was resuspended in buffer 2 and protein concentration was tested (BCA protein Assay, Pierce). The homogenate was kept cold during the whole procedure. The membranes were kept at −80° C. until use. Assay was performed in a 384 well Optiplate (PerkinElmer®) in a total volume of 40 ul. Membranes were mixed with SPA beads. Final concentration of membranes 35 ng/μL final and Final concentration of SPA beads was 0.05 mg/well. Test-compounds were dissolved in DMSO and further diluted in assay buffer (50 mM Hepes, pH 7.4, 1 mM CaCl2, 5 mM MgCl2, 0.1% OA and 0.02% Tween20). Radioligand $^{125}$I-Calcitonin was dissolved in assay buffer and added to the Optiplate at a final concentration of 75 pM/well (approx. 30.000 cpm/10 ul). The final mixture was incubated for 120 min with shaking at 400 rpm at 25° C. prior to centrifugation (1500 rpm, 10 min). Samples were analyzed on TopCounter™ (Packard). The $IC_{50}$ was calculated using (one site binding competition analysis) GraphPad Prism5 as a measure of receptor affinity.

Assay (VIIa)—Determination of Binding to the Human Calcitonin Receptor (Whole Cell Binding)

The binding assay was performed using a BHK tk'ts 13 cell line was stably transfected with the human calcitonin receptor, and a CRE-responsive luciferase reporter gene.

The day before the assay the cells were Seeded into Poly-D-Lysin coated 384 W Opaque White, BD BioCoat plates (10000 cells/well) and Incubated overnight at 37° C., 5% CO2, 95% humidity. Then, the cells were washed in HBSS (4° C.), and incubated overnight at 4° C. in a binding buffer containing test compounds, 50 pM [125I]-human calcitonin, media w/o phenol red, 500 ml 0.1% ovalbumin (5 ml 10% ovalbumin) 10 mM Hepes (5 ml 1M) 1× Glutamin (5 ml 100×) 1% P/S (5 ml 100%) Complete (1 tablet/50 ml) 0.1% Pluronic F68®. The morning after, the plates were washed three times in HBSS (4° C.), and lyzed in Lysis buffer (0.1 M NaOH), 1% SDS. Scintillation cocktail (MicroScint40®) was added and the plates were shaken at 500 rpm for a short period. The plate was incubated at room temperature in the dark for 1 hour and Read on a TopCounter™ (Packard). The $IC_{50}$ was calculated using (one site binding competition analysis) GraphPad Prism5 as a measure of receptor affinity.

Assay (VIII)—Determination of Binding to the Rat Calcitonin Receptor

The assay was performed as described above (Assay (VII)—Determination of binding to the human calcitonin receptor) with the exception that we used membranes prepared from BHK tk'ts 13 cells that were transiently transfected with the rat calcitonin receptor. The BHK tk'ts 13 cells were transiently transfected with rat calcitonin receptor using FuGENE® 6 (Roche), according to the manufacturer's recommendations. Cells were grown in DMEM with 10% FBS and 1% Pen/Strep. Approximately 48 hours after transfection, the cells were harvested and membranes were prepared.

Assay (IX)—pK—Determination of T½ in Mini-Pig

Pharmacokinetic (PK) studies in Göttingen mini-pigs were conducted in order to determine the T½ of the mimylin compound according to the Examples as indicated after i.v. administration.

T½ values of the amylin analogues of the invention is determined by pharmacokinetic studies in female Göttingen mini-pigs from Ellegaard Göttingen Minipigs ApS and the principles of laboratory animal care are followed.

An acclimatisation period of approximately 6-10 days was allowed before the animals entered the study. At start of the acclimatisation period the mini-pigs were about 5 to 12 months old and in the weight range of 15-35 kg. The mini-pigs had two central venous catheters inserted which were used for blood sampling.

The studies were conducted in an animal room which was illuminated to give a cycle of approximately 12 hours light and 12 hours darkness. The animals were housed individually.

The animals had free access to domestic quality drinking water during the study, and no food restrictions applied for PK studies. The animals were weighed on arrival and on the days of dosing.

In the present studies the test substances were administered intravenously in approximately 5 nmol/kg dose. The animals received a single intravenous injection in one central venous catheter and blood sampling was performed from the other catheter, where possible. Each test substance was given to typically three but in some cases two or four animals.

A full plasma concentration-time profile, employing 12-16 sampling points, was obtained from each animal. In example blood samples were collected according to the following schedule:
After intravenous administration:
Pre-dose (0), 0.5, 1, 2, 4, 6, 8, 12, 24, 48, 72, 96, 120, 168 and 240 hours after injection. In some cases also additional blood samples up to 288 hours post injection were taken.

At each sampling time, 0.5 to 2 ml of blood was drawn from each animal. The blood samples were taken via the central venous catheter.

The 0.8 mL blood samples were collected into EDTA test tubes (8 mM EDTA). Blood samples were kept on ice for max 20 min. before centrifugation. Plasma was separated using centrifugation (i.e. at 4° C., 10 min., 2000G) and was immediately transferred to Micronic tubes on dry ice. Approximately 200 µl plasma was transferred to each Micronic tube. The plasma was stored at −20° C. until assayed. The plasma samples were assayed for the content of compound using LCMS.

The plasma concentration-time profiles were analysed by a non-compartmental pharmacokinetic analysis (NCA) using Phoenix WinNonlin 6.3 (Pharsight Inc., Mountain View, Calif., USA). NCA was performed using the individual plasma concentration-time profiles from each animal. T½ is the terminal half-life=ln $2/\lambda_z$ and was determined from $\lambda_z$, the first order rate constant associated with the terminal (log-linear) portion of the curve, estimated by linear regression of time vs. log concentration.

MS-Method for Amylin and Mimylin Quantification

40 µl plasma is diluted with 120 µl 66.67% EtOH+1% HCOOH and mixed. Centrifuged for 20 min. at 13000 rpm, 4° C. The supernatant is analyzed by an LC-MS method on a Sciex API 3000 and quantitated with a standard made up in plasma Assay (X)—pK—Determination of T½ in Rat Pharmacokinetic (PK) studies rats were conducted in order to determine the T½ of mimylin peptide after i.v. and s.c. administration.

T½ values of the mimylin derivates of the invention is determined by pharmacokinetic studies in Sprague Dawley male rats, from Taconic Europe and the principles of laboratory animal care are followed.

An acclimatisation period of approximately 7 days was allowed before the animals entered the study. At start of the acclimatisation period the rats were in the weight range of 250-400 g.

The studies were conducted in an animal room which was illuminated to give a cycle of approximately 12 hours light and 12 hours darkness. The animals were group housed and had food and water ad lib. The animals were weighed on the days of dosing.

In the present studies the test substances were administered subcutaneously or intravenously in approximately 20 nmol/kg dose. The animals received a single subcutaneous injection to the neck for subcutaneous administration or directly into the tail vein for intravenous administration. Each test substance was given to typically three but in some cases two or four animals.

A full plasma concentration-time profile, employing 8-10 sampling points, was obtained from each animal. In example blood samples were collected according to the following schedule: After subcutaneous or intravenous administration:
Predose (0), 0.5, 1, 1.5, 2, 4, 6, 12, 24, 48 and 72 hours after injection.

At each sampling time, 0.08 to 0.10 ml of blood was drawn from each animal. The blood samples were taken in the sublingual vein via venous puncture and the use of a capillary tube.

The blood samples were stabilised with EDTA. Blood samples were kept on ice for max 20 min. before centrifugation. Plasma was separated using centrifugation (i.e. at 4° C., 10 min., 1500G) and was immediately transferred to Micronic tubes or PCR plates. Approximately 40 μl plasma was transferred and was stored at −20° C. until assayed. The plasma samples were assayed for the content of mimylin compound by LCMS The plasma concentration-time profiles were analysed by a non-compartmental pharmacokinetic analysis (NCA) using Phoenix WinNonlin 6.3 (Pharsight Inc., Mountain View, Calif., USA). NCA was performed using the individual plasma concentration-time profiles from each animal. T½ is the terminal half-life=ln $2/\lambda_z$ and was determined from $\lambda_z$, the first order rate constant associated with the terminal (log-linear) portion of the curve, estimated by linear regression of time vs. log concentration.

Assay (XI)—Determining Potential MHC Class II Binding Sites

The in-silico study investigated whether the novel peptides sequences that result from protein engineering to generate mimylin analogues could result in peptide sequences cap Termination Animals were sacrificed on day 28. Animals were anesthetized with $O_2/N_2O$/isoflurane, and blood was taken by cardiac puncture into EDTA tubes, kept on ice and centrifuged within 30 minutes of collection. All EDTA plasma samples were stored at −80° C. thereafter, until analyzed. Liver and brain samples were also collected and stored at −80° C. for later analysis Assay (XV)—Determination Subcutaneous Mimylin Derivative PK in LYD-Pigs when Co-Formulated with Liraglutide To determine if co-formulation with liraglutide would change the PK properties of either the mimylin derivatives or liraglutide co-formulation studies were performed in Landrace Yorkshire Duroc crossbreed (LYD) pigs and compared with co-dosing studies.

The studies were performed in female LYD pigs of SPF origin delivered from Lars Jonson, Hillerødvej 70, Lynge.

At start of the acclimatisation period, the body weight of the pigs was in the range of 55-70 kg and the pigs were of app. 5 month of age.

Before the animals arrived, the animal rooms and pens were cleaned and disinfected with Virkon S. During the study, the animal rooms were cleaned and washed regularly.

The pigs were group housed during the acclimatisation period. The pigs were fitted with a central venous catheter while under anaesthesia and after the single housed after catheterization in pens ≥3.1 $m^2$ with straw as bedding. The temperature in the rooms was set at 20-23° C. and the relative humidity to 30-70%. The rooms were illuminated to give a cycle of 12 hours light and 12 hours darkness. Light was on from 07.00 to 19.00 h.

The subcutaneous formulations used for co-dosing contained either 1.6 mM liraglutide or 1.6 mM mimylin derivative in 8 mM phosphate, 58 mM phenol, 14 mg/ml propylenglycol, pH 8.2. The co-formulation contained 1.6 mM liraglutide and 1.6 mM mimylin derivative in 8 mM phosphate, 58 mM phenol, 14 mg/ml propylenglycol, pH 8.2. The formulations was prepared similarly and filled in cartridges in all cases.

The animals were dosed subcutaneously as follows.

The s.c. dosing was performed in 4 mm depth, in a site of injection which was secured on beforehand by ultrasound to avoid muscular tissue or heavy vascularization. Dosing was made using NovoPen® 4 and needle Novofine 28 G and a needle stopper to ensure 4 mm depth of injection. The needle was kept in the subcutis for 10 seconds after the injection to secure deposition of compound. For co-dosing animals received two separate injections on different sides of the neck of liraglutide and Compound 2. The co-formulation was administered as one injection. Study was performed as a cross over study with adequate wash out between dosings. Animals were in all studies dosed with 2 nmol/kg liraglutide and 2 nmol/kg mimylin derivate.

Blood Sampling

Blood was sampled at predefined time points for up till 15 days post dosing to adequately cover the full plasma concentration-time profile of the mimylin derivative. Blood samples were drawn from a central venous catheter to jugularis made through the catheter which was afterwards flushed with 10 ml 0.9% NaCl.

For each blood sampling time point approximately 0.8 mL of whole blood was collected in a 1.5 mL EDTA coated tube, and the tube was gently turned to allowing mixing of the sample with the anticoagulant. Blood samples (for example 0.8 mL) were collected in EDTA buffer (8 mM) and then centrifuged at 4° C. and 2000G for 10 minutes. Plasma was pipetted into Micronic tubes on dry ice, and kept at −20° C. until analysis.

Analysis

The plasma concentration of the respective mimylin derivative was analysed using LC-MS and liraglutide by LOCI. Individual plasma concentration-time profiles were analysed by a non-compartmental model in Phoenix WinNonlin version 6.3 (Pharsight Inc., Mountain View, Calif., USA).

The area under the plasma concentration versus time curve (AUC, [time×concentration]) was calculated (by the Pharsight programme) after subcutaneous administration, typically until 240-288 hours post dosing, or until last measured concentration. The AUC was calculated and given as AUCinf-pred and dose normalized. However, in cases where the extrapoloated area in the profile exceeded 20% then $AUC_{last}$ was used to calculated AUC and dose-normalized.

Results of co-formulation studies in LYD-pigs are summarized below

Assay (XVI)—Determination of T½ and Subcutaneous Bioavailability in LYD-Pigs

Pharmacokinetic (PK) studies in Landrace Yorkshire Duroc crossbreed (LYD) pigs were conducted in order to determine a) the protraction of the mimylin derivative after i.v. administration, and b) the bioavailability of the mimylin derivative after s.c. administration The LYD pig were delivered, treated and acclimatised as described in ASSAY XV above.

In the i.v. and s.c. studies, the mimylin derivative was dissolved in 50 mM phosphate, 70 mM sodium chloride and 0.05% polysorbate 80, pH=8.0 to a concentration of approximately 100 nmol/mL. Animals were dosed with 2 nmol/kg s.c. and 5 nmol/kg i.v.

The animals were dosed subcutaneously or intravenously as follows.

The s.c. dosing was performed in 4 mm depth, in a site of injection which was secured on beforehand by ultrasound to avoid muscular tissue or heavy vascularization. Dosing was made using NovoPen®4 and needle Novofine 28 G and a needle stopper to ensure 4 mm depth of injection. The needle was kept in the subcutis for 10 seconds after the injection to secure deposition of compound.

Intravenous administration was performed either by an ear vein or through a venflon.

Blood Sampling

Blood was sampled at predefined time points for up till 10-12 days post dosing to adequately cover the full plasma concentration-time profile of the mimylin derivative. The remainder followed the protocol as described in ASSAY (XV) blood sampling above, Analysis The plasma concentration of the respective mimylin derivative was analysed using LC-MS. Individual plasma concentration-time profiles were analysed by a non-compartmental model in Phoenix WinNonlin version 6.3 (Pharsight Inc., Mountain View, Calif., USA).

The resulting terminal half-life was determined based on intravenous administration. T½ is the terminal half-life=ln $2/\lambda_z$ and was determined from $\lambda_z$, the first order rate constant associated with the terminal (log-linear) portion of the curve, estimated by linear regression of time vs. log concentration.

The absolute bioavailability (F) was calculated as follows:

The area under the plasma concentration versus time curve (AUC, [time×concentration]) was calculated (by the Pharsight programme) after both subcutaneous administration and intravenous administration, typically until 240-288 hours post dosing, or until last measured concentration. The AUC was calculated by extrapolating to infinity and dose normalized. The absolute bioavailability (F %) was then calculated based on the dose-corrected AUC values, namely as $AUC/D_{sc}$ divided by $AUC/D_{iv} \times 100$, where $D_{sc}$ is the subcutaneous dose per kg, and $D_{iv}$ the dose per kg given intravenously.

Assay (XVII)—Determination of T½ and Subcutaneous Bioavailability in Beagle Dogs Pharmacokinetic (PK) studies in Beagle dogs were conducted in order to determine a) the protraction of the mimylin derivative after i.v. administration, and b) the bioavailability of the mimylin derivative after s.c. administration.

By protraction is meant the prolongation of the time in the body and thereby the time of action of the mimylin derivatives. This was done in PK studies, where the terminal half-life of the derivative in question was determined following i.v. administration. By terminal half-life is generally meant the period of time it takes to halve a certain plasma concentration, measured after the initial distribution phase.

The mimylin compound was subjected to PK studies as described below.

For the studies with the mimylin derivative Compound 2 the Beagle dogs were 1 to 5 years of age and weighing approximately 10-12 kg at the start of the studies. The dogs were group housed in pens (12 hours light: 12 hours dark), and fed individually and restrictedly once daily with Royal Canin Medium Adult dog (Royal Canin Products, Brogaarden A/S, Denmark). Exercise and group social was permitted daily, whenever possible. The dogs were used for repeated pharmacokinetic studies with a suitable wash-out period between dosings. An appropriate acclimatisation period was given prior to initiation of the first pharmacokinetic study. All handling, dosing and blood sampling of the animals was performed by trained and skilled staff. Before the studies the dogs were fasted overnight and from 0 to 4 h after dosing. Besides, the dogs were restricted to water 1 hour before dosing until 4 hours after dosing, but otherwise had ad libitum access to water during the whole period.

Intravenous and Subcutaneous Administration

In the i.v. and s.c. studies, the mimylin derivative, dissolved 10 mM phosphate; 250 mM glycerol; 0.025% polysorbate 20, pH=7.4, to a concentration of approximately 10 nmol/ml (i.v.) and 50 nmol/ml (s.c.), were administered to the dogs by intravenous or subcutaneous injections (the volume corresponding to 1-5 nmol/kg, for example 0.1-0.2 ml/kg) in the cephalic or in subcutaneously in the dorsal part of the neck.

Blood Sampling

Blood was sampled at predefined time points for up till 10-12 days post dosing to adequately cover the full plasma concentration-time profile of the mimylin derivative.

For each blood sampling time point approximately 0.8 mL of whole blood was collected in a 1.5 mL EDTA coated tube (8 mM), and the tube was gently turned to allowing mixing of the sample with the anticoagulant, and then centrifuged at 4° C. and 1942G for 4 minutes. Plasma was pipetted into Micronic tubes on dry ice, and kept at −20° C. until analysis.

Blood samples were taken as appropriate, for example a) from the jugular vein using a standard 21G needle and a syringe, or b) from a venflon in the cephalic vein in the front leg for the first 2 hours and then with syringe from the jugular vein for the rest of the time points (the first few drops were allowed to drain from the venflon to avoid heparin saline from the venflon in the sample).

Analysis

The plasma concentration of the respective mimylin derivative was analysed using LC-MS. Individual plasma concentration-time profiles were analysed by a non-compartmental model in Phoenix WinNonlin version 6.3 (Pharsight Inc., Mountain View, Calif., USA).

The resulting terminal half-life was determined based on intravenous administration. T½ is the terminal half-life=ln $2/\lambda_z$ and was determined from $\lambda_z$, the first order rate constant associated with the terminal (log-linear) portion of the curve, estimated by linear regression of time vs. log concentration.

The absolute bioavailability (F) was calculated as follows:

The area under the plasma concentration versus time curve (AUC, [time×concentration]) was calculated (by the Pharsight programme) after both subcutaneous administration and intravenous administration, typically until 240-288 hours post dosing, or until last measured concentration. The AUC was calculated by extrapolating to infinity and dose normalized. The absolute bioavailability (F %) was then calculated based on the dose-corrected AUC values, namely as $AUC/D_{sc}$ divided by $AUC/D_{iv} \times 100$, where $D_{sc}$ is the subcutaneous dose per kg, and Di, the dose per kg given intravenously.

Results

TABLE 8

3 nmol/kg mimylin compound and effects on food intake reduction in the time spans 0-24 hours after administration and 24-48 hours after administration (Assay I)

| EX. # | PD rat 3 nmol/kg reduction (%) 0-24 h | PD rat 3 nmol/kg Reduction (%) 24-48 h |
|---|---|---|
| 2 | 79 | 60.66667 |
| 3 | 63 | 9 |
| 4 | 13.5 | −4 |
| 5 | 3 | −3 |
| 6 | 2 | −12 |
| 9 | 58.5 | 39 |
| 13 | 70 | 18 |
| 21 | 71 | 46 |
| 22 | 55.5 | 63.5 |
| 28 | 84 | 77 |
| 29 | 52 | 0 |
| 31 | 62 | 12 |
| 33 | 73 | 39 |
| 40 | 49 | 79 |
| 46 | 82 | 78 |
| 47 | 66 | 10 |
| 48 | 52 | 11 |
| 49 | 28 | −2 |
| 56 | 45 | 67 |
| 58 | 74 | 63 |
| 72 | 17 | 11 |
| 73 | 55 | 62 |
| 80 | 49 | 56 |
| 84 | 7 | 3 |
| 85 | 44 | 24 |
| 98 | 52 | 57 |
| 99 | 46 | 68 |
| 103 | 23 | 10 |
| 104 | 26 | 28 |
| 107 | 4 | −5 |

TABLE 8-continued 3 nmol/kg mimylin compound and effects on food intake reduction in the time spans 0-24 hours after administration and 24-48 hours after administration (Assay I)

| EX. # | PD rat 3 nmol/kg reduction (%) 0-24 h | PD rat 3 nmol/kg Reduction (%) 24-48 h |
|---|---|---|
| 108 | 27 | 26 |
| 109 | 40 | 42 |
| 110 | 44 | 8 |
| 113 | 21 | 6 |
| 117 | 20 | 14 |
| 118 | 26 | 15 |
| 119 | 25 | 29 |
| 120 | 22 | 19 |
| 121 | 0 | 0 |
| 125 | 9 | 5 |
| 126 | 34 | 24 |
| 127 | 36 | 21 |
| 129 | 32 | 0 |
| 130 | 25 | 10 |
| 131 | 8 | 9 |

TABLE 9

3 nmol/kg mimylin compound and effects on food intake reduction of above 0 in the period 0 h-24 h after administration (Assay I)
EX. #

| 2 | 21 | 46 | 73 | 104 | 118 | 130 |
| 3 | 22 | 47 | 80 | 107 | 119 | 131 |
| 4 | 28 | 48 | 84 | 108 | 120 | — |
| 5 | 29 | 49 | 85 | 109 | 125 | — |
| 6 | 31 | 56 | 98 | 110 | 126 | — |
| 9 | 33 | 58 | 99 | 113 | 127 | — |
| 13 | 40 | 72 | 103 | 117 | 129 | — |

TABLE 10

3 nmol/kg mimylin compound and effects on food intake reduction of 10 or more in the period 0 h-24 h after administration (Assay I)
EX. #

| 2 | 22 | 46 | 72 | 103 | 117 | 128 |
| 3 | 28 | 47 | 73 | 104 | 118 | 129 |
| 4 | 29 | 48 | 80 | 108 | 119 | 130 |
| 9 | 31 | 49 | 85 | 109 | 120 | |
| 13 | 33 | 56 | 98 | 110 | 126 | |
| 21 | 40 | 58 | 99 | 113 | 127 | |

TABLE 11

3 nmol/kg mimylin compound and effects on food intake reduction of above 0 in the period 24 h-48 h after administration (Assay I)
EX. #

| 2 | 28 | 48 | 84 | 108 | 119 | 131 |
| 3 | 31 | 56 | 85 | 109 | 120 | — |
| 9 | 33 | 58 | 98 | 110 | 125 | — |
| 13 | 40 | 72 | 99 | 113 | 126 | — |
| 21 | 46 | 73 | 103 | 117 | 127 | — |
| 22 | 47 | 80 | 104 | 118 | 130 | — |

TABLE 12

3 nmol/kg mimylin compound and effects on food intake reduction of 10 or more in the period 24 h-48 h after administration (Assay I)
EX. #

2
9
13
21
22
28
31
33
40
46
47
48
56
58
72
73
80
85
98
99
103
104
108
109
117
118
119
120
126
127
130
—
—
—
—

TABLE 13

EC50 (pM) of mimylin compounds in functinal human calcitonin and amylin receptor assay without HSA (Assay IIb)

| | Tested without HSA | |
|---|---|---|
| EX. # | hAmylin-R funct. EC50 (pM) | hCTR funct. EC50 (pM) |
| 1 | 3 | 1 |
| 2 | 8 | 5 |
| 3 | 8 | 4 |
| 4 | 6 | 2 |
| 5 | 27 | 7 |
| 6 | 23 | 8 |
| 7 | 10 | 13 |
| 8 | 7 | 7 |
| 9 | 12 | 9 |
| 10 | 16 | 5 |
| 11 | 7 | 5 |
| 12 | 6 | 5 |
| 13 | 4 | 3 |
| 14 | 28 | 13 |
| 15 | 9 | 7 |
| 16 | 15 | 9 |
| 17 | 8 | 6 |
| 18 | 20 | 17 |
| 19 | 8 | 3 |
| 20 | 11 | 7 |
| 21 | 9 | 6 |
| 22 | 11 | 9 |
| 23 | 9 | 4 |

TABLE 13-continued

| EC50 (pM) of mimylin compounds in functinal human calcitonin and amylin receptor assay without HSA (Assay IIb) | | |
|---|---|---|
| | Tested without HSA | |
| EX. # | hAmylin-R funct. EC50 (pM) | hCTR funct. EC50 (pM) |
| 24 | 20 | 14 |
| 25 | 10 | 7 |
| 26 | 7 | 6 |
| 27 | 8 | 4 |
| 28 | 8 | 7 |
| 29 | 10 | 7 |
| 30 | 14 | 7 |
| 31 | 14 | 6 |
| 32 | 31 | 12 |
| 33 | 8 | 7 |
| 34 | 12 | 14 |
| 35 | 13 | 8 |
| 36 | 23 | 54 |
| 37 | 10 | 5 |
| 38 | 12 | 6 |
| 39 | 16 | 8 |
| 40 | 13 | 14 |
| 41 | 27 | 18 |
| 42 | 17 | 12 |
| 43 | 18 | 11 |
| 44 | 24 | 13 |
| 45 | 15 | 10 |
| 46 | 16 | 17 |
| 47 | 18 | 15 |
| 48 | 18 | 17 |
| 49 | 10 | 10 |
| 50 | 6 | 4 |
| 51 | 7 | 5 |
| 52 | 39 | 34 |
| 53 | 22 | 31 |
| 54 | 28 | 19 |
| 55 | 41 | 29 |
| 56 | 22 | 23 |
| 57 | 20 | 22 |
| 58 | 10 | 10 |
| 59 | 46 | 37 |
| 60 | 53 | 48 |
| 61 | 50 | 40 |
| 62 | 55 | 31 |
| 63 | 63 | 38 |
| 64 | 142 | 66 |
| 65 | 67 | 40 |
| 66 | 41 | 25 |
| 67 | 20 | 14 |
| 68 | 36 | 27 |
| 69 | 21 | 28 |
| 70 | 32 | 19 |
| 71 | 53 | 30 |
| 72 | 17 | 12 |
| 73 | 27 | 18 |
| 74 | 50 | 45 |
| 75 | 80 | 19 |
| 76 | 10 | 14 |
| 77 | 10 | 6 |
| 78 | 9 | 11 |
| 79 | 38 | 42 |
| 80 | 32 | 29 |
| 81 | 37 | 41 |
| 82 | 33 | 27 |
| 83 | 17 | 15 |
| 84 | 26 | 12 |
| 85 | 33 | 28 |
| 86 | 32 | 13 |
| 87 | 9 | 13 |
| 88 | 461 | 127 |
| 89 | 187 | 64 |
| 90 | 239 | 88 |
| 91 | 37 | 41 |
| 92 | 22 | 23 |
| 93 | 64 | 24 |

TABLE 13-continued

| EC50 (pM) of mimylin compounds in functinal human calcitonin and amylin receptor assay without HSA (Assay IIb) | | |
|---|---|---|
| | Tested without HSA | |
| EX. # | hAmylin-R funct. EC50 (pM) | hCTR funct. EC50 (pM) |
| 94 | 42 | 30 |
| 95 | 65 | 32 |
| 96 | 11 | 8 |
| 97 | 50 | 34 |
| 98 | 47 | 28 |
| 99 | 20 | 23 |
| 100 | 17 | 16 |
| 101 | 51 | 37 |
| 102 | 12 | 6 |
| 103 | 43 | 23 |
| 104 | 67 | 70 |
| 105 | 235 | 45 |
| 106 | 386 | 66 |
| 107 | 68 | 36 |
| 108 | ND | ND |
| 109 | 37 | 25 |
| 110 | ND | ND |
| 111 | 22 | 24 |
| 112 | 54 | 18 |
| 113 | 36 | 21 |
| 114 | 76 | 60 |
| 115 | 66 | 56 |
| 116 | 62 | 63 |
| 117 | 41 | 27 |
| 118 | 57 | 65 |
| 119 | 72 | 49 |
| 120 | 89 | 52 |
| 121 | 50 | 22 |
| 122 | 53 | 52 |
| 123 | 24 | 28 |
| 124 | 40 | 34 |
| 125 | 70 | 57 |
| 126 | 52 | 40 |
| 127 | 31 | 31 |
| 128 | 23 | 19 |
| 129 | 25 | 25 |
| 130 | 54 | 45 |
| 131 | 18 | 15 |
| 132 | 16 | 15 |
| 133 | 10 | 12 |
| 134 | 481 | 45 |
| 72bb | 14 | 3 |
| 95bb | 46 | 9 |
| 127bb | 11 | 6 |
| 22bb | 5 | 2 |
| 86bb | 7 | 2 |
| 106bb | 629 | 103 |
| 135 | 23628 | 840 |
| 124bb | 5 | 4 |
| 118bb, 120bb, 121bb | 8 | 4 |

TABLE 14

| EC50 (pM) of mimylin compounds in functinal human calcitonin and amylin receptor assay withSA (Assay IIa) | | |
|---|---|---|
| | Tested with HSA | |
| EX. # | hAmylin-R funct. EC50 (pM) | hCTR funct. EC50 (pM) |
| 21 | 39 | 19 |
| 22 | 61 | 26 |
| 23 | 26 | 9 |
| 34 | 143 | 74 |

TABLE 14-continued

EC50 (pM) of mimylin compounds in functinal human calcitonin and amylin receptor assay withSA (Assay IIa)

| | Tested with HSA | |
|---|---|---|
| EX. # | hAmylin-R funct. EC50 (pM) | hCTR funct. EC50 (pM) |
| 35 | 39 | 19 |
| 40 | 51 | 29 |
| 41 | 73 | 30 |
| 42 | 67 | 35 |
| 43 | 68 | 25 |
| 44 | 62 | 25 |
| 45 | 66 | 27 |
| 46 | 26 | 11 |
| 47 | 4 | 2 |
| 48 | 9 | 8 |
| 49 | 4 | 3 |
| 50 | 4 | 4 |
| 51 | 6 | 4 |
| 52 | 74 | 30 |
| 53 | 57 | 48 |
| 54 | 49 | 28 |
| 55 | 140 | 42 |
| 56 | 67 | 24 |
| 57 | 82 | 51 |
| 58 | 24 | 15 |
| 59 | 62 | 49 |
| 60 | 125 | 72 |
| 61 | 94 | 73 |
| 62 | 168 | 78 |
| 63 | 328 | 154 |
| 64 | 435 | 239 |
| 65 | 265 | 102 |
| 66 | 85 | 40 |
| 67 | 94 | 23 |
| 68 | 72 | 37 |
| 69 | 100 | 44 |
| 70 | 47 | 22 |
| 71 | 164 | 59 |
| 72 | 230 | 48 |
| 73 | 185 | 22 |
| 74 | 134 | 56 |
| 75 | 413 | 95 |
| 76 | 17 | 11 |
| 79 | 71 | 45 |
| 80 | 93 | 71 |
| 81 | 100 | 37 |
| 82 | 58 | 30 |
| 83 | 181 | 113 |
| 84 | 440 | 123 |
| 85 | 19 | 9 |
| 86 | 356 | 87 |
| 88 | 976 | 418 |
| 89 | 210 | 50 |
| 90 | 209 | 53 |
| 91 | 81 | 42 |
| 92 | 150 | 105 |
| 93 | 729 | 109 |
| 94 | 30 | 75 |
| 95 | 52 | 13 |
| 96 | 38 | 11 |
| 97 | 64 | 48 |
| 98 | 66 | 35 |
| 99 | 92 | 40 |
| 100 | 143 | 108 |
| 101 | 93 | 73 |
| 102 | 106 | 28 |
| 103 | 128 | 92 |
| 104 | 122 | 53 |
| 105 | 179 | 22 |
| 106 | 157 | 31 |
| 107 | 335 | 113 |
| 108 | 150 | 68 |
| 109 | 158 | 108 |
| 110 | 70 | 53 |
| 111 | 52 | 49 |
| 112 | 291 | 67 |
| 113 | 159 | 57 |
| 114 | 142 | 97 |
| 115 | 546 | 366 |
| 116 | 67 | 36 |
| 117 | 212 | 99 |
| 118 | 105 | 54 |
| 119 | 86 | 61 |
| 120 | 123 | 68 |
| 121 | 80 | 38 |
| 122 | 77 | 37 |
| 123 | 64 | 34 |
| 124 | 122 | 92 |
| 125 | 152 | 72 |
| 126 | 223 | 142 |
| 127 | 140 | 73 |
| 128 | 173 | 77 |
| 129 | 565 | 852 |
| 130 | 185 | 99 |
| 131 | 154 | 62 |
| 132 | 37 | 50 |
| 133 | 44 | 50 |

TABLE 15

Stability of selected mimylin compounds (Assay III)

| Ex. # | ThT pH 7.5 lag time (h) | ThT pH 7.5 recovery (%) |
|---|---|---|
| 40 | >45 | 100 |
| 41 | >45 | 100 |
| 42 | >45 | 100 |
| 43 | >45 | 100 |
| 44 | >45 | 100 |
| 45 | >45 | 100 |
| 46 | >45 | 100 |
| 47 | >45 | 100 |
| 50 | >45 | 98 |
| 52 | >45 | 100 |
| 53 | >45 | 100 |
| 54 | >45 | 100 |
| 55 | >45 | 94 |
| 56 | >45 | 100 |
| 58 | >45 | 100 |
| 59 | >45 | 100 |
| 60 | >45 | 100 |
| 61 | >45 | 100 |
| 62 | >45 | 100 |
| 63 | >45 | 100 |
| 64 | >45 | 100 |
| 65 | >45 | 100 |
| 80 | >45 | 100 |
| 98 | >45 | 100 |
| 101 | 0 | 100 |
| 104 | >45 | 100 |
| 107 | 0.3 | 0 |
| 108 | >45 | 100 |
| 109 | >45 | 100 |
| 110 | >45 | 100 |
| 116 | 1 | 16 |
| 118 | 0 | 23 |
| 119 | 1.5 | 39.5 |
| 120 | >45 | 100 |
| 121 | >45 | 100 |
| 125 | >45 | 100 |
| 126 | 8.4 | 90 |
| 127 | >45 | 100 |
| 130 | 8 | 2 |

TABLE 16

Solubility of mimylin compounds (Assay IV)
Solubility (μM)

| Ex. # | pH 3.0 | pH 4.0 | pH 5.0 | pH 6.0 | pH 6.5 | pH 7.0 | pH 7.5 | pH 8.0 |
|---|---|---|---|---|---|---|---|---|
| 2 | ≥200 | ≥200 | ≥200 | ≥200 | ≥200 | ≥200 | ≥200 | ≥200 |
| 3 | ≥200 | ≥200 | ≥200 | ≥200 | ≥200 | ≥200 | ≥200 | ≥200 |
| 4 | ≥200 | ≥200 | ≥200 | ≥200 | ≥200 | ≥200 | ≥200 | ≥200 |
| 5 | ≥200 | ≥200 | ≥200 | ≥200 | ≥200 | ≥200 | ≥200 | ≥200 |
| 6 | ≥200 | ≥200 | ≥200 | ≥200 | ≥200 | ≥200 | ≥200 | ≥200 |
| 7 | ≥200 | ≥200 | ≥200 | ≥200 | ≥200 | ≥200 | ≥200 | ≥200 |
| 8 | ≥200 | 94 | 35 | ≥200 | ≥200 | ≥200 | ≥200 | ≥200 |
| 9 | ≥200 | ≥200 | ≥200 | ≥200 | ≥200 | ≥200 | ≥200 | ≥200 |
| 10 | ≥200 | 182 | ≥200 | ≥200 | ≥200 | ≥200 | ≥200 | ≥200 |
| 11 | ≥200 | ≥200 | ≥200 | ≥200 | ≥200 | ≥200 | ≥200 | ≥200 |
| 12 | ≥200 | ≥200 | ≥200 | ≥200 | ≥200 | ≥200 | ≥200 | ≥200 |
| 13 | ≥200 | ≥200 | ≥200 | ≥200 | ≥200 | ≥200 | ≥200 | ≥200 |
| 14 | ≥200 | ≥200 | ≥200 | ≥200 | ≥200 | ≥200 | ≥200 | ≥200 |
| 15 | ≥200 | ≥200 | ≥200 | ≥200 | ≥200 | ≥200 | ≥200 | ≥200 |
| 16 | ≥200 | ≥200 | ≥200 | ≥200 | ≥200 | ≥200 | ≥200 | ≥200 |
| 17 | ≥200 | ≥200 | ≥200 | ≥200 | ≥200 | ≥200 | ≥200 | ≥200 |
| 18 | ≥200 | ≥200 | ≥200 | ≥200 | ≥200 | ≥200 | ≥200 | ≥200 |
| 19 | ≥200 | ≥200 | ≥200 | ≥200 | ≥200 | ≥200 | ≥200 | ≥200 |
| 20 | ND | ND | ND | ND | ND | ND | ND | ND |
| 21 | ≥200 | ≥200 | ≥200 | ≥200 | ≥200 | ≥200 | ≥200 | ≥200 |
| 22 | ≥200 | ≥200 | ≥200 | ≥200 | ≥200 | ≥200 | ≥200 | ≥200 |
| 23 | ≥200 | ≥200 | ≥200 | ≥200 | ≥200 | ≥200 | ≥200 | ≥200 |
| 24 | ≥200 | 150 | 145 | ≥200 | ≥200 | ≥200 | ≥200 | ≥200 |
| 25 | ≥200 | 218 | ≥200 | ≥200 | ≥200 | ≥200 | ≥200 | ≥200 |
| 26 | ≥200 | ≥200 | ≥200 | ≥200 | ≥200 | ≥200 | ≥200 | ≥200 |
| 27 | ≥200 | ≥200 | ≥200 | ≥200 | ≥200 | ≥200 | ≥200 | ≥200 |
| 28 | ≥200 | ≥200 | ≥200 | ≥200 | ≥200 | ≥200 | ≥200 | ≥200 |
| 29 | ≥200 | ≥200 | ≥200 | ≥200 | ≥200 | ≥200 | ≥200 | ≥200 |
| 30 | ≥200 | ≥200 | ≥200 | ≥200 | ≥200 | ≥200 | ≥200 | ≥200 |
| 31 | ≥200 | ≥200 | ≥200 | ≥200 | ≥200 | ≥200 | ≥200 | ≥200 |
| 32 | ≥200 | ≥200 | ≥200 | ≥200 | ≥200 | ≥200 | ≥200 | ≥200 |
| 33 | ≥200 | 1 | ≥200 | ≥200 | ≥200 | ≥200 | ≥200 | ≥200 |
| 34 | ≥200 | ≥200 | ≥200 | ≥200 | ≥200 | ≥200 | ≥200 | ≥200 |
| 35 | ≥200 | ≥200 | ≥200 | ≥200 | ≥200 | ≥200 | ≥200 | ≥200 |
| 36 | 117 | 9 | 10 | ≥200 | ≥200 | ≥200 | ≥200 | ≥200 |
| 37 | ≥200 | 18 | ≥200 | ≥200 | ≥200 | ≥200 | ≥200 | ≥200 |
| 38 | ≥200 | ≥200 | ≥200 | ≥200 | ≥200 | ≥200 | ≥200 | ≥200 |
| 39 | ≥200 | ≥200 | ≥200 | ≥200 | ≥200 | ≥200 | ≥200 | ≥200 |
| 40 | ≥200 | ≥200 | ≥200 | ≥200 | ≥200 | ≥200 | ≥200 | ≥200 |
| 41 | ≥200 | ≥200 | ≥200 | ≥200 | ≥200 | ≥200 | ≥200 | ≥200 |
| 42 | ≥200 | ≥200 | ≥200 | ≥200 | ≥200 | ≥200 | ≥200 | ≥200 |
| 43 | ≥200 | ≥200 | ≥200 | ≥200 | ≥200 | ≥200 | ≥200 | ≥200 |
| 44 | ≥200 | ≥200 | ≥200 | ≥200 | ≥200 | ≥200 | ≥200 | ≥200 |
| 45 | ≥200 | ≥200 | ≥200 | ≥200 | ≥200 | ≥200 | ≥200 | ≥200 |
| 46 | ≥200 | ≥200 | ≥200 | ≥200 | ≥200 | ≥200 | ≥200 | ≥200 |
| 47 | ≥200 | ≥200 | ≥200 | ≥200 | ≥200 | ≥200 | ≥200 | ≥200 |
| 48 | ≥200 | ≥200 | ≥200 | ≥200 | ≥200 | ≥200 | ≥200 | ≥200 |
| 49 | ≥200 | ≥200 | ≥200 | ≥200 | ≥200 | ≥200 | ≥200 | ≥200 |
| 50 | ≥200 | ≥200 | ≥200 | ≥200 | ≥200 | ≥200 | ≥200 | ≥200 |
| 51 | ≥200 | ≥200 | ≥200 | ≥200 | ≥200 | ≥200 | ≥200 | ≥200 |
| 52 | ≥200 | ≥200 | ≥200 | ≥200 | ≥200 | ≥200 | ≥200 | ≥200 |
| 53 | ≥200 | ≥200 | ≥200 | ≥200 | ≥200 | ≥200 | ≥200 | ≥200 |
| 54 | ≥200 | ≥200 | ≥200 | ≥200 | ≥200 | ≥200 | ≥200 | ≥200 |
| 55 | ≥200 | ≥200 | ≥200 | ≥200 | ≥200 | ≥200 | ≥200 | ≥200 |
| 56 | ≥200 | ≥200 | ≥200 | ≥200 | ≥200 | ≥200 | ≥200 | ≥200 |
| 57 | ≥200 | ≥200 | ≥200 | ≥200 | ≥200 | ≥200 | ≥200 | ≥200 |
| 58 | ≥200 | ≥200 | ≥200 | ≥200 | ≥200 | ≥200 | ≥200 | ≥200 |
| 59 | ≥200 | ≥200 | 73 | ≥200 | ≥200 | ≥200 | ≥200 | ≥200 |
| 60 | ≥200 | ≥200 | ≥200 | ≥200 | ≥200 | ≥200 | ≥200 | ≥200 |
| 61 | ≥200 | ≥200 | 101 | ≥200 | ≥200 | ≥200 | ≥200 | ≥200 |
| 62 | ≥200 | ≥200 | ≥200 | ≥200 | ≥200 | ≥200 | ≥200 | ≥200 |
| 63 | ≥200 | ≥200 | ≥200 | ≥200 | ≥200 | ≥200 | ≥200 | ≥200 |
| 64 | ≥200 | ≥200 | ≥200 | ≥200 | ≥200 | ≥200 | ≥200 | ≥200 |
| 65 | ≥200 | ≥200 | ≥200 | ≥200 | ≥200 | ≥200 | ≥200 | ≥200 |
| 66 | ≥200 | ≥200 | ≥200 | ≥200 | ≥200 | ≥200 | ≥200 | ≥200 |
| 67 | ≥200 | ≥200 | ≥200 | ≥200 | ≥200 | ≥200 | ≥200 | ≥200 |
| 68 | ≥200 | ≥200 | ≥200 | ≥200 | ≥200 | ≥200 | ≥200 | ≥200 |
| 69 | ≥200 | ≥200 | ≥200 | ≥200 | ≥200 | ≥200 | ≥200 | ≥200 |
| 70 | ≥200 | ≥200 | ≥200 | ≥200 | ≥200 | ≥200 | ≥200 | ≥200 |
| 71 | ≥200 | ≥200 | ≥200 | ≥200 | ≥200 | ≥200 | ≥200 | ≥200 |
| 72 | ≥200 | ≥200 | ≥200 | ≥200 | ≥200 | ≥200 | ≥200 | ≥200 |
| 73 | ≥200 | ≥200 | ≥200 | ≥200 | ≥200 | ≥200 | ≥200 | ≥200 |
| 74 | ≥200 | ≥200 | ≥200 | ≥200 | ≥200 | ≥200 | ≥200 | ≥200 |
| 75 | ≥200 | ≥200 | ≥200 | ≥200 | ≥200 | ≥200 | ≥200 | ≥200 |
| 76 | ≥200 | ≥200 | ≥200 | ≥200 | ≥200 | ≥200 | ≥200 | ≥200 |
| 77 | ≥200 | 7 | 11 | ≥200 | ≥200 | ≥200 | ≥200 | ≥200 |
| 78 | ≥200 | ≥200 | ≥200 | ≥200 | ≥200 | ≥200 | ≥200 | ≥200 |
| 79 | ≥200 | ≥200 | ≥200 | ≥200 | ≥200 | ≥200 | ≥200 | ≥200 |
| 80 | ≥200 | ≥200 | 10 | ≥200 | ≥200 | ≥200 | ≥200 | ≥200 |
| 81 | ≥200 | ≥200 | ≥200 | ≥200 | ≥200 | ≥200 | ≥200 | ≥200 |
| 82 | ≥200 | ≥200 | 1 | ≥200 | ≥200 | ≥200 | ≥200 | ≥200 |
| 83 | ≥200 | ≥200 | ≥200 | ≥200 | ≥200 | ≥200 | ≥200 | ≥200 |
| 84 | ≥200 | ≥200 | ≥200 | ≥200 | ≥200 | ≥200 | ≥200 | ≥200 |
| 85 | ≥200 | ≥200 | ≥200 | ≥200 | ≥200 | ≥200 | ≥200 | ≥200 |
| 86 | ≥200 | ≥200 | ≥200 | 38 | ≥200 | ≥200 | ≥200 | ≥200 |
| 87 | ≥200 | ≥200 | ≥200 | ≥200 | ≥200 | ≥200 | ≥200 | ≥200 |
| 88 | ≥200 | 1 | 6 | ≥200 | ≥200 | ≥200 | ≥200 | ≥200 |
| 89 | ND | ND | ND | ND | ND | ND | ND | ND |
| 90 | ND | ND | ND | ND | ND | ND | ND | ND |
| 91 | ≥200 | 7 | 29 | ≥200 | ≥200 | ≥200 | ≥200 | ≥200 |
| 92 | ≥200 | ≥200 | 169 | ≥200 | ≥200 | ≥200 | ≥200 | ≥200 |
| 93 | ≥200 | ≥200 | ≥200 | ≥200 | ≥200 | ≥200 | ≥200 | ≥200 |
| 94 | ≥200 | ≥200 | ≥200 | ≥200 | ≥200 | ≥200 | ≥200 | ≥200 |
| 95 | ≥200 | ≥200 | ≥200 | ≥200 | ≥200 | ≥200 | ≥200 | ≥200 |
| 96 | ≥200 | 177 | 45 | ≥200 | ≥200 | ≥200 | ≥200 | ≥200 |
| 97 | ≥200 | ≥200 | 40 | ≥200 | ≥200 | ≥200 | ≥200 | ≥200 |
| 98 | ≥200 | ≥200 | ≥200 | ≥200 | ≥200 | ≥200 | ≥200 | ≥200 |
| 99 | ≥200 | ≥200 | 19 | ≥200 | ≥200 | ≥200 | ≥200 | ≥200 |
| 100 | ≥200 | 0 | 1 | 63 | 180 | ≥200 | ≥200 | ≥200 |
| 101 | ≥200 | ≥200 | ≥200 | ≥200 | ≥200 | ≥200 | ≥200 | ≥200 |
| 102 | 6 | 0 | ≥200 | ≥200 | ≥200 | ≥200 | ≥200 | ≥200 |
| 103 | ≥200 | ≥200 | 156 | ≥200 | ≥200 | ≥200 | ≥200 | ≥200 |
| 104 | ≥200 | ≥200 | 119 | ≥200 | ≥200 | ≥200 | ≥200 | ≥200 |
| 105 | ≥200 | ≥200 | ≥200 | ≥200 | ≥200 | ≥200 | ≥200 | ≥200 |
| 106 | ≥200 | ≥200 | ≥200 | ≥200 | ≥200 | ≥200 | ≥200 | ≥200 |
| 107 | ≥200 | ≥200 | ≥200 | 148 | 129 | 74 | ≥200 | ≥200 |
| 108 | ≥200 | ≥200 | 65 | ≥200 | ≥200 | ≥200 | ≥200 | ≥200 |
| 109 | ≥200 | ≥200 | 7 | ≥200 | ≥200 | ≥200 | ≥200 | ≥200 |
| 110 | ≥200 | ≥200 | 149 | ≥200 | ≥200 | ≥200 | ≥200 | ≥200 |
| 111 | ≥200 | 1 | 2 | 0 | 1 | 0 | 0 | 0 |
| 112 | ≥200 | 132 | 22 | ≥200 | ≥200 | ≥200 | ≥200 | ≥200 |
| 113 | ≥200 | 195 | 57 | ≥200 | ≥200 | ≥200 | ≥200 | ≥200 |
| 114 | ≥200 | 65 | 7 | ≥200 | ≥200 | ≥200 | ≥200 | ≥200 |
| 115 | ND | ND | ND | ND | ND | ND | ND | ND |
| 116 | ≥200 | ≥200 | 32 | ≥200 | ≥200 | ≥200 | ≥200 | ≥200 |
| 117 | ≥200 | ≥200 | 38 | ≥200 | ≥200 | ≥200 | ≥200 | ≥200 |
| 118 | ≥200 | 2 | 8 | 17 | 5 | 26 | 90 | 173 |
| 119 | ≥200 | 170 | 56 | ≥200 | ≥200 | ≥200 | ≥200 | ≥200 |
| 120 | ≥200 | ≥200 | 96 | ≥200 | ≥200 | ≥200 | ≥200 | ≥200 |
| 121 | ≥200 | ≥200 | 110 | ≥200 | ≥200 | ≥200 | ≥200 | ≥200 |
| 122 | ≥200 | ≥200 | 32 | ≥200 | ≥200 | ≥200 | ≥200 | ≥200 |
| 123 | ≥200 | ≥200 | 2 | ≥200 | ≥200 | ≥200 | ≥200 | ≥200 |
| 124 | ≥200 | ≥200 | 61 | ≥200 | ≥200 | ≥200 | ≥200 | ≥200 |
| 125 | ≥200 | 28 | ≥200 | ≥200 | ≥200 | ≥200 | ≥200 | ≥200 |
| 126 | ≥200 | 0 | 0 | 161 | ≥200 | ≥200 | ≥200 | ≥200 |
| 127 | ≥200 | 31 | 0 | ≥200 | ≥200 | ≥200 | ≥200 | ≥200 |
| 128 | ≥200 | 25 | ≥200 | ≥200 | ≥200 | ≥200 | ≥200 | ≥200 |
| 129 | ≥200 | ≥200 | 1 | 1 | 1 | 1 | 52 | 185 |
| 130 | ≥200 | 174 | 9 | ≥200 | ≥200 | ≥200 | ≥200 | ≥200 |
| 131 | ≥200 | 10 | ≥200 | ≥200 | ≥200 | ≥200 | ≥200 | ≥200 |

TABLE 17

Amylin and calcitonin receptor IC50 (pM)
for mimylin compounds (Assay V & VII)

| Ex. # | hAmylin-R binding IC50 (pM) | hCT-R binding IC50 (pM) | rAmylin-R binding IC50 (pM) | rCT-R binding IC50 (pM) |
|---|---|---|---|---|
| 41 | 141 | 85 | 146 | 44 |
| 42 | 159 | 50 | ND | ND |
| 43 | 164 | 50 | ND | ND |
| 45 | 389 | 112 | ND | ND |
| 46 | 516 | 84 | ND | ND |

TABLE 17-continued

Amylin and calcitonin receptor IC50 (pM) for mimylin compounds (Assay V & VII)

| Ex. # | hAmylin-R binding IC50 (pM) | hCT-R binding IC50 (pM) | rAmylin-R binding IC50 (pM) | rCT-R binding IC50 (pM) |
|---|---|---|---|---|
| 47 | 37 | 24 | 22 | 13 |
| 48 | 77 | 34 | 63 | 13 |
| 49 | 15 | 11 | 64 | 11 |
| 50 | 54 | 23 | 122 | 17 |
| 51 | 773 | 140 | ND | 123 |
| 52 | 724 | 136 | ND | 114 |
| 53 | 114 | 215 | 1302 | 65 |
| 54 | 442 | 85 | 455 | 44 |
| 55 | 202 | 84 | 242 | 27 |
| 56 | 394 | 70 | 3986 | 202 |
| 57 | 124 | 108 | 25 | 44 |
| 59 | 243 | 113 | 29 | 23 |
| 60 | 57 | 34 | 46 | 20 |
| 67 | 29 | 22 | 17 | 17 |
| 68 | 50 | 10 | 46 | 10 |
| 69 | 74 | 46 | 115 | 42 |
| 70 | 206 | 77 | 684 | 71 |
| 71 | 251 | 70 | 374 | 31 |
| 72 | 565 | 97 | 1529 | 85 |
| 81 | 141 | 102 | 26 | 39 |
| 99 | 159 | 154 | 45 | 69 |
| 100 | 171 | 100 | 46 | 62 |
| 105 | 309 | 222 | 162 | 72 |
| 109 | 131 | 51 | 78 | 12 |
| 110 | 122 | 57 | 13 | 13 |
| 114 | 297 | 85 | 146 | 21 |
| 117 | 166 | 150 | 26 | 31 |
| 119 | 152 | 67 | 53 | 16 |
| 120 | 166 | 91 | 29 | 27 |
| 121 | 371 | 120 | 357 | 32 |
| 126 | 225 | 193 | 91 | 31 |
| 128 | 216 | 53 | 98 | 28 |
| 131 | 720 | 651 | 385 | 246 |
| 132 | 390 | 131 | 1159 | 69 |

TABLE 18

T1/2 of mimylin compounds in mini pigs (Assay IX)

| Ex. # | PK mini pig iv T1/2 (h) |
|---|---|
| Salmon calcitonin | 0 |
| 1 | 0 |
| 2 | 85 |
| 3 | 17 |
| 4 | 2 |
| 6 | 1 |
| 9 | 90 |
| 13 | 86 |
| 21 | 118 |
| 22 | 108 |
| 40 | 171 |
| 46 | 118 |
| 56 | 88 |
| 110 | 32 |
| 116 | 87 |

TABLE 19

T1/2 of mimylin compounds in rats (Assay X)

| EX. # | PK rat iv T1/2 (hours) | PK rat sc T1/2 (hours) |
|---|---|---|
| Salmon Calcitonin | ND | 1 |
| 2 | 12 | 13 |
| 3 | 3 | 3 |
| 4 | 3 | 3 |
| 5 | 6 | 13 |

TABLE 20

Subcutaneous mimylin derivative PK in LYD-pigs co-formulated or co-dosed with liraglutide (Assay XV)

| | Co-formulation | | Co-dosing | |
|---|---|---|---|---|
| Pharmcokinetic parameter | Liraglutide | Ex #2 | Liraglutide | Ex #2 |
| T½ (hours) | 20 | 67 | 19 | 67 |
| Cmax/D (kg/L) | 3.9 | 5.8 | 3.4 | 6.9 |
| AUC/D (hr*kg/L) | 129 | 732 | 114 | 712 |
| Compound | Liraglutide | Ex #46 | Liraglutide | Ex #46 |
| T½ (hours) | 25 | 133 | 21 | 129 |
| Cmax/D (kg/L) | 3.7 | 5.7 | 3.4 | 5.2 |
| AUC/D (hr*kg/L) | 136 | 656 | 111 | 624 |

TABLE 21

T½ and subcutaneous bioavailability in LYD-pigs (Assay XVI)

| Ex. # | LYD-pigs iv PK, t½ (hours)* | Subcutaneous bioavailability (%) |
|---|---|---|
| 2 | 64 | 99 |

*terminal half-life (t½) is harmonic mean, n = 3

TABLE 22

In vivo pharmacokinetic evaluation in Beagle dogs after intravenous and subcutaneous administration (Assay XVII)

| Ex. # | Beagle dogs iv PK, t½ (hours)* | Subcutaneous bioavailability (%) |
|---|---|---|
| 2 | 95 | 98 |

*terminal half-life (t½) is harmonic mean, n = 2

Example A—Preparation of Formulations

Aqueous formulations are prepared by mixing aqueous stock solutions containing well-defined concentrations of excipients (antimicrobial agent, tonicity agent, pH buffer) with an aqueous stock solution containing a well-defined concentration of mimylin peptide and/or a GLP-1 compound. Alternatively, the mimylin peptide is dissolved directly in an aqueous solution containing well-defined concentrations of excipients and a GLP-1 compound. Following pH-adjustment, each formulation is sterile filtered (0.22 μm filter) to sterile glass containers.

Example B—Stability of Formulations Comprising Compounds of EX. #40 and EX. #46

Formulations containing 0.8 mM compound of EX. #40 or 0.8 mM compound of EX. #46 were prepared according to Example A. All formulations contained 8 mM phosphate and were pH-adjusted to pH 8.2. An additional set of formulations also containing 58 mM phenol and 14 mg/ml propylene glycol were prepared. Each formulation was tested according to ASSAY (IIIa).

TABLE 23

Stability of formulations comprising compounds of EX. #40 and EX. #46

| Form-ulation | EX.#40 (mM) | EX.#46 (mM) | Phosphate (mM) | Phenol (mM) | Propylene glycol (mg/ml) | ThT Lag-time (h) | Peptide Rec. (%) |
|---|---|---|---|---|---|---|---|
| F1 | 0.8 | — | 8 | — | — | >45 | 102 |
| F2 | 0.8 | — | 8 | 58 | 14 | >45 | 101 |
| F3 | — | 0.8 | 8 | — | — | >45 | 102 |
| F4 | — | 0.8 | 8 | 58 | 14 | >45 | 102 |

Each formulation was tested according to ASSAY (XIII), and the results are presented below.

TABLE 24

Stability of formulations comprising compounds of EX. #40 and EX. #46

| Form-ulation | EX.#40 (mM) | EX.#46 (mM) | Phosphate (mM) | Phenol (mM) | Propylene glycol (mg/ml) | Pep. Conc.* (%) | HMWP[£] (%) | Post monomer[$] (%) | Purity Loss[□] |
|---|---|---|---|---|---|---|---|---|---|
| F5 | 0.8 | — | 8 | — | — | 101 | 0.75 | 8.2 | 5.9 |
| F6 | 0.8 | — | 8 | 58 | 14 | 101 | 1.2 | 4.2 | 4.3 |
| F7 | — | 0.8 | 8 | — | — | 98 | 0.40 | 4.8 | 8.9 |
| F8 | — | 0.8 | 8 | 58 | 14 | 102 | 0.81 | 1.4 | 4.0 |

*Peptide concentration after 8 weeks at 37° C. relative to start value
[£]HMWP after 8 weeks at 37° C.
[$]Post monomer after 8 weeks at 37° C. minus start value
[□]Purity loss in %/month at 37° C.

Example C—Solubility of Formulations Comprising Compounds of EX. #40 and EX. #46

Formulations containing 0.5 mM compound of EX. #40 or 0.5 mM compound of EX. #46 were prepared according to Example A. All formulations contained 10 mM phosphate and were pH-adjusted to pH 7.4 or pH 8.2. An additional set of formulations also containing 50 mM NaCl and/or 50 mM phenol were prepared. Total peptide concentration was measured after 4-5 days storage at 5° C. or at room temperature.

TABLE 25

Solubility of formulations comrprising compounds of EX. #40 and EX. #46

| Form-ulation | EX.#40 (mM) | EX.#46 (mM) | Phosphate (mM) | NaCl (mM) | Phenol (mM) | Ph | Pep. Conc. 5° C. (mM) | Pep. Conc. 25° C. (mM) |
|---|---|---|---|---|---|---|---|---|
| F9 | 0.5 | | 10 | | | 7.4 | 0.47 | 0.47 |
| F10 | 0.5 | | 10 | 50 | | 7.4 | 0.48 | 0.48 |
| F11 | 0.5 | | 10 | | 50 | 7.4 | 0.48 | 0.48 |
| F12 | 0.5 | | 10 | 50 | 50 | 7.4 | 0.48 | 0.48 |
| F13 | | 0.5 | 10 | | | 7.4 | 0.48 | 0.48 |
| F14 | | 0.5 | 10 | 50 | | 7.4 | 0.50 | 0.49 |
| F15 | | 0.5 | 10 | | 50 | 7.4 | 0.50 | 0.50 |
| F16 | | 0.5 | 10 | 50 | 50 | 7.4 | 0.50 | 0.50 |
| F17 | 0.5 | | 10 | | | 8.2 | 0.4. | 0.48 |
| F18 | 0.5 | | 10 | 50 | | 8.2 | 0.48 | 0.48 |
| F19 | 0.5 | | 10 | | 50 | 8.2 | 0.48 | 0.49 |
| F20 | 0.5 | | 10 | 50 | 50 | 8.2 | 0.49 | 0.49 |
| F21 | | 0.5 | 10 | | | 8.2 | 0.49 | 0.50 |
| F22 | | 0.5 | 10 | 50 | | 8.2 | 0.50 | 0.50 |
| F23 | | 0.5 | 10 | | 50 | 8.2 | 0.50 | 0.50 |
| F24 | | 0.5 | 10 | 50 | 50 | 8.2 | 0.50 | 0.50 |

Example D—Stability of Formulations Compounds of EX. #46

Four formulations containing 0.3 mM or 0.03 mM compound of EX. #46 were prepared according to Example A.

All formulations contained 16 mg/ml glycerol and pH was adjusted to pH 7.4. On top of that, two of the formulations contained 19 mM phenol, 19 mM m-cresol, 5 mM phosphate, 20 mM NaCl and the other two formulations contained 28 mM m-cresol. All formulations were tested according to ASSAY (IIIa).

TABLE 26

Stability of formulations compounds of EX. #46

| Formulation | EX.#46 (mM) | Glycerol (mg/ml) | Phenol (mM) | m-Cresol (mM) | Phosphate (mM) | NaCl (mM) | pH | ThT Lag-time (h) | Peptide Rec. (%) |
|---|---|---|---|---|---|---|---|---|---|
| F25 | 0.3 | 16 | 19 | 19 | 5 | 20 | 7.4 | >45 | 98 |
| F26 | 0.03 | 16 | 19 | 19 | 5 | 20 | 7.4 | >45 | 105 |
| F27 | 0.3 | 16 | — | 28 | — | — | 7.4 | >45 | 104 |
| F28 | 0.03 | 16 | — | 28 | — | — | 7.4 | >45 | 84 |

Example E—Stability of Formulations Comprising Compound of EX. #40

Formulations containing 0.2 mM compound of EX. #40 were prepared according to Example A. All formulations contained 8 mM phosphate pH was adjusted to pH 8.2. On top of that, four of the formulations contained increasing concentration of propylene glycol (10-20-50-100 mg/ml) whereas four other formulations contained increasing concentration of glycerol (10-20-50-100 mg/ml). All formulations were tested according to ASSAY (XII) before and after 4 weeks storage at 5° C. and 37° C.

TABLE 27

Stability of analogue EX. #40

| Formulation | EX.#40 (mM) | Phosphate (mM) | Propylene glycol (mg/ml) | Glycerol (mg/ml) | pH | Total Pep. START (% of start) | Total Pep. 4w5° C. (% of start) | Total Pep. 4w25° C. (% of start) | HMWP. START(%) | HMWP 4w5° C.(%) | HMWP 4w37° C.(%) | Post mon. START(%) | Post mon. 4w5° C.(%) | Post mon. 4w37° C.(%) |
|---|---|---|---|---|---|---|---|---|---|---|---|---|---|---|
| F29 | 0.2 | 8 | — | — | 8.2 | 100 | 113 | 104 | 0.9 | 0.8 | 0.5 | 1.1 | 3.4 | 4.2 |
| F30 | 0.2 | 8 | 10 | — | 8.2 | 100 | 103 | 102 | 0.8 | 0.8 | 0.5 | 1.1 | 1.5 | 3.4 |
| F31 | 0.2 | 8 | 20 | — | 8.2 | 100 | 102 | 103 | 0.8 | 0.8 | 0.5 | 1.0 | 1.6 | 3.1 |
| F33 | 0.2 | 8 | 50 | — | 8.2 | 100 | 101 | 101 | 0.8 | 0.9 | 0.4 | 1.0 | 1.6 | 3.2 |
| F34 | 0.2 | 8 | 100 | — | 8.2 | 100 | 101 | 101 | 0.8 | 0.8 | 0.4 | 1.1 | 1.4 | 2.8 |
| F35 | 0.2 | 8 | — | 10 | 8.2 | 100 | 101 | 102 | 0.8 | 0.8 | 0.9 | 1.0 | 1.5 | 3.0 |
| F36 | 0.2 | 8 | — | 20 | 8.2 | 100 | 101 | 103 | 0.8 | 0.8 | 2.2 | 1.0 | 1.4 | 3.3 |
| F37 | 0.2 | 8 | — | 50 | 8.2 | 100 | 101 | 100 | 0.8 | 0.8 | 0.9 | 1.1 | 1.8 | 13 |
| F38 | 0.2 | 8 | — | 100 | 8.2 | 100 | 100 | 101 | 0.8 | 0.8 | 0.6 | 1.0 | 2.1 | 16 |

Example F—Stability of Formulations Comprising Compound of EX. #2

Formulations containing compound of Ex. #2 were prepared according to Example A and tested according to ASSAY (IIIa)

TABLE 28

Stability of formulation comprising compound of EX. #2

| Formulation | EX.#2 (mM) | Propylene glycol (mg/ml) | Phenol (mM) | Phosphate (mM) | HEPES (mM) | m-Cresol (mM) | NaCl (mM) | pH | ThT Lag-time (h) | Peptide Rec. (%) |
|---|---|---|---|---|---|---|---|---|---|---|
| F39 | 0.4 | 14 | 58 | 8 | — | — | — | 8.2 | >45 | 103 |
| F40 | 0.4 | 14 | 58 | 8 | — | — | — | 7.8 | >45 | 102 |
| F41 | 0.4 | 14 | 58 | 8 | — | — | — | 7.4 | >45 | 103 |
| F42 | 0.4 | 14 | 58 | 8 | — | — | — | 7.0 | >45 | 106 |
| F43 | 0.4 | 14 | 58 | 8 | — | — | — | 6.6 | >45 | 103 |
| F44 | 0.3 | 14 | 58 | 8 | — | — | — | 6.6 | >45 | 99 |
| F45 | 0.3 | 14 | 58 | 8 | — | — | — | 7.0 | >45 | 101 |
| F46 | 0.3 | 14 | 58 | 8 | — | — | — | 7.4 | >45 | 101 |
| F47 | 0.3 | 14 | 58 | 8 | — | — | — | 7.8 | >45 | 105 |
| F48 | 0.3 | 14 | 58 | 8 | — | — | — | 8.2 | >45 | 100 |

TABLE 28-continued

Stability of formulation comprising compound of EX. #2

| | EX.# 2 (mM) | Propylene glycol (mg/ml) | Phenol (mM) | Phosphate (mM) | HEPES (mM) | m-Cresol (mM) | NaCl (mM) | pH | ThT Lag-time (h) | Peptide Rec. (%) |
|---|---|---|---|---|---|---|---|---|---|---|
| F49 | 0.3 | 14 | 58 | 8 | — | — | — | 8.6 | >45 | 100 |
| F50 | 0.003 | 14 | 58 | 8 | — | — | — | 7.4 | >45 | 72 |
| F51 | 0.013 | 14 | 58 | 8 | — | — | — | 7.4 | >45 | 99 |
| F52 | 0.027 | 14 | 58 | 8 | — | — | — | 7.4 | >45 | 101 |
| F53 | 0.134 | 14 | 58 | 8 | — | — | — | 7.4 | >45 | 102 |
| F54 | 0.268 | 14 | 58 | 8 | — | — | — | 7.4 | >45 | 104 |
| F55 | 1.34 | 14 | 58 | 8 | — | — | — | 7.4 | >45 | 103 |
| F56 | 2.68 | 14 | 58 | 8 | — | — | — | 7.4 | >45 | 103 |
| F57 | 0.4 | 14 | 58 | 8 | — | — | — | 8.2 | >45 | 101 |
| F58 | 0.4 | 14 | 58 | — | 10 | — | — | 8.2 | >45 | 101 |
| F59 | 0.4 | 14 | — | — | 10 | 30 | — | 8.2 | >45 | 101 |
| F60 | 0.4 | 14 | 58 | 8 | — | — | — | 8.2 | >45 | 102 |
| F61 | 0.4 | 14 | 58 | 8 | — | — | 5 | 8.2 | >45 | 101 |
| F62 | 0.4 | 14 | 58 | 8 | — | — | 10 | 8.2 | >45 | 102 |
| F63 | 0.4 | 14 | 58 | 8 | — | — | 30 | 8.2 | >45 | 102 |
| F64 | 0.4 | 14 | 58 | 8 | — | — | 50 | 8.2 | >45 | 103 |
| F65 | 0.4 | 14 | 58 | 8 | — | — | 100 | 8.2 | >45 | 101 |
| F66 | 0.4 | 14 | 58 | 8 | — | — | 150 | 8.2 | >45 | 100 |
| F67 | 0.4 | 14 | 58 | 8 | — | — | — | 8.2 | >45 | 98 |
| F68 | 0.4 | 14 | 58 | — | — | — | — | 8.2 | >45 | 101 |
| F69 | 0.4 | 14 | 58 | — | 8 | — | — | 8.2 | >45 | 100 |
| F70 | 0.4 | 14 | — | 8 | — | — | — | 8.2 | >45 | 101 |
| F71 | 0.4 | 14 | — | — | 8 | — | — | 8.2 | >45 | 101 |
| F72 | 0.4 | — | 58 | 8 | — | — | — | 8.2 | >45 | 103 |
| F73 | 0.4 | — | — | — | 8 | — | — | 8.2 | >45 | 100 |

Example G—Stability of Formulations Comprising Compound of EX. #2

Formulations containing variable concentrations of compound of EX. #2 were prepared according to Example A. All formulations contained 14 mg/m propylene glycol, 58 mM phenol and 8 mM phosphate. pH was adjusted to specific levels between pH 6.6 and pH 8.6. All formulations were tested according to ASSAY (XIII).

TABLE 29

Stability of formulations comprising compound of EX. #2

| Form-ulation | EX.# 2 (mM) | Propylene glycol (mg/ml) | Phenol (mM) | Phosphate (mM) | pH | Pep. Conc.* (%) | HMWP£ (%) | Post monomer$ (%) | Purity Loss□ |
|---|---|---|---|---|---|---|---|---|---|
| F74 | 0.268 | 14 | 58 | 8 | 7.4 | 98 | 0.27 | 3.2 | 1.0 |
| F75 | 1.34 | 14 | 58 | 8 | 7.4 | 98 | 0.25 | 3.4 | 0.77 |
| F76 | 2.68 | 14 | 58 | 8 | 7.4 | 97 | 0.24 | 3.6 | 0.75 |
| F77 | 0.268 | 14 | 58 | 8 | 8.2 | 98 | 0.15 | 4.0 | 2.8 |
| F78 | 1.34 | 14 | 58 | 8 | 8.2 | 94 | 0.26 | 4.7 | 2.2 |
| F79 | 2.68 | 14 | 58 | 8 | 8.2 | 94 | 0.26 | 4.6 | 2.0 |
| F80 | 0.3 | 14 | 58 | 8 | 6.6 | — | 0.102 | — | 0.22 |
| F81 | 0.3 | 14 | 58 | 8 | 7.0 | — | 0.075 | — | 0.39 |
| F82 | 0.3 | 14 | 58 | 8 | 7.4 | — | 0.064 | — | 0.58 |
| F83 | 0.3 | 14 | 58 | 8 | 7.8 | — | 0.053 | — | 0.88 |
| F84 | 0.3 | 14 | 58 | 8 | 8.2 | — | 0.047 | — | 2.26 |
| F85 | 0.3 | 14 | 58 | 8 | 8.6 | — | 0.021 | — | 4.39 |

*Peptide concentration after 11 weeks at 37° C. relative to start value
£% HMWP after 11 weeks at 37° C. (Formulation F74-F79) or HMWP formation rate (%/month) at 37° C. (Formulation F80-F85)
$Post monomer after 11 weeks at 37° C. minus start value
□Purity loss in %/month at 37° C.

Example H—Stability of Formulations Comprising Compound of EX. #2

Formulations containing 0.05 to 2 mM compound of EX. #2 were prepared according to Example A. All formulations contained 14 mg/ml propylene glycol, 58 mM phenol and 8 mM phosphate, pH 8.2. All formulations were tested according to ASSAY (XIII).

TABLE 30

Stability of formulations comprising compound of EX. #2

| Formulation | EX.# 2 (mM) | Propylene glycol (mg/ml) | Phenol (mM) | Phosphate (mM) | pH | Pep. Conc.* (%) | HMWP£ (%) | Post monomer$ (%) | Purity Loss□ |
|---|---|---|---|---|---|---|---|---|---|
| F86 | 2 | 14 | 58 | 8 | 8.2 | 100 | 0.22 | 0.24 | 1.8 |
| F87 | 1 | 14 | 58 | 8 | 8.2 | 100 | 0.20 | 2.1 | 2.1 |
| F88 | 0.5 | 14 | 58 | 8 | 8.2 | 100 | 0.27 | 2.2 | 2.6 |
| F89 | 0.2 | 14 | 58 | 8 | 8.2 | 99 | 0.17 | 1.2 | 2.4 |
| F90 | 0.05 | 14 | 58 | 8 | 8.2 | 97 | 0.06 | nd | 3.0 |

*Peptide concentration after 8 weeks at 37° C. relative to start value
£HMWP after 8 weeks at 37° C.
$Post monomer after 8 weeks at 37° C. minus start value (nd = not possible to detect)
□Purity loss in %/month at 37° C.

Example I—Stability of Formulations Comprising Compound of Ex. #2

Formulations containing 0.01 to 0.5 mM compound of EX. #2 were prepared according to Example A. All formulations contained 14 mg/ml propylene glycol, 58 mM phenol and 8 mM phosphate, pH 8.2. All formulations were tested according to ASSAY (XIII).

TABLE 31

Stability of formulations comprising compound of EX. #2

| Formulation | EX.# 2 (mM) | Propylene glycol (mg/ml) | Phenol (mM) | Phosphate (mM) | pH | Pep. Conc.* (%) | Purity Loss□ |
|---|---|---|---|---|---|---|---|
| F91 | 0.01 | 14 | 58 | 8 | 8.2 | 84 | 2.8 |
| F92 | 0.02 | 14 | 58 | 8 | 8.2 | 94 | 2.7 |
| F93 | 0.05 | 14 | 58 | 8 | 8.2 | 98 | 2.7 |
| F94 | 0.1 | 14 | 58 | 8 | 8.2 | 98 | 2.7 |
| F95 | 0.2 | 14 | 58 | 8 | 8.2 | 99 | 2.9 |
| F96 | 0.5 | 14 | 58 | 8 | 8.2 | 99 | 2.5 |

*Peptide concentration after 8 weeks at 37° C. relative to start value
□Purity loss in %/month at 37° C.

Example J—Stability of Formulation Comprising Compound of EX. #2

Formulations containing 2.7 pM to 2.7 mM compound of EX. #2 were prepared according to Example A. All formulations contained 14 mg/ml propylene glycol, 58 mM phenol and 8 mM phosphate, pH 7.4. All formulations were tested according to ASSAY (XIII).

TABLE 32

Stability of formulations comprising compound of EX. #2

| Formulation | EX.# 2 (mM) | Propylene glycol (mg/ml) | Phenol (mM) | Phosphate (mM) | pH | Pep. Conc.* (%) | HMWP£ (%) | Purity Loss□ |
|---|---|---|---|---|---|---|---|---|
| F97 | 0.00268 | 14 | 58 | 8 | 7.4 | 77 | 0.09 | 6.1 |
| F98 | 0.0134 | 14 | 58 | 8 | 7.4 | 89 | 0.05 | 2.1 |
| F99 | 0.0268 | 14 | 58 | 8 | 7.4 | 92 | 0.04 | 1.2 |
| F100 | 0.134 | 14 | 58 | 8 | 7.4 | 94 | 0.24 | 1.1 |
| F101 | 0.268 | 14 | 58 | 8 | 7.4 | 94 | 0.28 | 0.9 |
| F102 | 1.34 | 14 | 58 | 8 | 7.4 | 99 | 0.41 | 1.0 |
| F103 | 2.68 | 14 | 58 | 8 | 7.4 | 99 | 0.42 | 0.7 |

*Peptide concentration after 11 weeks at 37° C. relative to start value
£HMWP after 11 weeks at 37° C.
□Purity loss in %/month at 37° C.

Example K—Stability of a Formulations Comprising Compound of EX. #2

Formulations containing a compound of EX. #2 were prepared according to Example A and tested according to ASSAY (XIII).

TABLE 33

Stability of formulations comprising compound of EX. #2

| Formulation | EX.# 2 (mM) | Propylene glycol (mg/ml) | Phenol (mM) | Phosphate (mM) | HEPES (mM) | m-Cresol (mM) | NaCl (mM) | pH | Pep. Conc.* (%) | HMWP£ (%) | Post monomer$ (%) |
|---|---|---|---|---|---|---|---|---|---|---|---|
| F104 | 0.4 | 14 | 58 | 8 | — | — | — | 8.2 | 107 | 0.30 | 3.4 |
| F105 | 0.4 | 14 | 58 | — | 10 | — | — | 8.2 | 105 | 0.25 | 3.2 |
| F106 | 0.4 | 14 | — | — | 10 | 30 | — | 8.2 | 105 | 0.23 | 3.0 |
| F107 | 0.4 | 14 | 58 | 8 | — | — | — | 8.2 | 99 | 0.31 | 0.77 |
| F108 | 0.4 | 14 | 58 | 8 | — | — | 5 | 8.2 | 99 | 0.38 | 0.99 |
| F109 | 0.4 | 14 | 58 | 8 | — | — | 10 | 8.2 | 99 | 0.36 | 0.85 |
| F110 | 0.4 | 14 | 58 | 8 | — | — | 30 | 8.2 | 97 | 0.41 | 0.71 |
| F111 | 0.4 | 14 | 58 | 8 | — | — | 50 | 8.2 | 98 | 0.53 | 0.43 |
| F112 | 0.4 | 14 | 58 | 8 | — | — | 100 | 8.2 | 99 | 0.67 | 0.94 |
| F113 | 0.4 | 14 | 58 | 8 | — | — | 150 | 8.2 | 99 | 0.69 | 0.66 |
| F114 | 0.4 | 14 | 58 | 8 | — | — | — | 8.2 | 104 | 0.27 | 0.51 |
| F115 | 0.4 | 14 | 58 | — | — | — | — | 8.2 | 99 | 0.14 | 0.72 |
| F116 | 0.4 | 14 | 58 | — | 8 | — | — | 8.2 | 101 | 0.20 | 0.66 |
| F117 | 0.4 | 14 | — | 8 | — | — | — | 8.2 | 101 | 0.18 | 1.02 |
| F118 | 0.4 | 14 | — | — | 8 | — | — | 8.2 | 101 | 0.17 | 0.68 |
| F119 | 0.4 | — | 58 | 8 | — | — | — | 8.2 | 101 | 0.37 | 0.70 |
| F120 | 0.4 | — | — | — | 8 | — | — | 8.2 | 102 | 0.20 | 0.73 |

*Peptide concentration after one month at 37° C. relative to start value
£HMWP after one month at 37° C.
$Post monomer after one month at 37° C. minus start value Example L—Stability of Co-Formulations Comprising Compound of EX. #2 in Combination with Liraglutide Co-formulations containing a compound of EX. #2 and liraglutide were prepared according to Example A together with mono-formulations containing the same amount of the two peptide components. All formulations (mono- and co-) were tested according to ASSAY (IIIa) and ASSAY (XIII).

TABLE 34

Stability of co-formulations comprising compound of EX. #2 in combination with liraglutide

| Formulation | EX.#2 (mg/ml)a | Liraglutide (mg/ml)a | Propylene glycol (mg/ml) | Phenol (mM) | Phosphate (mM) | pH | Pep. Conc.* (%) | HMWP£ (%) | ThT Lag-time (h) | EX.# 2 recovery (%)# | Liraglutide recovery (%)¤ |
|---|---|---|---|---|---|---|---|---|---|---|---|
| F121 | 0.6 | — | 14 | 58 | 8 | 8.2 | 97 | 0.02 | >45 | 107 | — |
| F122 | 1 | — | 14 | 58 | 8 | 8.2 | 98 | 0.03 | >45 | 96 | — |
| F123 | 2 | — | 14 | 58 | 8 | 8.2 | 98 | 0.03 | >45 | 106 | — |
| F124 | — | 1 | 14 | 58 | 8 | 8.2 | 99 | 2.54 | >45 | — | 104 |
| F125 | — | 3 | 14 | 58 | 8 | 8.2 | 101 | 1.17 | >45 | — | 105 |
| F126 | — | 6 | 14 | 58 | 8 | 8.2 | 100 | 0.62 | >45 | — | 100 |
| F127 | 0.6 | 1 | 14 | 58 | 8 | 8.2 | 98 | 1.78 | >45 | 105 | 97 |
| F128 | 0.6 | 3 | 14 | 58 | 8 | 8.2 | 99 | 1.06 | >45 | 98 | 106 |
| F129 | 0.6 | 6 | 14 | 58 | 8 | 8.2 | 99 | 0.67 | >45 | 107 | 103 |
| F130 | 1 | 1 | 14 | 58 | 8 | 8.2 | 98 | 1.55 | >45 | 110 | 98 |
| F131 | 1 | 3 | 14 | 58 | 8 | 8.2 | 99 | 0.85 | >45 | 99 | 95 |
| F132 | 1 | 6 | 14 | 58 | 8 | 8.2 | 100 | 0.75 | >45 | 102 | 104 |
| F133 | 2 | 1 | 14 | 58 | 8 | 8.2 | 99 | 1.14 | >45 | 97 | 95 |
| F134 | 2 | 3 | 14 | 58 | 8 | 8.2 | 99 | 0.79 | >45 | 99 | 98 |
| F135 | 2 | 6 | 14 | 58 | 8 | 8.2 | 100 | 0.66 | >45 | 110 | 98 | a1 mg/ml EX #2~0.27 mM; 1 mg/ml liraglutide ~0.27 mM
*Peptide concentration after twelve weeks at 37° C. relative to start value
£HMWP formation rate at 37° C. (%/month)
UV-215 nm detection; not baseline separated from liraglutide
¤UV-280 nm detection Example M—Stability of Co Formulations Comprising Compound of EX. #2 in Combination with Semaglutide Co-formulations containing compound of EX. #2 and semaglutide were prepared according to Example A together with mono-formulations containing the same amount of the two peptide components. All formulations (mono- and co-) were tested according to ASSAY (IIIa) and ASSAY (XIII).

TABLE 35

Stability of co formulations comprising compound of EX. #2 in combonation with semaglutide

| Form- ulation | EX.#2 (mg/ml)[a] | Semaglutide (mg/ml)[a] | Propylene glycol (mg/ml) | Phenol (mM) | Phosphate (mM) | pH | Pep. Conc.* (%) | HMWP[£] (%) | ThT Lag-time (h) | Total peptide recovery (%)[$] | Semaglutide recovery (%)[¤] |
|---|---|---|---|---|---|---|---|---|---|---|---|
| F136 | 0.6 | — | 14 | 58 | 8 | 7.4 | 95 | 0.00 | >45 | 101 | — |
| F137 | 6 | — | 14 | 58 | 8 | 7.4 | 96 | 0.08 | >45 | 102 | — |
| F138 | 12 | — | 14 | 58 | 8 | 7.4 | 90 | 0.09 | >45 | 103 | — |
| F139 | — | 0.5 | 14 | 58 | 8 | 7.4 | 98 | 1.36 | >45 | 96 | 107 |
| F140 | — | 2 | 14 | 58 | 8 | 7.4 | 97 | 0.68 | >45 | 117 | 97 |
| F141 | — | 4.1 | 14 | 58 | 8 | 7.4 | 99 | 0.47 | >45 | 100 | 106 |
| F142 | 0.6 | 0.5 | 14 | 58 | 8 | 7.4 | 97 | 0.74 | >45 | 100 | 101 |
| F143 | 0.6 | 2 | 14 | 58 | 8 | 7.4 | 95 | 0.37 | >45 | 102 | 102 |
| F144 | 0.6 | 4.1 | 14 | 58 | 8 | 7.4 | 96 | 0.34 | >45 | 95 | 97 |
| F145 | 6 | 0.5 | 14 | 58 | 8 | 7.4 | 95 | 0.14 | >45 | 104 | 96 |
| F146 | 6 | 2 | 14 | 58 | 8 | 7.4 | 96 | 0.20 | >45 | 103 | 91 |
| F147 | 6 | 4.1 | 14 | 58 | 8 | 7.4 | 97 | 0.26 | >45 | 98 | 98 |
| F148 | 12 | 0.5 | 14 | 58 | 8 | 7.4 | 96 | 0.13 | >45 | 100 | 96 |
| F159 | 12 | 2 | 14 | 58 | 8 | 7.4 | 96 | 0.17 | >45 | 107 | 92 |
| F150 | 12 | 4.1 | 14 | 58 | 8 | 7.4 | 95 | 0.19 | >45 | 98 | 99 |

[a] 1 mg/ml EX #2~0.27 mM; 1 mg/ml semaglutide ~0.27 mM
*Peptide concentration after twelve weeks at 37° C. relative to start value
[£] HMWP formation rate at 37° C. (%/month)
[$] Total peptide recovery reflects the recovery of EX.* 2 and semaglutide in total (EX.# 2 co-elutes with semaglutide)
[¤] UV-280 nm detection of semaglutide Example N—Compound EX. #2 when Co-Formulated with Liraglutide: Effect on Body Weight Using DIO Rat Model ASSAY(XIV)

Monotherapy with liraglutide and compound of EX. #2 induced a 5.9% and 10.9% reduction in body weight at the given doses, respectively. Addition of compound EX. #2 on day 15 to the treatment regimen with liraglutide caused an additional 9.7% reduction in body weight by day 28 relative to monotherapy with liraglutide. See FIG. 1 and Table 36.

TABLE 36

Effects on body weight reduction with liraglutide and compound of Ex. #2 at the given doses ASSAY (XIV)

| Group | Absolute BW (g) | | | Relative BW (% of initial BW) | |
|---|---|---|---|---|---|
| | Day 0 | Day 15 | Day 28 | Day 15 | Day 28 |
| Vehicle | 834.7 ± 40 [a] | 824.4 ± 39.6 [a] | 833.2 ± 41 [a] | 98.8 ± 0.8 [a] | 99.8 ± 1.1 [a] |
| Liraglutide, 0.1 mg/kg | 824.6 ± 44.7 [a] | 774.2 ± 42.9 [a] | 773.9 ± 41.2 [a] | 93.9 ± 0.5 [b] | 93.9 ± 0.7 [b] |
| EX. #2, 3.7 µg/kg | 815.5 ± 33.3 [a] | 740.3 ± 34.3 [a] | 726.5 ± 33.9 [a] | 90.6 ± 0.6 [c] | 88.9 ± 0.7 [c] |
| Liraglutide, 0.1 mg/kg + EX. #2, 3.7 µg/kg | 819.3 ± 27.7 [a] | 765.1 ± 27.1 [a] | 681.5 ± 26 [b] | 93.4 ± 0.5 [b] | 83.2 ± 1.3 [d] |

[a-d] p < 0.05, one-way ANOVA and Tukey's multiple comparison test for each day; groups not connected by the same letter (in each column) are significantly different from each other. Results expressed as mean ± SEM, n = 10.

TABLE 37

Amylin and calcitonin receptor IC50 (pM) for mimylin compounds (Assay Va & VIIa)

| Ex. # | Amylin-R binding IC50 (pM) | hCT-R binding IC50 (PM) |
|---|---|---|
| 1 | 511 | 431 |
| 2 | 902 | 798 |
| 3 | 498 | 413 |
| 4 | 1189 | 1050 |
| 5 | 8377 | 6506 |
| 6 | 8972 | 5684 |
| 7 | 435 | 834 |
| 8 | 429 | 368 |
| 9 | 796 | 736 |
| 10 | 417 | 523 |
| 11 | 1475 | 1369 |
| 12 | 511 | 419 |
| 13 | 329 | 279 |
| 15 | 275 | 473 |
| 16 | 1312 | 981 |
| 17 | 832 | 577 |
| 18 | 1265 | 1172 |
| 19 | 1144 | 515 |
| 21 | 187 | 315 |
| 22 | 240 | 188 |
| 23 | 830 | 541 |
| 24 | 824 | 749 |
| 25 | 400 | 413 |
| 26 | 891 | 570 |
| 27 | 374 | 219 |
| 28 | 375 | 351 |
| 29 | 352 | 309 |
| 30 | 323 | 478 |

TABLE 37-continued

Amylin and calcitonin receptor IC50 (pM) for mimylin compounds (Assay Va & VIIa)

| Ex. # | Amylin-R binding IC50 (pM) | hCT-R binding IC50 (PM) |
|---|---|---|
| 31 | 383 | 506 |
| 32 | 9000 | 3348 |
| 33 | 745 | 752 |
| 34 | 1592 | 2266 |
| 43 | 432 | 352 |
| 56 | 2609 | 2935 |
| 57 | 1231 | 2536 |
| 60 | 1067 | 1527 |
| 61 | 1360 | 1760 |
| 62 | 3053 | 2332 |
| 63 | 4066 | 2597 |
| 64 | 4360 | 3632 |
| 65 | 1888 | 1246 |
| 72 | 697 | 438 |
| 73 | 608 | 442 |
| 74 | 606 | 1085 |
| 75 | 21984 | 20475 |
| 76 | 764 | 855 |
| 77 | 998 | 1100 |
| 78 | 587 | 605 |
| 79 | 111 | 385 |
| 81 | 2015 | 4929 |
| 83 | 1916 | 1567 |
| 85 | 653 | 821 |
| 86 | 812 | 943 |
| 87 | 428 | 590 |
| 88 | 92023 | 24195 |
| 89 | 7260 | 3600 |
| 90 | 21010 | 6843 |
| 92 | 2609 | 2935 |
| 93 | 1507 | 1028 |
| 94 | 652 | 651 |
| 95 | 2147 | 1696 |
| 96 | 1170 | 767 |
| 97 | 186 | 307 |
| 100 | 3167 | 2824 |
| 101 | 588 | 628 |
| 102 | 1649 | 1242 |
| 105 | 22900 | 17318 |
| 106 | 19721 | 9146 |
| 107 | 5445 | 1267 |
| 111 | 222 | 747 |
| 112 | 431 | 547 |
| 114 | 278 | 326 |
| 115 | 338 | 796 |
| 117 | 142 | 450 |
| 121 | 801 | 300 |
| 122 | 244 | 318 |
| 123 | 11784 | 5624 |
| 124 | 79 | 312 |
| 126 | 1481 | 1833 |
| 128 | 116 | 200 |
| 129 | 2560 | 3624 |
| 132 | 3701 | 1549 |
| 133 | 10698 | 9664 |
| 134 | 297898 | 42425 |
| 135 | 294388 | 630425 |
| 106bb | 71390 | 62870 |
| 127bb | 1183 | 959 |
| 22bb | 469 | 481 |
| 72bb | 5100 | 4529 |
| 86bb | 982 | 520 |
| 95bb | 20158 | 15330 |

The invention claimed is:

1. A mimylin peptide comprising a sequence which is at least 66% identical to EASELSTAALGRLSAELHELATL-PRTETGPESP (SEQ ID NO: 1) and does not comprise any N.

2. The mimylin peptide according to claim 1, wherein said mimylin peptide comprises up to 11 of the following amino acids or modifications relative to SEQ ID NO: 1:
   a. E or no amino acid in position −1,
   b. E, A or no amino acid in position 1,
   c. A, L or P in position 2,
   d. S or P in position 3,
   e. E, P, K, Q or G in position 4,
   f. L, V, I or H in position 5,
   g. S, T or H in position 6,
   h. T in position 7,
   i. L or A in position 8,
   j. A, V, I, S or T in position 9,
   k. L, A, I, H or V in position 10,
   l. G in position 11,
   m. R, H or K in position 12,
   n. L in position 13,
   o. S, T or E in position 14,
   p. A, Q, E, e or T in position 15,
   q. E, R, K or Q in position 16,
   r. L or I in position 17,
   s. H or A in position 18,
   t. E, R or K in position 19,
   u. L, I or V in position 20,
   v. A, Q, S, E or T in position 21,
   w. T in position 22,
   x. L or Y in position 23, y. P in position 24,
z. R, P, H or K in position 25,
aa. T in position 26,
bb. E, Q, G or K in position 27,
cc. T or P in position 28,
dd. G in position 29,
ee. P, S or T in position 30,
ff. E, Q, G, A, P or K in position 31,
gg. T, S, H, P or A in position 32,
hh. P, Y, H, F, L, S, G or A in position 33,
ii. G or K in position 34 or no amino acid.

3. The mimylin peptide according to claim 1, wherein said mimylin peptide comprises up to 11 of the following amino acids or modifications relative to SEQ ID NO: 1:
a. E or no amino acid in position −1,
b. E in position 1,
c. A, L or P in position 2,
d. S or P in position 3,
e. E, P, K, Q or G in position 4,
f. L, V, I or H in position 5,
g. S in position 6,
h. T in position 7,
i. A in position 8,
j. A, V, or I in position 9,
k. L, or I in position 10,
l. G in position 11,
m. R, H or K in position 12,
n. L in position 13,
o. S, T or E in position 14,
p. A in position 15,
q. E in position 16,
r. L or I in position 17,
s. H or A in position 18,
t. E in position 19,
u. L in position 20,
v. A in position 21,
w. T in position 22,
x. L or Y in position 23,
y. P in position 24,
z. R in position 25,
aa. T in position 26,
bb. E in position 27,
cc. T or P in position 28,
dd. G in position 29,
ee. P, S or T in position 30,
ff. E or G in position 31,
gg. S or T in position 32,
hh. P or Y in position 33,
ii. G or K in position 34 or no amino acid.

4. The mimylin peptide according to claim 1, wherein position 30 is S and position 31 is G, wherein the amino acid numbering corresponds to SEQ ID NO: 1.

5. The mimylin peptide according to claim 1, wherein position 9 is V and/or position 1 is E, wherein the amino acid numbering corresponds to SEQ ID NO: 1.

6. The mimylin peptide according to claim 1, wherein position 33 is P, wherein the amino acid numbering corresponds to SEQ ID NO: 1.

7. The mimylin peptide according to claim 1, wherein said peptide has a c-terminal amide.

8. The mimyin peptide according to claim 1, wherein said mimylin peptide is derivatised in the N-terminal amino acid or any K within said mimylin peptide sequence.

9. The mimylin peptide according to claim 1, wherein said mimylin peptide does not comprise a disulfide bridge between the amino acids in positions 2 and 8, wherein the amino acid numbering corresponds to SEQ ID NO: 1.

10. A mimylin derivative, wherein a mimylin peptide according to claim 1 is derivatised with a side chain comprising a protracting moiety and a linker.

11. The mimylin derivative according to claim 10, wherein said protracting moiety is a fatty acid or diacid.

12. The mimylin derivative according to claim 10, which is an agonist of the amylin and calcitonin receptor.

13. A method of treating overweight comprising administering a mimylin peptide according to claim 1 to a subject in need thereof.

14. A method of treating overweight comprising administering a mimylin derivative according to claim 10 to a subject in need thereof.

15. A method of reducing food intake comprising administering a mimylin peptide according to claim 1 to a subject in need thereof.

16. A method of reducing food intake comprising administering a mimylin derivative according to claim 10 to a subject in need thereof.

17. An aqueous pharmaceutical formulation comprising a mimylin derivative according to claim 10 and a pharmaceutically acceptable ingredient.

18. The aqueous pharmaceutical formulation according to claim 17, wherein said pharmaceutically acceptable ingredient is selected from the group consisting of glycerol, phosphate, propylene glycol, phenol, m-cresol, or a combination of phenol and m-cresol.

19. An aqueous pharmaceutical formulation comprising a mimylin derivative of claim 10 in a concentration of from about 0.001 mM to about 15 mM, phosphate in a range of between about 4 mM to about 12 mM, propylene glycol from about 1 mg/ml to about 30 mg/ml, m-cresol from about 5 mM to about 40 mM, phenol from about 5 mM to about 90 mM, and glycerol from about 1 mg/ml to about 30 mg/ml.

20. An aqueous pharmaceutical formulation comprising a mimylin derivative of claim 10, 8 mM phosphate, 14 mg/ml propylene glycol, and 58 mM phenol, wherein said mimylin derivative is in a concentration selected from the group consisting of from 0.005 mM to 2 mM, from 0.01 to 0.5 mM, and from 0.0027 mM to 2.7 mM.

21. A mimylin derivative, wherein a mimylin peptide according to claim 1 is derivatised with a side chain comprising a protracting moiety.

22. The mimylin derivative according to claim 21, wherein said protracting moiety is a fatty acid or diacid.

23. The mimylin derivative according to claim 21, wherein said protracting moiety is a fatty acid or diacid comprising between 14 and 20 carbon atoms.

24. The mimylin derivative according to claim 21, which is an agonist of the amylin and calcitonin receptor.

25. A method of treating overweight comprising administering a mimylin derivative according to claim 21 to a subject in need thereof.

26. A method of reducing food intake comprising administering a mimylin peptide according to claim 21 to a subject in need thereof.

27. An aqueous pharmaceutical formulation comprising a mimylin derivative according to claim 21 and a pharmaceutically acceptable ingredient.

28. The aqueous pharmaceutical formulation according to claim 27, wherein said pharmaceutically acceptable ingredient is selected from the group consisting of glycerol, phosphate, propylene glycol, phenol, m-cresol, or a combination of phenol and m-cresol.

29. An aqueous pharmaceutical formulation comprising a mimylin derivative of claim 21 in a concentration of from about 0.001 mM to about 15 mM, phosphate in a range of between about 4 mM to about 12 mM, propylene glycol from about 1 mg/ml to about 30 mg/ml, m-cresol from about 5 mM to about 40 mM, phenol from about 5 mM to about 90 mM, and glycerol from about 1 mg/ml to about 30 mg/ml.

30. An aqueous pharmaceutical formulation comprising a mimylin derivative of claim 21, 8 mM phosphate, 14 mg/ml propylene glycol, and 58 mM phenol, wherein said mimylin derivative is in a concentration selected from the group consisting of from 0.05 mM to 2 mM, from 0.01 to 0.5 mM, and from 0.0027 mM to 2.7 mM.

31. The mimylin peptide according to claim 2, wherein said mimylin peptide comprises 10, 9, 8 or 7 of the amino acids or modifications as set forth in (a)-(ii) in claim 2 relative to SEQ ID NO: 1.

32. The mimylin peptide according to claim 2, wherein said mimylin peptide comprises 6, 5, 3, 2 or 1 of the amino acids or modifications as set forth in (a)-(ii) in claim 2 relative to SEQ ID NO: 1.

33. The mimylin peptide according to claim 3, wherein said mimylin peptide comprises 10, 9, 8 or 7 of the amino acids or modifications as set forth in (a)-(ii) in claim 3 relative to SEQ ID NO: 1.

34. The mimylin peptide according to claim 3, wherein said mimylin peptide comprises 6, 5, 3, 2 or 1 of the amino acids or modifications as set forth in (a)-(ii) in claim 3, relative to SEQ ID NO: 1.

35. The mimylin derivative according to claim 10, wherein said linker is selected from the list consisting of gGlu, gGlu-OEG, gGlu-OEG-OEG, gGlu-OEG-OEG-OEG, gGlu-OEG-OEG-OEG-OEG, and gGlu-OEG-OEG-OEG-OEG-OEG.

36. The mimylin derivative according to claim 11, wherein said fatty acid or diacid comprises between 14 and 20 carbon atoms.

37. The mimylin derivative according to claim 35, wherein said protracting moiety is a fatty acid or diacid comprising between 14 and 20 carbon atoms.

38. A method of treating obesity comprising administering a mimylin peptide according to claim 1 to a subject in need thereof.

39. A method of treating obesity comprising administering a mimylin derivative according to claim 10 to a subject in need thereof.

40. A method of treating obesity comprising administering a mimylin derivative according to claim 21 to a subject in need thereof.

* * * * *

UNITED STATES PATENT AND TRADEMARK OFFICE
CERTIFICATE OF CORRECTION

PATENT NO. : 10,174,082 B2
APPLICATION NO. : 15/417671
DATED : January 8, 2019
INVENTOR(S) : Thomas Kruse et al.

Page 1 of 1

It is certified that error appears in the above-identified patent and that said Letters Patent is hereby corrected as shown below:

In the Claims

At Column 282, Claim number 2, Line number 53, amend as follows:
j. A, V, I, S or T in position 9, Signed and Sealed this
Fourteenth Day of May, 2019

Andrei Iancu
*Director of the United States Patent and Trademark Office*